United States Patent
Schwabe et al.

(10) Patent No.: US 12,358,991 B2
(45) Date of Patent: Jul. 15, 2025

(54) ANTI-SORTILIN ANTIBODIES AND METHODS OF USE THEREOF

(71) Applicant: Alector LLC, South San Francisco, CA (US)

(72) Inventors: Tina Schwabe, San Francisco, CA (US); Michael Kurnellas, San Francisco, CA (US); Arnon Rosenthal, Woodside, CA (US); Robert Pejchal, Lebanon, NH (US); Anthony B. Cooper, White River Junction, VT (US)

(73) Assignee: Alector LLC, South San Francisco, CA (US)

( * ) Notice: Subject to any disclaimer, the term of this patent is extended or adjusted under 35 U.S.C. 154(b) by 261 days.

(21) Appl. No.: 17/836,644

(22) Filed: Jun. 9, 2022

(65) Prior Publication Data

US 2023/0047941 A1    Feb. 16, 2023

Related U.S. Application Data

(62) Division of application No. 16/510,773, filed on Jul. 12, 2019, now Pat. No. 11,396,546.

(60) Provisional application No. 62/868,849, filed on Jun. 28, 2019, provisional application No. 62/860,184, filed on Jun. 11, 2019, provisional application No. 62/698,007, filed on Jul. 13, 2018.

(51) Int. Cl.
*C07K 16/28* (2006.01)

(52) U.S. Cl.
CPC ........ *C07K 16/286* (2013.01); *C07K 2317/31* (2013.01); *C07K 2317/52* (2013.01); *C07K 2317/76* (2013.01); *C07K 2317/92* (2013.01); *C07K 2317/94* (2013.01)

(58) Field of Classification Search
CPC ............. C07K 16/286; C07K 2317/31; C07K 2317/52; C07K 2317/76; C07K 2317/92; C07K 2317/94
See application file for complete search history.

(56) References Cited

U.S. PATENT DOCUMENTS

| RE30,985 E | 6/1982 | Cartaya |
|---|---|---|
| 4,560,655 A | 12/1985 | Baker |
| 4,657,760 A | 4/1987 | Kung et al. |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,927,762 A | 5/1990 | Darfler |
| 5,122,469 A | 6/1992 | Mather et al. |
| 5,206,344 A | 4/1993 | Katre et al. |
| 5,225,212 A | 7/1993 | Martin et al. |
| 5,229,275 A | 7/1993 | Goroff et al. |
| 5,530,101 A | 6/1996 | Queen et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,825 A | 10/1996 | Lonberg et al. |
| 5,571,894 A | 11/1996 | Wels et al. |
| 5,573,905 A | 11/1996 | Lerner et al. |
| 5,585,089 A | 12/1996 | Queen et al. |
| 5,587,458 A | 12/1996 | King et al. |
| 5,591,669 A | 1/1997 | Krimpenfort et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,648,237 A | 7/1997 | Carter et al. |
| 5,661,016 A | 8/1997 | Lonberg et al. |
| 5,693,761 A | 12/1997 | Queen et al. |
| 5,693,762 A | 12/1997 | Queen et al. |
| 5,731,168 A | 3/1998 | Carter et al. |
| 5,739,277 A | 4/1998 | Presta et al. |
| 5,750,373 A | 5/1998 | Garrard et al. |
| 5,766,886 A | 6/1998 | Studnicka et al. |
| 5,770,429 A | 6/1998 | Lonberg et al. |
| 5,789,199 A | 8/1998 | Joly et al. |
| 5,821,337 A | 10/1998 | Carter et al. |
| 5,840,523 A | 11/1998 | Simmons et al. |
| 5,869,046 A | 2/1999 | Presta et al. |
| 5,869,619 A | 2/1999 | Studnicka |
| 5,959,177 A | 9/1999 | Hein et al. |
| 6,040,498 A | 3/2000 | Stomp et al. |
| 6,075,181 A | 6/2000 | Kucherlapati et al. |

(Continued)

FOREIGN PATENT DOCUMENTS

| CN | 101835489 A | 9/2010 |
|---|---|---|
| EP | 308936 B1 | 7/1994 |

(Continued)

OTHER PUBLICATIONS

Alegre et al. (1994). "A Non-Activating "Humanized" Anti-CD3 Monoclonal Antibody Retains Immunosuppressive Properties In Vivo," Transplantation 57(11):1537-1543.

(Continued)

*Primary Examiner* — Gyan Chandra

(74) *Attorney, Agent, or Firm* — MORRISON & FOERSTER LLP

(57) ABSTRACT

The present disclosure is generally directed to compositions that include antibodies, e.g., monoclonal, chimeric, affinity-matured, humanized antibodies, antibody fragments, etc., that specifically bind a Sortilin protein, e.g., human Sortilin or mammalian Sortilin, and have improved and/or enhanced functional characteristics, and use of such compositions in preventing, reducing risk, or treating an individual in need thereof.

52 Claims, 6 Drawing Sheets

Specification includes a Sequence Listing.

(56) References Cited

U.S. PATENT DOCUMENTS

| | | |
|---|---|---|
| 6,150,584 A | 11/2000 | Kucherlapati et al. |
| 6,248,516 B1 | 6/2001 | Winter et al. |
| 6,417,429 B1 | 7/2002 | Hein et al. |
| 6,420,548 B1 | 7/2002 | Vézina et al. |
| 6,982,321 B2 | 1/2006 | Winter |
| 7,041,870 B2 | 5/2006 | Tomizuka et al. |
| 7,087,409 B2 | 8/2006 | Barbas, III et al. |
| 7,125,978 B1 | 10/2006 | Vézina et al. |
| 7,189,826 B2 | 3/2007 | Rodman |
| 7,527,791 B2 | 5/2009 | Adams et al. |
| 8,008,009 B2 | 8/2011 | Choquet-Kastylevsky et al. |
| 8,066,997 B2 | 11/2011 | Nykjaer et al. |
| 8,460,657 B2 | 6/2013 | Nykjaer et al. |
| 8,614,299 B2 | 12/2013 | Baurin et al. |
| 8,703,125 B2 | 4/2014 | Pedersen et al. |
| 8,748,384 B2 | 6/2014 | Andersen et al. |
| 8,795,627 B2 | 8/2014 | Starr et al. |
| 8,815,808 B2 | 8/2014 | Nykjaer et al. |
| 8,877,714 B2 | 11/2014 | Starr et al. |
| 8,986,690 B2 | 3/2015 | Nykjaer et al. |
| 9,061,045 B2 | 6/2015 | Choquet-Kastylevsky et al. |
| 9,062,126 B2 | 6/2015 | Zankel et al. |
| 9,084,745 B2 | 7/2015 | Nykjaer et al. |
| 9,234,036 B2 | 1/2016 | Anderson et al. |
| 9,605,073 B2 | 3/2017 | Nykjaer et al. |
| 9,670,263 B2 | 6/2017 | Pedersen et al. |
| 9,822,366 B2 | 11/2017 | Aikawa et al. |
| 10,087,255 B2 | 10/2018 | Rosenthal et al. |
| 10,308,718 B2 | 6/2019 | Rosenthal et al. |
| 10,428,150 B2 | 10/2019 | Rosenthal et al. |
| 10,478,421 B1 | 11/2019 | Sparks et al. |
| 10,849,896 B2 | 12/2020 | Patel et al. |
| 10,849,992 B1 | 12/2020 | Rosenthal et al. |
| 11,186,645 B2 | 11/2021 | Rosenthal et al. |
| 11,208,488 B2 | 12/2021 | Rosenthal et al. |
| 11,339,223 B2 | 5/2022 | Rosenthal et al. |
| 11,396,546 B2 | 7/2022 | Schwabe et al. |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2006/0025576 A1 | 2/2006 | Miller et al. |
| 2007/0061900 A1 | 3/2007 | Murphy et al. |
| 2007/0148167 A1 | 6/2007 | Strohl |
| 2007/0292936 A1 | 12/2007 | Barthelemy et al. |
| 2008/0069820 A1 | 3/2008 | Fuh et al. |
| 2009/0002360 A1 | 1/2009 | Chen et al. |
| 2009/0055944 A1 | 2/2009 | Korman et al. |
| 2009/0068200 A1 | 3/2009 | Choquet-Kastylevsky et al. |
| 2009/0181855 A1 | 7/2009 | Vasquez et al. |
| 2010/0028333 A1 | 2/2010 | Getty et al. |
| 2010/0056386 A1 | 3/2010 | Vasquez et al. |
| 2010/0092481 A1 | 4/2010 | Lanzavecchia et al. |
| 2010/0280227 A1 | 11/2010 | Ambrose et al. |
| 2012/0039865 A1 | 2/2012 | Strittmatter et al. |
| 2012/0315244 A1 | 12/2012 | Yuan et al. |
| 2013/0115222 A1 | 5/2013 | Hempstead et al. |
| 2013/0171173 A1 | 7/2013 | Choquet-Kastylevsky et al. |
| 2013/0336988 A1 | 12/2013 | Hempstead et al. |
| 2014/0004108 A1 | 1/2014 | Yuan et al. |
| 2015/0299304 A1 | 10/2015 | Nykjaer et al. |
| 2016/0024172 A1 | 1/2016 | Zankel et al. |
| 2016/0060346 A1 | 3/2016 | Andersen et al. |
| 2016/0194631 A1 | 7/2016 | Yuan et al. |
| 2016/0349276 A1 | 12/2016 | Jepsen et al. |
| 2017/0049855 A1 | 2/2017 | Liu et al. |
| 2017/0096486 A1 | 4/2017 | Landberg |
| 2017/0158766 A1 | 6/2017 | Nykjaer et al. |
| 2017/0210808 A1 | 7/2017 | Rosenthal et al. |
| 2017/0240611 A1 | 8/2017 | Pedersen et al. |
| 2017/0246263 A1 | 8/2017 | Concino et al. |
| 2017/0267761 A1 | 9/2017 | Ronn et al. |
| 2017/0318057 A1 | 11/2017 | Nykjaer et al. |
| 2018/0265586 A1 | 9/2018 | Rosenthal et al. |
| 2019/0023788 A1 | 1/2019 | Ronn et al. |
| 2019/0062433 A1 | 2/2019 | Rosenthal et al. |
| 2019/0085084 A1 | 3/2019 | Rosenthal et al. |
| 2019/0127475 A1 | 5/2019 | Rosenthal et al. |
| 2020/0024348 A1 | 1/2020 | Schwabe et al. |
| 2020/0223928 A1 | 7/2020 | Rosenthal et al. |
| 2020/0330553 A1 | 10/2020 | Ito et al. |
| 2020/0392229 A1 | 12/2020 | Paul et al. |
| 2022/0185898 A1 | 6/2022 | Rosenthal et al. |
| 2022/0185899 A1 | 6/2022 | Rosenthal et al. |
| 2022/0251219 A1 | 8/2022 | Rosenthal et al. |
| 2022/0348656 A1 | 11/2022 | Schwabe et al. |
| 2024/0101681 A1 | 3/2024 | Rosenthal et al. |
| 2024/0132597 A1 | 4/2024 | Paul et al. |
| 2025/0092144 A1 | 3/2025 | Rosenthal et al. |

FOREIGN PATENT DOCUMENTS

| | | |
|---|---|---|
| EP | 404097 B1 | 9/1996 |
| EP | 546073 B1 | 9/1997 |
| JP | 2014519517 A | 8/2014 |
| JP | 2018517401 A | 7/2018 |
| WO | WO-198700195 A1 | 1/1987 |
| WO | WO-198704462 A1 | 7/1987 |
| WO | WO-199003430 A1 | 4/1990 |
| WO | WO-199100360 A1 | 1/1991 |
| WO | WO-199110741 A1 | 7/1991 |
| WO | WO-199220373 A1 | 11/1992 |
| WO | WO-199301161 A1 | 1/1993 |
| WO | WO-199308829 A1 | 5/1993 |
| WO | WO-199311161 A1 | 6/1993 |
| WO | WO-199316185 A2 | 8/1993 |
| WO | WO-199404690 A1 | 3/1994 |
| WO | WO-199627011 A1 | 9/1996 |
| WO | WO-199633735 A1 | 10/1996 |
| WO | WO-199634096 A1 | 10/1996 |
| WO | WO-199711971 A1 | 4/1997 |
| WO | WO-199717852 A1 | 5/1997 |
| WO | WO-199824893 A2 | 6/1998 |
| WO | WO-199958572 A1 | 11/1999 |
| WO | WO-2004042072 A2 | 5/2004 |
| WO | WO-2004056385 A2 | 7/2004 |
| WO | WO-2005044293 A2 | 5/2005 |
| WO | WO-2006138343 A2 | 12/2006 |
| WO | WO-2007035716 A2 | 3/2007 |
| WO | WO-2007088305 A1 | 8/2007 |
| WO | WO-2007106585 A1 | 9/2007 |
| WO | WO-2008036682 A2 | 3/2008 |
| WO | WO-2008052016 A2 | 5/2008 |
| WO | WO-2008074329 A2 | 6/2008 |
| WO | WO-2008076262 A2 | 6/2008 |
| WO | WO-2008079246 A2 | 7/2008 |
| WO | WO-2008086452 A2 | 7/2008 |
| WO | WO-2009036379 A2 | 3/2009 |
| WO | WO-2009089004 A1 | 7/2009 |
| WO | WO-2009132656 A2 | 11/2009 |
| WO | WO-2009140972 A2 | 11/2009 |
| WO | WO-2009155932 A2 | 12/2009 |
| WO | WO-2010022175 A1 | 2/2010 |
| WO | WO-2010028333 A2 | 3/2010 |
| WO | WO-2010069331 A2 | 6/2010 |
| WO | WO-2010105256 A1 | 9/2010 |
| WO | WO-2011041582 A2 | 4/2011 |
| WO | WO-2011159762 A1 | 12/2011 |
| WO | WO-2012009568 A2 | 1/2012 |
| WO | WO-2012068332 A2 | 5/2012 |
| WO | WO-2013026833 A1 | 8/2012 |
| WO | WO-2012171057 A1 | 12/2012 |
| WO | WO-2014071131 A1 | 5/2014 |
| WO | WO-2014179363 A1 | 11/2014 |
| WO | WO-2015006504 A1 | 1/2015 |
| WO | WO-2015119989 A1 | 8/2015 |
| WO | WO-2015121166 A1 | 8/2015 |
| WO | WO-2015144860 A1 | 10/2015 |
| WO | WO-2015147506 A1 | 10/2015 |
| WO | WO-2016025523 A1 | 2/2016 |

(56) References Cited

FOREIGN PATENT DOCUMENTS

| | | |
|---|---|---|
| WO | WO-2016164608 A1 | 10/2016 |
| WO | WO-2016164637 A1 | 10/2016 |
| WO | WO-2017009327 A1 | 1/2017 |
| WO | WO-2017024137 A1 | 2/2017 |
| WO | WO-2018191786 A1 | 10/2018 |
| WO | WO-2019016247 A2 | 1/2019 |
| WO | WO-2019246071 A1 | 12/2019 |
| WO | WO-2020014617 A1 | 1/2020 |
| WO | WO-2020037434 A1 | 2/2020 |
| WO | WO-2020051624 A1 | 3/2020 |
| WO | WO-2020120749 A1 | 6/2020 |
| WO | WO-2020191212 A1 | 9/2020 |
| WO | WO-2020252066 A1 | 12/2020 |

OTHER PUBLICATIONS

Almagro et al. (2008). "Humanization of Antibodies," Frontiers in Bio-Science 13:1619-1633.
Al-Shawi et al. (2007). "ProNGF, Sortilin, and Age-Related Neurodegeneration," Annals of the New York Academy of Sciences, pp. 208-215.
Al-Shawi et al. (2008). "Neurotoxic and Neurotrophic Roles of proNGF and the Receptor Sortilin in the Adult and Ageing Nervous System," European Journal of Neuroscience 27:2103-2114.
Altmann et al., (2016). "Progranulin overexpression in sensory neurons attenuates neuropathic pain in mice: Role of autophagy," Neurobiology of Disease, 96:294-311.
Altshuler et al., (2010). "Generation of Recombinant Antibodies and Means for Increasing Their Affinity," Biochemistry (Moscow), 75(13):1584-1605.
Andersen et al. (2010). "Identification of a Linear Epitope in Sortilin that Partakes in Pro-Neurotrophin Binding," J. Biol. Chem. 285(16):12210-12222.
Angal et al. (1993). "A Single Amino Acid Substitution Abolishes The Heterogeneity Of Chimeric Mouse/Human (IgG4) Antibody," Molecular Immunology 30(1):105-108.
Armour et al. (1999). "Recombinant Human IgG Molecules Lacking FcGamma Receptor I Binding and Monocyte Triggering Activities," Eur. J. Immunol. 29:2613-2624.
Armour et al. (2003). "Differential Binding To Human Fcγrila and Fcγriib Receptors by Human IgG Wildtype and Mutant Antibodies," Molecular Immunology 40:585-593.
Armour et al. (Jun. 25-28, 2000). "Mutant IgG Lacking FcγRIII Binding and ADCC Activities," The Haematology Journal, poster Session 1, Presented at the 5th Annual Meeting of the European Haematology Association, Birmingham, UK, 1(Suppl. 1):27, 2 pages.
Arnett et al. (2007). "proNGF, sortilin, and p75NTR: Potential Mediators Of Injury-Induced Apoptosis In The Mouse Dorsal Root Ganglion," Brain Research1183:32-42.
Arrant et al., (2018). "Progranulin Gene Therapy Improves Lysosomal Dysfunction and Microglial Pathology Associated with Frontotemporal Dementia and Neuronal Ceroid Lipofuscinosis," Journal of Neuroscience, 38:2341-2358.
Asquith et al. (2009). "Animal Models of Rheumatoid Arthritis," Eur. J. Immunol. 39:2040-2044.
Baca et al. (1997). "Antibody Humanization Using Monovalent Phage Display," The Journal of Biological Chemistry 272(16):10678-10684.
Baker et al. (2006). "Mutations In Progranulin Cause Tau-Negative Frontotemporal Dementia Linked To Chromosome 17," Nature 442:916-919.
Barbas et al. (1994). "In Vitro Evolution of A Neutralizing Human Antibody To Human Immunodeficiency Virus Type 1 To Enhance Affinity And Broaden Strain Cross-Reactivity," Proc Nat. Acad. Sci. USA 9:3809-3813.
Barnes et al. (1980). "Methods For Growth Of Cultured Cells In Serum-Free Medium," Analytical Biochemistry. 102:255-270.

Bath et al. (2006). "Variant BDNF (Val66Met) impact On Brain Structure And Function," Cognitive, Affective, & Behavioral Neuroscience 6(1):79-85.
BD Transduction Laboratories, (2008). "Purified Mouse Anti-Neurotensin Receptor 3 Product Information—Technical Data Sheet," available online at <http://www.bdbiosciences.com/ds/pm/tds/612100.pdf>, 2 pages.
Beattie et al. (2002). "ProNGF Induces p75-Mediated Death of Oligodendrocytes following Spinal Cord Injury," Neuron 36(3):375-386.
Birch et al., (2007). "Age-related macular degeneration: a target for nanotechnology derived medicines," International Journal of Nanomedicine, 2:65-77.
Boerner et al. (1991). "Production Of Antigen-Specific Human Monoclonal Antibodies From In Vitro-Primed Human Splenocytes," Journal of Immunology 147(1):86-95.
Bolt et al. (1993). "The Generation Of A Humanized, Non-Mitogenic Cd3 Monoclonal Antibody Which Retains In Vitro Immunosuppressive Properties," European Journal Immunol. 23:403-411.
Bostrom et al., (2009). "Improving antibody binding affinity and specificity for therapeutic development," Methods Mol Biol., 525:353-376.
Brennan et al. (1985). "Preparation Of Bispecific Antibodies By Chemical Recombination Of Monoclonal Immunoglobulin G1 Fragments," Science 229:81-83.
Bruggemann et al. (1993). "Designer Mice: The Production of Human Antibody Repertoires in Transgenic Animals," Year Immunol. 7:33-40.
Cantoni et al. (2015). "Trem2 Regulates Microglial Cell Activation In Response To Demyelination In Vivo," Acta Neuropathol, 129(3):429-447.
Cao et al. (2011). "Macrophage Polarization In The Maculae Of Age-Related Macular Degeneration: A Pilot Study," Pathology International 61:528-535.
Capel et al. (1994). "Heterogeneity of Human IgG Fc Receptors," Immunomethods 4:25-34.
Carecchio et al. (2011). "Cerebrospinal Fluid Biomarkers In Progranulin Mutations Carriers," Journal of Alzheimer's Disease 27:781-790.
Carlo et al. (2013). "The Pro-neurotrophin Receptor Sortilin is a Major neuronal APOE Receptor for Catabolismof Amyloid-β peptide in the Brain," J. Neurosc, 33(1):358-370.
Carrasquillo et al. (2010). "Genome-Wide Screen Identifies rs646776 near Sortilin as a Regulator of Progranulin Levels in Human Plasma," The American Journal of Human Genetics 87:890-897.
Carter et al. (1992). "High Level Escherichia coli Expression and Production of a Bivalent Humanized Antibody Fragment," Bio/technology10:163-167.
Carter et al. (1992). "Humanization of an Anti-p185HER2 Antibody for Human Cancer Therapy," Proc. Natl. Acad. Sci. USA 89:4285-4289.
Chamow et al., (1996). "Immunoadhesins: principles and applications," Trends Biotechnol., 14:52-60.
Chang et al. (2002). "Retinal Degeneration Mutants In The Mouse," Vision Research 42:517-525.
Chang et al., (2017). "Progranulin deficiency causes impairment of autophagy and TDP-43 accumulation," J Exp Med, 214:2611-2628.
Chao et al. (2006). "Isolating And Engineering Human Antibodies Using Yeast Surface Display," Nature Protocols 1(2):755-768.
Chen et al. (2005). "Sortilin Controls Intracellular Sorting of Brain-Derived Neurotrophic Factor to the Regulated Secretory Pathway," The Journal of Neuroscience 25(26):6156-6166.
Chesselet. (2008). "In Vivo Alpha-Synuclein Overexpression In Rodents: A Useful Model Of Parkinson's Disease?," Exp Neurol 209(1):22-27.
Chothia et al. (1987). "Canonical Structures for the Hypervariable Regions of Immunoglobulins," J. Mol. Biol, 196:901-917.
Chu et al. (2008). "Inhibition of B Cell Receptor-Mediated Activation of Primary Human B Cells by Coengagement of CD19 and FcγRIIb With Fc-Engineered Antibodies," Mol. Immunol. 45(15):3926-3933.
Clackson et al. (1991). "Making Antibody Fragments Using Phage Display Libraries," Nature 352(15):624-628.

(56) References Cited

OTHER PUBLICATIONS

Counts et al. (2004). "Reduction Of Cortical TrkA But Not p75NTR Protein In Early-Stage Alzheimer's Disease," Ann. Neurol. 56:520-531.
Counts et al. (2005). "The Role of Nerve Growth Factor Receptors in Cholinergic BasalForebrain Degeneration in Prodromal Alzheimer Disease," J. Neuropathol. Exp. Neurol, 64(4):263-272.
Cruts et al. (2008). "Loss of Progranulin Function in Frontotemporal Lobar Degeneration," Trends Genetics 24(4):186-194.
Cunningham et al. (1989). "High-Resolution Epitope Mapping Of Hgh-Receptor Interactions By Alanine-Scanning Mutagenesis," Science 244:1081-1085.
Daeron (1997). "FC Receptor Biology," Annu. Rev. Immunol. 15:203-234.
Dall'acqua et al. (2006). "Properties of Human IgG1s Engineered for Enhanced Binding to the Neonatal Fc Receptor (FcRn)," The Journal Of Biological Chemistry 281(33):23514-23524.
Daneman et al. (2010). "The Mouse Blood-Brain Barrier Transcriptome: A New Resource for Understanding the Development and Function of Brain Endothelial Cells," PLoS One 5(10):1-16.
Davidson et al. (2014). "A High-Throughput Shotgun Mutagenesis Approach to Mapping B-Cell Antibody Epitopes," Immunology 143(1):13-20.
Davis et al. (2007). "Abatacept Binds To The Fc Receptor Cd64 But Does Not Mediate Complement-Dependent Cytotoxicity Or Antibody-Dependent Cellular Cytotoxicity," The Journal of Rheumatology 34(11):2204-2210.
De Haas et al. (1995). "Fcγ Receptors of Phagocytes," J. Lab. Clin. Med. 126(4):330-341.
De Muynck, L. et al. (2013). "The Neurotrophic Properties of Progranulin Depend on the Granulin E Domain But Do Not Require Sortilin Binding," Neurobiol Aging. 34(11):2541-2547.
Demetriades et al. (2013). "AAV-Mediated Neurotrophin-4 Is Neuroprotective In Murine Model Of Microbead-Induced Glaucoma with Neurotrophin Expression in the Visual Pathway," Investigative Ophthalmology & Visual Science, vol. 54, 3 pages.
Ducry et al. (2010). "Antibody-Drug Conjugates: Linking Cytotoxic Payloads to Monoclonal Antibodies," Bioconjug. Chem. 21(1):5-13.
Duman et al. (1997). "A Molecular and Cellular Theory of Depression," Arch Gen Psychiatry 54(7):597-606.
Egan et al. (2003). "The BDNF val66met Polymorphism Affects Activity-Dependent Secretion Of Bdnf And Human Memory And Hippocampal Function," Cell 112:257-269.
Egashira et al. (2013). "The Growth Factor Progranulin Attenuates Neuronal Injury Induced By Cerebral Ischemia-Reperfusion Through The Suppression Of Neutrophil Recruitment," Journal of Neuroinflammation 10(105):1-13.
El-Danaf et al. (2015). "Characteristic Patterns of Dendritic Remodeling in Early-Stage Glaucoma: Evidence from Genetically Identified Retinal Ganglion Cell Types," The Journal of Neuroscience 35(6):2329-2343.
Estep et al. (2013). "High Throughput Solution-Based Measurement Of Antibody-Antigen Affinity And Epitope Binning," mAbs. 5(2):270-278.
Fahnestock et al. (2001). "The Precursor Pro-Nerve Growth Factor Is the Predominant Form of Nerve Growth Factor in Brain and Is Increased in Alzheimer's Disease," Molecular and Cellular Neuroscience 18:210-220.
Fan. (2008). "Differential effects of Pro-BDNF on Sensory Neurons after Sciatic Nerve Transection in Neonatal Rats," European Journal of Neuroscience 27:2380-2390.
Feldhaus et al. (2004). "Yeast Display of Antibody Fragments: A Discovery and Characterization Platform," Journal of Immunological Methods 290:69-80.
Fellouse et al. (2004). "Synthetic Antibodies from a Four-Amino-Acid Code: A Dominant Role for Tyrosine in Antigen Recognition," PNAS 101(34):12467-12472.
Finan. (2011). "BACE1 Retrograde Trafficking Is Uniquely Regulated by the Cytoplasmic Domain of Sortilin," The Journal of Biological Chemistry 286(14):12602-12616.
Fishwild. (1996). "High-Avidity Human Iggκ Monoclonal Antibodies from a Novel Strain of Minilocus Transgenic Mice," Nature Biotechnology 14:845-851.
Fournier et al. (2011). "Identification of a Receptor Mediating Nogo-66 Inhibition of Axonal Regeneration," Nature 409(6818):341-346.
Frank. (2002). "The SPOT—Synthesis Technique Synthetic Peptide Arrays on Membrane Supports-Principles and Applications," Journal of Immunological Methods 267:13-26.
Gabathuler. (2010). "Approaches to Transport Therapeutic Drugs across the Blood-Brain Barrier to Treat Brain Diseases", Neurobiology of Disease 37:48-57.
Galimberti et al. (2010). "GRN Variability Contributes to Sporadic Frontotemporal Lobar Degeneration," Journal of Alzheimer's Disease 19(1):171-177.
Gargini et al. (2007). "Retinal Organization in the Retinal Degeneration 10 (Rd10) Mutant Mouse: A Morphological and Erg Study," The Journal of Comparative Neurology 500(2):222-238.
Gerngross (2004). "Advances in the Production of Human Therapeutic Proteins in Yeasts and Filamentous Fungi," Nature Biotechnology 22(11):1409-1414.
Gonzales et al., (2005). "Minimizing the Immunogenicity of Antibodies for Clinical Application," Tumour Biol., 26(1):31-43.
Gorno et al., (2011). "Classification of primary progressive aphasia and its variants," Neurology, 76(11):1006-1014.
Graham et al. (1977). "Characteristics of a Human Cell Line Transformed by DNA from Human Adenovirus Type 5," Journal of General Virology 36(1):59-74.
Griffiths et al. (1993). "Human Anti-self Antibodies with High Specificity from Phage Display Libraries," The EMBO Journal 12(2):725-734.
Grossniklaus et al. (2010). "Animal Models of Choroidal and Retinal Neovascularization," Progress in Retinal and Eye Research 29(6):500-519.
Gruber et al. (1994). "Efficient Tumor Cell Lysis Mediated by a Bispecific Single Chain Antibody Expressed in *Escherichia coli*," The Journal of Immunology 152(11):5368-5374.
Guo et al. (2012). "Prevention of LPS-Induced Acute Lung Injury in Mice by Progranulin," Mediators of Inflammation 2012(540794):1-10.
Gupta et al. (2003). "Activated Microglia in Human Retinitis Pigmentosa, Late-Onset Retinal Degeneration, and Age-Related Macular Degeneration," Experimental Eye Research 76:463-471.
Gustafsen et al. (2014). "The Hypercholesterolemia-Risk Gene SORT1 Facilitates PCSK9 Secretion," Cell Metabolism 19:310-318.
Gustafsen. (2013). "Sortilin and SorLA Display Distinct Roles in Processing and Trafficking of Amyloid Precursor Protein," The Journal of Neuroscience 33(1):64-71.
Ham et al. (1979). "Media and Growth Requirements," Methods in Enzymology LVII:44-93.
Hamers-Casterman et al. (1993). "Naturally Occurring Antibodies Devoid of Light Chains." Nature 363:446-448.
Harrington et al. (Apr. 20, 2004). "Secreted proNGF is a Pathophysiological Death-Inducing Ligand after Adult CNS Injury," PNAS 101(16):6226-6230.
Harris. (1995). "Production of Humanized Monoclonal Antibodies for in Vivo Imaging and Therapy," Therapeutic Monoclonals, Biochemical Society Transactions 23:1035-1038.
Hawkins et al. (1992). "Selection of Phage Antibodies by Binding Affinity: Mimicking Affinity Maturation," Journal of Molecular Biology 226:889-896.
Hezareh et al. (2001). "Effector Function Activities of a Panel of Mutants of a Broadly Neutralizing Antibody against Human Immunodeficiency Virus Type 1," Journal of Virology vol. 75(24):12161-12168.
Holliger et al. (1993). ""Diabodies": Small Bivalent and Bispecific Antibody Fragments," Proceedings of the National Academy of Sciences 90:6444-6448.

(56) References Cited

OTHER PUBLICATIONS

Hongo et al. (1995). "Development and Characterization of Murine Monoclonal Antibodies to the Latency-Associated Peptide of Transforming Growth Factor β1," Hybridoma 14(3):253-260.
Hoogenboom et al. (1992). "By-Passing Immunisation. Human Antibodies from Synthetic Repertoires of Germline Hh Gene Segments Rearranged in Vitro," Journal of Molecular Biology 227:381-388.
Hu et al. (2005). "Nogo-A Interacts with the Nogo-66 Receptor through Multiple Sites to Create an Isoform-Selective Subnanomolar Agonist," The Journal of Neuroscience 25(22):5298-5304.
Hu et al. (2010). "Sortilin-Mediated Endocytosis Determines Levels of the Frontotemporal Dementia Protein, Progranulin," Neuron 68:654-667.
Hudson et al. (2003). "Engineered Antibodies," Nat. Med. 9(1):129-134.
Hurle et al. (1994). "Protein Engineering Techniques for Antibody Humanization," Current Opinion in Biotechnology 5:428-433.
Hutchins et al. (1995). "Improved Biodistribution, Tumor Targeting, and Reduced Immunogenicity in Mice with a Gamma 4 Variant of Campath-IH," Proc. Natl. Acad. Sci. 92:11980-11984.
Hutton et al. (1998). "Association of Missense and 5'-Splice-Site Mutations in Tau with the Inherited Dementia FTDP-17," Nature 393:702-705.
Jackson et al. (1995). "In Vitro Antibody Maturation. Improvement of a High Affinity, Neutralizing Antibody against IL-1 Beta," The Journal of Immunology 157(7):3310-3319.
Jakobovits et al. (1993) "Germ-line Transmission and Expression of a Human-derived Yeast Artificial Chromosome," Nature 362:255-258.
Jakobovits et al. (1993). "Analysis of Homozygous Mutant Chimeric Mice: Deletion of The Immunoglobulin Heavy-chain Joining Region Blocks B-Cell Development and Antibody Production," Proceedings of the National Academy of Sciences 90:2551-2555.
Jansen et al. (2007). "Roles for the Pro-Neurotrophin Receptor Sortilin in Neuronal Development, Aging and Brain Injury," Nature Neuroscience 10(11):1449-1457.
Jefferis et al. (2009). "Human Immunoglobulin Allotypes: Possible Implications for Immunogenicity," MAbs 1(4):332-338.
Johnson et al. (1993). "Human antibody engineering: Current Opinion in Structural Biology," Current Opinion in Structural Biology 3(4):564-571.
Johnson et al. (2011). "Apolipoprotein E4 Exaggerates Diabetic Dyslipidemia and Atherosclerosis in Mice Lacking the LDL Receptor," Diabetes 60(9):2285-2294.
Jones et al. (1986). "Replacing the Complementarity-Determining Regions in a Human Antibody with Those from a Mouse," Nature 321:522-525.
Kanazawa et al., (2015). "Multiple therapeutic effects of progranulin on experimental acute ischaemic stroke," Brain, 138:1932-1948.
Kanda et al. (2006). "Comparison of Cell Lines for Stable Production of Fucose-Negative Antibodies With Enhanced ADCC," Biotechnol. Bioeng. 94(4):680-688.
Karch et al., (2018). "Selective Genetic Overlap Between Amyotrophic Lateral Sclerosis and Diseases of the Frontotemporal Dementia Spectrum," JAMA Neurol, 75:860-875.
Kjolby et al. (2010). "Sort1, Encoded by the Cardiovascular Risk Locus 1p13.3, Is a Regulator of Hepatic Lipoprotein Export," Cell Metabolism 12:213-223.
Klinger et al. (2011). "SorLA Regulates the Activity of Lipoprotein Lipase by Intracellular Trafficking," Journal of Cell Science 124(7):1095-1105.
Kohler et al. (1975). "Continuous Cultures of Fused Cells Secreting Antibody of Predefined Specificity," Nature 256:495-497.
Kostelny et al. (1992). "Formation of a Bispecific Antibody by the Use of Leucine Zippers," The Journal of Immunology 148(5):1547-1553.
Kozbor et al. (1984). "A Human Hybrid Myeloma for Production of Human Monoclonal Antibodies," The Journal of Immunology 133(6):3001-3005.

Kuipers et al. (2006). "Brain-Derived Neurotrophic Factor Mechanisms and Function in Adult Synaptic Plasticity: New Insights and Implications for Therapy," Current Opinion in Drug Discovery & Development 9(5):580-586.
Kunik et al., (2012). "Structural consensus among antibodies defines the antigen binding site." PLoS Comput Biol., 8(2):e1002388, 12 pages.
Kyte et al. (1982). "A Simple Method For Displaying the Hydropathic Character of a Protein," J. Mol. Biol. 157(1):105-132.
Lagier-Tourenne et al., (2009). "Rethinking ALS: the FUS about TDP-43," Cell, 136:1001-4.
Laird et al. (2010). "Progranulin is Neurotrophic in Vivo and Protects against a Mutant TDP-43 Induced Axonopathy," PLOS ONE 5(10):1-7.
Langer. (1990). "New Methods of Drug Delivery," Science 249(4976):1527-1533.
Lauren et al. (2009). "Cellular Prion Protein Mediates Impairment of Synaptic Plasticity by Amyloid-β Oligomers," Nature 457:1128-1132.
Lavail et al. (2011). "Retinal Degeneration Rat Model Resource Availability of P23H and S334ter Mutant Rhodopsin Transgenic Rats and RCS Inbred and RCS Congenic Strains of Rats," UCSF School of Medicine, 12 pages.
Lazar et al. (2006). "Engineered Antibody Fc variants with Enhanced Effector Function," PNAS 103(11):4005-4010.
Lee et al. (2004). "Bivalent Antibody Phage Display Mimics Natural Immunoglobulin," Journal of Immunological Methods 284:119-132.
Lee et al. (2004). "High-affinity Human Antibodies from Phage-displayed Synthetic Fab Libraries with a Single Framework Scaffold," Journal of Molecular Biology 340:1073-1093.
Lee et al. (2014). "Targeted Manipulation of the Sortilin-Progranulin Axis Rescues Progranulin Haploinsufficiency," Human Molecular Genetics 23(6):1467-1478.
Li et al. (2006). "Human Antibodies for Immunotherapy Development Generated via a Human B Cell Hybridoma Technology," PNAS 103(10):3557-3562.
Li et al. (2006). "Optimization of Humanized IgGs in Glycoengineered Pichia Pastoris," Nature Biotechnology 24(2):210-215.
Lightle et al. (2010). "Mutations Within a Human IgG2 Antibody Form Distinct and Homogeneous Disulfide Isomers but do not Affect Fc Gamma Receptor or C1q Binding," Protein Sci. 19(4):753-762.
Lipovsek et al. (2004). "In-vitro protein evolution by ribosome display and mRNA display," Journal of Immunological Methods 290:51-67.
Lonberg et al. (1994). "Antigen-Specific Human Antibodies from Mice Comprising Four Distinct Genetic Modifications," Nature 368:856-859.
Lonberg et al. (1995). "Human Antibodies from Transgenic Mice," International Reviews of Immunology. 13:65-93.
Lonberg. (2008). "Fully Human Antibodies From Transgenic Mouse and Phage Display Platforms," Curr. Opin. Immunol. 20(4):450-459.
Lutje et al. (2014). "Anti-CEA Antibody Fragments Labeled with [18F]AIF for PET Imaging of CEA-Expressing Tumors," Bioconjugate Chemistry 25:335-341.
Lynaugh et al. (2013). "Rapid Fc Glycosylation Analysis of Fc Fusions with IdeS and Liquid Chromatography Mass Spectrometry," mAbs 5:641-645.
Maguire-Zeiss. (2008). "α-Synuclein: A Therapeutic Target for Parkinson's Disease?," Pharmacological Research 58(5-6): 271-280.
Marks et al. (1991). "By-Passing Immunization: Human Antibodies From V-Gene Libraries Displayed on Phage," Journal of Molecular Biology 222(3): 581-597.
Marks et al. (1992)."By-Passing Immunization: Building High Affinity Human Antibodies By Chain Shuffling," Bio/Technology 10:779-782.
Martens et al. (2012). "Progranulin Deficiency Promotes Neuroinflammation and Neuron Loss Following Toxin-Induced Injury," The Journal of Clinical Investigation 122(11):3955-3959.

(56) References Cited

OTHER PUBLICATIONS

Mather et al. (1982). "Culture of Testicular Cells in Hormone-Supplemented Serum-Free Medium," Annals of the New York Academy of Sciences, Testicular Cell Culture 383:44-68.

Mather. (1980). "Establishment and Characterization of Two Distinct Mouse Testicular Epithelial Cell Lines," Biology of Reproduction 23:243-252.

Mccafferty et al. (1990). "Phage Antibodies: Filamentous Phage Displaying Antibody Variable Domains," Nature 348:552-554.

Mcearchern et al. (2007). "Engineered Anti-CD70 Antibody with Multiple Effector Functions Exhibits in Vitro and in Vivo Antitumor Activities," Blood 109(3):1185-1192.

Meeter et al., (2016). "Progranulin Levels in Plasma and Cerebrospinal Fluid in Granulin Mutation Carriers," Dement Geriatr Cogn Disord Extra, 6:330-340.

Menzel et al., (2016). "Progranulin Protects Against Exaggerated Axonal Injury and Astrogliosis Following Traumatic Brain Injury," GLIA, 65:278-292.

Michalski et al. (2003). "Pro-Brain-Derived Neurotrophic Factor is Decreased in Parietal Cortex in Alzheimer's Disease," Molecular Brain Research 111:148-154.

Milstein et al. (1983). "Hybrid Hybridomas and their use in Immunohistochemistry," Nature 305:537-540.

Minami et al. (2014). "Progranulin Protects against Amyloid β Deposition and Toxicity in Alzheimer's disease Mouse Models," Nature Medicine 20(10):1157-1164.

Mizoguchi. (2012). "Animal models of inflammatory bowel disease," Progress in Molecular Biology and Translational Science 105:263-320.

Morimoto et al. (1992). "Single-Step Purification of F(ab')2 Fragments of Mouse Monoclonal Antibodies (Immunoglobulins G1) by Hydrophobic Interaction High Performance Liquid Chromatography Using TSKgel Phenyl-5PW," Journal of Biochemical and Biophysical Methods 24:107-117.

Morrison et al. (1984). "Chimeric Human Antibody Molecules: Mouse Antigen-binding Domains with Human Constant Region Domains," Proc. Nat'l Acad. Sci 81:6851-6855.

Morrison. (1994). "Success in Specification," Nature 368:812-813.

Munson et al. (1980). "Ligand: A Versatile Computerized Approach for Characterization of Ligand-binding Systems," Analytical Biochemistry 107:220-239.

Nakamura et al. (2007). "Intracellular Sortilin Expression Pattern Regulates proNGF-Induced Naturally Occurring Cell Death during Development," Cell Death and Differentiation 14:1552-1554.

Neary et al. (1998). "Frontotemporal Lobar Degeneration: A Consensus on Clinical Diagnostic Criteria," Neurology 51:1546-1554.

Neuberger. (1996). "Generating high-avidity human Mabs in mice," Nature Biotechnology 14:826.

Neumann et al. (2007). "TDP-43 Proteinopathy in Frontotemporal Lobar Degeneration and Amyotrophic Lateral Sclerosis," Arch Neurol. 64(10):1388-1394.

Nguyen et al. (2013). "Progranulin: at the Interface of Neurodegenerative and Metabolic Diseases," Trends in Endocrinology and Metabolism 24(12):597-606.

Nguyen et al., (2013). Trends in Endocrinology and Metabolism, 24, 597-606.

Nilsson et al. (2007). "Apolipoprotein A-V Interaction with Members of the Low Density Lipoprotein Receptor Gene Family," Biochemistry 46(12):3896-3904.

Nilsson et al. (2008). "Endocytosis of Apolipoprotein A-V by Members of the Low Density Lipoprotein Receptor and the Vps10p Domain Receptor Families," The Journal of Biological Chemistry 283(38):25920-25927.

Novusbio, (2020). "Datasheet: Sortilin Antibody (1B3) H00006272-M01," Online catalogue NovusBio, May 6, 2020, available online at <https://www.novusbio.com/products/sortilin-antibody-1b3_h00006272-m01>, 4 pages.

Nykjaer et al. (2004). "Sortilin is Essential for proNGF Induced Neuronal Cell Death," Nature 427:843-848.

Nykjaer et al. (2005). "p75NTR—Live or Let Die," Current Opinion in Neurobiology 15:49-57.

Nykjaer et al. (2012). "Sortilin: A Receptor to Regulate Neuronal Viability and Function," Trends in Neurosciences 35(4):261-270.

Oganesyan et al. (2008). "Structural characterization of a Human Fc Fragment Engineered for Lack of Effector Functions," Acta Crystallography 64:700-704.

Okazaki et al. (2004). "Fucose Depletion From Human IgG1 Oligosaccharide Enhances Binding Enthalpy and Association Rate Between IgG1 and FcγRIIIa," J. Mol. Biol. 336(5):1239-1249.

Pang et al. (2004). "Cleavage of proBDNF by tPA/ Plasmin Is Essential for Long-Term Hippocampal Plasticity," Science 306:487-491.

Pedraza et al. (2005). "Pro-NGF Isolated from the Human Brain Affected by Alzheimer's Disease Induces Neuronal Apoptosis Mediated by p75NTR," American Journal of Pathology 166(2):533-543.

Peng et al. (2005). "Precursor form of Brain-Derived Neurotrophic Factor and Mature Brain-Derived Neurotrophic Factor are Decreased in the Pre-Clinical Stages of Alzheimer's Disease," Journal of Neurochemistry 93:1412-1421.

Peng et al. (2010). "TREM2- and DAP12-Dependent Activation of PI3K Requires DAP10 and Is Inhibited by SHIP1," Science Signaling 3(122): 1-15.

Pennesi et al. (2012). "Animal Models of Age Related Macular Degeneration," Molecular Aspects of Medicine 33(4):1-40.

Peters et al. (2012). "Engineering an Improved IgG4 Molecule with Reduced Disulfide Bond Heterogeneity and Increased Fab Domain Thermal Stability," The Journal of Biological Chemistry 287(29):24525-24533.

Plückthun. (1992). "Mono- and Bivalent Antibody Fragments Produced in *Escherichia coli*: Engineering, Folding and Antigen Binding," Immunological Reviews130:151-188.

Presta et al. (1993). "Humanization of an Antibody Directed Against IgE," The Journal of Immunology 151(5):2623-2632.

Presta. (1992). "Antibody Engineering," Current Opinion in Structural Biology 2:593-596.

Provenzano. (2008). "p75NTR and Sortilin Increase After Facial Nerve Injury," Laryngoscope 118:87-93.

Quistgaard et al. (2009). "Ligands Bind to Sortilin in the Tunnel of a Ten-Bladed β-Propeller Domain," Nature Structural & Molecular Biology 16(1):96-98.

Quistgaard et al. (2014). "Revisiting the Structure of the Vps10 Domain of Human Sortilin and its Interaction With Neurotensin," Protein Sci. 23(9):1291-1300.

Ratnavalli et al. (2002). "The Prevalence of Frontotemporal Dementia," Neurology 58(1 of 2):1615-1621.

Ravetch et al. (1991). "Fc Receptors," Annual Review Immunology 9:457-492.

Reddy et al. (2000). "Elimination of Fc Receptor-Dependent Effector Functions of a Modified IgG4 Monoclonal Antibody to Human CD4," The Journal of Immunology 164:1925-1933.

Reineke et al. (2002). "Identification of Distinct Antibody Epitopes and Mimotopes from A Peptide Array of 5520 Randomly Generated Sequences," J. Immunol. Methods 267(1):37-51.

Riechmann et al. (1988). "Reshaping Human Antibodies for Therapy," Nature 332:323-327.

Ripka et al. (1986). "Two Chinese Hamster Ovary Glycosylation Mutants Affected in the Conversion of GDP-Mannose to GDP-Fucose," Arch Biochem. Biophys. 249(2):533-545.

Rizo et al. (1992). "Constrained Peptides: Models of Bioactive Peptides and Protein Substructures," Annu. Rev. Biochem. 61:387-418.

Roberts et al. (1997). "RNA-Peptide Fusions for the In Vitro Selection of Peptides and Proteins," Proc. Natl. Acad. Sci. USA 94:12297-12302.

Rosok et al. (1996). "Combinatorial Library Strategy for the Rapid Humanization of Anticarcinoma BR96 Fab," The Journal of Biological Chemistry 271(37):22611-22618.

Rudikoff et al., (1982). "Single amino acid substitution altering antigen-binding specificity," Proc. Natl. Acad. Sci., 79(6):1979-83.

Sazinsky et al. (2008). "Aglycosylated Immunoglobulin G1 Variants Productively Engage Activating Fc Receptors," PNAS 105(51):20167-20172.

(56) References Cited

OTHER PUBLICATIONS

Schaffitzel et al. (1999). "Ribosome Display: An In Vitro Method for Selection and Evolution of Antibodies from Libraries," Journal of Immunological Methods 231:119-135.

Scharn et al. (2000). "Spatially Addressed Synthesis of Amino- and Amino-Oxy-Substituted 1,3,5-Triazine Arrays on Polymeric Membranes," Journal of Combinatorial Chemistry 2(4):361-369.

Schier et al. (1996). "Identification of Functional and Structural Amino-Acid Residues by Parsimonious Mutagenesis," Gene 169:147-155.

Schofield et al., (2010). "Low serum progranulin predicts the presence of mutations: a prospective study," J Alzheimers Dis, 22(3):981-4.

Schymick et al. (2007). "Progranulin Mutations and Amyotrophic Lateral Sclerosis or Amyotrophic Lateral Sclerosis-Frontotemporal Dementia Phenotypes," Journal of Neurology, Neurosurgery and Psychiatry 78:754-756.

Seelaar et al. (2011). "Clinical, Genetic and Pathological Heterogeneity of Frontotemporal Dementia: A Review," J Neurol Neurosurg Psychiatry 82:476-486.

Seidah et al. (1996). "Cellular Processing of the Nerve Growth Factor Precursor by the Mammalian Pro-Protein Convertases," Biochem. J. 314:951-960.

Sela-Chung et al., (2013). "The Structural Basis of Antibody-Antigen Recognition," Front Immunol., 4:302, 13 pages.

Seno et al. (2009). "Efficient Colonic Mucosal Wound Repair Requires Trem2 Signaling," PNAS 106(1):256-261.

Shalaby et al. (1992). "Development of Humanized Bispecific Antibodies Reactive with Cytotoxic Lymphocytes and Tumor Cells Overexpressing the HER2 Protooncogene," The Journal of Experimental Medicine 175:217-225.

Sheriff et al. (1996). "Redefining the Minimal Antigen-binding Fragment," Nature Structural & Molecular Biology 3(9):733-736.

Shields et al. (2001). "High Resolution Mapping of the Binding Site on Human IgG1 for FcγRI, FcγRII, FcγRIII, and FcRn and Design of IgG1 Variants with Improved Binding to the FcγR," The Journal Of Biological Chemistry 276(9):6591-6604.

Shirayama et al. (2002). "Brain-Derived Neurotrophic Factor Produces Antidepressant Effects in Behavioral Models of Depression," The Journal of Neuroscience 22(8):3251-3261.

Sidhu et al. (2004). "Phage-displayed Antibody Libraries of Synthetic Heavy Chain Complementarity Determining Regions," Journal of Molecular Biology 338(2):299-310.

Sieber et al. (2013). "Attenuated Inflammatory Response in Triggering Receptor Expressed on Myeloid Cells 2 (TREM2) Knock-Out Mice Following Stroke," PLoS One 8(1):e52982.

Siegel et al. (2004). "High Efficiency Recovery and Epitope-Specific Sorting of an scFv Yeast Display Library," Journal of Immunological Methods 286:141-153.

Sims et al. (1993). "A Humanized CD18 Antibody Can Block Function Without Cell Destruction," The Journal of Immunology 151(4):2296-2308.

Skeldal et al. (2012). "Mapping of the Interaction Site between Sortilin and the p75 Neurotrophin Receptor Reveals a Regulatory Role for the Sortilin Intracellular Domain in p75 Neurotrophin Receptor Shedding and Apoptosis," The Journal of Biological Chemistry 287(52):43798-43809.

Skerra. (1993). "Bacterial Expression of Immunoglobulin Fragments," Current Opinion in Immunology 5:256-262.

Sleegers et al., (2008). "Progranulin genetic variability contributes to amyotrophic lateral sclerosis," Neurology, 71:253-9.

Smith et al., (2012). "Strikingly different clinicopathological phenotypes determined by progranulin-mutation dosage," Am J Hum Genet, 90:1102-7.

Strohl. (2009). "Optimization of Fc-mediated Effector Functions of Monoclonal Antibodies," Current Opinion in Biotechnology 20:685-691.

Suresh et al. (1986). "Bispecific Monoclonal Antibodies from Hybrid Hybridomas," Methods In Enzymology 121:210-228.

Tanaka et al. (2013). "Exacerbated Inflammatory Responses Related to Activated Microglia After Traumatic Brain Injury in Progranulin-Deficient Mice," Neuroscience 231:49-60.

Tanaka et al. (2013). "Increased Lysosomal Biogenesis in Activated Microglia and Exacerbated Neuronal Damage After Traumatic Brain Injury in Progranulin-Deficient Mice," Neuroscience 250:8-19.

Tang et al. (2011). "The Growth Factor Progranulin Binds to TNF Receptors and Is Therapeutic against Inflammatory Arthritis in Mice," Science 332:478-484.

Tao et al. (2012). "Neuroprotective Effects of Progranulin in Ischemic Mice," Brain Research 1436:130-136.

Tauffenberger et al., (2013). "Reduction of polyglutamine toxicity by TDP-43, FUS and progranulin in Huntington's disease models," Hum Mol Genet, 22:782-94.

Tavaré et al. (2014). "Engineered Antibody Fragments for Immuno-PET Imaging of Endogenous CD8+ T Cells in Vivo," PNAS 111(3):1108-1113.

Teng et al. (2005). "ProBDNF Induces Neuronal Apoptosis via Activation of a Receptor Complex of p75 NTR and Sortilin," The Journal of Neuroscience 25(22):5455-5463.

Traunecker et al. (1991). "Bispecific Single Chain Molecules (Janusins) Target Cytotoxic Lymphocytes on HIV Infected Cells," The EMBO Journal 10(12):3655-3659.

Tutt et al. (1991). "Trispecific F(ab')3 Derivatives that Use Cooperative Signaling Via the TCR/CD3 Complex and CD2 to Activate and Redirect Resting Cytotoxic T Cells1," The Journal of Immunology 147(1):60-69.

Urlaub et al. (1980). "Isolation of Chinese Hamster Cell Mutants Deficient in Dihydrofolate Reductase Activity," Proc. Natl. Acad. Sci. 77(7):4216-4220.

Vaegter et al. (2011). "Sortilin Associates with Trk Receptors to Enhance Anterograde Transport and Neurotrophin Signaling," Nature Neuroscience 14(1):54-61.

Vafa et al. (2014). "An Engineered Fc Variant of an Igg Eliminates All Immune Effector Functions Via Structural Perturbations," Methods 65:114-126.

Van Dijk et al. (2001). "Human Antibodies as Next Generation Therapeutics," Current Opinion in Chemical Biology 5:368-374.

Van Kampen et al. (2014). "Progranulin Gene Delivery Protects Dopaminergic Neurons in a Mouse Model of Parkinson's Disease," Plos One 9(5):1-10.

Vaswani et al. (1998). "Humanized Antibodies as Potential Therapeutic Drugs," Annals of Allergy, Asthma & Immunology 81:105-115.

Vercellino et al., (2016). "Progranulin genetic polymorphisms influence progression of disability and relapse recovery in multiple sclerosis," 22(8):1007-1012.

Verhoeyen et al. (1988). "Reshaping Human Antibodies: Grafting an Antilysozyme Activity," Science 239:1534-1536.

Vollmers et al. (2005). "Death by Stress: Natural IgM-Induced Apoptosis," Methods Find. Exp. Clin. Pharmacol. 27(3):185-191.

Vollmers et al. (2005). "The "Early Birds": Natural IgM Antibodies and Immune Surveillance," Histol. Histopathol. 20(3):927-937.

Volosin et al. (2006). "Interaction of Survival and Death Signaling in Basal Forebrain Neurons: Roles of Neurotrophins and Proneurotrophins," The Journal of Neuroscience 26(29):7756-7766.

Volosin et al. (2008). "Induction of Proneurotrophins and Activation of P75ntr-Mediated Apoptosis Via Neurotrophin Receptor-Interacting Factor in Hippocampal Neurons After Seizures," The Journal of Neuroscience 28(39):1-25.

Wang et al. (2015). "TREM2 Lipid Sensing Sustains the Microglial Response in an Alzheimer's Disease Model," Cell 160(6):1061-1071.

Wang et al., (2019). "Progranulin deficiency exacerbates spinal cord injury by promoting neuroinflammation and cell apoptosis in mice," Journal of Neuroinflammation, 16:238, 12 pages.

Wark et al., (2006). "Latest technologies for the enhancement of antibody affinity," Adv Drug Deliv Rev., 58:657-670.

Waterhouse et al. (1993). "Combinatorial Infection and In Vivo Recombination: A Strategy for Making Large Phage Antibody Repertoires," Nucleic Acids Research 21(9):2265-2266.

(56) References Cited

OTHER PUBLICATIONS

Wei et al. (2007). "Enhanced Protein Expressions of Sortilin and p75NTR in Retina of Rat Following Elevated Intraocular Pressure-Induced Retinal Ischemia," Neuroscience Letters 429(2-3):169-174.
Weishaupt et al., (2016). "Common Molecular Pathways in Amyotrophic Lateral Sclerosis and Frontotemporal Dementia," Trends Mol Med, 22:769-783.
White et al. (2015). "Conformation of the Human Immunoglobulin G2 Hinge Imparts Superagonistic Properties to Immunostimulatory Anticancer Antibodies," Cancer Cell 27(1):138-148.
Wiehr et al. (2014). "Pharmacokinetics and PET Imaging Properties of Two Recombinant Anti-PSMA Antibody Fragments in Comparison to their Parental Antibody," The Prostate 24:743-755.
Wilkinson et al. (2013). "Monovalent IgG4 Molecules: Immunoglobulin Fc Mutations that Result in a Monomeric Structure," mAbs 5(3):406-417.
Willnow et al. (2008). "VPS10P-Domain Receptors-Regulators of Neuronal Viability and Function," Nature Reviews Neuroscience 9:899-909.
Willnow et al. (2011). "Sortilins: New Players in Lipoprotein Metabolism," Current Opinion in Lipidology 22(2):79-85.
Wilson et al. (2011). "An Fcγ Receptor-Dependent Mechanism Drives Antibody-Mediated Target-Receptor Signaling in Cancer Cells," Cancer Cell 19(1):101-113.
Winter et al. (1994). "Making Antibodies by Phage Display Technology," Annu. Rev. Immunol. 12:433-455.
Xu et al. (2000). "Diversity in the CDR3 Region of VH Is Sufficient for Most Antibody Specificities," Immunity 13:37-45.
Xu et al. (2000). "In Vitro Characterization of Five Humanized OKT3 Effector Function Variant Antibodies," Cell Immunol. 200(1):16-26.
Xu et al. (2013). "Addressing Polyspecificity of Antibodies Selected from an in Vitro Yeast presentation system: a FACS-based, high-throughput selection and analytical tool," Protein Engineering, Design & Selection 26(10):663-670.
Yamane-Ohnuki et al. (2004). "Establishment of FUT8 Knockout Chinese Hamster Ovary Cells: An Ideal Host Cell Line For Producing Completely Defucosylated Antibodies With Enhanced Antibody-Dependent Cellular Cytotoxicity," Biotechnol. Bioeng., 87(5):614-622.
Yano et al. (2009)."Proneurotrophin-3 Is a Neuronal Apoptotic Ligand: Evidence for Retrograde-Directed Cell Killing," The Journal of Neuroscience 29(47):14790-14802.
Yelton et al. (1995). "Affinity maturation of the BR96 anti-carcinoma antibody by codon-based mutagenesis," The Journal of Immunology 155:1994-2004.
Yin et al. (2009). "Exaggerated Inflammation, Impaired Host Defense, and Neuropathology in Progranulin-Deficient Mice," J. Exp. Med. 207(1):117-128.
Yu et al., (2010). "The spectrum of mutations in progranulin: a collaborative study screening 545 cases of neurodegeneration," Arch Neurol, 67(2):161-170, 18 pages.
Yu et al., (2016). "Progranulin deficiency leads to severe inflammation, lung injury and cell death in a mouse model of endotoxic shock," J. Cell Mol. Med., 20(3):506-517.
Yune et al. (2007). "Minocycline Alleviates Death of Oligodendrocytes by Inhibiting Pro-Nerve Growth Factor Production in Microglia after Spinal Cord Injury," The Journal of Neuroscience 27(29):7751-7761.
Zapata et al. (1995). "Engineering Linear F(ab')2 Fragments for Efficient Production in *Escherichia coli* And Enhanced Antiproliferative Activity," Protein Engineering Designs and Selections 8(10):1057-1062.
Zhao et al. (2015). "Progranulin Knockout Accelerates Intervertebral Disc Degeneration in Aging Mice," Scientific Reports 5(Article No. 9102), 9 pages.
Zheng et al. (2011)."C-Terminus of Progranulin Interacts with the Beta-Propeller Region of Sortilin to Regulate Progranulin Trafficking," PLoS One 6(6), 7 pages.
European Search Report mailed on Aug. 13, 2018 for EP Application No. 16777311.8 filed on Oct. 20, 2017, 10 pages.
International Preliminary Report on Patentability received for PCT Patent Application No. PCT/US2016/026519 mailed on Oct. 19, 2017, 13 pages.
International Preliminary Report on Patentability received for PCT Patent Application No. PCT/US2019/041614 mailed on Jan. 19, 2021, 7 pages.
International Search Report and Written Opinion received for PCT Patent Application No. PCT/US2016/026519 mailed on Sep. 14, 2016, 18 pages.
International Search Report and Written Opinion received for PCT Patent Application No. PCT/US2019/041614 mailed on Sep. 25, 2019, 13 pages.
Singaporean Search Report and Written Opinion mailed on Dec. 5, 2018 for SG Application No. 11201708220R, filed Apr. 7, 2016, 12 pages.
Extended European Search Report received for European Patent Application No. 21191834.7 mailed on Jul. 22, 2022, 16 pages.
Paul et al., (2019). "P4-664: A Phase 1 Study Of AL001 In Healthy Volunteers And Frontotemporal Dementia Patients Carrying A Granulin Mutation," Alzheimer's Association International Conference 2019, 15(7S):p. 1585-p. 1586.
Ward et al., (2021). "A First-In-Human Study of the Anti-Sortilin Antibody AL101," available online at <https://investors.alector.com/static-files/1746ff73-897a-4c27-ad14-8ee3f4680e84>, 1 page.
Singaporean Search Report and Written Opinion completed on Aug. 26, 2022 for SG Application No. 11201910148X, 3 pages.
Extended European Search Report received for European Patent Application No. 22212523.9 mailed on May 17, 2023, 11 pages.
Unpublished U.S. Appl. No. 18/776,646, filed Jul. 18, 2024, titled "Methods of Use of Anti-Sortilin Antibodies," (Copy not submitted herewith pursuant to the waiver of 37 C.F.R. § 1.98(a)(2)(iii)).

SEQUENCE LISTING

```
<160> NUMBER OF SEQ ID NOS: 146

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct

<400> SEQUENCE: 1

Tyr Ser Ile Ser Ser Gly Tyr Tyr Trp Gly
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Synthetic Construct

<400> SEQUENCE: 2

Thr Ile Tyr His Ser Gly Ser Thr Tyr Tyr Asn Pro Ser Leu Lys Ser
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Synthetic Construct

<400> SEQUENCE: 3

Thr Ile Tyr His Ser Gly Ser Thr Tyr Tyr Asn Pro Ser Leu Glu Ser
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 15
<223> OTHER INFORMATION: Xaa = Lys or Glu

<400> SEQUENCE: 4

Thr Ile Tyr His Ser Gly Ser Thr Tyr Tyr Asn Pro Ser Leu Xaa Ser
1               5                   10                  15

<210> SEQ ID NO 5
```

```
<211> LENGTH: 15
<212> TYPE: PRT
<213> ORGANISM: Artificial Sequence
<220> FEATURE:
<223> OTHER INFORMATION: Synthetic Construct

<400> SEQUENCE: 5

Ala Arg Gln Gly Ser Ile Gln Gln Gly Tyr Tyr Gly Met Asp Val
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic Construct

<400> SEQUENCE: 6

Ala Arg Gln Gly Ser Ile Lys Gln Gly Tyr Tyr Gly Met Asp Val
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 7
<223> OTHER INFORMATION: Xaa = Gln or Lys

<400> SEQUENCE: 7

Ala Arg Gln Gly Ser Ile Xaa Gln Gly Tyr Tyr Gly Met Asp Val
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthetic Construct

<400> SEQUENCE: 8

Arg Ser Ser Gln Ser Leu Leu Arg Ser Asn Gly Tyr Asn Tyr Leu Asp
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Synthetic Construct

<400> SEQUENCE: 9

Arg Ser Ser Gln Ser Leu Leu Arg Ser Thr Gly Tyr Asn Tyr Leu Asp
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Synthetic Construct

<400> SEQUENCE: 10

Arg Ser Ser Gln Ser Leu Leu Arg Ser Ser Gly Tyr Asn Tyr Leu Asp
1               5                   10                  15
```

```
<210> SEQ ID NO 11
<211> LENGTH: 16
<212> TYPE: PRT
<213> ORGANISM: Artificial Sequence
<220> FEATURE:
<223> OTHER INFORMATION: Synthetic Construct

<400> SEQUENCE: 11

Arg Ser Ser Gln Ser Leu Leu Arg Ser Gly Gly Tyr Asn Tyr Leu Asp
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Synthetic Construct

<400> SEQUENCE: 12

Arg Ser Ser Gln Ser Leu Leu Arg Ser Arg Gly Tyr Asn Tyr Leu Asp
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Synthetic Construct

<400> SEQUENCE: 13

Arg Ser Ser Gln Ser Leu Leu Arg Ser Asp Gly Tyr Asn Tyr Leu Asp
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Synthetic Construct

<400> SEQUENCE: 14

Arg Ser Ser Gln Ser Leu Leu Arg Ser His Gly Tyr Asn Tyr Leu Asp
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Synthetic Construct

<400> SEQUENCE: 15

Arg Ser Ser Gln Ser Leu Leu Arg Ser Lys Gly Tyr Asn Tyr Leu Asp
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Synthetic Construct

<400> SEQUENCE: 16

Arg Ser Ser Gln Ser Leu Leu Arg Ser Gln Gly Tyr Asn Tyr Leu Asp
1               5                   10                  15
```

```
<210> SEQ ID NO 17
<211> LENGTH: 16
<212> TYPE: PRT
<213> ORGANISM: Artificial Sequence
<220> FEATURE:
<223> OTHER INFORMATION: Synthetic Construct

<400> SEQUENCE: 17

Arg Ser Ser Gln Ser Leu Leu Arg Ser Tyr Gly Tyr Asn Tyr Leu Asp
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Synthetic Construct

<400> SEQUENCE: 18

Arg Ser Ser Gln Ser Leu Leu Arg Ser Glu Gly Tyr Asn Tyr Leu Asp
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Synthetic Construct

<400> SEQUENCE: 19

Arg Ser Ser Gln Ser Leu Leu Arg Ser Trp Gly Tyr Asn Tyr Leu Asp
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Synthetic Construct

<400> SEQUENCE: 20

Arg Ser Ser Gln Ser Leu Leu Arg Ser Phe Gly Tyr Asn Tyr Leu Asp
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Synthetic Construct

<400> SEQUENCE: 21

Arg Ser Ser Gln Ser Leu Leu Arg Ser Ile Gly Tyr Asn Tyr Leu Asp
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Synthetic Construct

<400> SEQUENCE: 22

Arg Ser Ser Gln Ser Leu Leu Arg Ser Val Gly Tyr Asn Tyr Leu Asp
1               5                   10                  15
```

-continued

```
<210> SEQ ID NO 23
<211> LENGTH: 16
<212> TYPE: PRT
<213> ORGANISM: Artificial Sequence
<220> FEATURE:
<223> OTHER INFORMATION: Synthetic Construct

<400> SEQUENCE: 23

Arg Ser Ser Gln Ser Leu Leu Arg Ser Ala Gly Tyr Asn Tyr Leu Asp
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Synthetic Construct

<400> SEQUENCE: 24

Arg Ser Ser Gln Ser Leu Leu Arg Ser Met Gly Tyr Asn Tyr Leu Asp
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Synthetic Construct

<400> SEQUENCE: 25

Arg Ser Ser Gln Ser Leu Leu Arg Ser Leu Gly Tyr Asn Tyr Leu Asp
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Synthetic Construct

<400> SEQUENCE: 26

Arg Ser Ser Gln Ser Leu Leu His Ser Asn Gly Tyr Asn Tyr Leu Asp
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Synthetic Construct

<400> SEQUENCE: 27

Arg Ser Ser Gln Gly Leu Leu Arg Ser Asn Gly Tyr Asn Tyr Leu Asp
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Ser or Gly
<220> FEATURE:
<221> NAME/KEY: VARIANT
<222> LOCATION: 8
<223> OTHER INFORMATION: Xaa = Arg or His
```

```
<220> FEATURE:
<221> NAME/KEY: VARIANT
<222> LOCATION: 10
<223> OTHER INFORMATION: Xaa = Asn, Thr, Ser, Gly, Arg, Asp, His, Lys,
      Gln, Tyr, Glu, Trp, Phe, Ile, Val, Ala, Met, or Leu

<400> SEQUENCE: 28

Arg Ser Ser Gln Xaa Leu Leu Xaa Ser Xaa Gly Tyr Asn Tyr Leu Asp
1               5                   10                  15

<210> SEQ ID NO 29
<211> LENGTH: 7
<212> TYPE: PRT
<213> ORGANISM: Artificial Sequence
<220> FEATURE:
<223> OTHER INFORMATION: Synthetic Construct

<400> SEQUENCE: 29

Leu Gly Ser Asn Arg Ala Ser
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic Construct

<400> SEQUENCE: 30

Leu Gly Ser Asn Arg Val Ser
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Ala or Val

<400> SEQUENCE: 31

Leu Gly Ser Asn Arg Xaa Ser
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic Construct

<400> SEQUENCE: 32

Met Gln Gln Gln Glu Ala Pro Leu Thr
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic Construct

<400> SEQUENCE: 33

Met Gln Gln Gln Glu Thr Pro Leu Thr
1               5
```

```
<210> SEQ ID NO 34
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Ala or Thr

<400> SEQUENCE: 34

Met Gln Gln Gln Glu Xaa Pro Leu Thr
1               5

<210> SEQ ID NO 35
<211> LENGTH: 26
<212> TYPE: PRT
<213> ORGANISM: Artificial Sequence
<220> FEATURE:
<223> OTHER INFORMATION: Synthetic Construct

<400> SEQUENCE: 35

Gln Val Gln Leu Gln Glu Ser Gly Pro Gly Leu Val Lys Pro Ser Glu
1               5                   10                  15

Thr Leu Ser Leu Thr Cys Ala Val Ser Gly
            20                  25

<210> SEQ ID NO 36
<211> LENGTH: 14
<212> TYPE: PRT
<213> ORGANISM: Artificial Sequence
<220> FEATURE:
<223> OTHER INFORMATION: Synthetic Construct

<400> SEQUENCE: 36

Trp Ile Arg Gln Pro Pro Gly Lys Gly Leu Glu Trp Ile Gly
1               5                   10

<210> SEQ ID NO 37
<211> LENGTH: 30
<212> TYPE: PRT
<213> ORGANISM: Artificial Sequence
<220> FEATURE:
<223> OTHER INFORMATION: Synthetic Construct

<400> SEQUENCE: 37

Gln Val Thr Ile Ser Val Asp Thr Ser Lys Asn Gln Phe Ser Leu Glu
1               5                   10                  15

Leu Ser Ser Val Thr Ala Ala Asp Thr Ala Val Tyr Tyr Cys
            20                  25                  30

<210> SEQ ID NO 38
<211> LENGTH: 30
<212> TYPE: PRT
<213> ORGANISM: Artificial Sequence
<220> FEATURE:
<223> OTHER INFORMATION: Synthetic Construct

<400> SEQUENCE: 38

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30
```

```
<210> SEQ ID NO 39
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Gln or Arg
<220> FEATURE:
<221> NAME/KEY: VARIANT
<222> LOCATION: 16
<223> OTHER INFORMATION: Xaa = Glu or Lys

<400> SEQUENCE: 39

Xaa Val Thr Ile Ser Val Asp Thr Ser Lys Asn Gln Phe Ser Leu Xaa
1               5                   10                  15

Leu Ser Ser Val Thr Ala Ala Asp Thr Ala Val Tyr Tyr Cys
            20                  25                  30

<210> SEQ ID NO 40
<211> LENGTH: 11
<212> TYPE: PRT
<213> ORGANISM: Artificial Sequence
<220> FEATURE:
<223> OTHER INFORMATION: Synthetic Construct

<400> SEQUENCE: 40

Trp Gly Gln Gly Thr Thr Val Thr Val Ser Ser
1               5                   10

<210> SEQ ID NO 41
<211> LENGTH: 23
<212> TYPE: PRT
<213> ORGANISM: Artificial Sequence
<220> FEATURE:
<223> OTHER INFORMATION: Synthetic Construct

<400> SEQUENCE: 41

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 42
<211> LENGTH: 23
<212> TYPE: PRT
<213> ORGANISM: Artificial Sequence
<220> FEATURE:
<223> OTHER INFORMATION: Synthetic Construct

<400> SEQUENCE: 42

Asp Ile Val Met Thr Gln Ser Pro Leu Ser Leu Pro Val Thr Pro Gly
1               5                   10                  15

Gly Pro Ala Ser Ile Ser Cys
            20

<210> SEQ ID NO 43
<211> LENGTH: 23
<212> TYPE: PRT
<213> ORGANISM: Artificial Sequence
<220> FEATURE:
<223> OTHER INFORMATION: Synthetic Construct

<400> SEQUENCE: 43
```

Asp Ile Val Met Thr Gln Ser Pro Leu Ser Leu Pro Val Thr Pro Gly
1               5                   10                  15

Glu Ser Ala Ser Ile Ser Cys
            20

<210> SEQ ID NO 44
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 17
<223> OTHER INFORMATION: Xaa = Glu or Gly
<220> FEATURE:
<221> NAME/KEY: VARIANT
<222> LOCATION: 18
<223> OTHER INFORMATION: Xaa = Pro or Ser

<400> SEQUENCE: 44

Asp Ile Val Met Thr Gln Ser Pro Leu Ser Leu Pro Val Thr Pro Gly
1               5                   10                  15

Xaa Xaa Ala Ser Ile Ser Cys
            20

<210> SEQ ID NO 45
<211> LENGTH: 15
<212> TYPE: PRT
<213> ORGANISM: Artificial Sequence
<220> FEATURE:
<223> OTHER INFORMATION: Synthetic Construct

<400> SEQUENCE: 45

Trp Tyr Leu Gln Lys Pro Gly Gln Ser Pro Gln Leu Leu Ile Tyr
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Synthetic Construct

<400> SEQUENCE: 46

Trp Tyr Leu Gln Lys Pro Gly Gln Pro Pro Gln Leu Leu Ile Tyr
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 9
<223> OTHER INFORMATION: Xaa = Ser or Pro

<400> SEQUENCE: 47

Trp Tyr Leu Gln Lys Pro Gly Gln Xaa Pro Gln Leu Leu Ile Tyr
1               5                   10                  15

<210> SEQ ID NO 48
<211> LENGTH: 32
<212> TYPE: PRT
<213> ORGANISM: Artificial Sequence
<220> FEATURE:

<223> OTHER INFORMATION: Synthetic Construct

<400> SEQUENCE: 48

Gly Val Pro Asp Arg Phe Ser Gly Ser Gly Ser Gly Thr Asp Phe Thr
1               5                   10                  15

Leu Lys Ile Ser Arg Ala Glu Ala Glu Asp Val Gly Val Tyr Tyr Cys
            20                  25                  30

<210> SEQ ID NO 49
<211> LENGTH: 32
<212> TYPE: PRT
<213> ORGANISM: Artificial Sequence
<220> FEATURE:
<223> OTHER INFORMATION: Synthetic Construct

<400> SEQUENCE: 49

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 50
<211> LENGTH: 32
<212> TYPE: PRT
<213> ORGANISM: Artificial Sequence
<220> FEATURE:
<223> OTHER INFORMATION: Synthetic Construct

<400> SEQUENCE: 50

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Ala Tyr Tyr Cys
            20                  25                  30

<210> SEQ ID NO 51
<211> LENGTH: 32
<212> TYPE: PRT
<213> ORGANISM: Artificial Sequence
<220> FEATURE:
<223> OTHER INFORMATION: Synthetic Construct

<400> SEQUENCE: 51

Gly Val Pro Asp Arg Leu Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Phe or Leu
<220> FEATURE:
<221> NAME/KEY: VARIANT
<222> LOCATION: 22
<223> OTHER INFORMATION: Xaa = Ala or Val
<220> FEATURE:
<221> NAME/KEY: VARIANT
<222> LOCATION: 29
<223> OTHER INFORMATION: Xaa = Val or Ala

<400> SEQUENCE: 52

```
Gly Val Pro Asp Arg Xaa Ser Gly Ser Gly Thr Asp Phe Thr
1               5                   10                  15

Leu Lys Ile Ser Arg Xaa Glu Ala Glu Asp Val Gly Xaa Tyr Tyr Cys
                20                  25                  30
```

<210> SEQ ID NO 53
<211> LENGTH: 10
<212> TYPE: PRT
<213> ORGANISM: Artificial Sequence
<220> FEATURE:
<223> OTHER INFORMATION: Synthetic Construct

<400> SEQUENCE: 53

```
Phe Gly Gly Gly Thr Lys Val Glu Ile Lys
1               5                   10
```

<210> SEQ ID NO 54
<211> LENGTH: 122
<212> TYPE: PRT
<213> ORGANISM: Artificial Sequence
<220> FEATURE:
<223> OTHER INFORMATION: Synthetic Construct

<400> SEQUENCE: 54

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
                20                  25                  30

Tyr Tyr Trp Gly Trp Ile Arg Gln Pro Pro Gly Lys Gly Leu Glu Trp
            35                  40                  45

Ile Gly Thr Ile Tyr His Ser Gly Ser Thr Tyr Tyr Asn Pro Ser Leu
        50                  55                  60

Lys Ser Gln Val Thr Ile Ser Val Asp Thr Ser Lys Asn Gln Phe Ser
65                  70                  75                  80

Leu Glu Leu Ser Ser Val Thr Ala Ala Asp Thr Ala Val Tyr Tyr Cys
                85                  90                  95

Ala Arg Gln Gly Ser Ile Gln Gln Gly Tyr Tyr Gly Met Asp Val Trp
                100                 105                 110

Gly Gln Gly Thr Thr Val Thr Val Ser Ser
            115                 120
```

<210> SEQ ID NO 55
<211> LENGTH: 122
<212> TYPE: PRT
<213> ORGANISM: Artificial Sequence
<220> FEATURE:
<223> OTHER INFORMATION: Synthetic Construct

<400> SEQUENCE: 55

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
                20                  25                  30

Tyr Tyr Trp Gly Trp Ile Arg Gln Pro Pro Gly Lys Gly Leu Glu Trp
            35                  40                  45

Ile Gly Thr Ile Tyr His Ser Gly Ser Thr Tyr Tyr Asn Pro Ser Leu
        50                  55                  60

Glu Ser Arg Val Thr Ile Ser Val Asp Thr Ser Lys Asn Gln Phe Ser
65                  70                  75                  80
```

```
Leu Lys Leu Ser Ser Val Thr Ala Ala Asp Thr Ala Val Tyr Tyr Cys
                85                  90                  95

Ala Arg Gln Gly Ser Ile Gln Gln Gly Tyr Tyr Gly Met Asp Val Trp
            100                 105                 110

Gly Gln Gly Thr Thr Val Thr Val Ser Ser
        115                 120

<210> SEQ ID NO 56
<211> LENGTH: 122
<212> TYPE: PRT
<213> ORGANISM: Artificial Sequence
<220> FEATURE:
<223> OTHER INFORMATION: Synthetic Construct

<400> SEQUENCE: 56

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Thr Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gln Gly Ser Ile Lys Gln Gly Tyr Tyr Gly Met Asp Val Trp
            100                 105                 110

Gly Gln Gly Thr Thr Val Thr Val Ser Ser
        115                 120

<210> SEQ ID NO 57
<211> LENGTH: 112
<212> TYPE: PRT
<213> ORGANISM: Artificial Sequence
<220> FEATURE:
<223> OTHER INFORMATION: Synthetic Construct

<400> SEQUENCE: 57

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
                85                  90                  95

Gln Glu Ala Pro Leu Thr Phe Gly Gly Gly Thr Lys Val Glu Ile Lys
            100                 105                 110

<210> SEQ ID NO 58
<211> LENGTH: 112
<212> TYPE: PRT
<213> ORGANISM: Artificial Sequence
```

```
<220> FEATURE:
<223> OTHER INFORMATION: Synthetic Construct

<400> SEQUENCE: 58

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gln
                85                  90                  95

Gln Glu Ala Pro Leu Thr Phe Gly Gly Gly Thr Lys Val Glu Ile Lys
            100                 105                 110

<210> SEQ ID NO 59
<211> LENGTH: 112
<212> TYPE: PRT
<213> ORGANISM: Artificial Sequence
<220> FEATURE:
<223> OTHER INFORMATION: Synthetic Construct

<400> SEQUENCE: 59

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Asn Gly Tyr Asn Tyr Leu Asp Trp Tyr Leu Gln Lys Pro Gly Gln Pro
        35                  40                  45

Pro Gln Leu Leu Ile Tyr Leu Gly Ser Asn Arg Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gln
                85                  90                  95

Gln Glu Thr Pro Leu Thr Phe Gly Gly Gly Thr Lys Val Glu Ile Lys
            100                 105                 110

<210> SEQ ID NO 60
<211> LENGTH: 112
<212> TYPE: PRT
<213> ORGANISM: Artificial Sequence
<220> FEATURE:
<223> OTHER INFORMATION: Synthetic Construct

<400> SEQUENCE: 60

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Thr Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
                85                  90                  95

Gln Glu Ala Pro Leu Thr Phe Gly Gly Gly Thr Lys Val Glu Ile Lys
            100                 105                 110

<210> SEQ ID NO 61
<211> LENGTH: 112
<212> TYPE: PRT
<213> ORGANISM: Artificial Sequence
<220> FEATURE:
<223> OTHER INFORMATION: Synthetic Construct

<400> SEQUENCE: 61

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Ser Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
                85                  90                  95

Gln Glu Ala Pro Leu Thr Phe Gly Gly Gly Thr Lys Val Glu Ile Lys
            100                 105                 110

<210> SEQ ID NO 62
<211> LENGTH: 112
<212> TYPE: PRT
<213> ORGANISM: Artificial Sequence
<220> FEATURE:
<223> OTHER INFORMATION: Synthetic Construct

<400> SEQUENCE: 62

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Gly Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
                85                  90                  95

Gln Glu Ala Pro Leu Thr Phe Gly Gly Gly Thr Lys Val Glu Ile Lys
            100                 105                 110

<210> SEQ ID NO 63
<211> LENGTH: 112
<212> TYPE: PRT
<213> ORGANISM: Artificial Sequence
<220> FEATURE:
<223> OTHER INFORMATION: Synthetic Construct

<400> SEQUENCE: 63

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Arg Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
                85                  90                  95

Gln Glu Ala Pro Leu Thr Phe Gly Gly Gly Thr Lys Val Glu Ile Lys
            100                 105                 110

<210> SEQ ID NO 64
<211> LENGTH: 112
<212> TYPE: PRT
<213> ORGANISM: Artificial Sequence
<220> FEATURE:
<223> OTHER INFORMATION: Synthetic Construct

<400> SEQUENCE: 64

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Asp Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
                85                  90                  95

Gln Glu Ala Pro Leu Thr Phe Gly Gly Gly Thr Lys Val Glu Ile Lys
            100                 105                 110

<210> SEQ ID NO 65
<211> LENGTH: 112
<212> TYPE: PRT
<213> ORGANISM: Artificial Sequence
<220> FEATURE:
<223> OTHER INFORMATION: Synthetic Construct

<400> SEQUENCE: 65

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

His Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Ala Glu Ala Glu Asp Val Gly Val Tyr Tyr Cys Met Gln Gln
            85                  90                  95

Gln Glu Ala Pro Leu Thr Phe Gly Gly Gly Thr Lys Val Glu Ile Lys
        100                 105                 110
```

<210> SEQ ID NO 66
<211> LENGTH: 112
<212> TYPE: PRT
<213> ORGANISM: Artificial Sequence
<220> FEATURE:
<223> OTHER INFORMATION: Synthetic Construct

<400> SEQUENCE: 66

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Lys Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
            85                  90                  95

Gln Glu Ala Pro Leu Thr Phe Gly Gly Gly Thr Lys Val Glu Ile Lys
        100                 105                 110
```

<210> SEQ ID NO 67
<211> LENGTH: 112
<212> TYPE: PRT
<213> ORGANISM: Artificial Sequence
<220> FEATURE:
<223> OTHER INFORMATION: Synthetic Construct

<400> SEQUENCE: 67

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Gln Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
            85                  90                  95

Gln Glu Ala Pro Leu Thr Phe Gly Gly Gly Thr Lys Val Glu Ile Lys
        100                 105                 110
```

<210> SEQ ID NO 68
<211> LENGTH: 112
<212> TYPE: PRT
<213> ORGANISM: Artificial Sequence
<220> FEATURE:
<223> OTHER INFORMATION: Synthetic Construct

<400> SEQUENCE: 68

```
Asp Ile Val Met Thr Gln Ser Pro Leu Ser Leu Pro Val Thr Pro Gly
```

-continued

```
                1               5                   10                  15
Glu Pro Ala Ser Ile Ser Cys Arg Ser Ser Gln Ser Leu Leu Arg Ser
            20                  25                  30

Tyr Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
            50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
            85                  90                  95

Gln Glu Ala Pro Leu Thr Phe Gly Gly Gly Thr Lys Val Glu Ile Lys
            100                 105                 110
```

<210> SEQ ID NO 69
<211> LENGTH: 112
<212> TYPE: PRT
<213> ORGANISM: Artificial Sequence
<220> FEATURE:
<223> OTHER INFORMATION: Synthetic Construct

<400> SEQUENCE: 69

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Glu Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
            50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
            85                  90                  95

Gln Glu Ala Pro Leu Thr Phe Gly Gly Gly Thr Lys Val Glu Ile Lys
            100                 105                 110
```

<210> SEQ ID NO 70
<211> LENGTH: 112
<212> TYPE: PRT
<213> ORGANISM: Artificial Sequence
<220> FEATURE:
<223> OTHER INFORMATION: Synthetic Construct

<400> SEQUENCE: 70

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Trp Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
            50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
            85                  90                  95
```

Gln Glu Ala Pro Leu Thr Phe Gly Gly Gly Thr Lys Val Glu Ile Lys
            100                 105                 110

<210> SEQ ID NO 71
<211> LENGTH: 112
<212> TYPE: PRT
<213> ORGANISM: Artificial Sequence
<220> FEATURE:
<223> OTHER INFORMATION: Synthetic Construct

<400> SEQUENCE: 71

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Phe Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
                85                  90                  95

Gln Glu Ala Pro Leu Thr Phe Gly Gly Gly Thr Lys Val Glu Ile Lys
            100                 105                 110

<210> SEQ ID NO 72
<211> LENGTH: 112
<212> TYPE: PRT
<213> ORGANISM: Artificial Sequence
<220> FEATURE:
<223> OTHER INFORMATION: Synthetic Construct

<400> SEQUENCE: 72

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Ile Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
                85                  90                  95

Gln Glu Ala Pro Leu Thr Phe Gly Gly Gly Thr Lys Val Glu Ile Lys
            100                 105                 110

<210> SEQ ID NO 73
<211> LENGTH: 112
<212> TYPE: PRT
<213> ORGANISM: Artificial Sequence
<220> FEATURE:
<223> OTHER INFORMATION: Synthetic Construct

<400> SEQUENCE: 73

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser

```
                    20                  25                  30
Val Gly Tyr Asn Tyr Leu Asp Trp Tyr Leu Gln Lys Pro Gly Gln Ser
                35                  40                  45
Pro Gln Leu Leu Ile Tyr Leu Gly Ser Asn Arg Ala Ser Gly Val Pro
         50                  55                  60
Asp Arg Phe Ser Gly Ser Gly Ser Gly Thr Asp Phe Thr Leu Lys Ile
 65                  70                  75                  80
Ser Arg Ala Glu Ala Glu Asp Val Gly Val Tyr Tyr Cys Met Gln Gln
                 85                  90                  95
Gln Glu Ala Pro Leu Thr Phe Gly Gly Gly Thr Lys Val Glu Ile Lys
                100                 105                 110

<210> SEQ ID NO 74
<211> LENGTH: 112
<212> TYPE: PRT
<213> ORGANISM: Artificial Sequence
<220> FEATURE:
<223> OTHER INFORMATION: Synthetic Construct

<400> SEQUENCE: 74

Asp Ile Val Met Thr Gln Ser Pro Leu Ser Leu Pro Val Thr Pro Gly
 1               5                  10                  15
Glu Pro Ala Ser Ile Ser Cys Arg Ser Ser Gln Ser Leu Leu Arg Ser
                20                  25                  30
Ala Gly Tyr Asn Tyr Leu Asp Trp Tyr Leu Gln Lys Pro Gly Gln Ser
                35                  40                  45
Pro Gln Leu Leu Ile Tyr Leu Gly Ser Asn Arg Ala Ser Gly Val Pro
         50                  55                  60
Asp Arg Phe Ser Gly Ser Gly Ser Gly Thr Asp Phe Thr Leu Lys Ile
 65                  70                  75                  80
Ser Arg Ala Glu Ala Glu Asp Val Gly Val Tyr Tyr Cys Met Gln Gln
                 85                  90                  95
Gln Glu Ala Pro Leu Thr Phe Gly Gly Gly Thr Lys Val Glu Ile Lys
                100                 105                 110

<210> SEQ ID NO 75
<211> LENGTH: 112
<212> TYPE: PRT
<213> ORGANISM: Artificial Sequence
<220> FEATURE:
<223> OTHER INFORMATION: Synthetic Construct

<400> SEQUENCE: 75

Asp Ile Val Met Thr Gln Ser Pro Leu Ser Leu Pro Val Thr Pro Gly
 1               5                  10                  15
Glu Pro Ala Ser Ile Ser Cys Arg Ser Ser Gln Ser Leu Leu Arg Ser
                20                  25                  30
Met Gly Tyr Asn Tyr Leu Asp Trp Tyr Leu Gln Lys Pro Gly Gln Ser
                35                  40                  45
Pro Gln Leu Leu Ile Tyr Leu Gly Ser Asn Arg Ala Ser Gly Val Pro
         50                  55                  60
Asp Arg Phe Ser Gly Ser Gly Ser Gly Thr Asp Phe Thr Leu Lys Ile
 65                  70                  75                  80
Ser Arg Ala Glu Ala Glu Asp Val Gly Val Tyr Tyr Cys Met Gln Gln
                 85                  90                  95
Gln Glu Ala Pro Leu Thr Phe Gly Gly Gly Thr Lys Val Glu Ile Lys
                100                 105                 110
```

<210> SEQ ID NO 76
<211> LENGTH: 112
<212> TYPE: PRT
<213> ORGANISM: Artificial Sequence
<220> FEATURE:
<223> OTHER INFORMATION: Synthetic Construct

<400> SEQUENCE: 76

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Leu Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Tyr Tyr Cys Met Gln Gln
            85                  90                  95

Gln Glu Ala Pro Leu Thr Phe Gly Gly Gly Thr Lys Val Glu Ile Lys
            100                 105                 110
```

<210> SEQ ID NO 77
<211> LENGTH: 112
<212> TYPE: PRT
<213> ORGANISM: Artificial Sequence
<220> FEATURE:
<223> OTHER INFORMATION: Synthetic Construct

<400> SEQUENCE: 77

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ala Tyr Tyr Cys Met Gln Gln
            85                  90                  95

Gln Glu Ala Pro Leu Thr Phe Gly Gly Gly Thr Lys Val Glu Ile Lys
            100                 105                 110
```

<210> SEQ ID NO 78
<211> LENGTH: 112
<212> TYPE: PRT
<213> ORGANISM: Artificial Sequence
<220> FEATURE:
<223> OTHER INFORMATION: Synthetic Construct

<400> SEQUENCE: 78

```
Asp Ile Val Met Thr Gln Ser Pro Leu Ser Leu Pro Val Thr Pro Gly
1               5                   10                  15

Gly Pro Ala Ser Ile Ser Cys Arg Ser Ser Gln Ser Leu Leu Arg Ser
            20                  25                  30

Asn Gly Tyr Asn Tyr Leu Asp Trp Tyr Leu Gln Lys Pro Gly Gln Ser
```

```
                35                  40                  45

Pro Gln Leu Leu Ile Tyr Leu Gly Ser Asn Arg Ala Ser Gly Val Pro
         50                  55                  60

Asp Arg Leu Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gln
                 85                  90                  95

Gln Glu Thr Pro Leu Thr Phe Gly Gly Gly Thr Lys Val Glu Ile Lys
            100                 105                 110

<210> SEQ ID NO 79
<211> LENGTH: 112
<212> TYPE: PRT
<213> ORGANISM: Artificial Sequence
<220> FEATURE:
<223> OTHER INFORMATION: Synthetic Construct

<400> SEQUENCE: 79

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gln
                 85                  90                  95

Gln Glu Thr Pro Leu Thr Phe Gly Gly Gly Thr Lys Val Glu Ile Lys
            100                 105                 110

<210> SEQ ID NO 80
<211> LENGTH: 112
<212> TYPE: PRT
<213> ORGANISM: Artificial Sequence
<220> FEATURE:
<223> OTHER INFORMATION: Synthetic Construct

<400> SEQUENCE: 80

Asp Ile Val Met Thr Gln Ser Pro Leu Ser Leu Pro Val Thr Pro Gly
 1               5                  10                  15

Glu Ser Ala Ser Ile Ser Cys Arg Ser Ser Gln Gly Leu Leu Arg Ser
                 20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gln
                 85                  90                  95

Gln Glu Ala Pro Leu Thr Phe Gly Gly Gly Thr Lys Val Glu Ile Lys
            100                 105                 110

<210> SEQ ID NO 81
<211> LENGTH: 831
```

<212> TYPE: PRT
<213> ORGANISM: Homo sapiens

<400> SEQUENCE: 81

```
Met Glu Arg Pro Trp Gly Ala Ala Asp Gly Leu Ser Arg Trp Pro His
1               5                   10                  15

Gly Leu Gly Leu Leu Leu Leu Gln Leu Leu Pro Pro Ser Thr Leu
            20                  25                  30

Ser Gln Asp Arg Leu Asp Ala Pro Pro Pro Ala Ala Pro Leu Pro
            35                  40                  45

Arg Trp Ser Gly Pro Ile Gly Val Ser Trp Gly Leu Arg Ala Ala Ala
        50                  55                  60

Ala Gly Gly Ala Phe Pro Arg Gly Gly Arg Trp Arg Arg Ser Ala Pro
65                  70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
        115                 120                 125

Thr Phe His Val Pro Leu Val Ile Met Thr Phe Gly Gln Ser Lys Leu
130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
            260                 265                 270

Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
370                 375                 380

Val Tyr Ser Lys Ser Leu Asp Arg His Leu Tyr Thr Thr Thr Gly Gly
385                 390                 395                 400
```

-continued

Glu Thr Asp Phe Thr Asn Val Thr Ser Leu Arg Gly Val Tyr Ile Thr
                405                 410                 415
Ser Val Leu Ser Glu Asp Asn Ser Ile Gln Thr Met Ile Thr Phe Asp
                420                 425                 430
Gln Gly Gly Arg Trp Thr His Leu Arg Lys Pro Glu Asn Ser Glu Cys
                435                 440                 445
Asp Ala Thr Ala Lys Asn Lys Asn Glu Cys Ser Leu His Ile His Ala
            450                 455                 460
Ser Tyr Ser Ile Ser Gln Lys Leu Asn Val Pro Met Ala Pro Leu Ser
465                 470                 475                 480
Glu Pro Asn Ala Val Gly Ile Val Ile Ala His Gly Ser Val Gly Asp
                485                 490                 495
Ala Ile Ser Val Met Val Pro Asp Val Tyr Ile Ser Asp Asp Gly Gly
                500                 505                 510
Tyr Ser Trp Thr Lys Met Leu Glu Gly Pro His Tyr Tyr Thr Ile Leu
                515                 520                 525
Asp Ser Gly Gly Ile Ile Val Ala Ile Glu His Ser Ser Arg Pro Ile
            530                 535                 540
Asn Val Ile Lys Phe Ser Thr Asp Glu Gly Gln Cys Trp Gln Thr Tyr
545                 550                 555                 560
Thr Phe Thr Arg Asp Pro Ile Tyr Phe Thr Gly Leu Ala Ser Glu Pro
                565                 570                 575
Gly Ala Arg Ser Met Asn Ile Ser Ile Trp Gly Phe Thr Glu Ser Phe
                580                 585                 590
Leu Thr Ser Gln Trp Val Ser Tyr Thr Ile Asp Phe Lys Asp Ile Leu
                595                 600                 605
Glu Arg Asn Cys Glu Gly Lys Asp Tyr Thr Ile Trp Leu Ala His Ser
            610                 615                 620
Thr Asp Pro Glu Asp Tyr Glu Asp Gly Cys Ile Leu Gly Tyr Lys Glu
625                 630                 635                 640
Gln Phe Leu Arg Leu Arg Lys Ser Ser Val Cys Gln Asn Gly Arg Asp
                645                 650                 655
Tyr Val Val Thr Lys Gln Pro Ser Ile Cys Leu Cys Ser Leu Glu Asp
                660                 665                 670
Phe Leu Cys Asp Phe Gly Tyr Tyr Arg Pro Glu Asn Asp Ser Lys Cys
            675                 680                 685
Val Glu Gln Pro Glu Leu Lys Gly His Asp Leu Glu Phe Cys Leu Tyr
            690                 695                 700
Gly Arg Glu Glu His Leu Thr Thr Asn Gly Tyr Arg Lys Ile Pro Gly
705                 710                 715                 720
Asp Lys Cys Gln Gly Gly Val Asn Pro Val Arg Glu Val Lys Asp Leu
                725                 730                 735
Lys Lys Lys Cys Thr Ser Asn Phe Leu Ser Pro Glu Lys Gln Asn Ser
                740                 745                 750
Lys Ser Asn Ser Val Pro Ile Ile Leu Ala Ile Val Gly Leu Met Leu
            755                 760                 765
Val Thr Val Val Ala Gly Val Leu Ile Val Lys Lys Tyr Val Cys Gly
770                 775                 780
Gly Arg Phe Leu Val His Arg Tyr Ser Val Leu Gln Gln His Ala Glu
                785                 790                 795                 800
Ala Asn Gly Val Asp Gly Val Asp Ala Leu Asp Thr Ala Ser His Thr
                805                 810                 815

```
Asn Lys Ser Gly Tyr His Asp Asp Ser Asp Glu Asp Leu Leu Glu
            820                 825                 830

<210> SEQ ID NO 82
<211> LENGTH: 825
<212> TYPE: PRT
<213> ORGANISM: Mus musculus

<400> SEQUENCE: 82

Met Glu Arg Pro Arg Gly Ala Ala Asp Gly Leu Leu Arg Trp Pro Leu
1               5                   10                  15

Gly Leu Leu Leu Leu Leu Gln Leu Leu Pro Pro Ala Ala Val Gly Gln
                20                  25                  30

Asp Arg Leu Asp Ala Pro Pro Pro Ala Pro Pro Leu Leu Arg Trp
            35                  40                  45

Ala Gly Pro Val Gly Val Ser Trp Gly Leu Arg Ala Ala Pro Gly
        50                  55                  60

Gly Pro Val Pro Arg Ala Gly Arg Trp Arg Gly Ala Pro Ala Glu
65                  70                  75                  80

Asp Gln Asp Cys Gly Arg Leu Pro Asp Phe Ile Ala Lys Leu Thr Asn
                85                  90                  95

Asn Thr His Gln His Val Phe Asp Asp Leu Ser Gly Ser Val Ser Leu
            100                 105                 110

Ser Trp Val Gly Asp Ser Thr Gly Val Ile Leu Val Leu Thr Thr Phe
        115                 120                 125

Gln Val Pro Leu Val Ile Val Ser Phe Gly Gln Ser Lys Leu Tyr Arg
    130                 135                 140

Ser Glu Asp Tyr Gly Lys Asn Phe Lys Asp Ile Thr Asn Leu Ile Asn
145                 150                 155                 160

Asn Thr Phe Ile Arg Thr Glu Phe Gly Met Ala Ile Gly Pro Glu Asn
                165                 170                 175

Ser Gly Lys Val Ile Leu Thr Ala Glu Val Ser Gly Gly Ser Arg Gly
            180                 185                 190

Gly Arg Val Phe Arg Ser Ser Asp Phe Ala Lys Asn Phe Val Gln Thr
        195                 200                 205

Asp Leu Pro Phe His Pro Leu Thr Gln Met Met Tyr Ser Pro Gln Asn
    210                 215                 220

Ser Asp Tyr Leu Leu Ala Leu Ser Thr Glu Asn Gly Leu Trp Val Ser
225                 230                 235                 240

Lys Asn Phe Gly Glu Lys Trp Glu Glu Ile His Lys Ala Val Cys Leu
                245                 250                 255

Ala Lys Trp Gly Pro Asn Asn Ile Ile Phe Phe Thr Thr His Val Asn
            260                 265                 270

Gly Ser Cys Lys Ala Asp Leu Gly Ala Leu Glu Leu Trp Arg Thr Ser
        275                 280                 285

Asp Leu Gly Lys Thr Phe Lys Thr Ile Gly Val Lys Ile Tyr Ser Phe
    290                 295                 300

Gly Leu Gly Gly Arg Phe Leu Phe Ala Ser Val Met Ala Asp Lys Asp
305                 310                 315                 320

Thr Thr Arg Arg Ile His Val Ser Thr Asp Gln Gly Asp Thr Trp Ser
                325                 330                 335

Met Ala Gln Leu Pro Ser Val Gly Gln Glu Gln Phe Tyr Ser Ile Leu
            340                 345                 350

Ala Ala Asn Glu Asp Met Val Phe Met His Val Asp Glu Pro Gly Asp
        355                 360                 365
```

```
Thr Gly Phe Gly Thr Ile Phe Thr Ser Asp Asp Arg Gly Ile Val Tyr
    370                 375                 380

Ser Lys Ser Leu Asp Arg His Leu Tyr Thr Thr Gly Gly Glu Thr
385                 390                 395                 400

Asp Phe Thr Asn Val Thr Ser Leu Arg Gly Val Tyr Ile Thr Ser Thr
                405                 410                 415

Leu Ser Glu Asp Asn Ser Ile Gln Ser Met Ile Thr Phe Asp Gln Gly
                420                 425                 430

Gly Arg Trp Glu His Leu Arg Lys Pro Glu Asn Ser Lys Cys Asp Ala
            435                 440                 445

Thr Ala Lys Asn Lys Asn Glu Cys Ser Leu His Ile His Ala Ser Tyr
    450                 455                 460

Ser Ile Ser Gln Lys Leu Asn Val Pro Met Ala Pro Leu Ser Glu Pro
465                 470                 475                 480

Asn Ala Val Gly Ile Val Ile Ala His Gly Ser Val Gly Asp Ala Ile
                485                 490                 495

Ser Val Met Val Pro Asp Val Tyr Ile Ser Asp Asp Gly Gly Tyr Ser
            500                 505                 510

Trp Ala Lys Met Leu Glu Gly Pro His Tyr Tyr Thr Ile Leu Asp Ser
    515                 520                 525

Gly Gly Ile Ile Val Ala Ile Glu His Ser Asn Arg Pro Ile Asn Val
    530                 535                 540

Ile Lys Phe Ser Thr Asp Glu Gly Gln Cys Trp Gln Ser Tyr Val Phe
545                 550                 555                 560

Thr Gln Glu Pro Ile Tyr Phe Thr Gly Leu Ala Ser Glu Pro Gly Ala
                565                 570                 575

Arg Ser Met Asn Ile Ser Ile Trp Gly Phe Thr Glu Ser Phe Ile Thr
                580                 585                 590

Arg Gln Trp Val Ser Tyr Thr Val Asp Phe Lys Asp Ile Leu Glu Arg
            595                 600                 605

Asn Cys Glu Glu Asp Asp Tyr Thr Thr Trp Leu Ala His Ser Thr Asp
    610                 615                 620

Pro Gly Asp Tyr Lys Asp Gly Cys Ile Leu Gly Tyr Lys Glu Gln Phe
625                 630                 635                 640

Leu Arg Leu Arg Lys Ser Ser Val Cys Gln Asn Gly Arg Asp Tyr Val
                645                 650                 655

Val Ala Lys Gln Pro Ser Val Cys Pro Cys Ser Leu Glu Asp Phe Leu
            660                 665                 670

Cys Asp Phe Gly Tyr Phe Arg Pro Glu Asn Ala Ser Glu Cys Val Glu
    675                 680                 685

Gln Pro Glu Leu Lys Gly His Glu Leu Glu Phe Cys Leu Tyr Gly Lys
    690                 695                 700

Glu Glu His Leu Thr Thr Asn Gly Tyr Arg Lys Ile Pro Gly Asp Lys
705                 710                 715                 720

Cys Gln Gly Gly Met Asn Pro Ala Arg Glu Val Lys Asp Leu Lys Lys
                725                 730                 735

Lys Cys Thr Ser Asn Phe Leu Asn Pro Thr Lys Gln Asn Ser Lys Ser
            740                 745                 750

Asn Ser Val Pro Ile Ile Leu Ala Ile Val Gly Leu Met Leu Val Thr
        755                 760                 765

Val Val Ala Gly Val Leu Ile Val Lys Lys Tyr Val Cys Gly Gly Arg
    770                 775                 780
```

Phe Leu Val His Arg Tyr Ser Val Leu Gln Gln His Ala Glu Ala Asp
785                 790                 795                 800

Gly Val Glu Ala Leu Asp Ser Thr Ser His Ala Lys Ser Gly Tyr His
            805                 810                 815

Asp Asp Ser Asp Glu Asp Leu Leu Glu
            820                 825

<210> SEQ ID NO 83
<211> LENGTH: 825
<212> TYPE: PRT
<213> ORGANISM: Rattus norvegicus

<400> SEQUENCE: 83

Met Glu Arg Pro Arg Gly Ala Ala Asp Gly Leu Leu Arg Trp Pro Leu
1               5                   10                  15

Gly Leu Leu Leu Leu Leu Gln Leu Leu Pro Ala Ala Val Gly Gln
            20                  25                  30

Asp Arg Leu Asp Ala Pro Pro Pro Ala Pro Pro Leu Leu Arg Trp
            35                  40                  45

Ala Gly Pro Val Gly Val Ser Trp Gly Leu Arg Ala Ala Pro Gly
50                  55                  60

Gly Pro Val Pro Arg Ala Gly Arg Trp Arg Arg Gly Ala Pro Ala Glu
65                  70                  75                  80

Asp Gln Asp Cys Gly Arg Leu Pro Asp Phe Ile Ala Lys Leu Thr Asn
            85                  90                  95

Asn Thr His Gln His Val Phe Asp Asp Leu Ser Gly Ser Val Ser Leu
            100                 105                 110

Ser Trp Val Gly Asp Ser Thr Gly Val Ile Leu Val Leu Thr Thr Phe
        115                 120                 125

Gln Val Pro Leu Val Ile Val Ser Phe Gly Gln Ser Lys Leu Tyr Arg
        130                 135                 140

Ser Glu Asp Tyr Gly Lys Asn Phe Lys Asp Ile Thr Asn Leu Ile Asn
145                 150                 155                 160

Asn Thr Phe Ile Arg Thr Glu Phe Gly Met Ala Ile Gly Pro Glu Asn
                165                 170                 175

Ser Gly Lys Val Ile Leu Thr Ala Glu Val Ser Gly Ser Arg Gly
            180                 185                 190

Gly Arg Val Phe Arg Ser Ser Asp Phe Ala Lys Asn Phe Val Gln Thr
                195                 200                 205

Asp Leu Pro Phe His Pro Leu Thr Gln Met Met Tyr Ser Pro Gln Asn
        210                 215                 220

Ser Asp Tyr Leu Leu Ala Leu Ser Thr Glu Asn Gly Leu Trp Val Ser
225                 230                 235                 240

Lys Asn Phe Gly Glu Lys Trp Glu Glu Ile His Lys Ala Val Cys Leu
                245                 250                 255

Ala Lys Trp Gly Pro Asn Asn Ile Ile Phe Phe Thr Thr His Val Asn
            260                 265                 270

Gly Ser Cys Lys Ala Asp Leu Gly Ala Leu Glu Leu Trp Arg Thr Ser
        275                 280                 285

Asp Leu Gly Lys Thr Phe Lys Thr Ile Gly Val Lys Ile Tyr Ser Phe
        290                 295                 300

Gly Leu Gly Gly Arg Phe Leu Phe Ala Ser Val Met Ala Asp Lys Asp
305                 310                 315                 320

Thr Thr Arg Arg Ile His Val Ser Thr Asp Gln Gly Asp Thr Trp Ser
                325                 330                 335

```
Met Ala Gln Leu Pro Ser Val Gly Gln Glu Gln Phe Tyr Ser Ile Leu
            340                 345                 350

Ala Ala Asn Asp Asp Met Val Phe Met His Val Asp Glu Pro Gly Asp
            355                 360                 365

Thr Gly Phe Gly Thr Ile Phe Thr Ser Asp Asp Arg Gly Ile Val Tyr
    370                 375                 380

Ser Lys Ser Leu Asp Arg His Leu Tyr Thr Thr Thr Gly Gly Glu Thr
385                 390                 395                 400

Asp Phe Thr Asn Val Thr Ser Leu Arg Gly Val Tyr Ile Thr Ser Thr
                405                 410                 415

Leu Ser Glu Asp Asn Ser Ile Gln Ser Met Ile Thr Phe Asp Gln Gly
            420                 425                 430

Gly Arg Trp Glu His Leu Gln Lys Pro Glu Asn Ser Lys Cys Asp Ala
            435                 440                 445

Thr Ala Lys Asn Lys Asn Glu Cys Ser Leu His Ile His Ala Ser Tyr
            450                 455                 460

Ser Ile Ser Gln Lys Leu Asn Val Pro Met Ala Pro Leu Ser Glu Pro
465                 470                 475                 480

Asn Ala Val Gly Ile Val Ile Ala His Gly Ser Val Gly Asp Ala Ile
                485                 490                 495

Ser Val Met Val Pro Asp Val Tyr Ile Ser Asp Asp Gly Gly Tyr Ser
            500                 505                 510

Trp Ala Lys Met Leu Glu Gly Pro His Tyr Tyr Thr Ile Leu Asp Ser
            515                 520                 525

Gly Gly Ile Ile Val Ala Ile Glu His Ser Asn Arg Pro Ile Asn Val
            530                 535                 540

Ile Lys Phe Ser Thr Asp Glu Gly Gln Cys Trp Gln Ser Tyr Val Phe
545                 550                 555                 560

Ser Gln Glu Pro Val Tyr Phe Thr Gly Leu Ala Ser Glu Pro Gly Ala
                565                 570                 575

Arg Ser Met Asn Ile Ser Ile Trp Gly Phe Thr Glu Ser Phe Leu Thr
            580                 585                 590

Arg Gln Trp Val Ser Tyr Thr Ile Asp Phe Lys Asp Ile Leu Glu Arg
            595                 600                 605

Asn Cys Glu Glu Asn Asp Tyr Thr Thr Trp Leu Ala His Ser Thr Asp
            610                 615                 620

Pro Gly Asp Tyr Lys Asp Gly Cys Ile Leu Gly Tyr Lys Glu Gln Phe
625                 630                 635                 640

Leu Arg Leu Arg Lys Ser Ser Val Cys Gln Asn Gly Arg Asp Tyr Val
                645                 650                 655

Val Ala Lys Gln Pro Ser Ile Cys Pro Cys Ser Leu Glu Asp Phe Leu
            660                 665                 670

Cys Asp Phe Gly Tyr Phe Arg Pro Glu Asn Ala Ser Glu Cys Val Glu
            675                 680                 685

Gln Pro Glu Leu Lys Gly His Glu Leu Glu Phe Cys Leu Tyr Gly Lys
            690                 695                 700

Glu Glu His Leu Thr Thr Asn Gly Tyr Arg Lys Ile Pro Gly Asp Arg
705                 710                 715                 720

Cys Gln Gly Gly Met Asn Pro Ala Arg Glu Val Lys Asp Leu Lys Lys
                725                 730                 735

Lys Cys Thr Ser Asn Phe Leu Asn Pro Lys Lys Gln Asn Ser Lys Ser
            740                 745                 750
```

```
Ser Ser Val Pro Ile Ile Leu Ala Ile Val Gly Leu Met Leu Val Thr
        755                 760                 765

Val Val Ala Gly Val Leu Ile Val Lys Lys Tyr Val Cys Gly Gly Arg
    770                 775                 780

Phe Leu Val His Arg Tyr Ser Val Leu Gln Gln His Ala Glu Ala Asp
785                 790                 795                 800

Gly Val Glu Ala Leu Asp Thr Ala Ser His Ala Lys Ser Gly Tyr His
                805                 810                 815

Asp Asp Ser Asp Glu Asp Leu Leu Glu
            820                 825

<210> SEQ ID NO 84
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Ser or Thr
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 3
<223> OTHER INFORMATION: Xaa = Asp or Asn
<220> FEATURE:
<221> NAME/KEY: VARIANT
<222> LOCATION: 4, 5, 6, 7
<223> OTHER INFORMATION: Xaa = Any Amino Acid
<220> FEATURE:
<221> NAME/KEY: VARIANT
<222> LOCATION: 8
<223> OTHER INFORMATION: Xaa = Trp, Phe, or Tyr

<400> SEQUENCE: 84

Xaa Xaa Xaa Xaa Xaa Xaa Xaa Xaa
1               5

<210> SEQ ID NO 85
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2
<223> OTHER INFORMATION: Xaa = Any Amino Acid
<220> FEATURE:
<221> NAME/KEY: VARIANT
<222> LOCATION: 3
<223> OTHER INFORMATION: Xaa = Ser or Thr
<220> FEATURE:
<221> NAME/KEY: VARIANT
<222> LOCATION: 4
<223> OTHER INFORMATION: Xaa = Any Amino Acid
<220> FEATURE:
<221> NAME/KEY: VARIANT
<222> LOCATION: 5
<223> OTHER INFORMATION: Xaa = Asp or Asn
<220> FEATURE:
<221> NAME/KEY: VARIANT
<222> LOCATION: 6, 8
<223> OTHER INFORMATION: Xaa = Any Amino Acid
<220> FEATURE:
<221> NAME/KEY: VARIANT
<222> LOCATION: 9
<223> OTHER INFORMATION: Xaa = Thr or Ser
```

```
<220> FEATURE:
<221> NAME/KEY: VARIANT
<222> LOCATION: 10
<223> OTHER INFORMATION: Xaa = Trp, Phe, or Tyr
<220> FEATURE:
<221> NAME/KEY: VARIANT
<222> LOCATION: 11
<223> OTHER INFORMATION: Xaa = Any Amino Acid

<400> SEQUENCE: 85

Xaa Xaa Xaa Xaa Xaa Xaa Gly Xaa Xaa Xaa Xaa
1               5                   10

<210> SEQ ID NO 86
<211> LENGTH: 8
<212> TYPE: PRT
<213> ORGANISM: Artificial Sequence
<220> FEATURE:
<223> OTHER INFORMATION: Synthetic Construct

<400> SEQUENCE: 86

Ser Ser Asp Phe Ala Lys Asn Phe
1               5

<210> SEQ ID NO 87
<211> LENGTH: 6
<212> TYPE: PRT
<213> ORGANISM: Artificial Sequence
<220> FEATURE:
<223> OTHER INFORMATION: Synthetic Construct

<400> SEQUENCE: 87

Asn Gln Phe Ser Leu Lys
1               5

<210> SEQ ID NO 88
<211> LENGTH: 23
<212> TYPE: PRT
<213> ORGANISM: Artificial Sequence
<220> FEATURE:
<223> OTHER INFORMATION: Synthetic Construct

<400> SEQUENCE: 88

Gln Gly Tyr Tyr Gly Met Asp Val Trp Gly Gln Gly Thr Thr Val Thr
1               5                   10                  15

Val Ser Ser Ala Ser Thr Lys
            20

<210> SEQ ID NO 89
<211> LENGTH: 49
<212> TYPE: PRT
<213> ORGANISM: Artificial Sequence
<220> FEATURE:
<223> OTHER INFORMATION: Synthetic Construct

<400> SEQUENCE: 89

Asp Tyr Phe Pro Glu Pro Val Thr Val Ser Trp Asn Ser Gly Ala Leu
1               5                   10                  15

Thr Ser Gly Val His Thr Phe Pro Ala Val Leu Gln Ser Ser Gly Leu
            20                  25                  30

Tyr Ser Leu Ser Ser Val Val Thr Val Pro Ser Ser Ser Leu Gly Thr
        35                  40                  45

Lys

<210> SEQ ID NO 90
```

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 90

Asp Thr Leu Met Ile Ser Arg
1               5

<210> SEQ ID NO 91
<211> LENGTH: 33
<212> TYPE: PRT
<213> ORGANISM: Artificial Sequence
<220> FEATURE:
<223> OTHER INFORMATION: Synthetic Construct

<400> SEQUENCE: 91

Thr Pro Glu Val Thr Cys Val Val Val Asp Val Ser Gln Glu Asp Pro
1               5                   10                  15

Glu Val Gln Phe Asn Trp Tyr Val Asp Gly Val Glu Val His Asn Ala
            20                  25                  30

Lys

<210> SEQ ID NO 92
<211> LENGTH: 16
<212> TYPE: PRT
<213> ORGANISM: Artificial Sequence
<220> FEATURE:
<223> OTHER INFORMATION: Synthetic Construct

<400> SEQUENCE: 92

Val Val Ser Val Leu Thr Val Leu His Gln Asp Trp Leu Asn Gly Lys
1               5                   10                  15

<210> SEQ ID NO 93
<211> LENGTH: 16
<212> TYPE: PRT
<213> ORGANISM: Artificial Sequence
<220> FEATURE:
<223> OTHER INFORMATION: Synthetic Construct

<400> SEQUENCE: 93

Glu Pro Gln Val Tyr Thr Leu Pro Pro Ser Gln Glu Glu Met Thr Lys
1               5                   10                  15

<210> SEQ ID NO 94
<211> LENGTH: 10
<212> TYPE: PRT
<213> ORGANISM: Artificial Sequence
<220> FEATURE:
<223> OTHER INFORMATION: Synthetic Construct

<400> SEQUENCE: 94

Asn Gln Val Ser Leu Thr Cys Leu Val Lys
1               5                   10

<210> SEQ ID NO 95
<211> LENGTH: 22
<212> TYPE: PRT
<213> ORGANISM: Artificial Sequence
<220> FEATURE:
<223> OTHER INFORMATION: Synthetic Construct

<400> SEQUENCE: 95

Gly Phe Tyr Pro Ser Asp Ile Ala Val Glu Trp Glu Ser Asn Gly Gln
```

```
                1               5                   10                  15
Pro Glu Asn Asn Tyr Lys
            20

<210> SEQ ID NO 96
<211> LENGTH: 23
<212> TYPE: PRT
<213> ORGANISM: Artificial Sequence
<220> FEATURE:
<223> OTHER INFORMATION: Synthetic Construct

<400> SEQUENCE: 96

Trp Gln Glu Gly Asn Val Phe Ser Cys Ser Val Met His Glu Ala Leu
1               5                   10                  15

His Asn His Tyr Thr Gln Lys
            20

<210> SEQ ID NO 97
<211> LENGTH: 24
<212> TYPE: PRT
<213> ORGANISM: Artificial Sequence
<220> FEATURE:
<223> OTHER INFORMATION: Synthetic Construct

<400> SEQUENCE: 97

Asp Ile Val Met Thr Gln Ser Pro Leu Ser Leu Pro Val Thr Pro Gly
1               5                   10                  15

Glu Pro Ala Ser Ile Ser Cys Arg
            20

<210> SEQ ID NO 98
<211> LENGTH: 7
<212> TYPE: PRT
<213> ORGANISM: Artificial Sequence
<220> FEATURE:
<223> OTHER INFORMATION: Synthetic Construct

<400> SEQUENCE: 98

Ser Ser Gln Ser Leu Leu Arg
1               5

<210> SEQ ID NO 99
<211> LENGTH: 28
<212> TYPE: PRT
<213> ORGANISM: Artificial Sequence
<220> FEATURE:
<223> OTHER INFORMATION: Synthetic Construct

<400> SEQUENCE: 99

Ser Asn Gly Tyr Asn Tyr Leu Asp Trp Tyr Leu Gln Lys Pro Gly Gln
1               5                   10                  15

Ser Pro Gln Leu Leu Ile Tyr Leu Gly Ser Asn Arg
            20                  25

<210> SEQ ID NO 100
<211> LENGTH: 26
<212> TYPE: PRT
<213> ORGANISM: Artificial Sequence
<220> FEATURE:
<223> OTHER INFORMATION: Synthetic Construct

<400> SEQUENCE: 100

Ala Glu Ala Glu Asp Val Gly Val Tyr Tyr Cys Met Gln Gln Gln Glu
1               5                   10                  15
```

Ala Pro Leu Thr Phe Gly Gly Gly Thr Lys
            20                  25

<210> SEQ ID NO 101
<211> LENGTH: 16
<212> TYPE: PRT
<213> ORGANISM: Artificial Sequence
<220> FEATURE:
<223> OTHER INFORMATION: Synthetic Construct

<400> SEQUENCE: 101

Ser Gly Thr Ala Ser Val Val Cys Leu Leu Asn Asn Phe Tyr Pro Arg
1               5                   10                  15

<210> SEQ ID NO 102
<211> LENGTH: 20
<212> TYPE: PRT
<213> ORGANISM: Artificial Sequence
<220> FEATURE:
<223> OTHER INFORMATION: Synthetic Construct

<400> SEQUENCE: 102

Val Asp Asn Ala Leu Gln Ser Gly Asn Ser Gln Glu Ser Val Thr Glu
1               5                   10                  15

Gln Asp Ser Lys
            20

<210> SEQ ID NO 103
<211> LENGTH: 330
<212> TYPE: PRT
<213> ORGANISM: Artificial Sequence
<220> FEATURE:
<223> OTHER INFORMATION: Synthetic Construct

<400> SEQUENCE: 103

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn

```
                195                 200                 205
Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 104
<211> LENGTH: 329
<212> TYPE: PRT
<213> ORGANISM: Artificial Sequence
<220> FEATURE:
<223> OTHER INFORMATION: Synthetic Construct

<400> SEQUENCE: 104

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Asp Glu
```

```
            225                 230                 235                 240
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 105
<211> LENGTH: 452
<212> TYPE: PRT
<213> ORGANISM: Artificial Sequence
<220> FEATURE:
<223> OTHER INFORMATION: Synthetic Construct

<400> SEQUENCE: 105

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
                20                  25                  30

Tyr Tyr Trp Gly Trp Ile Arg Gln Pro Pro Gly Lys Gly Leu Glu Trp
            35                  40                  45

Ile Gly Thr Ile Tyr His Ser Gly Ser Thr Tyr Tyr Asn Pro Ser Leu
        50                  55                  60

Lys Ser Gln Val Thr Ile Ser Val Asp Thr Ser Lys Asn Gln Phe Ser
65                  70                  75                  80

Leu Glu Leu Ser Ser Val Thr Ala Ala Asp Thr Ala Val Tyr Tyr Cys
                85                  90                  95

Ala Arg Gln Gly Ser Ile Gln Gln Gly Tyr Tyr Gly Met Asp Val Trp
                100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
        210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
```

```
                   260                 265                 270
His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 106
<211> LENGTH: 451
<212> TYPE: PRT
<213> ORGANISM: Artificial Sequence
<220> FEATURE:
<223> OTHER INFORMATION: Synthetic Construct

<400> SEQUENCE: 106

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Thr Ile Tyr His Ser Gly Ser Thr Tyr Tyr Asn Pro Ser Leu
    50                  55                  60

Lys Ser Gln Val Thr Ile Ser Val Asp Thr Ser Lys Asn Gln Phe Ser
65                  70                  75                  80

Leu Glu Leu Ser Ser Val Thr Ala Ala Asp Thr Ala Val Tyr Tyr Cys
                85                  90                  95

Ala Arg Gln Gly Ser Ile Gln Gln Gly Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
```

-continued

```
                165                 170                 175
Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
            210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Ser
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly
    450

<210> SEQ ID NO 107
<211> LENGTH: 122
<212> TYPE: PRT
<213> ORGANISM: Artificial Sequence
<220> FEATURE:
<223> OTHER INFORMATION: Synthetic Construct

<400> SEQUENCE: 107

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Val
            20                  25                  30

Arg Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
```

```
                65                  70                  75                  80
Leu Lys Leu Ser Ser Val Thr Ala Ala Asp Thr Ala Val Tyr Tyr Cys
                85                  90                  95

Ala Arg Gln Gly Ser Ile Lys Gln Gly Tyr Tyr Gly Met Asp Val Trp
            100                 105                 110

Gly Gln Gly Thr Thr Val Thr Val Ser Ser
            115                 120

<210> SEQ ID NO 108
<211> LENGTH: 122
<212> TYPE: PRT
<213> ORGANISM: Artificial Sequence
<220> FEATURE:
<223> OTHER INFORMATION: Synthetic Construct

<400> SEQUENCE: 108

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Val
                20                  25                  30

Arg Tyr Trp Gly Trp Ile Arg Gln Pro Pro Gly Lys Gly Leu Glu Trp
            35                  40                  45

Ile Gly Ala Ile Tyr Pro Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gln Gly Ser Ile Lys Gln Gly Tyr Tyr Gly Met Asp Val Trp
            100                 105                 110

Gly Gln Gly Thr Thr Val Thr Val Ser Ser
            115                 120

<210> SEQ ID NO 109
<211> LENGTH: 122
<212> TYPE: PRT
<213> ORGANISM: Artificial Sequence
<220> FEATURE:
<223> OTHER INFORMATION: Synthetic Construct

<400> SEQUENCE: 109

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
                20                  25                  30

Tyr Tyr Trp Gly Trp Ile Arg Gln Pro Pro Gly Lys Gly Leu Glu Trp
            35                  40                  45

Ile Gly Thr Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gln Gly Ser Ile Lys Gln Gly Tyr Tyr Gly Met Asp Val Trp
            100                 105                 110

Gly Gln Gly Thr Thr Val Thr Val Ser Ser
            115                 120
```

<210> SEQ ID NO 110
<211> LENGTH: 122
<212> TYPE: PRT
<213> ORGANISM: Artificial Sequence
<220> FEATURE:
<223> OTHER INFORMATION: Synthetic Construct

<400> SEQUENCE: 110

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Thr Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gln Gly Ser Ile Lys Gly Tyr Tyr Gly Met Asp Val Trp
            100                 105                 110

Gly Gln Gly Thr Thr Val Thr Val Ser Ser
        115                 120
```

<210> SEQ ID NO 111
<211> LENGTH: 122
<212> TYPE: PRT
<213> ORGANISM: Artificial Sequence
<220> FEATURE:
<223> OTHER INFORMATION: Synthetic Construct

<400> SEQUENCE: 111

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Thr Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gln Gly Ser Ile Lys Gly Tyr Tyr Gly Met Asp Val Trp
            100                 105                 110

Gly Gln Gly Thr Thr Val Thr Val Ser Ser
        115                 120
```

<210> SEQ ID NO 112
<211> LENGTH: 122
<212> TYPE: PRT
<213> ORGANISM: Artificial Sequence
<220> FEATURE:
<223> OTHER INFORMATION: Synthetic Construct

<400> SEQUENCE: 112

```
Gln Val Gln Leu Gln Glu Ser Gly Pro Gly Leu Val Lys Pro Ser Glu
```

-continued

```
                1               5                  10                  15
            Thr Leu Ser Leu Thr Cys Ala Val Ser Gly Tyr Ser Ile Ser Ser Gly
                        20                  25                  30

Tyr Tyr Trp Gly Trp Ile Arg Gln Pro Pro Gly Lys Gly Leu Glu Trp
                        35                  40                  45

Ile Gly Thr Ile Tyr His Ser Gly Ser Thr Tyr Tyr Asn Pro Ser Leu
                        50                  55                  60

Lys Ser Arg Val Thr Ile Ser Val Asp Thr Ser Lys Asn Gln Phe Ser
             65                  70                  75                  80

Leu Lys Leu Ser Ser Val Thr Ala Ala Asp Thr Ala Val Tyr Tyr Cys
                        85                  90                  95

Ala Arg Gln Gly Ser Ile Lys Gln Gly Tyr Tyr Gly Met Asp Val Trp
                        100                 105                 110

Gly Gln Gly Thr Thr Val Thr Val Ser Ser
                        115                 120

<210> SEQ ID NO 113
<211> LENGTH: 112
<212> TYPE: PRT
<213> ORGANISM: Artificial Sequence
<220> FEATURE:
<223> OTHER INFORMATION: Synthetic Construct

<400> SEQUENCE: 113

Asp Ile Val Met Thr Gln Ser Pro Leu Ser Leu Pro Val Thr Pro Gly
             1               5                  10                  15

Glu Pro Ala Ser Ile Ser Cys Arg Ser Ser Gln Ser Leu Leu His Ser
                        20                  25                  30

Asn Gly Tyr Asn Tyr Leu Asp Trp Tyr Leu Gln Lys Pro Gly Gln Ser
                        35                  40                  45

Pro Gln Leu Leu Ile Tyr Leu Gly Ser Asn Arg Ala Ser Gly Val Pro
                        50                  55                  60

Asp Arg Phe Ser Gly Ser Gly Ser Gly Thr Asp Phe Thr Leu Lys Ile
             65                  70                  75                  80

Ser Arg Val Glu Ala Glu Asp Val Gly Val Tyr Tyr Cys Met Gln Gln
                        85                  90                  95

Gln Glu Thr Pro Leu Thr Phe Gly Gly Gly Thr Lys Val Glu Ile Lys
                        100                 105                 110

<210> SEQ ID NO 114
<211> LENGTH: 112
<212> TYPE: PRT
<213> ORGANISM: Artificial Sequence
<220> FEATURE:
<223> OTHER INFORMATION: Synthetic Construct

<400> SEQUENCE: 114

Asp Ile Val Met Thr Gln Ser Pro Leu Ser Leu Pro Val Thr Pro Gly
             1               5                  10                  15

Glu Pro Ala Ser Ile Ser Cys Arg Ser Ser Gln Ser Leu Leu His Ser
                        20                  25                  30

Asn Gly Tyr Asn Tyr Leu Asp Trp Tyr Leu Gln Lys Pro Gly Gln Ser
                        35                  40                  45

Pro Gln Leu Leu Ile Tyr Leu Gly Ser Asn Arg Ala Ser Gly Val Pro
                        50                  55                  60

Asp Arg Phe Ser Gly Ser Gly Ser Gly Thr Asp Phe Thr Leu Lys Ile
             65                  70                  75                  80
```

```
Ser Arg Val Glu Ala Glu Asp Val Gly Val Tyr Tyr Cys Met Gln Gln
            85                  90                  95

Gln Glu Thr Pro Leu Thr Phe Gly Gly Gly Thr Lys Val Glu Ile Lys
        100                 105                 110

<210> SEQ ID NO 115
<211> LENGTH: 112
<212> TYPE: PRT
<213> ORGANISM: Artificial Sequence
<220> FEATURE:
<223> OTHER INFORMATION: Synthetic Construct

<400> SEQUENCE: 115

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Asn Gly Tyr Asn Tyr Leu Asp Trp Tyr Leu Gln Lys Pro Gly Gln Pro
        35                  40                  45

Pro Gln Leu Leu Ile Tyr Leu Gly Ser Asn Arg Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gln
            85                  90                  95

Gln Glu Thr Pro Leu Thr Phe Gly Gly Gly Thr Lys Val Glu Ile Lys
        100                 105                 110

<210> SEQ ID NO 116
<211> LENGTH: 112
<212> TYPE: PRT
<213> ORGANISM: Artificial Sequence
<220> FEATURE:
<223> OTHER INFORMATION: Synthetic Construct

<400> SEQUENCE: 116

Asp Ile Val Met Thr Gln Ser Pro Leu Ser Leu Pro Val Thr Pro Gly
1               5                   10                  15

Glu Ser Ala Ser Ile Ser Cys Arg Ser Ser Gln Gly Leu Leu Arg Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gln
            85                  90                  95

Gln Glu Thr Pro Leu Thr Phe Gly Gly Gly Thr Lys Val Glu Ile Lys
        100                 105                 110

<210> SEQ ID NO 117
<211> LENGTH: 112
<212> TYPE: PRT
<213> ORGANISM: Artificial Sequence
<220> FEATURE:
<223> OTHER INFORMATION: Synthetic Construct

<400> SEQUENCE: 117

Asp Ile Val Met Thr Gln Ser Pro Leu Ser Leu Pro Val Thr Pro Gly
```

-continued

```
                1               5                  10                 15
Glu Pro Ala Ser Ile Ser Cys Arg Ser Ser Gln Ser Leu Leu Arg Ser
            20                  25                 30

Asn Gly Tyr Asn Tyr Leu Asp Trp Tyr Leu Gln Lys Pro Gly Gln Ser
            35                  40                 45

Pro Gln Leu Leu Ile Tyr Leu Gly Ser Asn Arg Ala Ser Gly Val Pro
        50                  55                 60

Asp Arg Phe Ser Gly Ser Gly Ser Gly Thr Asp Phe Thr Leu Lys Ile
65                  70                  75                 80

Ser Arg Val Glu Ala Glu Asp Val Gly Val Tyr Tyr Cys Met Gln Gln
                85                  90                 95

Gln Glu Thr Pro Leu Thr Phe Gly Gly Gly Thr Lys Val Glu Ile Lys
            100                 105                110
```

<210> SEQ ID NO 118
<211> LENGTH: 112
<212> TYPE: PRT
<213> ORGANISM: Artificial Sequence
<220> FEATURE:
<223> OTHER INFORMATION: Synthetic Construct

<400> SEQUENCE: 118

```
Asp Ile Val Met Thr Gln Ser Pro Leu Ser Leu Pro Val Thr Pro Gly
1               5                  10                 15

Gly Pro Ala Ser Ile Ser Cys Arg Ser Ser Gln Ser Leu Leu Arg Ser
            20                  25                 30

Asn Gly Tyr Asn Tyr Leu Asp Trp Tyr Leu Gln Lys Pro Gly Gln Ser
            35                  40                 45

Pro Gln Leu Leu Ile Tyr Leu Gly Ser Asn Arg Ala Ser Gly Val Pro
        50                  55                 60

Asp Arg Phe Ser Gly Ser Gly Ser Gly Thr Asp Phe Thr Leu Lys Ile
65                  70                  75                 80

Ser Arg Val Glu Ala Glu Asp Val Gly Val Tyr Tyr Cys Met Gln Gln
                85                  90                 95

Gln Glu Thr Pro Leu Thr Phe Gly Gly Gly Thr Lys Val Glu Ile Lys
            100                 105                110
```

<210> SEQ ID NO 119
<211> LENGTH: 219
<212> TYPE: PRT
<213> ORGANISM: Artificial Sequence
<220> FEATURE:
<223> OTHER INFORMATION: Synthetic Construct

<400> SEQUENCE: 119

```
Asp Ile Val Met Thr Gln Ser Pro Leu Ser Leu Pro Val Thr Pro Gly
1               5                  10                 15

Glu Pro Ala Ser Ile Ser Cys Arg Ser Ser Gln Ser Leu Leu Arg Ser
            20                  25                 30

His Gly Tyr Asn Tyr Leu Asp Trp Tyr Leu Gln Lys Pro Gly Gln Ser
            35                  40                 45

Pro Gln Leu Leu Ile Tyr Leu Gly Ser Asn Arg Ala Ser Gly Val Pro
        50                  55                 60

Asp Arg Phe Ser Gly Ser Gly Ser Gly Thr Asp Phe Thr Leu Lys Ile
65                  70                  75                 80

Ser Arg Ala Glu Ala Glu Asp Val Gly Val Tyr Tyr Cys Met Gln Gln
                85                  90                 95
```

```
Gln Glu Ala Pro Leu Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
210                 215
```

<210> SEQ ID NO 120
<211> LENGTH: 219
<212> TYPE: PRT
<213> ORGANISM: Artificial Sequence
<220> FEATURE:
<223> OTHER INFORMATION: Synthetic Construct

<400> SEQUENCE: 120

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Lys Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
                85                  90                  95

Gln Glu Ala Pro Leu Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
210                 215
```

<210> SEQ ID NO 121
<211> LENGTH: 219

```
<212> TYPE: PRT
<213> ORGANISM: Artificial Sequence
<220> FEATURE:
<223> OTHER INFORMATION: Synthetic Construct

<400> SEQUENCE: 121

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Gln Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
                85                  90                  95

Gln Glu Ala Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 122
<211> LENGTH: 219
<212> TYPE: PRT
<213> ORGANISM: Artificial Sequence
<220> FEATURE:
<223> OTHER INFORMATION: Synthetic Construct

<400> SEQUENCE: 122

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Tyr Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
                85                  90                  95

Gln Glu Ala Pro Leu Thr Phe Gly Gly Gly Thr Lys Val Glu Ile Lys
            100                 105                 110
```

Arg Thr Val Ala Ala Pro Ser Val Phe Ile Phe Pro Pro Ser Asp Glu
          115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 123
<211> LENGTH: 219
<212> TYPE: PRT
<213> ORGANISM: Artificial Sequence
<220> FEATURE:
<223> OTHER INFORMATION: Synthetic Construct

<400> SEQUENCE: 123

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
                20                  25                  30

Glu Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
                85                  90                  95

Gln Glu Ala Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 124
<211> LENGTH: 219
<212> TYPE: PRT
<213> ORGANISM: Artificial Sequence
<220> FEATURE:
<223> OTHER INFORMATION: Synthetic Construct

<400> SEQUENCE: 124

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Trp Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
                85                  90                  95

Gln Glu Ala Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 125
<211> LENGTH: 219
<212> TYPE: PRT
<213> ORGANISM: Artificial Sequence
<220> FEATURE:
<223> OTHER INFORMATION: Synthetic Construct

<400> SEQUENCE: 125

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Phe Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
                85                  90                  95

Gln Glu Ala Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
```

```
                    115                 120                 125
Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 126
<211> LENGTH: 219
<212> TYPE: PRT
<213> ORGANISM: Artificial Sequence
<220> FEATURE:
<223> OTHER INFORMATION: Synthetic Construct

<400> SEQUENCE: 126

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
                20                  25                  30

Ile Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
                85                  90                  95

Gln Glu Ala Pro Leu Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 127
<211> LENGTH: 219
<212> TYPE: PRT
<213> ORGANISM: Artificial Sequence
<220> FEATURE:
<223> OTHER INFORMATION: Synthetic Construct
```

<400> SEQUENCE: 127

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Val Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
                85                  90                  95

Gln Glu Ala Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 128
<211> LENGTH: 219
<212> TYPE: PRT
<213> ORGANISM: Artificial Sequence
<220> FEATURE:
<223> OTHER INFORMATION: Synthetic Construct

<400> SEQUENCE: 128

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Ala Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
                85                  90                  95

Gln Glu Ala Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

```
Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 129
<211> LENGTH: 219
<212> TYPE: PRT
<213> ORGANISM: Artificial Sequence
<220> FEATURE:
<223> OTHER INFORMATION: Synthetic Construct

<400> SEQUENCE: 129

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Met Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
                85                  90                  95

Gln Glu Ala Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 130
<211> LENGTH: 219
<212> TYPE: PRT
<213> ORGANISM: Artificial Sequence
<220> FEATURE:
<223> OTHER INFORMATION: Synthetic Construct

<400> SEQUENCE: 130
```

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Leu Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
                85                  90                  95

Gln Glu Ala Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 131
<211> LENGTH: 219
<212> TYPE: PRT
<213> ORGANISM: Artificial Sequence
<220> FEATURE:
<223> OTHER INFORMATION: Synthetic Construct

<400> SEQUENCE: 131

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ala Tyr Tyr Cys Met Gln Gln
                85                  90                  95

Gln Glu Ala Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140
```

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 132
<211> LENGTH: 219
<212> TYPE: PRT
<213> ORGANISM: Artificial Sequence
<220> FEATURE:
<223> OTHER INFORMATION: Synthetic Construct

<400> SEQUENCE: 132

Asp Ile Val Met Thr Gln Ser Pro Leu Ser Leu Pro Val Thr Pro Gly
1               5                   10                  15

Gly Pro Ala Ser Ile Ser Cys Arg Ser Ser Gln Ser Leu Leu Arg Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Leu Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gln
                85                  90                  95

Gln Glu Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 133
<211> LENGTH: 219
<212> TYPE: PRT
<213> ORGANISM: Artificial Sequence
<220> FEATURE:
<223> OTHER INFORMATION: Synthetic Construct

<400> SEQUENCE: 133

Asp Ile Val Met Thr Gln Ser Pro Leu Ser Leu Pro Val Thr Pro Gly

-continued

```
1               5                   10                  15
Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
                35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gln
                85                  90                  95

Gln Glu Thr Pro Leu Thr Phe Gly Gly Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215
```

<210> SEQ ID NO 134
<211> LENGTH: 219
<212> TYPE: PRT
<213> ORGANISM: Artificial Sequence
<220> FEATURE:
<223> OTHER INFORMATION: Synthetic Construct

<400> SEQUENCE: 134

```
Asp Ile Val Met Thr Gln Ser Pro Leu Ser Leu Pro Val Thr Pro Gly
1               5                   10                  15

Glu Ser Ala Ser Ile Ser Cys Arg Ser Ser Gln Gly Leu Leu Arg Ser
                20                  25                  30

Asn Gly Tyr Asn Tyr Leu Asp Trp Tyr Leu Gln Lys Pro Gly Gln Ser
                35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gln
                85                  90                  95

Gln Glu Ala Pro Leu Thr Phe Gly Gly Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
```

```
145                 150                 155                 160
Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
        210                 215

<210> SEQ ID NO 135
<211> LENGTH: 452
<212> TYPE: PRT
<213> ORGANISM: Artificial Sequence
<220> FEATURE:
<223> OTHER INFORMATION: Synthetic Construct

<400> SEQUENCE: 135

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Thr Ile Tyr His Ser Gly Ser Thr Tyr Tyr Asn Pro Ser Leu
    50                  55                  60

Glu Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gln Gly Ser Ile Gln Gln Gly Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
```

```
                    290                 295                 300
Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Ser
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
                355                 360                 365

Ser Leu Thr Cys Leu Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly Lys
    450

<210> SEQ ID NO 136
<211> LENGTH: 451
<212> TYPE: PRT
<213> ORGANISM: Artificial Sequence
<220> FEATURE:
<223> OTHER INFORMATION: Synthetic Construct

<400> SEQUENCE: 136

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
                20                  25                  30

Tyr Tyr Trp Gly Trp Ile Arg Gln Pro Pro Gly Lys Gly Leu Glu Trp
                35                  40                  45

Ile Gly Thr Ile Tyr His Ser Gly Ser Thr Tyr Tyr Asn Pro Ser Leu
50                  55                  60

Glu Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gln Gly Ser Ile Gln Gln Gly Tyr Tyr Gly Met Asp Val Trp
                100                 105                 110

Gly Gln Gly Thr Thr Val Thr Val Ser Ser Ala Ser Thr Lys Gly Pro
                115                 120                 125

Ser Val Phe Pro Leu Ala Pro Ser Ser Lys Ser Thr Ser Gly Gly Thr
                130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
```

```
                   195                 200                 205
His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 137
<211> LENGTH: 452
<212> TYPE: PRT
<213> ORGANISM: Artificial Sequence
<220> FEATURE:
<223> OTHER INFORMATION: Synthetic Construct

<400> SEQUENCE: 137

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Thr Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gln Gly Ser Ile Lys Gln Gly Tyr Tyr Gly Met Asp Val Trp
```

```
                100                 105                 110
Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 138
<211> LENGTH: 451
<212> TYPE: PRT
<213> ORGANISM: Artificial Sequence
<220> FEATURE:
<223> OTHER INFORMATION: Synthetic Construct

<400> SEQUENCE: 138

Gln Val Gln Leu Gln Glu Ser Gly Pro Gly Leu Val Lys Pro Ser Glu
```

```
  1               5                   10                  15
Thr Leu Ser Leu Thr Cys Ala Val Ser Gly Tyr Ser Ile Ser Ser Gly
                20                  25                  30

Tyr Tyr Trp Gly Trp Ile Arg Gln Pro Pro Gly Lys Gly Leu Glu Trp
                35                  40                  45

Ile Gly Thr Ile Tyr His Ser Gly Ser Thr Tyr Tyr Asn Pro Ser Leu
                50                  55                  60

Lys Ser Arg Val Thr Ile Ser Val Asp Thr Ser Lys Asn Gln Phe Ser
 65                 70                  75                  80

Leu Lys Leu Ser Ser Val Thr Ala Ala Asp Thr Ala Val Tyr Tyr Cys
                85                  90                  95

Ala Arg Gln Gly Ser Ile Lys Gln Gly Tyr Tyr Gly Met Asp Val Trp
                100                 105                 110

Gly Gln Gly Thr Thr Val Thr Val Ser Ser Ala Ser Thr Lys Gly Pro
                115                 120                 125

Ser Val Phe Pro Leu Ala Pro Ser Ser Lys Ser Thr Ser Gly Gly Thr
                130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
                210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
                290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Ser
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
                355                 360                 365

Ser Leu Thr Cys Leu Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430
```

```
Met His Glu Ala Leu His Asn His Tyr Thr Gln Lys Ser Leu Ser Leu
        435                 440                 445

Ser Pro Gly
    450

<210> SEQ ID NO 139
<211> LENGTH: 219
<212> TYPE: PRT
<213> ORGANISM: Artificial Sequence
<220> FEATURE:
<223> OTHER INFORMATION: Synthetic Construct

<400> SEQUENCE: 139

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
                85                  90                  95

Gln Glu Ala Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 140
<211> LENGTH: 219
<212> TYPE: PRT
<213> ORGANISM: Artificial Sequence
<220> FEATURE:
<223> OTHER INFORMATION: Synthetic Construct

<400> SEQUENCE: 140

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
```

```
                50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gln
                 85                  90                  95

Gln Glu Ala Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 141
<211> LENGTH: 219
<212> TYPE: PRT
<213> ORGANISM: Artificial Sequence
<220> FEATURE:
<223> OTHER INFORMATION: Synthetic Construct

<400> SEQUENCE: 141

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu Arg Ser
             20                  25                  30

Asn Gly Tyr Asn Tyr Leu Asp Trp Tyr Leu Gln Lys Pro Gly Gln Pro
         35                  40                  45

Pro Gln Leu Leu Ile Tyr Leu Gly Ser Asn Arg Val Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gln
                 85                  90                  95

Gln Glu Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
```

```
                195                 200                 205
Pro Val Thr Lys Ser Phe Asn Arg Gly Glu Cys
    210                 215

<210> SEQ ID NO 142
<211> LENGTH: 219
<212> TYPE: PRT
<213> ORGANISM: Artificial Sequence
<220> FEATURE:
<223> OTHER INFORMATION: Synthetic Construct

<400> SEQUENCE: 142

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Thr Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
                85                  90                  95

Gln Glu Ala Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 143
<211> LENGTH: 219
<212> TYPE: PRT
<213> ORGANISM: Artificial Sequence
<220> FEATURE:
<223> OTHER INFORMATION: Synthetic Construct

<400> SEQUENCE: 143

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Ser Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60
```

Asp Arg Phe Ser Gly Ser Gly Ser Gly Thr Asp Phe Thr Leu Lys Ile
 65                  70                  75                  80

Ser Arg Ala Glu Ala Glu Asp Val Gly Val Tyr Tyr Cys Met Gln Gln
                 85                  90                  95

Gln Glu Ala Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 144
<211> LENGTH: 219
<212> TYPE: PRT
<213> ORGANISM: Artificial Sequence
<220> FEATURE:
<223> OTHER INFORMATION: Synthetic Construct

<400> SEQUENCE: 144

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
                20                  25                  30

Gly Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
 65                  70                  75                  80

Ser Arg Ala Glu Ala Glu Asp Val Gly Val Tyr Tyr Cys Met Gln Gln
                 85                  90                  95

Gln Glu Ala Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

```
Pro Val Thr Lys Ser Phe Asn Arg Gly Glu Cys
    210                 215

<210> SEQ ID NO 145
<211> LENGTH: 219
<212> TYPE: PRT
<213> ORGANISM: Artificial Sequence
<220> FEATURE:
<223> OTHER INFORMATION: Synthetic Construct

<400> SEQUENCE: 145

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Arg Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Ala Glu Ala Glu Asp Val Gly Val Tyr Tyr Cys Met Gln Gln
                85                  90                  95

Gln Glu Ala Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 146
<211> LENGTH: 219
<212> TYPE: PRT
<213> ORGANISM: Artificial Sequence
<220> FEATURE:
<223> OTHER INFORMATION: Synthetic Construct

<400> SEQUENCE: 146

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Arg Ser
            20                  25                  30

Asp Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80
```

-continued

```
Ser Arg Ala Glu Ala Glu Asp Val Gly Val Tyr Tyr Cys Met Gln Gln
            85                  90                  95

Gln Glu Ala Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215
```

ANTI-SORTILIN ANTIBODIES AND METHODS OF USE THEREOF

CROSS-REFERENCE TO RELATED APPLICATIONS

This application is a divisional application of U.S. application Ser. No. 16/510,773, filed Jul. 12, 2019, now U.S. Pat. No. 11,396,546, which claims the benefit of U.S. Provisional Application No. 62/698,007, filed Jul. 13, 2018, U.S. Provisional Application No. 62/860,184, filed Jun. 11, 2019, and U.S. Provisional Application No. 62/868,849, filed Jun. 28, 2019, each of which is hereby incorporated by reference in its entirety.

STATEMENT REGARDING FEDERALLY SPONSORED RESEARCH OR DEVELOPMENT

This invention was made with government support under Award Number R44AG050363 awarded by the National Institutes of Health. The government has certain rights in the invention.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 735022001911SEQLIST.TXT, date recorded: Apr. 27, 2022, size: 156,708 bytes.

FIELD

This present disclosure relates to anti-Sortilin antibodies, and therapeutic uses of such antibodies.

BACKGROUND

Sortilin is a Type I transmembrane protein that acts both as a receptor of several ligands, and in the sorting of select cargo from the trans-Golgi network (TGN) to late endosomes and lysosomes for degradation. Sortilin harbors a large extracellular domain that is part of the VPS10 family, homologous to yeast VPS10P, and contains of a 10-blade beta-propeller structure and a cysteine-rich 10 CC module (Nykjaer, A et al., (2012) *Trends Neurosci* 35: 261-270; and Zheng, Y et al., (2011) *PLoS One* 6: e21023). A small fraction of Sortilin may be shed by activity of ADAM10 or gamma-Secretase (<5%) (Nykjaer, A et al., (2012) *Trends Neurosci* 35: 261-270; and Willnow, T E et al., (2011) *Curr Opin Lipidol* 22: 79-85).

Sortilin binds the secreted protein Progranulin (PGRN) and targets it for lysosomal degradation, thus negatively regulating extracellular levels of PGRN (Hu, F et al. (2010) *Neuron* 68, 654-667. In line with this, deficiency of Sortilin significantly increases plasma PGRN levels both in mouse models in vivo and human cells in vitro (Carrasquillo, M. M et al., (2010) *Am J Hum Genet* 87, 890-897; Lee, W. C et al., (2014) *Hum Mol Genet* 23, 1467-1478). Moreover, a polymorphism in Sortilin was shown to be strongly associated with PGRN serum levels in humans (Carrasquillo M M e al., (2010), *Am J Hum Genet.* 10; 87(6):890-7).

Progranulin (PGRN) is a secreted, growth factor-like, trophic, and anti-inflammatory protein, which also plays a role as an adipokine involved in diet-induced obesity and insulin resistance (Nguyen D A et al., (2013). *Trends in Endocrinology and Metabolism*, 24, 597-606). Progranulin deficiency accounts for roughly 25% of all heritable forms of frontotemporal dementia (FTD), an early-onset neurodegenerative disease. Patients with heterozygous loss-of-function mutations in PGRN have ~50% reduced extracellular levels of the protein and they will invariably develop FTD, making PGRN a causal gene for the disease (Baker, M et al., (2006) *Nature* 442, 916-919; Carecchio M et al., (2011) *J Alzheimers Dis* 27, 781-790; Cruts, M et al., (2008) *Trends Genet* 24, 186-194; Galimberti, D et al., (2010) *J Alzheimers Dis* 19, 171-177). In addition, PGRN mutant alleles have been identified in Alzheimer's disease patients (Seelaar, H et al., (2011). *Journal of neurology, neurosurgery, and psychiatry* 82, 476-486). Importantly, PGRN acts protectively in several disease models with increased PGRN levels, accelerating behavioral recovery from ischemia (Tao, J et al., (2012) *Brain Res* 1436, 130-136; Egashira, Y. et al., (2013). *J Neuroinflammation* 10, 105), suppressing locomotor deficits in a Parkinson's disease model (Van Kampen, J. M et al. (2014). *PLOS One* 9, e97032), attenuating pathology in a model of amyotrophic lateral sclerosis (Laird, A. S et al., (2010). *PLOS One* 5, e13368.) and arthritis (Tang, W et al., (2011). *Science* 332, 478-484) and preventing memory deficits in an Alzheimer's disease model (Minami, S. S et al., (2014). *Nat Med* 20, 1157-1164).

Sortilin also binds directly to pro-neurotrophins, such as pro-nerve growth factor (pro-NGF), pro-BDNF, pro-neurotrophin-3, etc., which harbor a pro-domain and are typically pro-apoptotic. Such pro-neurotrophin precursors are released during stress, and Sortilin is involved in regulating their release as well as binding on the receiving cell and stimulation of apoptosis in conjunction with p75NTR (Willnow, T E et al., (2008) *Nat Rev Neurosci* 9: 899-909; Nykjaer, A et al., *Trends Neurosci* 35: 261-270; and Nykjaer, A et al., (2004) *Nature* 427: 843-848; Hiroko Yano et al., (2009) *J Neurosci.*; 29: 14790-14802. Teng H. K., et al., *J. Neurosci.* 25:5455-5463(2005)). Sortilin also binds to p75NTR directly (Skeldal S et al., (2012) *J Biol Chem.*; 287:43798). Sortilin also binds to neurotensin in a region that partially overlaps with Progranulin binding (Quistgaard, E M et al., (2009) *Nat Struct Mol Biol* 16: 96-98; and Zheng, Y et al., *PLoS One* 6: e21023). Sortilin also interacts with the Trk receptors NTRK1, NTRK2, and NTRK3; and can regulate their anterograde axonal transport and signaling (Vaegter, C B et al., (2011) *Nat. Neurosci.* 14:54-61). Sortilin also interacts with and regulates the processing and trafficking of amyloid precursor protein and the resulting production of pathological beta amyloid peptides (Gustafsen C et al., (2013). *J Neurosci.* 2; 33(1):64-71).

Sortilin has also been shown to bind to apolipoproteins and lipoprotein lipase; thus, deficiency leads to reduced VLDL release from liver and reduced cholesterol (Willnow, T E et al., (2011) *Curr Opin Lipidol* 22: 79-85; Kjolby, M et al., (2010) *Cell Metab* 12: 213-223; Nilsson, S K et al., (2007) *Biochemistry* 46: 3896-3904.; Nilsson, S K et al., (2008) *J Biol Chem* 283: 25920-25927; and Klinger, S C et al., (2011) *J Cell Sci* 124: 1095-1105). Recently, Sortilin has also been implicated in binding to APP directly (Gustafsen, C et al., (2013) *J. Neurosc.* 33:64-71) and also to the APP processing enzyme BACE1 (Gustafsen, C et al., (2013) *J. Neurosc.* 33:64-71; and Finan, G M et al., *J Biol Chem* 286: 12602-12616). Sortilin also binds to apolipoprotein E (APOE), to the A beta peptide (Carlo, A S et al., (2013) *J. Neurosc,* 33: 358-370), and to PCSK9 (Gustafsen et al, (2014) *Cell Metab,* 19: 310-318). Sortilin has also been shown to bind to and regulate extracellular levels of PCSK9, which directs low-density lipoprotein receptor for degradation in lysosomes, resulting in increased levels of LDL cholesterol (Gustafsen C et al., (2014). *Cell Metab.* 2014 Feb. 4; 19(2):310-8).

When present at intracellular vesicles such as endosomes, the amino-terminal extracellular domain of Sortilin is directed towards the lumen, where cargo of the vesicle is present. The carboxy-terminal intracellular/cytoplasmic domain of Sortilin, however, binds to a series of adaptor proteins, which regulate its trafficking from the surface and within intracellular compartments. These include AP2 (a clathrin adaptor to modulate endocytosis from the cell surface), and the Retromer Complex/AP1, which modulate movement from early endosomes to Golgi for recycling; and interaction with GGA (Golgi-localizing, gamma-ear containing, ADP-ribosylation factor binding) family proteins for movement from Golgi directly to early endosomes, usually for subsequent degradation through lysosomes. Thus, Sortilin can bind to ligands at its luminal domain, while engaging the cytoplasmic adaptors that determine its destination to determine intracellular fates, such as degradation for Progranulin and other factors.

Through its various interactions with proteins, such as Progranulin, Sortilin and its multiple ligands have been shown to be involved in various diseases, disorders, and conditions, such as frontotemporal dementia, amyotrophic lateral sclerosis, amyotrophic lateral sclerosis-frontotemporal dementia phenotypes, Alzheimer's disease, Parkinson's disease, depression, neuropsyciatric disorders, vascular dementia, seizures, retinal dystrophy, age related macular degeneration, glaucoma, traumatic brain injury, aging, seizures, wound healing, stroke, arthritis, and atherosclerotic vascular diseases.

Accordingly, there is a need for therapeutic antibodies that specifically bind Sortilin proteins and block the binding of Sortilin to its ligands, such as Progranulin, or otherwise modulate the effective concentration of the ligands, in order to treat one or more diseases, disorders, and conditions associated with Sortilin activity.

All references cited herein, including patents, patent applications and publications, are hereby incorporated by reference in their entirety.

SUMMARY

The present disclosure is generally directed to compositions that include antibodies, e.g., monoclonal, chimeric, humanized antibodies, antibody fragments, etc., that specifically bind human Sortilin, and to methods of using such compositions.

In some aspects, the present disclosure provides an antibody that binds to a Sortilin protein, wherein the antibody comprises a heavy chain variable region and a light chain variable region, wherein the heavy chain variable region comprises an HVR-H1 comprising SEQ ID NO: 1, an HVR-H2 comprising SEQ ID NO: 2 or SEQ ID NO:3, and an HVR-H3 comprising SEQ ID NO: 5 or SEQ ID NO: 6; and the light chain variable region comprises an HVR-L1 comprising any of SEQ ID NOs: 8-27, an HVR-L2 comprising SEQ ID NO: 29 or SEQ ID NO: 30, and an HVR-L3 comprising SEQ ID NO: 32.

In some embodiments, an anti-Sortilin antibody of the present disclosure comprises a heavy chain variable region comprising the HVR-H1 comprising the amino acid sequence YSISSGYYWG (SEQ ID NO: 1), the HVR-H2 comprising the amino acid sequence TIYHSGSTYYNPSLKS (SEQ ID NO: 2), the HVR-H3 comprising the amino acid sequence ARQGSIQQGYYGMDV (SEQ ID NO: 5); and a light chain variable region comprising the HVR-L1 comprising the amino acid sequence RSSQSLLRSNGYNYLD (SEQ ID NO: 8), the HVR-L2 comprising the amino acid sequence LGSNRAS (SEQ ID NO: 29), and the HVR-L3 comprising the amino acid sequence MQQQEAPLT (SEQ ID NO: 32).

In some embodiments, an anti-Sortilin antibody of the present disclosure comprises a heavy chain variable region comprising the HVR-H1 comprising the amino acid sequence YSISSGYYWG (SEQ ID NO: 1), the HVR-H2 comprising the amino acid sequence TIYHSGSTYYNPSLKS (SEQ ID NO: 2), the HVR-H3 comprising the amino acid sequence ARQGSIQQGYYGMDV (SEQ ID NO: 5); and a light chain variable region comprising the HVR-L1 comprising the amino acid sequence RSSQSLLRSNGYNYLD (SEQ ID NO: 8), the HVR-L2 comprising the amino acid sequence LGSNRVS (SEQ ID NO: 30), and the HVR-L3 comprising the amino acid sequence MQQQETPLT (SEQ ID NO: 33).

In some embodiments, an anti-Sortilin antibody of the present disclosure comprises a heavy chain variable region comprising the HVR-H1 comprising the amino acid sequence YSISSGYYWG (SEQ ID NO: 1), the HVR-H2 comprising the amino acid sequence TIYHSGSTYYNPSLES (SEQ ID NO: 3), the HVR-H3 comprising the amino acid sequence ARQGSIQQGYYGMDV (SEQ ID NO: 5); and a light chain variable region comprising the HVR-L1 comprising the amino acid sequence RSSQSLLRSNGYNYLD (SEQ ID NO: 8), the HVR-L2 comprising the amino acid sequence LGSNRAS (SEQ ID NO: 29), and the HVR-L3 comprising the amino acid sequence MQQQEAPLT (SEQ ID NO: 32).

In some aspects, an anti-Sortilin antibody of the present disclosure comprises a heavy chain variable region comprising the HVR-H1 comprising the amino acid sequence YSISSGYYWG (SEQ ID NO: 1), the HVR-H2 comprising the amino acid sequence TIYHSGSTYYNPSLKS (SEQ ID NO: 2), the HVR-H3 comprising the amino acid sequence ARQGSIKQGYYGMDV (SEQ ID NO: 6); and a light chain variable region comprising the HVR-L1 comprising the amino acid sequence RSSQSLLRSNGYNYLD (SEQ ID NO: 8), the HVR-L2 comprising the amino acid sequence LGSNRAS (SEQ ID NO: 29), and the HVR-L3 comprising the amino acid sequence MQQQEAPLT (SEQ ID NO: 32).

In some aspects, an anti-Sortilin antibody of the present disclosure comprises a heavy chain variable region comprising the HVR-H1 comprising the amino acid sequence YSISSGYYWG (SEQ ID NO: 1), the HVR-H2 comprising the amino acid sequence TIYHSGSTYYNPSLKS (SEQ ID NO: 2), the HVR-H3 comprising the amino acid sequence ARQGSIKQGYYGMDV (SEQ ID NO: 6); and a light chain variable region comprising the HVR-L1 comprising the amino acid sequence RSSQSLLRSTGYNYLD (SEQ ID NO: 9), the HVR-L2 comprising the amino acid sequence LGSNRAS (SEQ ID NO: 29), and the HVR-L3 comprising the amino acid sequence MQQQEAPLT (SEQ ID NO: 32).

In some aspects, an anti-Sortilin antibody of the present disclosure comprises a heavy chain variable region comprising the HVR-H1 comprising the amino acid sequence YSISSGYYWG (SEQ ID NO: 1), the HVR-H2 comprising the amino acid sequence TIYHSGSTYYNPSLKS (SEQ ID NO: 2), the HVR-H3 comprising the amino acid sequence ARQGSIKQGYYGMDV (SEQ ID NO: 6); and a light chain variable region comprising the HVR-L1 comprising the amino acid sequence RSSQSLLRSTGYNYLD (SEQ ID NO: 10), the HVR-L2 comprising the amino acid sequence LGSNRAS (SEQ ID NO: 29), and the HVR-L3 comprising the amino acid sequence MQQQEAPLT (SEQ ID NO: 32).

In some aspects, an anti-Sortilin antibody of the present disclosure comprises a heavy chain variable region comprising the HVR-H1 comprising the amino acid sequence YSISSGYYWG (SEQ ID NO: 1), the HVR-H2 comprising the amino acid sequence TIYHSGSTYYNPSLKS (SEQ ID NO: 2), the HVR-H3 comprising the amino acid sequence ARQGSIKQGYYGMDV (SEQ ID NO: 6); and a light chain variable region comprising the HVR-L1 comprising the amino acid sequence RSSQSLLRSTGYNYLD (SEQ ID NO: 21), the HVR-L2 comprising the amino acid sequence LGSNRAS (SEQ ID NO: 29), and the HVR-L3 comprising the amino acid sequence MQQQEAPLT (SEQ ID NO: 32).

In some embodiments, an anti-Sortilin antibody of the present disclosure comprises a heavy chain variable region comprising the HVR-H1 comprising the amino acid sequence YSISSGYYWG (SEQ ID NO: 1), the HVR-H2 comprising the amino acid sequence TIYHSGSTYYNPSLKS (SEQ ID NO: 2), the HVR-H3 comprising the amino acid sequence ARQGSIKQGYYGMDV (SEQ ID NO: 6); and a light chain variable region comprising the HVR-L1 comprising the amino acid sequence RSSQSLLRSNGYNYLD (SEQ ID NO: 8), the HVR-L2 comprising the amino acid sequence LGSNRAS (SEQ ID NO: 29), and the HVR-L3 comprising the amino acid sequence MQQQETPLT (SEQ ID NO: 33).

In some embodiments, an anti-Sortilin antibody of the present disclosure comprises a heavy chain variable region comprising the HVR-H1 comprising the amino acid sequence YSISSGYYWG (SEQ ID NO: 1), the HVR-H2 comprising the amino acid sequence TIYHSG-STYYNPSLKS (SEQ ID NO: 2), the HVR-H3 comprising the amino acid sequence ARQGSIQQGYYGMDV (SEQ ID NO: 5); and a light chain variable region comprising the HVR-L1 comprising the amino acid sequence RSSQSLLHSNGYNYLD (SEQ ID NO: 26), the HVR-L2 comprising the amino acid sequence LGSNRAS (SEQ ID NO: 29), and the HVR-L3 comprising the amino acid sequence MQQQETPLT (SEQ ID NO: 33).

In some embodiments, an anti-Sortilin antibody of the present disclosure comprises a heavy chain variable region comprising the HVR-H1 comprising the amino acid sequence YSISSGYYWG (SEQ ID NO: 1), the HVR-H2 comprising the amino acid sequence TIYHSG-STYYNPSLKS (SEQ ID NO: 2), the HVR-H3 comprising the amino acid sequence ARQGSIKQGYYGMDV (SEQ ID NO: 6); and a light chain variable region comprising the HVR-L1 comprising the amino acid sequence RSSQGLLRSNGYNYLD (SEQ ID NO: 27), the HVR-L2 comprising the amino acid sequence LGSNRAS (SEQ ID NO: 29), and the HVR-L3 comprising the amino acid sequence MQQQEAPLT (SEQ ID NO: 32).

In some aspects, the present disclosure provides an antibody that binds to a Sortilin protein, wherein the antibody comprises a heavy chain variable region and a light chain variable region, wherein the heavy chain variable region comprises an HVR-H1 comprising the amino acid sequence YSISSGYYWG (SEQ ID NO: 1), an HVR-H2 comprising the amino acid sequence TIYHSGSTYYNPSLKS (SEQ ID NO: 2), and an HVR-H3 comprising the amino acid sequence ARQGSIKQGYYGMDV (SEQ ID NO: 6); and the light chain variable region comprises an HVR-L1 comprising the amino acid sequence RSSQSLLRSNGYNYLD (SEQ ID NO: 8), an HVR-L2 comprising the amino acid sequence LGSNRAS (SEQ ID NO: 29), and an HVR-L3 comprising the amino acid sequence MQQQEAPLT (SEQ ID NO: 32).

In some aspects, the present disclosure provides an antibody that binds to a Sortilin protein, wherein the antibody comprises a heavy chain variable region and a light chain variable region, wherein the antibody comprises a heavy chain variable region with an HVR-H1 comprising the amino acid sequence YSISSGYYWG (SEQ ID NO: 1), an HVR-H2 comprising the amino acid sequence TIYHSG-STYYNPSLKS (SEQ ID NO: 2), and an HVR-H3 comprising the amino acid sequence ARQGSIKQGYYGMDV (SEQ ID NO: 6); and the light chain variable region comprises an HVR-L1 comprising the amino acid sequence RSSQSLLRSTGYNYLD (SEQ ID NO: 9), an HVR-L2 comprising the amino acid sequence LGSNRAS (SEQ ID NO: 29), and an HVR-L3 comprising the amino acid sequence MQQQEAPLT (SEQ ID NO: 32).

In some embodiments of any of the above aspects, the anti-Sortilin antibody: (a) decreases cell surface levels of Sortilin more than the level of decrease caused by an anti-Sortilin antibody comprising a heavy chain variable region comprising the sequence of SEQ ID NO: 56 and a light chain variable region comprising the sequence of SEQ ID NO: 79; (b) increases extracellular levels of Progranulin more than the level of increase caused by an anti-Sortilin antibody comprising a heavy chain variable region comprising the sequence of SEQ ID NO: 56 and a light chain variable region comprising the sequence of SEQ ID NO: 79; (c) inhibits the interaction between Sortilin and Progranulin more than the level of inhibition caused by an anti-Sortilin antibody comprising a heavy chain variable region comprising the sequence of SEQ ID NO: 56 and a light chain variable region comprising the sequence of SEQ ID NO: 79; or (d) any combination of (a)-(c). In some embodiments of any of the above aspects, the anti-Sortilin antibody: (a) decreases cell surface levels of Sortilin more than the level of decrease caused by an anti-Sortilin antibody selected from the group consisting of S-60-1, S-60-2, S-60-3, S-60-4, S-60-7, or S-60-8; (b) increases extracellular levels of Progranulin more than the level of increase caused by an anti-Sortilin antibody selected from the group consisting of S-60-1, S-60-2, S-60-3, S-60-4, S-60-7, or S-60-8; (c) inhibits the interaction between Sortilin and Progranulin more than the level of inhibition caused by an anti-Sortilin antibody selected from the group consisting of S-60-1, S-60-2, S-60-3, S-60-4, S-60-7, or S-60-8; or (d) any combination of (a)-(c).

Certain aspects of the present disclosure provide an anti-Sortilin antibody with a heavy chain variable region comprising an amino acid sequence selected from the group consisting of SEQ ID NOs: 54-56; and/or a light chain variable region comprising an amino acid sequence selected from the group consisting of SEQ ID NOs: 57-58, 60-78, or 80.

In some embodiments, an anti-Sortilin antibody of the present disclosure comprises a heavy chain variable region comprising the amino acid sequence of SEQ ID NO: 54, and a light chain variable region comprising the amino acid sequence of SEQ ID NO: 57.

In some embodiments, an anti-Sortilin antibody of the present disclosure comprises a heavy chain variable region comprising the amino acid sequence of SEQ ID NO: 54, and a light chain variable region comprising the amino acid sequence of SEQ ID NO: 58.

In some embodiments, an anti-Sortilin antibody of the present disclosure comprises a heavy chain variable region comprising the amino acid sequence of SEQ ID NO: 54, and a light chain variable region comprising the amino acid sequence of SEQ ID NO: 59.

In some embodiments, an anti-Sortilin antibody of the present disclosure comprises a heavy chain variable region comprising the amino acid sequence of SEQ ID NO: 55, and a light chain variable region comprising the amino acid sequence of SEQ ID NO: 57.

In some embodiments, an anti-Sortilin antibody of the present disclosure comprises a heavy chain variable region comprising the amino acid sequence of SEQ ID NO: 55, and a light chain variable region comprising the amino acid sequence of SEQ ID NO: 58.

In some embodiments, an anti-Sortilin antibody of the present disclosure comprises a heavy chain variable region comprising the amino acid sequence of SEQ ID NO: 56, and a light chain variable region comprising the amino acid sequence of SEQ ID NO: 57.

In some embodiments, an anti-Sortilin antibody of the present disclosure comprises a heavy chain variable region comprising the amino acid sequence of SEQ ID NO: 56, and a light chain variable region comprising the amino acid sequence of SEQ ID NO: 77.

In some embodiments, an anti-Sortilin antibody of the present disclosure comprises a heavy chain variable region comprising the amino acid sequence of SEQ ID NO: 56, and a light chain variable region comprising the amino acid sequence of SEQ ID NO: 78.

In some embodiments, an anti-Sortilin antibody of the present disclosure comprises a heavy chain variable region comprising the amino acid sequence of SEQ ID NO: 54, and a light chain variable region comprising the amino acid sequence of SEQ ID NO: 79.

In some embodiments, an anti-Sortilin antibody of the present disclosure comprises a heavy chain variable region comprising the amino acid sequence of SEQ ID NO: 56, and a light chain variable region comprising the amino acid sequence of SEQ ID NO: 80.

In some aspects, the present disclosure provides an antibody that binds to a Sortilin protein, wherein the antibody comprises a heavy chain variable region comprising the amino acid sequence of SEQ ID NO: 56 and a light chain variable region comprising the amino acid sequence of SEQ ID NO: 57.

In certain aspects, the present disclosure provides an antibody that binds to a Sortilin protein, wherein the antibody comprises a heavy chain variable region comprising the amino acid sequence of SEQ ID NO: 56 and a light chain variable region comprising the amino acid sequence of SEQ ID NO: 60.

In certain aspects, the present disclosure provides an antibody that binds to a Sortilin protein, wherein the antibody comprises a heavy chain variable region comprising the amino acid sequence of SEQ ID NO: 56 and a light chain variable region comprising the amino acid sequence of SEQ ID NO: 61.

In certain aspects, the present disclosure provides an antibody that binds to a Sortilin protein, wherein the antibody comprises a heavy chain variable region comprising the amino acid sequence of SEQ ID NO: 56 and a light chain variable region comprising the amino acid sequence of SEQ ID NO: 72.

In some embodiments that may be combined with any of the previous aspects, an anti-Sortilin antibody of the present disclosure is of the IgG class, the IgM class, or the IgA class. In certain specific embodiments, the anti-Sortilin antibody is of the IgG class and has an IgG1, IgG2, IgG3, or IgG4 isotype. In some embodiments of the present disclosure, provided is an anti-Sortilin antibody of the IgG1, IgG2, IgG3, or IgG4 isotype, wherein (a) the antibody is an IgG1 or IgG2 isotype and the Fc region comprises an amino acid substitution at position P331S, wherein the numbering of the residue position is according to EU numbering; (b) the antibody is an IgG1 isotype and the Fc region comprises amino acid substitutions at positions L234A, L235A, and P331S, wherein the numbering of the residue position is according to EU numbering; (c) the antibody is an IgG1, IgG2, or IgG4 isotype and the Fc region comprises an amino acid substitution at position N297A, wherein the numbering of the residue position is according to EU numbering; or (d) the Fc region comprises an amino acid substitution at positions S267E and L328F, wherein the numbering of the residue position is according to EU numbering. In some embodiments, the antibody is an IgG1 isotype and the Fc region comprises amino acid substitutions at positions L234A, L235A, and P331S, wherein the numbering of the residue position is according to EU numbering.

In some aspects, the present disclosure provides an antibody that binds to a Sortilin protein, wherein the antibody comprises a heavy chain comprising the amino acid sequence of SEQ ID NO: 137 and a light chain comprising the amino acid sequence of SEQ ID NO: 142.

In some aspects, the present disclosure provides an antibody that binds to a Sortilin protein, wherein the antibody comprises a heavy chain comprising the amino acid sequence of SEQ ID NO: 138 and a light chain comprising the amino acid sequence of SEQ ID NO: 142.

In certain embodiments of the present disclosure, the Sortilin protein is a human protein. In some embodiments, the Sortilin protein is a wild-type protein. In certain embodiments, the Sortilin protein is a naturally occurring variant. In some embodiments, an anti-Sortilin antibody of the present disclosure binds specifically to a human Sortilin protein. In some embodiments that may be combined with any of the previous embodiments, the antibody is a human antibody, a bispecific antibody, a monoclonal antibody, a multivalent antibody, a conjugated antibody, or a chimeric antibody. In certain embodiments, an anti-Sortilin antibody of the present disclosure is a monoclonal antibody.

In some embodiments, an anti-Sortilin antibody of the present disclosure is a bispecific antibody recognizing a first antigen and a second antigen. In certain embodiments, bispecific antibodies of the present disclosure recognize both Sortilin and an antigen facilitating transport across the blood-brain-barrier. In some specific embodiments, the first antigen is Sortilin and the second antigen is Sortilin, transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, basigin, Glut1, CD98hc, or ANG1005.

In certain embodiments of the present disclosure, the anti-Sortilin antibody is an antibody fragment that binds to a human Sortilin protein. In some embodiments, the anti-Sortilin antibody is an antibody fragment that binds to one or more human proteins selected from the group consisting of human Sortilin, a naturally occurring variant of human Sortilin, and a disease variant of human Sortilin. In certain embodiments that may be combined with any of the preceding embodiments, the anti-Sortilin antibody fragment is an Fab, Fab', Fab'-SH, F(ab')2, Fv, or scFv fragment.

In certain embodiments, the present disclosure provides an anti-Sortilin antibody, wherein (a) the anti-Sortilin antibody has increases extracellular levels of Progranulin, decreases cellular levels of Sortilin, inhibits the interaction between Sortilin and Progranulin, or any combination thereof; (b) the anti-Sortilin antibody decreases cell surface levels of Sortilin, increases extracellular levels of Progranulin, inhibits interaction between Sortilin and Progranulin, or any combination thereof; (c) the anti-Sortilin antibody decreases cell surface levels of Sortilin, decreases intracellular levels of Sortilin, decreases total levels of Sortilin, or any combination thereof; (d) the anti-Sortilin antibody induces Sortilin degradation, Sortilin cleavage, Sortilin internalization, Sortilin down regulation, or any combination thereof; (e) the anti-Sortilin antibody decreases cellular levels of Sortilin and inhibits the interaction between Sortilin and Progranulin; (f) the anti-Sortilin antibody decreases cellular levels of Sortilin and increases cellular levels of Progranulin; and/or (g) the anti-Sortilin antibody increases the effective concentration of Progranulin.

In certain embodiments, the present disclosure provides an anti-Sortilin antibody, wherein the anti-Sortilin antibody decreases cell surface levels of Sortilin, increases extracellular levels of Progranulin, inhibits interaction between Sortilin and Progranulin, or any combination thereof. In some embodiments, the anti-Sortilin antibody has a dissociation constant ($K_D$) for human Sortilin that is up to 2.5-fold lower than an anti-Sortilin antibody comprising a heavy chain variable region comprising the sequence of SEQ ID NO: 56 and a light chain variable region comprising the sequence of SEQ ID NO: 79, wherein the $K_D$ is determined by FACS (see, e.g., Example 1). In some embodiments, the antibody has a dissociation constant ($K_D$) for human Sortilin that is greater than 1- and up to about 2.1-fold lower than an anti-Sortilin antibody comprising a heavy chain variable region comprising the sequence of SEQ ID NO: 56 and a light chain variable region comprising the sequence of SEQ ID NO: 79, wherein the $K_D$ is determined by FACS. In some embodiments, the anti-Sortilin antibody has a dissociation constant ($K_D$) for human Sortilin that ranges from about 1.10E-8 M to about 4.68E-10 M wherein the $K_D$ is determined by FACS (see, e.g., Example 1), or about 270 to about 2910 pM wherein the $K_D$ is determined by Bio-layer interferometry (see, e.g., Example 4). In some embodiments, the antibody has a dissociation constant ($K_D$) for human Sortilin that ranges from about 5.0E-10 M to about 1.0E-9 M wherein the $K_D$ is determined by FACS, or about 250-500 pM wherein the $K_D$ is determined by Bio-layer interferometry.

In some embodiments that may be combined with any of the previous embodiments, an anti-Sortilin antibody of the present disclosure (a) reduces cell surface levels of Sortilin with a half maximal effective concentration ($EC_{50}$) that is less than 150 pM, as measured by flow cytometry; (b) reduces cell surface levels of Sortilin by more than about 50% at 1.25 nM IgG, by more than about 80% at 0.63 nM IgG, or by more than about 69% at 150 nM IgG relative to control, as measured by flow cytometry; increases Progranulin secretion by more than about 1.13 fold over control at 0.63 nM IgG, or by more than about 1.22 fold over control at 50 nM IgG, as measured by standard ELISA; blocks binding of Progranulin to Sortilin with a half maximal effective concentration ($EC_{50}$) that is less than 0.325 nM, as measured by flow cytometry; (e) blocks binding of Progranulin to Sortilin by more than about 88% at 50 nM IgG, or by more than about 27.5% at 150 nM IgG relative to control, as measured by flow cytometry; or (f) any combination thereof.

In some embodiments, an anti-Sortilin antibody of the present disclosure (a) reduces cell surface levels of Sortilin with a half maximal effective concentration ($EC_{50}$) that is less than 681 pM, as measured by flow cytometry; (b) reduces cell surface levels of Sortilin by more than about 40% at 1.25 nM IgG, by more than about 29% at 0.6 nM IgG, or by more than about 62% at 150 nM IgG relative to control, as measured by flow cytometry; (c) increases Progranulin secretion by more than about 1.11 fold over control at 0.63 nM IgG, or by more than about 1.75 fold over control at 50 nM IgG, as measured by standard ELISA; (d) blocks binding of Progranulin to Sortilin with a half maximal effective concentration ($EC_{50}$) that is less than 0.751 nM, as measured by flow cytometry; (e) blocks binding of Progranulin to Sortilin by more than about 90% at 50 nM IgG, or by more than about 95% at 150 nM IgG relative to control, as measured by flow cytometry; or (f) any combination thereof.

In some embodiments, an anti-Sortilin antibody of the present disclosure competes with an antibody comprising the heavy chain variable domain and the light chain variable domain of an antibody selected from the group consisting of S-60-10, S-60-11, S-60-12, S-60-13, S-60-14, S-60-15 [N33 (wt)], S-60-15.1 [N33T], S-60-16, S-60-18, S-60-19, S-60-24, and any combination thereof for binding to Sortilin. In some embodiments that may be combined with any of the previous embodiments, an anti-Sortilin antibody of the present disclosure binds essentially the same Sortilin epitope as an antibody comprising the heavy chain variable domain and the light chain variable domain of an antibody selected from the group consisting of S-60-10, S-60-11, S-60-12, S-60-13, S-60-14, S-60-15 [N33 (wt)], S-60-15.1 [N33T], S-60-16, S-60-18, S-60-19, and S-60-24.

In another aspect, the present disclosure relates to an antibody produced by any of the methods described herein. In some aspects, the present disclosure provides an isolated nucleic acid comprising a nucleic acid sequence encoding an anti-Sortilin antibody of any one of the preceding aspects and embodiments. Accordingly, some aspects provide a vector containing a nucleic acid encoding an anti-Sortilin antibody, and some aspects provide an isolated host cell containing such a vector. In certain aspects, the present disclosure provides a method of producing an anti-Sortilin antibody that binds to Sortilin, comprising culturing such an isolated host cell so that the anti-Sortilin antibody is produced. In certain embodiments, the method further comprises recovering the antibody produced by the cell. In some aspects, provide herein is an isolated antibody that binds to Sortilin and is produced by a method of the present disclosure.

In another aspect, the present disclosure relates to a pharmaceutical composition comprising any of the anti-Sortilin antibodies described herein and a pharmaceutically acceptable carrier. In some embodiments, the present disclosure relates to the use of any of the antibodies or compositions described herein for the preparation or manufacture of a medicament. In some embodiments, the present disclosure relates to the use of any of the antibodies or compositions described herein for the preparation or manufacture of a medicament for the treatment of frontotemporal dementia, progressive supranuclear palsy, Alzheimer's disease, vascular dementia, seizures, retinal dystrophy, amyotrophic lateral sclerosis, traumatic brain injury, a spinal cord injury, neuropathic pain, dementia, stroke, Parkinson's disease, acute disseminated encephalomyelitis, retinal degeneration, age related macular degeneration, glaucoma, multiple sclerosis, septic shock, bacterial infection, arthritis, or osteoarthritis. Some embodiments provide an antibody or composition described herein for use in a method of treatment. Some embodiments provide an antibody or composition described herein for use in a method of treatment of frontotemporal dementia, progressive supranuclear palsy, Alzheimer's disease, vascular dementia, seizures, retinal dystrophy, amyotrophic lateral sclerosis, traumatic brain injury, a spinal cord injury, neuropathic pain, dementia, stroke, Parkinson's disease, acute disseminated encephalomyelitis, retinal degeneration, age related macular degeneration, glaucoma, multiple sclerosis, septic shock, bacterial infection, arthritis, or osteoarthritis.

In certain aspects, provided herein is a method of preventing, reducing risk for, or treating an individual having a disease, disorder, or injury, comprising administering to an individual in need thereof a therapeutically effective amount of an anti-Sortilin antibody of the present disclosure. In some embodiments, the disease, disorder or injury is selected from the group consisting of frontotemporal dementia, progressive supranuclear palsy, Alzheimer's disease, vascular dementia, seizures, retinal dystrophy, amyotrophic lateral sclerosis, traumatic brain injury, a spinal cord injury, neuropathic pain, dementia, stroke, Parkinson's disease, acute disseminated encephalomyelitis, retinal degeneration, age related macular degeneration, glaucoma, multiple sclerosis, septic shock, bacterial infection, arthritis, and osteoarthritis. In some embodiments, the disease, disorder, or injury is selected from frontotemporal dementia, progressive supranuclear palsy, Alzheimer's disease, and amyotrophic lateral sclerosis.

In certain aspects, provided herein is a method of inhibiting one or more of neuroinflammation, axonopathy characterized by short axonal outgrowth and aberrant branching, microglial activation, and inflammatory response, comprising administering to the individual a therapeutically effective amount of an anti-Sortilin antibody of the present disclosure.

In certain aspects, provided herein is a method of promoting one or more of wound healing, autophagy, and clearance of aggregate proteins, comprising administering to the individual a therapeutically effective amount of an anti-Sortilin antibody of the present disclosure.

In certain aspects, provided herein is a method of preventing, reducing risk, or treating an individual having arthritis, comprising administering to the individual a therapeutically effective amount of an anti-Sortilin antibody of the present disclosure.

In certain aspects, provided herein is a method of decreasing expression of one or more pro-inflammatory mediators, comprising administering to the individual a therapeutically effective amount of an anti-Sortilin antibody of the present disclosure. In some embodiments, the one or more pro-inflammatory mediators are selected from the group consisting of IL-6, IL12p70, IL12p40, IL-1β, TNF-α, CXCL1, CCL2, CCL3, CCL4, and CCL5.

In some aspects, provided herein is a method of inhibiting the interaction between Sortilin and Progranulin, the method comprising exposing a cell expressing Sortilin to an anti-Sortilin antibody or a pharmaceutical composition of the present disclosure. In some embodiments, the cell is in vitro. In some embodiments, the cell is in vivo. In some embodiments, the method further comprises decreasing the level of Sortilin expressed on the cell surface. In some embodiments, extracellular levels of Progranulin are increased.

In some aspects, provided herein is a method of increasing levels of Progranulin in an individual in need thereof, the method comprising administering to the individual a therapeutically effective amount of the anti-Sortilin antibody or a pharmaceutical composition of the present disclosure. In some embodiments, levels of Progranulin are increased in plasma. In some embodiments, levels of Progranulin are increased in cerebrospinal fluid. In some aspects, provided herein is a method of decreasing levels of Sortilin in an individual in need thereof, the method comprising administering to the individual a therapeutically effective amount of an anti-Sortilin antibody or a pharmaceutical composition of the present disclosure. In some embodiments, the levels of Sortilin are decreased in peripheral white blood cells. In some embodiments, the individual has one or more mutations in the gene encoding Progranulin. In some the individual is heterozygous for one or more loss-of-function mutations in the gene encoding Progranulin. In some embodiments, the individual has a c9orf72 hexanucleotide repeat expansion. the individual has or is at risk for frontotemporal dementia, Alzheimer's disease, or amyotrophic lateral sclerosis.

In some embodiments that may be combined with any of the previous aspects or embodiments, the present disclosure provides a method, wherein the anti-Sortilin antibody comprises two or more anti-Sortilin antibodies.

BRIEF DESCRIPTION OF THE DRAWINGS

FIG. 1A provides the level of SORT1 in peripheral white blood cells as a percentage from baseline at the indicated times after treatment (hours) with the specified anti-Sortilin antibody doses. SORT1 expression decreased with all of the anti-Sortilin antibody doses tested. Higher antibody doses (60 mg/kg, 200 mg/kg) resulted in both an earlier and more prolonged decrease of SORT1 levels compared to lower anti-Sortilin antibody doses (5 mg/kg, 20 mg/kg).

FIG. 1B provides the levels of PGRN in the plasma as a percentage from baseline at the indicated times after treatment (hours) with the specified anti-Sortilin antibody doses. The levels of PGRN increased in a time- and dose-dependent manner. In particular, plasma PGRN levels increased 3- to 4-fold at $C_{max}$, compared to baseline levels, for all anti-Sortilin antibody doses tested and remained elevated for longer periods of time at the higher antibody doses. FIG. 1C provides the levels of PGRN in CSF as a percentage from baseline at the indicated times after treatment (hours) with the specified anti-Sortilin antibody doses. CSF PGRN levels increased 2- to 3-fold above baseline in animals administered either 20 mg/kg, 60 mg/kg, or 200 mg/kg. As observed with plasma PGRN levels (FIG. 1B), CSF PGRN levels remained elevated over time in the higher antibody dose groups. For FIGS. 1A-1C, n=3 animals per dose.

FIG. 2A provides the mean (+/−standard deviation) of the concentration of SORT1 in peripheral white blood cells (WBCs) as a percentage of baseline at the indicated times (days). SORT1 levels in peripheral white blood cells remained decreased throughout the duration of the study. FIG. 2B provides the mean (+/−standard deviation) of the concentration of PGRN in plasma as a percentage of baseline (normalized) at the indicated times (days). Plasma PGRN levels increased to 5- to 6-fold above baseline at peak levels. A decrease in plasma PGRN was observed following the fourth and final administration of anti-Sortilin antibody; however, the plasma PGRN levels remained elevated by 2-fold above baseline. FIG. 2C provides the mean (+/−standard deviation) of the concentration of PGRN in CSF as a percentage of baseline (normalized) at the indicated times (days). CSF PGRN levels were increased 3- to 4-fold above baseline (FIG. 2C).

DETAILED DESCRIPTION

Definitions

Figure 1A:
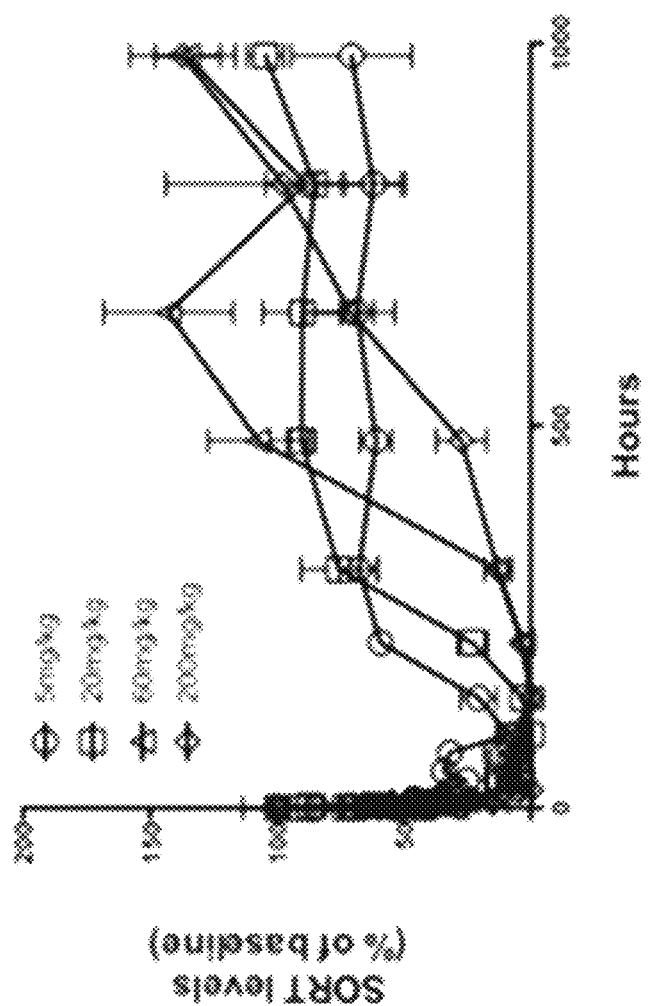
FIGS. 1A-1C provide pharmacokinetic and pharmacodynamic studies of non-human primates administered single doses of anti-Sortilin antibody S-60-15.1 [N33T] LALAPS (S-60-15.1 [N33T] with huIgG1 with L234A/L235A/P331S mutations).

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations. An effective amount herein may vary according to factors such as the disease state, age, sex, and weight of the individual, and the ability of the treatment to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration.

An "individual" for purposes of treatment, prevention, or reduction of risk refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. Preferably, the individual is human.

The terms "Sortilin" or "Sortilin polypeptide" are used interchangeably herein refer herein to any native Sortilin from any mammalian source, including primates (e.g., humans and cynos) and rodents (e.g., mice and rats), unless otherwise indicated. In some embodiments, the term encompasses both wild-type sequences and naturally occurring variant sequences, e.g., splice variants or allelic variants. In some embodiments, the term encompasses "full-length," unprocessed Sortilin as well as any form of Sortilin that results from processing in the cell. In some embodiments, the Sortilin is human Sortilin. In some embodiments, the amino acid sequence of an exemplary human Sortilin is SEQ ID NO: 81.

The terms "anti-Sortilin antibody," an "antibody that binds to Sortilin," and "antibody that specifically binds Sortilin" refer to an antibody that is capable of binding Sortilin with sufficient affinity such that the antibody is useful as a diagnostic and/or therapeutic agent in targeting Sortilin. In one embodiment, the extent of binding of an anti-Sortilin antibody to an unrelated, non-Sortilin polypeptide is less than about 10% of the binding of the antibody to Sortilin as measured, e.g., by a radioimmunoassay (RIA). In certain embodiments, an antibody that binds to Sortilin has a dissociation constant (KD) of <1 µM, <100 nM, <10 nM, <1 nM, <0.1 nM, <0.01 nM, or <0.001 nM (e.g., 10-8 M or less, e.g. from 10-8 M to 10-13 M, e.g., from 10-9 M to 10-13 M). In certain embodiments, an anti-Sortilin antibody binds to an epitope of Sortilin that is conserved among Sortilin from different species.

The term "immunoglobulin" (Ig) is used interchangeably with "antibody" herein. The term "antibody" herein is used in the broadest sense and specially covers monoclonal antibodies, polyclonal antibodies, multispecific antibodies (e.g., bispecific antibodies) including those formed from at least two intact antibodies, and antibody fragments so long as they exhibit the desired biological activity.

"Native antibodies" are usually heterotetrameric glycoproteins of about 150,000 Daltons, composed of two identical Light ("L") chains and two identical heavy ("H") chains. Each light chain is linked to a heavy chain by one covalent disulfide bond, while the number of disulfide linkages varies among the heavy chains of different immunoglobulin isotypes. Each heavy and light chain also has regularly spaced intra-chain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

For the structure and properties of the different classes of antibodies, see, e.g., *Basic and Clinical Immunology*, 8th Ed., Daniel P. Stites, Abba I. Terr and Tristram G. Parslow (eds.), Appleton & Lange, Norwalk, CT, 1994, page 71 and Chapter 6.

The light chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ"), and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three-dimensional configurations of different classes of immunoglobulins are well known and described generally in, for example, Abbas et al., Cellular and Molecular Immunology, $4^{th}$ ed. (W.B. Saunders Co., 2000).

The "variable region" or "variable domain" of an antibody, such as an anti-Sortilin antibody of the present disclosure, refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies, such as anti-Sortilin antibodies of the present disclosure. The variable domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Immunological Interest*, Fifth Edition, National Institute of Health, Bethesda, MD (1991)). The constant domains are not involved directly in the binding of antibody to an antigen, but exhibit various effector functions, such as participation of the antibody in antibody-dependent-cellular toxicity.

An "isolated" antibody, such as an anti-Sortilin antibody of the present disclosure, is one that has been identified, separated and/or recovered from a component of its production environment (e.g., naturally or recombinantly). Preferably, the isolated polypeptide is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant T cells since at least one component of the antibody's natural environment will not be present. Ordinarily, however, an isolated polypeptide or antibody will be prepared by at least one purification step.

The term "monoclonal antibody" as used herein refers to an antibody, such as a monoclonal anti-Sortilin antibody of the present disclosure, obtained from a population of substantially homogeneous antibodies, i.e., the individual antibodies comprising the population are identical except for possible naturally occurring mutations and/or post-translation modifications (e.g., isomerizations, amidations, etc.) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, but not limited to one or more of the following methods, immunization methods of animals including, but not limited to rats, mice, rabbits, guinea pigs, hamsters and/or chickens with one or more of DNA(s), virus-like particles, polypetide(s), and/or cell(s), the hybridoma methods, B-cell cloning methods, recombinant DNA methods, and technologies for producing human or human-like antibodies in animals that have parts or all of the human immunoglobulin loci or genes encoding human immunoglobulin sequences.

The terms "full-length antibody," "intact antibody" or "whole antibody" are used interchangeably to refer to an antibody, such as an anti-Sortilin antibody of the present disclosure, in its substantially intact form, as opposed to an antibody fragment. Specifically, whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10):1057-1062 (1995)); single-chain antibody molecules and multispecific antibodies formed from antibody fragments.

Papain digestion of antibodies, such as anti-Sortilin antibodies of the present disclosure, produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

"Functional fragments" of antibodies, such as anti-Sortilin antibodies of the present disclosure, comprise a portion of an intact antibody, generally including the antigen binding or variable region of the intact antibody or the F region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the variable domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains.

As used herein, a "chimeric antibody" refers to an antibody (immunoglobulin), such as a chimeric anti-Sortilin antibody of the present disclosure, in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity. Chimeric antibodies of interest herein include PRI-MATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies, such as humanized forms of anti-Sortilin antibodies of the present disclosure, are chimeric antibodies comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is one that possesses an amino-acid sequence corresponding to that of an antibody, such as an anti-Sortilin antibody of the present disclosure, produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries and yeast-based platform technologies. Human antibodies can be prepared by administering the antigen to a transgenic animal that has been modified to produce such antibodies in response to antigenic challenge, but whose endogenous loci have been disabled, e.g., immunized xeno-mice as well as generated via a human B-cell hybridoma technology.

The term "hypervariable region," "HVR," or "HV," when used herein refers to the regions of an antibody-variable domain, such as that of an anti-Sortilin antibody of the present disclosure, that are hypervariable in sequence and/or form structurally defined loops. Generally, antibodies comprise six HVRs; three in the $V_H$ (H1, H2, H3), and three in the $V_L$ (L1, L2, L3). In native antibodies, H3 and L3 display the most diversity of the six HVRs, and H3 in particular is believed to play a unique role in conferring fine specificity to antibodies. Naturally occurring camelid antibodies consisting of a heavy chain only are functional and stable in the absence of light chain.

A number of HVR delineations are in use and are encompassed herein. In some embodiments, the HVRs may be Kabat complementarity-determining regions (CDRs) based on sequence variability and are the most commonly used (Kabat et al., supra). In some embodiments, the HVRs may be Chothia CDRs. Chothia refers instead to the location of the structural loops (Chothia and Lesk *J. Mol. Biol.* 196: 901-917 (1987)). In some embodiments, the HVRs may be AbM HVRs. The AbM HVRs represent a compromise between the Kabat CDRs and Chothia structural loops, and are used by Oxford Molecular's AbM antibody-modeling software. In some embodiments, the HVRs may be "contact" HVRs. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (a preferred embodiment) (H2), and 93-102, 94-102, or 95-102 (H3) in the VH. The variable-domain residues are numbered according to Kabat et al., supra, for each of these extended-HVR definitions.

"Framework" or "FR" residues are those variable-domain residues other than the HVR residues as herein defined.

An "acceptor human framework" as used herein is a framework comprising the amino acid sequence of a $V_L$ or $V_H$ framework derived from a human immunoglobulin framework or a human consensus framework. An acceptor human framework "derived from" a human immunoglobulin framework or a human consensus framework may comprise the same amino acid sequence thereof, or it may comprise pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferable those changes occur at only three, two, or one of positions 71H, 73H and 78H; for instance, the amino acid residues at those positions may by 71A, 73T and/or 78A. In one embodiment, the VL acceptor human framework is identical in sequence to the $V_L$ human immunoglobulin framework sequence or human consensus framework sequence.

A "human consensus framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., *Sequences of Proteins of Immunological Interest*, 5th Ed. Public Health Service, National Institutes of Health, Bethesda, MD (1991). Examples include for the $V_L$, the subgroup may be subgroup kappa I, kappa II, kappa III or kappa IV as in Kabat et al., supra. Additionally, for the $V_H$, the subgroup may be subgroup I, subgroup II, or subgroup III as in Kabat et al., supra.

An "amino-acid modification" at a specified position, e.g., of an anti-Sortilin antibody of the present disclosure, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody, such as an anti-Sortilin antibody of the present disclosure, is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by VH- and VL-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As use herein, the term "specifically recognizes" or "specifically binds" refers to measurable and reproducible interactions such as attraction or binding between a target and an antibody, such as an anti-Sortilin antibody of the present disclosure, that is determinative of the presence of the target in the presence of a heterogeneous population of molecules including biological molecules. For example, an antibody, such as an anti-Sortilin antibody of the present disclosure, that specifically or preferentially binds to a target or an epitope is an antibody that binds this target or epitope with greater affinity, avidity, more readily, and/or with greater duration than it binds to other targets or other epitopes of the target. It is also understood by reading this definition that, for example, an antibody (or a moiety) that specifically or preferentially binds to a first target may or may not specifically or preferentially bind to a second target. As such, "specific binding" or "preferential binding" does not necessarily require (although it can include) exclusive binding. An antibody that specifically binds to a target may have an association constant of at least about $10^3$ M$^{-1}$ or $10^4$ M$^{-1}$, sometimes about $10^5$ M$^{-1}$ or $10^6$ M$^{-1}$, in other instances about $10^6$ M$^{-1}$ or $10^7$ M$^{-1}$, about $10^8$ M$^{-1}$ to $10^9$ M$^{-1}$, or about $10^{10}$ M$^{-1}$ to $10^{11}$ M$^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) *Antibodies, A Laboratory Manual*, Cold Spring Harbor Publications, New York, for a description of immunoassay formats and conditions that can be used to determine specific immunoreactivity.

As used herein, an "interaction" between a Sortilin protein and a second protein encompasses, without limitation, protein-protein interaction, a physical interaction, a chemical interaction, binding, covalent binding, and ionic binding. As used herein, an antibody "inhibits interaction" between two proteins when the antibody disrupts, reduces, or completely eliminates an interaction between the two proteins. An antibody of the present disclosure, or fragment thereof, "inhibits interaction" between two proteins when the antibody or fragment thereof binds to one of the two proteins.

An "agonist" antibody or an "activating" antibody is an antibody, such as an agonist anti-Sortilin antibody of the present disclosure, that induces (e.g., increases) one or more activities or functions of the antigen after the antibody binds the antigen.

A "blocking" antibody, an "antagonist" antibody, or an "inhibitory" antibody is an antibody, such as an anti-Sortilin antibody of the present disclosure, that inhibits or reduces (e.g., decreases) antigen binding to one or more ligand after the antibody binds the antigen, and/or that inhibits or reduces (e.g., decreases) one or more activities or functions of the antigen after the antibody binds the antigen. In some embodiments, blocking antibodies, antagonist antibodies, or inhibitory antibodies substantially or completely inhibit antigen binding to one or more ligand and/or one or more activities or functions of the antigen.

Antibody "effector functions" refer to those biological activities attributable to the Fc region (a native sequence Fc region or amino acid sequence variant Fc region) of an antibody, and vary with the antibody isotype.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the present disclosure include human IgG1, IgG2, IgG3 and IgG4.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain. Other FcRs, including those to be identified in the future, are encompassed by the term "FcR" herein. FcRs can also increase the serum half-life of antibodies. As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full length of the sequences being compared.

An "isolated" cell is a molecule or a cell that is identified and separated from at least one contaminant cell with which it is ordinarily associated in the environment in which it was produced. In some embodiments, the isolated cell is free of association with all components associated with the production environment. The isolated cell is in a form other than in the form or setting in which it is found in nature. Isolated cells are distinguished from cells existing naturally in tissues, organs, or individuals. In some embodiments, the isolated cell is a host cell of the present disclosure.

An "isolated" nucleic acid molecule encoding an antibody, such as an anti-Sortilin antibody of the present disclosure, is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of the present disclosure.

"Carriers" as used herein include pharmaceutically acceptable carriers, excipients, or stabilizers that are non-toxic to the cell or mammal being exposed thereto at the dosages and concentrations employed.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and embodiments of the present disclosure described herein include "comprising," "consisting," and "consisting essentially of" aspects and embodiments.

Overview

The present disclosure relates, in part, to anti-Sortilin antibodies that exhibit one or more improved and/or enhanced functional characteristics relative to an anti-Sortilin antibody, S-60, having a heavy chain variable region and a light chain variable region as described in WO2016164637. Non-limiting improved and/or enhanced functional properties include, for example, antibodies capable of binding Sortilin with higher affinity, reducing cell surface levels of Sortilin, decreasing the half-maximal effective concentration ($EC_{50}$) to reduce cell surface levels of Sortilin, improving the maximal reduction of cell surface levels of Sortilin, increasing extracellular secretion of a Sortilin ligand: e.g Progranulin (PGRN), decreasing the half-maximal effective concentration ($EC_{50}$) to block PGRN binding to Sortilin, improving the maximal blocking of PGRN binding to Sortilin, or any combination thereof. Also contemplated herein are anti-Sortilin antibodies with different Fc variants that exhibit one or more improved and/or enhanced functional characteristics, including decreasing the half-maximal effective concentration ($EC_{50}$) to reduce cell surface levels of Sortilin, improving the maximal reduction of cell surface levels of Sortilin, increasing extracellular secretion of a Sortilin ligand: e.g Progranulin (PGRN), decreasing the half-maximal effective concentration ($EC_{50}$) to block PGRN binding to Sortilin, and improving the maximal blocking of PGRN binding to Sortilin.

In some embodiments, anti-Sortilin antibodies of the present disclosure have higher potencies in reducing cell surface levels of Sortilin relative to an anti-Sortilin antibody having a heavy chain variable region and a light chain variable region corresponding to S-60. In some embodiments, potency is measured by half maximal effective concentration ($EC_{50}$) for reduction of cell surface cell levels of SORT1.

The present disclosure further relates to methods of making and using anti-Sortilin antibodies as described herein; pharmaceutical compositions containing such antibodies; nucleic acids encoding such antibodies; and host cells containing nucleic acids encoding such antibodies.

In some embodiments, the anti-Sortilin antibodies of the present disclosure may have one or more activities that are due, at least in part, to the ability of the antibodies to reduce levels (e.g., cell surface levels) of Sortilin by inducing degradation, down regulation, cleavage, receptor desensitization, and/or lysosomal targeting of Sortilin. In some embodiments, the anti-Sortilin antibodies exhibit one or more of the following properties: a. have a dissociation constant ($K_D$) for human Sortilin that is lower than that of an anti-Sortilin antibody having a heavy chain variable region and a light chain variable region corresponding to S-60; b. decrease cell surface levels of Sortilin (e.g., decrease cell surface levels of Sortilin on engineered cells expressing human Sortilin in vitro) with a half-maximal effective concentration ($EC_{50}$) that is lower than that of an anti-Sortilin antibody having a heavy chain variable region and a light chain variable region corresponding to S-60; c. have a dissociation constant ($K_D$) for human Sortilin that may range from about 0.560 nM to about 1.63 nM, for example when the $K_D$ is determined by fluorescent activated cell sorting (FACS); d. have a dissociation constant ($K_D$) for human Sortilin that may range from about 0.270 nM to about 2.910 nM, for example when the $K_D$ is determined by BioLayer Interferometry; e. decrease cell surface levels of Sortilin (e.g., decreases cell surface levels of Sortilin on engineered cells expressing human Sortilin in vitro) with a half-maximal effective concentration ($EC_{50}$) that may range from about 72.58 pM to about 103.6 pM, for example when the $EC_{50}$ is determined in vitro by FACS; f. reduce cell surface levels of Sortilin with a maximum reduction that may range from about 51.33% to 88.76%; g. increase extracellular secretion of PGRN higher than that of an anti-Sortilin antibody having a heavy chain variable region and a light chain variable region corresponding to S-60; h. block PGRN binding to Sortilin (e.g., block binding of PGRN of Sortilin on engineered cells expressing human Sortilin in vitro) with a half-maximal effective concentration ($EC_{50}$) that may range from about 0.325 nM to about 2.27 nM, for example when the $EC_{50}$ is determined in vitro by FACS; and/or i. improve the maximal blocking of PGRN binding to Sortilin higher than that of an anti-Sortilin antibody having a heavy chain variable region and a light chain variable region corresponding to S-60.

Advantageously, anti-Sortilin antibodies of the present disclosure reduce cell surface levels (e.g., up to approximately 3.02-fold) of Sortilin more potently (e.g., with a lower $EC_{50}$) as compared to a control anti-Sortilin antibody (e.g., a control anti-Sortilin antibody having a heavy chain variable region and a light chain variable region corresponding to S-60) (See e.g., Example 2). In some embodiments, anti-Sortilin antibodies of the present disclosure reduce binding of PGRN to Sortilin with a lower $EC_{50}$ (up to approximately 5.36-fold) more potently as compared to a control anti-Sortilin antibody (e.g., a control anti-Sortilin antibody having a heavy chain variable region and a light chain variable region corresponding to S-60) (See e.g., Example 3). Moreover, advantageously, anti-Sortilin antibodies of the present disclosure have a higher affinity (e.g., up to approximately 2.79-fold higher affinity) for Sortilin (e.g., a lower $K_D$ value as measured by FACS or BioLayer Interferometry) as compared to a control anti-Sortilin antibody (e.g., a control anti-Sortilin antibody having a heavy chain variable region and a light chain variable region corresponding to S-60 (See e.g., Examples 1 and 4). Surprisingly, higher affinity for Sortilin does not necessarily correlate with an increase in ability or potency of reduction of cell surface levels of Sortilin (See, e.g., Examples 2 and 4) nor an increase in ability or potency of blocking binding of PGRN to Sortilin (See, e.g., Examples 3 and 4).

The present disclosure further relates to anti-Sortilin antibodies with improved stability during manufacturing, storage, and in vivo administration. In some embodiments, anti-Sortilin antibodies of the present disclosure have improved stability under various stress conditions (See, e.g., Example 4).

Sortilin Proteins

In one aspect, the present disclosure provides antibodies, such as isolated (e.g., monoclonal) antibodies, that interact with or otherwise bind to a region, such as an epitope, within a Sortilin protein of the present disclosure. In some embodiments, the antibodies interact with or otherwise bind to a region, such as an epitope, within a Sortilin protein of the present disclosure with improved/enhanced kinetics (e.g., relative to an anti-Sortilin antibody having a heavy chain variable region and a light chain variable region corresponding to S-60). In some embodiments, the antibodies interact with or otherwise bind to a region, such as an epitope, within a human Sortilin protein, with a half-maximal effective concentration ($EC_{50}$) that is lower than that of a control antibody (e.g., relative to an anti-Sortilin antibody having a heavy chain variable region and a light chain variable region corresponding to S-60). In some embodiments, anti-Sortilin antibodies of the present disclosure bind to a Sortilin protein and modulate one or more Sortilin activities after binding to the Sortilin protein, for example, an activity associated with Sortilin expression on a cell. Sortilin proteins of the present disclosure include, without limitation, a mammalian Sortilin protein, human Sortilin protein, mouse Sortilin protein, and rat Sortilin protein. Exemplary Sortilin protein sequences are shown in Table 32.

Sortilin is variously referred to as sortilin 1, SORT1, 100 kDa NT receptor, glycoprotein 95 (GP95), Progranulin receptor (PGRN-R), and neurotensin receptor 3 (NT-3 or NTR-3). Sortilin is an 831 amino acid protein that encodes a type I membrane receptor. Various Sortilin homologs are known, including without limitation, human Sortilin, rat Sortilin, and mouse Sortilin. The amino acid sequence of human Sortilin is set forth below as SEQ ID NO: 81 (with key amino acid residues predicted to participate in Progranulin binding depicted in bold and, and the predicted pro-NGF binding region underlined):

```
         10         20         30         40
MERPWGAADG LSRWPHGLGL LLLLQLLPPS TLSQDRLDAP 50         60         70         80
PPPAAPLPRW SGPIGVSWGL RAAAAGGAFP RGGRWRRSAP 90        100        110        120
GEDEECGRVR DFVAKLANNT HQHVFDDLRG SVSLSWVGDS 130        140        150        160
TGVILVLTTF HVPLVIMTFG QSKLYRSEDY GKNFKDITDL 170        180        190        200
INNTFIRTEF GMAIGPENSG KVVLTAEVSG GSRGGRIFRS 210        220        230        240
SDFAKNFVQT DLPFHPLTQM MYSPQNSDYL LALSTENGLW 250        260        270        280
VSKNFGGKWE EIHKAVCLAK WGSDNTIFFT TYANGSCKAD 290        300        310        320
LGALELWRTS DLGKSFKTIG VKIYSFGLGG RFLFASVMAD 330        340        350        360
KDTTRRIHVS TDQGDTWSMA QLPSVGQEQF YSILAANDDM 370        380        390        400
VFMHVDEPGD TGFGTIFTSD DRGIVYSKSL DRHLYTTTGG 410        420        430        440
ETDFTNVTSL RGVYITSVLS EDNSIQTMIT FDQGGRWTHL 450        460        470        480
RKPENSECDA TAKNKNECSL HIHASYSISQ KLNVPMAPLS 490        500        510        520
EPNAVGIVIA HGSVGDAISV MVPDVYISDD GGYSWTKMLE 530        540        550        560
GPHYYTILDS GGIIVAIEHS SRPINVIKFS TDEGQCWQTY 570        580        590        600
TFTRDPIYFT GLASEPGARS MNISIWGFTE SFLTSQWVSY 610        620        630        640
TIDFKDILER NCEEKDYTIW LAHSTDPEDY EDGCILGYKE 650        660        670        680
QFLRLRKSSV CQNGRDYVVT KQPSICLCSL EDFLCDFGYY 690        700        710        720
RPENDSKCVE QPELKGHDLE FCLYGREEHL TTNGYRKIPG 730        740        750        760
DKCQGGVNPV REVKDLKKKC TSNFLSPEKQ NSKSNSVPII 770        780        790        800
LAIVGLMLVT VVAGVLIVKK YVCGGRFLVH RYSVLQQHAE 810        820        830
ANGVDGVDAL DTASHTNKSG YHDDSDEDLL E
```

The amino acid sequence of mouse Sortilin is set forth in SEQ ID NO: 82:

```
MERPRGAADG LLRWPLGLLL LLQLLPPAAV GQDRLDAPPP

PAPPLLRWAG PVGVSWGLRA AAPGGPVPRA GRWRRGAPAE

DQDCGRLPDF IAKLTNNTHQ HVFDDLSGSV SLSWVGDSTG

VILVLTTFQV PLVIVSFGQS KLYRSEDYGK NFKDITNLIN
```

```
NTFIRTEFGM AIGPENSGKV ILTAEVSGGS RGGRVFRSSD

FAKNFVQTDL PFHPLTQMMY SPQNSDYLLA LSTENGLWVS

KNFGEKWEEI HKAVCLAKWG PNNIIFFTTH VNGSCKADLG

ALELWRTSDL GKTFKTIGVK IYSFGLGGRF LFASVMADKD

TTRRIHVSTD QGDTWSMAQL PSVGQEQFYS ILAANEDMVF

MHVDEPGDTG FGTIFTSDDR GIVYSKSLDR HLYTTTGGET

DFTNVTSLRG VYITSTLSED NSIQSMITFD QGGRWEHLRK

PENSKCDATA KNKNECSLHI HASYSISQKL NVPMAPLSEP

NAVGIVIAHG SVGDAISVMV PDVYISDDGG YSWAKMLEGP

HYYTILDSGG IIVAIEHSNR PINVIKFSTD EGQCWQSYVF

TQEPIYFTGL ASEPGARSMN ISIWGFTESF ITRQWVSYTV

DFKDILERNC EEDDYTTWLA HSTDPGDYKD GCILGYKEQF

LRLRKSSVCQ NGRDYVVAKQ PSVCPCSLED FLCDFGYFRP

ENASECVEQP ELKGHELEFC LYGKEEHLTT NGYRKIPGDK

CQGGMNPARE VKDLKKKCTS NFLNPTKQNS KSNSVPIILA

CGGRFLVHRY IVGLMLVTVV AGVLIVKKYV SVLQQHAEAD

GVEALDSTSH AKSGYHDDSD EDLLE
```

The amino acid sequence of rat Sortilin is set forth in SEQ ID NO: 83:

```
MERPRGAADG LLRWPLGLLL LLQLLPPAAV GQDRLDAPPP

PAPPLLRWAG PVGVSWGLRA AAPGGPVPRA GRWRRGAPAE

DQDCGRLPDF IAKLTNNTHQ HVFDDLSGSV SLSWVGDSTG

VILVLTTFQV PLVIVSFGQS KLYRSEDYGK NFKDITNLIN

NTFIRTEFGM AIGPENSGKV ILTAEVSGGS RGGRVFRSSD

FAKNFVQTDL PFHPLTQMMY SPQNSDYLLA LSTENGLWVS

KNFGEKWEEI HKAVCLAKWG PNNIIFFTTH VNGSCKADLG

ALELWRTSDL GKTFKTIGVK IYSFGLGGRF LFASVMADKD

TTRRIHVSTD QGDTWSMAQL PSVGQEQFYS ILAANDDMVF

MHVDEPGDTG FGTIFTSDDR GIVYSKSLDR HLYTTTGGET

DFTNVTSLRG VYITSTLSED NSIQSMITFD QGGRWEHLQK

PENSKCDATA KNKNECSLHI HASYSISQKL NVPMAPLSEP

NAVGIVIAHG SVGDAISVMV PDVYISDDGG YSWAKMLEGP

HYYTILDSGG IIVAIEHSNR PINVIKFSTD EGQCWQSYVF

SQEPVYFTGL ASEPGARSMN ISIWGFTESF LTRQWVSYTI

DFKDILERNC EENDYTTWLA HSTDPGDYKD GCILGYKEQF

LRLRKSSVCQ NGRDYVVAKQ PSICPCSLED FLCDFGYFRP

ENASECVEQP ELKGHELEFC LYGKEEHLTT NGYRKIPGDR

CQGGMNPARE VKDLKKKCTS NFLNPKKQNS KSSSVPIILA

IVGLMLVTVV AGVLIVKKYV CGGRFLVHRY SVLQQHAEAD

GVEALDTASH AKSGYHDDSD EDLLE
```

In some embodiments, the Sortilin is a preprotein that includes a signal sequence. In some embodiments, the Sortilin is a mature protein. In some embodiments, the mature Sortilin protein does not include a signal sequence. In some embodiments, the mature Sortilin protein is expressed on a cell.

Sortilin proteins of the present disclosure include several domains, including without limitation, a signal sequence, a propeptide, a luminal domain, a Vps10p domain, a 10 CC domain, a transmembrane domain and a cytoplasmic domain. Additionally, proteins of the present disclosure are expressed at high levels in a number of tissues, including without limitation, the brain, spinal cord, heart and skeletal muscle, thyroid, placenta, and testis.

Accordingly, as used herein a "Sortilin" protein of the present disclosure includes, without limitation, a mammalian Sortilin protein, human Sortilin protein, primate Sortilin protein, mouse Sortilin protein, and rat Sortilin protein. Additionally, anti-Sortilin antibodies of the present disclosure may bind an epitope within one or more of a mammalian Sortilin protein, human Sortilin protein, primate Sortilin, mouse Sortilin protein, and rat Sortilin protein.

Sortilin Protein Domains

Sortilin proteins of the present disclosure contain several domains, such as a Vps10p domain that contains an Asp-box motif, a ten-bladed beta-propeller structure, and a hydrophobic loop; and a 10 CC domain.

As disclosed herein, interactions between Sortilin proteins of the present disclosure and pro-neurotrophins or neurotrophins are mediated by the Vps10p domain that contains a ten-bladed beta-propeller structure and an Asp-box motif. In certain embodiments, Sortilin proteins of the present disclosure contain a Vps10p domain that includes a ten-bladed beta-propeller structure and is located within amino acid residues 78-611 of human Sortilin (SEQ ID NO: 81) or amino acid residues of a mammalian Sortilin that correspond to amino acid residues 78-611 of SEQ ID NO: 81. In certain embodiments, amino acid residues 190-220 of human Sortilin (SEQ ID NO: 81) or amino acid residues of a mammalian Sortilin that correspond to amino acid residues 190-220 of SEQ ID NO: 81 are located within the Vps10p domain.

Vps10p domains of the present disclosure may include an Asp-box motif. As used herein, Asp-box motifs have the following sequence: (S/T)-X-(D/N)-X-X-X-X-(W/F/Y) (SEQ ID NO: 84), or X-X-(S/T)-X-(D/N)-X-G-X-(T/S)-(W/F/Y)-X (SEQ ID NO: 85), where X represents any amino acid. In human Sortilin, the Asp-box motif is SSDFAKNF (SEQ ID NO:86), located at amino acid residues 200-207 of human Sortilin. Accordingly, in certain embodiments, an Asp-box motif is located at amino acid residues 200-207 of human Sortilin (SEQ ID NO: 81) or amino acid residues of a mammalian Sortilin that correspond to amino acid residues 200-207 of SEQ ID NO: 81.

As disclosed herein, interactions between Sortilin proteins of the present disclosure and p75 are mediated by the 10 CC domain of the hydrophobic loop of the Vps10p domain.

In certain embodiments, Sortilin proteins of the present disclosure contain a 10 CC domain that is located within amino acid residues 610-757 of human Sortilin (SEQ ID NO: 81) or amino acid residues of a mammalian Sortilin that correspond to amino acid residues 610-757 of SEQ ID NO: 81. In preferred embodiments, amino acid residues 592-593, 610-660, and/or 667-749 of human Sortilin (SEQ ID NO: 81) or amino acid residues of a mammalian Sortilin that correspond to amino acid residues 592-593, 610-660, and/or 667-749 of SEQ ID NO: 81 are located within the 10 CC domain of Sortilin.

In other embodiments, Sortilin proteins of the present disclosure contain a hydrophobic loop within the Vps10p domain that is located within amino acid residues 130-141 of human Sortilin (SEQ ID NO: 81) or amino acid residues of a mammalian Sortilin that correspond to amino acid residues 130-141 of SEQ ID NO: 81.

As one of skill in the art will appreciate, the beginning and ending residues of the domains of the present disclosure may vary depending upon the computer modeling program used or the method used for determining the domain.

Sortilin Binding Partners

Sortilin proteins of the present disclosure can interact with (e.g., bind to) one or more proteins including, without limitation, Progranulin (PGRN) protein; neurotrophins, such as pro-neurotrophins, pro-neurotrophin-3, neurotrophin-3, pro-neurotrophin-4/5, neurotrophin-4/5, pro-nerve growth factor (Pro-NGF), nerve growth factor (NGF), pro-brain-derived neurotrophic factor (Pro-BDNF), and brain-derived neurotrophic factor (BDNF); neurotensin, p75, lipoprotein lipase (LpL), apolipoprotein AV (APOA5), apolipoprotein E (APOE), amyloid precursor protein, A beta peptide, PCSK9, p75NTR, and receptor associated protein (RAP).

Progranulin (PGRN)

Sortilin proteins of the present disclosure have been shown to interact (e.g., bind to) directly with Progranulin and mediate the degradation of Progranulin (e.g., Zheng, Y et al., (2011) *PLoS ONE* 6(6): e21023).

Progranulin is variously referred to as PGRN, proepithelin, granulin-epithelin precursor, PC (prostate cancer) cell-derived growth factor (PCDGF), and acrogranin. Progranulin is a 593 amino acid protein that encodes a 68.5 kD a secreted glycoprotein that has 7.5 repeats of smaller granulin (epithelin) motifs, ranging from 6-25 kDa, which can be proteolytically cleaved from the precursor PGRN. Examples of Progranulin cleavage products include, without limitation, granulin A/Epithelins 1, granulin B Epithelins 2, granulin C, granulins D, granulin E, granulin F, granulin G and any other known peptide products derived from Progranulin.

Accordingly, anti-Sortilin antibodies of the present disclosure that increase Progranulin levels, decrease cell surface levels of Sortilin, and/or block the interaction (e.g., binding) between Sortilin and Progranulin would be beneficial for preventing, lowering the risk of, or treating conditions and/or diseases associated with decreased levels of Progranulin expression and/or activity, cell death (e.g., neuronal cell death), frontotemporal dementia, Alzheimer's disease, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotrophic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, intervertebral disc degeneration, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arthritis, multiple sclerosis, metabolic disorder, obesity, insulin resistance, type 2 diabetes, tissue or vascular damage, an injury, and/or one or more undesirable symptoms of normal aging. Additionally, anti-Sortilin antibodies of the present disclosure that increase Progranulin levels, decrease cell surface levels of Sortilin, and/or block the interaction (e.g., binding) between Sortilin and Progranulin may inhibit interaction between Sortilin and Progranulin, may induce one or more Progranulin activities, may reduce the endosomal internalization of Progranulin, or fragments thereof, and/or may increase the effective concentration of Progranulin.

In some embodiments, anti-Sortilin antibodies of the present disclosure that increase Progranulin levels, decrease cell surface levels of Sortilin, and/or block the interaction (e.g., binding) between Sortilin and Progranulin bind to one or more amino acids within amino acid residues 131-138, 175-181, 190-220, 199-220, 190-211, 196-207, 196-199, 200-207, 203-207, 207-231, 207-227, 212-221, 233-243, 237-247, 237-260, 297-317, 314-338, 367-391, 429-443, 623-632, and/or 740-749 of human Sortilin (SEQ ID NO: 81); or within amino acid residues of a mammalian Sortilin that corresponds to amino acid residues 131-138, 175-181, 190-220, 199-220, 190-211, 196-207, 196-199, 200-207, 203-207, 207-231, 207-227, 212-221, 233-243, 237-247, 237-260, 297-317, 314-338, 367-391, 429-443, 623-632, and/or 740-749 of SEQ ID NO: 81. In other embodiments, anti-Sortilin antibodies of the present disclosure that increase Progranulin levels, decrease cell surface levels of Sortilin, and/or block the interaction (e.g., binding) between Sortilin and Progranulin may bind one or more amino acids of amino acid residues His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe314, Ser316, Arg325, Arg326, Ile327, Phe350, Tyr351, Ser352, Ile353, Asn373, Ser379, Arg382, Tyr386, Ser595, and/or Glu700 of human Sortilin (SEQ ID NO: 81); or of amino acid residues of a mammalian Sortilin that corresponds to one or more amino acid residues His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe314, Ser316, Arg325, Arg326, Ile327, Phe350, Tyr351, Ser352, Ile353, Asn373, Ser379, Arg382, Tyr386, Ser595, and/or Glu700 of SEQ ID NO: 81.

Other Sortilin Ligands

Sortilin proteins of the present disclosure have been shown to interact (e.g., bind) directly with pro-neurotrophins (e.g., pro-NGF), which harbor a pro-domain and are typically pro-apoptotic. This binding may be mediated through a linear epitope on Sortilin that corresponds to amino acid residues 163-174 of SEQ ID NO: 81. Sortilin proteins of the present disclosure also have been shown to interact (e.g., bind) with neurotensin within the beta-propeller structure of Sortilin, and an important contact has been shown to at serine 283 of human Sortilin.

Sortilin proteins of the present disclosure have also been shown to interact (e.g., bind) with the low affinity nerve growth factor (NGF) receptor (p75) within the 10 CC domain of Sortilin or the hydrophobic loop of the Vps10p domain of Sortilin. As disclosed herein, Sortilin proteins of the present disclosure can function as a co-receptor with p75 for pro-neurotrophins, which induce apoptotic signaling. Sortilin proteins of the present disclosure have further been shown to interact (e.g., bind) with amyloid precursor protein (APP).

Sortilin proteins of the present disclosure have been shown to interact (e.g., bind) with the lipoprotein lipase (LpL). As disclosed herein, Sortilin proteins of the present disclosure bind to and modify the degradation of LpL. Sortilin proteins of the present disclosure have been shown to interact (e.g., bind) with the apolipoprotein AV (APOA5). As disclosed herein, Sortilin proteins of the present disclosure bind to and modify the degradation of APOA5.

Sortilin proteins of the present disclosure have been shown to interact (e.g., bind) with the apolipoprotein E (APOE, APOE2, APOE3, APOE4). As disclosed herein, Sortilin proteins of the present disclosure bind to and modify the degradation and transport of APOE as well as agents that APOE carries such as the A beta peptide. In addition, Sortilin proteins of the present disclosure have been shown to interact (e.g., bind) with receptor-associate protein (RAP). Further, Sortilin proteins of the present disclosure have been shown to interact (e.g., bind) with Proprotein convertase subtilisin/kexin type 9 (PCSK9), and secrete it to the circulation.

In some embodiments of any of the anti-Sortilin antibodies, anti-Sortilin antibodies of the present disclosure may also inhibit (e.g., block) the interaction between Sortilin and one or more other Sortilin ligands of the present disclosure. In some embodiments, the one or more other ligands is one or more of pro-neurotrophins, neurotensin, low affinity nerve growth factor (NGF) receptor (p75), amyloid precursor protein, lipoprotein lipase, apolipoprotein AV, apolipoprotein, receptor-associated protein, and/or proprotein convertase subtilisin/kexin type 9. Such antibodies may be beneficial for preventing, lowering the risk of, or treating conditions and/or diseases associated with decreased levels of one or more other Sortilin ligands expression and/or activity, cell death (e.g., neuronal cell death). In some embodiments, the one or more other ligands is one or more of pro-neurotrophins, neurotensin, low affinity nerve growth factor (NGF) receptor (p75), amyloid precursor protein, lipoprotein lipase, apolipoprotein AV, apolipoprotein, receptor-associated protein, and/or proprotein convertase subtilisin/kexin type 9.

Anti-Sortilin antibodies of the present disclosure that inhibit (e.g., block) the interaction between Sortilin and one or more other Sortilin ligands of the present disclosure may also prevent cell death (e.g., apoptosis) induced by one or more other Sortilin ligands. In some embodiments, the one or more other ligands is one or more of pro-neurotrophins, neurotensin, low affinity nerve growth factor (NGF) receptor (p75), amyloid precursor protein, lipoprotein lipase, apolipoprotein AV, apolipoprotein, receptor-associated protein, and/or proprotein convertase subtilisin/kexin type 9.

In some embodiments of any of the anti-Sortilin antibodies, anti-Sortilin antibodies of the present disclosure that inhibit (e.g., block) the interaction between Sortilin and one or more Sortilin ligands of the present disclosure bind one or more amino acids within amino acid residues within amino acid residues 131-138, 175-181, 190-220, 199-220, 190-211, 196-207, 196-199, 200-207, 203-207, 207-231, 207-227, 212-221, 233-243, 237-247, 237-260, 297-317, 314-338, 367-391, 429-443, 623-632, and/or 740-749 of human Sortilin (SEQ ID NO: 81); or within amino acid residues of a mammalian Sortilin that corresponds to amino acid residues 131-138, 175-181, 190-220, 199-220, 190-211, 196-207, 196-199, 200-207, 203-207, 207-231, 207-227, 212-221, 233-243, 237-247, 237-260, 297-317, 314-338, 367-391, 429-443, 623-632, and/or 740-749 of SEQ ID NO: 81. In some embodiments, the one or more other ligands is one or more of pro-neurotrophins, neurotensin, low affinity nerve growth factor (NGF) receptor (p75), amyloid precursor protein, lipoprotein lipase, apolipoprotein AV, apolipoprotein, receptor-associated protein, and/or proprotein convertase subtilisin/kexin type 9.

In other embodiments of any of the anti-Sortilin antibodies, anti-Sortilin antibodies of the present disclosure that inhibit (e.g., block) the interaction between Sortilin and one or more Sortilin ligands of the present disclosure bind one or more amino acids of amino acid residues His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe314, Ser316, Arg325, Arg326, Ile327, Phe350, Tyr351, Ser352, Ile353, Asn373, Ser379, Arg382, Tyr386, Ser595, and/or Glu700 of human Sortilin (SEQ ID NO: 81); or of amino acid residues of a mammalian Sortilin that corresponds to one or more amino acid residues His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe314, Ser316, Arg325, Arg326, Ile327, Phe350, Tyr351, Ser352, Ile353, Asn373, Ser379, Arg382, Tyr386, Ser595, and/or Glu700 of SEQ ID NO: 81. In some embodiments, the one or more other ligands is one or more of pro-neurotrophins, neurotensin, low affinity nerve growth factor (NGF) receptor (p75), amyloid precursor protein, lipoprotein lipase, apolipoprotein AV, apolipoprotein, receptor-associated protein, and/or proprotein convertase subtilisin/kexin type 9.

Sortilin Antibodies

Certain aspects of the present disclosure relate to anti-Sortilin antibodies comprising one or more improved and/or enhanced functional characteristics. In some embodiments, anti-Sortilin antibodies of the present disclosure comprise one or more improved and/or enhanced functional characteristics relative to an anti-Sortilin antibody, S-60, having a heavy chain variable region and a light chain variable region as described in WO2016164637. In some embodiments, anti-Sortilin antibodies of the present disclosure have an affinity for Sortilin (e.g., human Sortilin) that is higher than that of a control anti-Sortilin antibody (e.g., a control anti-Sortilin antibody comprising a heavy chain variable region and a light chain variable region corresponding to S-60). In some embodiments, anti-Sortilin antibodies of the present disclosure decrease cellular levels (e.g., cell surface levels) of Sortilin to a greater degree and with a half-maximal effective concentration (EC50) that is lower than that of a control antibody (e.g., a control anti-Sortilin antibody comprising a heavy chain variable region and a light chain variable region corresponding to S-60). In some embodiments, anti-Sortilin antibodies of the present disclosure improve the maximal reduction of cell surface levels of Sortilin relative to an anti-Sortilin antibody comprising a heavy chain variable region and a light chain variable region corresponding to S-60. In some embodiments, anti-Sortilin antibodies of the present disclosure increase the secretion of extracellular Progranulin (PGRN) relative to an anti-Sortilin antibody comprising a heavy chain variable region and a light chain variable region corresponding to S-60. In some embodiments, anti-Sortilin antibodies of the present disclosure blocking binding of PGRN to Sortilin to a greater degree and with a half-maximal effective concentration (EC50) that is lower than that of a control antibody (e.g., a control anti-Sortilin antibody comprising a heavy chain variable region and a light chain variable region corresponding to S-60). In some embodiments, anti-Sortilin antibodies of the present disclosure improve the maximal blocking of PGRN binding to Sortilin relative to an anti-Sortilin antibody comprising a heavy chain variable region and a light chain variable region corresponding to S-60.

Also contemplated herein are anti-Sortilin antibodies with different Fc variants that exhibit one or more improved and/or enhanced functional characteristics relative to an anti-Sortilin antibody comprising a heavy chain variable region and a light chain variable region corresponding to S-60, including decreasing the half-maximal effective concentration (EC50) to reduce cell surface levels of Sortilin, improving the maximal reduction of cell surface levels of Sortilin, increasing extracellular secretion of PGRN, decreasing the half-maximal effective concentration (EC50) to block PGRN binding to Sortilin, and improving the maximal blocking of PGRN binding to Sortilin.

In some embodiments, an anti-Sortilin antibody of the present disclosure is a human antibody, a bispecific antibody, a monoclonal antibody, a multivalent antibody, a conjugated antibody, or a chimeric antibody In a preferred embodiment, an anti-Sortilin antibody of the present disclosure is a monoclonal antibody.

Anti-Sortilin Antibody Binding Epitope

In some embodiments, anti-Sortilin antibodies of the present disclosure bind to a Sortilin protein of the present disclosure and/or naturally occurring variants. In some embodiments, anti-Sortilin antibodies of the present disclosure bind to a Sortilin protein, wherein the Sortilin protein is a human protein. In some embodiments, anti-Sortilin antibodies of the present disclosure bind to a Sortilin protein, wherein the Sortilin protein is a wild-type protein. In some embodiments, anti-Sortilin antibodies of the present disclosure bind to a Sortilin protein, wherein the Sortilin protein is a naturally occurring variant.

In certain preferred embodiments, anti-Sortilin antibodies of the present disclosure bind specifically to a human Sortilin protein.

Certain aspects of the present disclosure provide anti-Sortilin antibodies that bind a discontinuous Sortilin epitope. In some embodiments, the discontinuous Sortilin epitope comprises two or more peptides, three or more peptides, four or more peptides, five or more peptides, six or more peptides, seven or more peptide, eight or more peptides, nine or more peptides, or 10 or more peptides. In some embodiments, each of the peptides comprise five or more, six or more, seven or more, eight or more, nine or more, 10 or more, 11 or more, 12 or more, 13 or more 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, or 30 or more amino acid residues of the amino acid sequence of SEQ ID NO: 81; or five or more, six or more, seven or more, eight or more, nine or more, 10 or more, 11 or more, 12 or more, 13 or more 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, or 30 or more amino acid residues on a mammalian Sortilin protein corresponding to the amino acid sequence of SEQ ID NO: 81. Other aspects of the present disclosure provide anti-Sortilin antibodies that bind to a conformational epitope of Sortilin.

Certain aspects of the present disclosure provide anti-Sortilin antibodies that bind to one or more amino acids within amino acid residues 207-231 of human Sortilin (SEQ ID NO: 81); or within amino acid residues on a mammalian Sortilin corresponding to amino acid residues 207-231 of SEQ ID NO: 81. In some embodiments, the anti-Sortilin antibodies bind to one or more amino acids of amino acid residues Thr218, Tyr222, Ser223, and/or Ser227 of human Sortilin (SEQ ID NO: 81); or of amino acid residues on a mammalian Sortilin corresponding to amino acid residues Thr218, Tyr222, Ser223, and/or Ser227 of SEQ ID NO: 81. In some embodiments, the anti-Sortilin antibodies bind to one or more amino acids of amino acid residues F105, L108, R109, G110, I537, F569, E590, F592, L593, S595, and/or W597 of human Sortilin (SEQ ID NO: 81); or of amino acid residues on a mammalian Sortilin corresponding to amino acid residues F105, L108, R109, G110, I537, F569, E590, F592, L593, S595, and/or W597 of SEQ ID NO: 81. Other aspects of the present disclosure provide anti-Sortilin antibodies that bind to an epitope having amino acid residues (S/T)-X-(D/N)-X-X-X-X-(W/F/Y), where X represents any amino acid (SEQ ID NO: 84).

In some embodiments, anti-Sortilin antibodies of the present disclosure bind to a Sortilin protein of the present disclosure expressed on the surface of cell and the naked antibodies inhibit interaction (e.g., binding) between the Sortilin protein and a protein selected from Progranulin (PGRN), a pro-neurotrophin, a neurotrophin, pro-neurotrophin-3, neurotrophin-3, pro-neurotrophin-4/5, neurotrophin-4/5, pro-nerve growth factor (pro-NGF), nerve growth factor (NGF), pro-brain-derived neurotrophic factor (pro-BDNF), brain-derived neurotrophic factor (BDNF), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), PCSK9, and receptor associated protein (RAP). In some embodiments, anti-Sortilin antibodies of the present disclosure bind to a Sortilin protein of the present disclosure expressed on the surface of cell and the naked antibodies inhibit interaction (e.g., binding) between the Sortilin protein and PGRN.

In some embodiments, anti-Sortilin antibodies of the present disclosure that bind to a Sortilin protein of the present disclosure inhibit interaction (e.g., binding) between the Sortilin protein and Progranulin, a pro-neurotrophin, a neurotrophin, pro-neurotrophin-3, neurotrophin-3, pro-neurotrophin-4/5, neurotrophin-4/5, pro-nerve growth factor (pro-NGF), nerve growth factor (NGF), pro-brain-derived neurotrophic factor (pro-BDNF), brain-derived neurotrophic factor (BDNF), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), PCSK9, and receptor associated protein (RAP) by reducing the effective levels of Sortilin that is available to interact with these proteins either on the cell surface or inside the cell.

In some embodiments, anti-Sortilin antibodies of the present disclosure that bind to a Sortilin protein of the present disclosure inhibit interaction (e.g., binding) between the Sortilin protein and Progranulin, a pro-neurotrophin, a neurotrophin, pro-neurotrophin-3, neurotrophin-3, pro-neurotrophin-4/5, neurotrophin-4/5, pro-nerve growth factor (pro-NGF), nerve growth factor (NGF), pro-brain-derived neurotrophic factor (pro-BDNF), brain-derived neurotrophic factor (BDNF), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), PCSK9, and receptor associated protein (RAP) by inducing degradation of Sortilin.

In some embodiments, anti-Sortilin antibodies of the present disclosure bind to a human Sortilin, or a homolog thereof, including without limitation, a mammalian Sortilin protein, or a non-human primate Sortilin protein. In some embodiments, anti-Sortilin antibodies of the present disclosure specifically bind to human Sortilin. In some embodiments, anti-Sortilin antibodies of the present disclosure bind to human Sortilin and are not cross-reactive with Sortilin orthologs or homologs from other species.

Anti-Sortilin Antibody Competitive Binding

In some embodiments, anti-Sortilin antibodies of the present disclosure competitively inhibit binding of at least one other anti-Sortilin antibody selected from any of the antibodies listed in Tables 1-29. In some embodiments, anti-Sortilin antibodies of the present disclosure competitively inhibit binding of at least one antibody selected from: S-60, S-60-1, S-60-2, S-60-3, S-60-4, S-60-5, S-60-6, S-60-7, S-60-8, and S-60-9 (described in WO2016164637); or S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, S-60-24; and any combination thereof.

In some embodiments, an anti-Sortilin antibody of the present disclosure competes with one or more anti-Sortilin antibodies selected from: S-60, S-60-1, S-60-2, S-60-3, S-60-4, S-60-5, S-60-6, S-60-7, S-60-8, and S-60-9 (described in WO2016164637); or S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, S-60-24 and any combination thereof, for binding to Sortilin when the anti-Sortilin antibody reduces the binding of one or more antibodies selected from: S-60, S-60-1, S-60-2, S-60-3, S-60-4, S-60-5, S-60-6, S-60-7, S-60-8, and S-60-9 (described in WO2016164637); or S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, S-60-24; and any combination thereof to Sortilin by an amount the ranges from about 50% to 100%, as compared to binding to Sortilin in the absence of the anti-Sortilin antibody.

In some embodiments, an anti-Sortilin antibody of the present disclosure competes with one or more anti-Sortilin antibodies selected from: S-60, S-60-1, S-60-2, S-60-3, S-60-4, S-60-5, S-60-6, S-60-7, S-60-8, and S-60-9 (described in WO2016164637); or S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, S-60-24; and any combination thereof, for binding to Sortilin when the anti-Sortilin antibody reduces the binding of one or more antibodies selected from: S-60, S-60-1, S-60-2, S-60-3, S-60-4, S-60-5, S-60-6, S-60-7, S-60-8, and S-60-9 (described in WO2016164637); or S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, S-60-24; and any combination thereof to Sortilin by at least 50%, at least 55%, by at least 60%, at least 65%, at least 70%, at least 75%, at least 80%, at least 85%, at least 90%, at least 95%, or 100%, as compared to binding to Sortilin in the absence of the anti-Sortilin antibody.

In some embodiments, an anti-Sortilin antibody of the present disclosure that reduces the binding of one or more antibodies selected from: S-60, S-60-1, S-60-2, S-60-3, S-60-4, S-60-5, S-60-6, S-60-7, S-60-8, and S-60-9 (described in WO2016164637); or S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, S-60-24, and any combination thereof, to Sortilin by 100% indicates that the anti-Sortilin antibody essential completely blocks the binding of one or more antibodies selected from S-60, S-60-1, S-60-2, S-60-3, S-60-4, S-60-5, S-60-6, S-60-7, S-60-8, and S-60-9 (described in WO2016164637); or S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, S-60-24, and any combination thereof, to Sortilin. In some embodiments, the anti-Sortilin antibody and the one or more antibodies selected from S-60, S-60-1, S-60-2, S-60-3, S-60-4, S-60-5, S-60-6, S-60-7, S-60-8, and S-60-9 (described in WO2016164637); or S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, S-60-24, and any combination thereof, are present in an amount that corresponds to a 10:1 ratio, 9:1 ratio, 8:1 ratio, 7:1 ratio, 6:1 ratio, 5:1 ratio, 4:1 ratio, 3:1 ratio, 2:1 ratio, 1:1 ratio, 0.75:1 ratio, 0.5:1 ratio, 0.25:1 ratio, 0.1:1 ratio, 0.075:1 ratio, 0.050:1 ratio, 0.025:1 ratio, 0.01:1 ratio, 0.0075: ratio, 0.0050:1 ratio, 0.0025:1 ratio, 0.001: ratio, 0.00075:1 ratio, 0.00050:1 ratio, 0.00025:1 ratio, 0.0001: ratio, 1:10 ratio, 1:9 ratio, 1:8 ratio, 1:7 ratio, 1:6 ratio, 1:5 ratio, 1:4 ratio, 1:3 ratio, 1:2 ratio, 1:0.75 ratio, 1:0.5 ratio, 1:0.25 ratio, 1:0.1 ratio, 1:0.075 ratio, 1:0.050 ratio, 1:0.025 ratio, 1:0.01 ratio, 1:0.0075 ratio, 1:0.0050 ratio, 1:0.0025 ratio, 1:0.001 ratio, 1:0.00075 ratio, 1:0.00050 ratio, 1:0.00025 ratio, or 1:0.0001 ratio of anti-Sortilin antibody to one or more antibodies selected from S-60, S-60-1, S-60-2, S-60-3, S-60-4, S-60-5, S-60-6, S-60-7, S-60-8, and S-60-9 (described in WO2016164637); or S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5

[N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, S-60-24, and any combination thereof. In some embodiments, the anti-Sortilin antibody is present in excess by an amount that ranges from about 1.5-fold to 100-fold, or greater than 100-fold compared to the amount of the one or more antibodies selected from S-60, S-60-1, S-60-2, S-60-3, S-60-4, S-60-5, S-60-6, S-60-7, S-60-8, and S-60-9 (described in WO2016164637); or S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, S-60-24, and any combination thereof. In some embodiments, the anti-Sortilin antibody is present in an amount that is about a 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold excess compared to the amount of the one or more antibodies selected from S-60, S-60-1, S-60-2, S-60-3, S-60-4, S-60-5, S-60-6, S-60-7, S-60-8, and S-60-9 (described in WO2016164637); or S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, S-60-24, and any combination thereof.

In some embodiments, anti-Sortilin antibodies of the present disclosure bind to an epitope of human Sortilin that is the same as or overlaps with the Sortilin epitope bound by at least one antibody selected from any of the antibodies listed in Tables 1-29. In some embodiments, anti-Sortilin antibodies of the present disclosure bind to an epitope of human Sortilin that is the same as or overlaps with the Sortilin epitope bound by at least one antibody selected from: S-60, S-60-1, S-60-2, S-60-3, S-60-4, S-60-5, S-60-6, S-60-7, S-60-8, and S-60-9 (described in WO2016164637); or S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, S-60-24; and any combination thereof. In some embodiments, anti-Sortilin antibodies of the present disclosure bind essentially the same Sortilin epitope bound by at least one antibody selected from any of the antibodies listed in Tables 1-29. In some embodiments, anti-Sortilin antibodies of the present disclosure bind essentially the same Sortilin epitope bound by at least one antibody selected from: S-60, S-60-1, S-60-2, S-60-3, S-60-4, S-60-5, S-60-6, S-60-7, S-60-8, and S-60-9 (described in WO2016164637); or S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, S-60-24; and any combination thereof. Detailed exemplary methods for mapping an epitope to which an antibody binds are provided in Morris (1996) "Epitope Mapping Protocols," in *Methods in Molecular Biology* vol. 66 (Humana Press, Totowa, NJ).

Any suitable competition assay or Sortilin binding assay known in the art, such as BIAcore analysis, ELISA assays, or flow cytometry, may be utilized to determine whether an anti-Sortilin antibody competes with one or more antibodies selected from: S-60, S-60-1, S-60-2, S-60-3, S-60-4, S-60-5, S-60-6, S-60-7, S-60-8, and S-60-9 (described in WO2016164637); or S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, S-60-24; and any combination thereof for binding to Sortilin. In an exemplary competition assay, immobilized Sortilin or cells expressing Sortilin on the cell surface are incubated in a solution comprising a first labeled antibody that binds to Sortilin (e.g., human or non-human primate) and a second unlabeled antibody that is being tested for its ability to compete with the first antibody for binding to Sortilin. The second antibody may be present in a hybridoma supernatant. As a control, immobilized Sortilin or cells expressing Sortilin is incubated in a solution comprising the first labeled antibody but not the second unlabeled antibody. After incubation under conditions permissive for binding of the first antibody to Sortilin, excess unbound antibody is removed, and the amount of label associated with immobilized Sortilin or cells expressing Sortilin is measured. If the amount of label associated with immobilized Sortilin or cells expressing Sortilin is substantially reduced in the test sample relative to the control sample, then that indicates that the second antibody is competing with the first antibody for binding to Sortilin. See, Harlow and Lane (1988) *Antibodies: A Laboratory Manual* ch. 14 (Cold Spring Harbor Laboratory, Cold Spring Harbor, NY).

In some embodiments, an anti-Sortilin antibody of the present disclosure competes with an antibody comprising the heavy chain variable domain and the light chain variable domain of an antibody selected from the group consisting of S-60-10, S-60-11, S-60-12, S-60-13, S-60-14, S-60-15 [N33 (wt)], S-60-15.1 [N33T], S-60-16, S-60-18, S-60-19, S-60-24, and any combination thereof for binding to Sortilin.

In some embodiments, an anti-Sortilin antibody of the present disclosure binds essentially the same Sortilin epitope as an antibody comprising the heavy chain variable domain and the light chain variable domain of an antibody selected from the group consisting of S-60-10, S-60-11, S-60-12, S-60-13, S-60-14, S-60-15 [N33 (wt)], S-60-15.1 [N33T], S-60-16, S-60-18, S-60-19, and S-60-24.

Additional anti-Sortilin antibodies, e.g., antibodies that specifically bind to a Sortilin protein of the present disclosure, may be identified, screened, and/or characterized for their physical/chemical properties and/or biological activities by various assays known in the art.

Anti-Sortilin Antibody Heavy Chain and Light Chain Variable Regions

A. Heavy Chain HVRs

In some embodiments, anti-Sortilin antibodies of the present disclosure include a heavy chain variable region comprising one or more (e.g., one or more, two or more, or all three) HVRs selected from HVR-H1, HVR-H2, and HVR-H3 (as shown in Tables 14-16). In some embodiments, the heavy chain variable region comprises an HVR-H1, an HVR-H2, and an HVR-H3 (as shown in Tables 14-16).

In some embodiments, the HVR-H1 comprises a sequence of YSISSGYYWG (SEQ ID NO: 1). In some embodiments, the HVR-H2 comprises a sequence according to Formula I: TIYHSGSTYYNPSLX$_1$S (SEQ ID NO: 4), wherein $X_1$ is K or E. In some embodiments, the HVR-H2 comprises a sequence selected from SEQ ID NOs: 2-3. In some embodiments, the HVR-H3 comprises a sequence according to Formula II: ARQGSIX$_1$QGYYGMDV (SEQ ID NO: 7). In some embodiments, the HVR-H3 comprises a sequence selected from SEQ ID NOs: 5-6.

In some embodiments, the HVR-H1 comprises an amino acid sequence with at least about 90%, at least about 91%, at least about 92%, at least about 93%, at least about 94%, at least about 95%, at least about 96%, at least about 97%, at least about 98%, at least about 99%, or 100% identity to an amino acid sequence of SEQ ID NO: 1. In some embodiments, the HVR-H1 comprises an amino acid sequence containing substitutions (e.g., conservative substitutions, insertions, or deletions relative to an amino acid sequence of SEQ ID NO: 1), but retains the ability to bind to Sortilin. In certain embodiments, up to 1, up to 2, up to 3, up to 4, or up to 5 amino acids been substituted, inserted, and/or deleted in the HVR-H1 amino acid sequence of SEQ ID NO: 1. In some embodiments, the HVR-H2 comprises an amino acid sequence with at least about 90%, at least about 91%, at least about 92%, at least about 93%, at least about 94%, at least about 95%, at least about 96%, at least about 97%, at least about 98%, at least about 99%, or 100% identity to an amino acid sequence selected from SEQ ID NOs: 2-3. In some embodiments, the HVR-H2 comprises an amino acid sequence containing substitutions (e.g., conservative substitutions, insertions, or deletions relative to an amino acid sequence selected from SEQ ID NOs: 2-3), but retains the ability to bind to Sortilin. In certain embodiments, up to 1, up to 2, up to 3, up to 4, or up to 5 amino acids been substituted, inserted, and/or deleted in the HVR-H2 amino acid sequence selected from SEQ ID NOs: 2-3. In some embodiments, the HVR-H3 comprises an amino acid sequence with at least about 90%, at least about 91%, at least about 92%, at least about 93%, at least about 94%, at least about 95%, at least about 96%, at least about 97%, at least about 98%, at least about 99%, or 100% identity to an amino acid sequence selected from SEQ ID NOs: 5-6. In some embodiments, the HVR-H3 comprises an amino acid sequence containing substitutions (e.g., conservative substitutions, insertions, or deletions relative to an amino acid sequence selected from SEQ ID NOs: 5-6), but retains the ability to bind to Sortilin. In certain embodiments, up to 1, up to 2, up to 3, up to 4, or up to 5 amino acids been substituted, inserted, and/or deleted in the HVR-H3 amino acid sequence selected from SEQ ID NOs: 5-6.

In some embodiments, the heavy chain variable region comprises an HVR-H1 comprising a sequence of YSISSGYYWG (SEQ ID NO: 1), an HVR-H2 comprising a sequence according to Formula I, and an HVR-H3 comprising a sequence according to Formula II.

In some embodiments, the heavy chain variable region comprises an HVR-H1 comprising a sequence of SEQ ID NO: 1, an HVR-H2 comprising a sequence selected from SEQ ID NOs: 2-3, and an HVR-H3 comprising a sequence selected from SEQ ID NOs: 5-6.

In some embodiments, the heavy chain variable region comprises the HVR-H1, HVR-H2, and HVR-H3 of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, S-60-24, or any combination thereof (as shown in Tables 14-16).

In some embodiments, anti-Sortilin antibodies of the present disclosure include a heavy chain variable region, wherein the heavy chain variable region comprises one or more of: (a) an HVR-H1 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-H1 amino acid sequence of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, or S-60-24; (b) an HVR-H2 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-H2 amino acid sequence of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, or S-60-24; and (c) an HVR-H3 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-H3 amino acid sequence of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, or S-60-24.

In some embodiments, anti-Sortilin antibodies of the present disclosure comprise an HVR-H1 comprising the amino acid sequence YSISSGYYWG (SEQ ID NO: 1), an HVR-H2 comprising the amino acid sequence TIYHSGSTYYNPSLKS (SEQ ID NO: 2), and an HVR-H3 comprising the amino acid sequence ARQGSIKQGYYGMDV (SEQ ID NO: 6).

B. Light Chain HVRs

In some embodiments, anti-Sortilin antibodies of the present disclosure comprise a light chain variable region comprising one or more (e.g., one or more, two or more, or all three) HVRs selected from HVR-L1, HVR-L2, and HVR-L3 (as shown in Tables 17-19). In some embodiments, the light chain variable region comprises an HVR-L1, an HVR-L2, and an HVR-L3 (as shown in Tables 17-19).

In some embodiments, the HVR-L1 comprises a sequence according to Formula III: RSSQX$_1$LLX$_2$SX$_3$GYNYLD (SEQ ID NO: 28), wherein X$_1$ is S or G, X$_2$ is R or H, and X$_3$ is N, T, S, G, R, D, H, K, Q, Y, E, W, F, I, V, A, M, or L. In some embodiments, the HVR-L1 comprises a sequence selected from SEQ ID NOs: 8-27. In some embodiments, the HVR-L1 comprises a sequence of RSSQSLLRSNGYNYLD (SEQ ID NO:8), RSSQSLLRSTGYNYLD (SEQ ID NO:9), RSSQSLLRSSGYNYLD (SEQ ID NO:10), RSSQSLLRSGGYNYLD (SEQ ID NO:11), RSSQSLLRSRGYNYLD (SEQ ID NO:12), RSSQSLLRSDGYNYLD (SEQ ID NO:13), RSSQSLLRSHGYNYLD (SEQ ID NO:14), RSSQSLLRSKGYNYLD (SEQ ID NO:15), RSSQSLLRSQGYNYLD (SEQ ID NO:16), RSSQSLLRSYGYNYLD (SEQ ID NO:17), RSSQSLLRSEGYNYLD (SEQ ID NO:18), RSSQSLLRSWGYNYLD (SEQ ID NO:19), RSSQSLLRSFGYNYLD (SEQ ID NO:20), RSSQSLLRSIGYNYLD (SEQ ID NO:21), RSSQSLLRSVGYNYLD (SEQ ID NO:22), RSSQSLLRSAGYNYLD (SEQ ID NO:23), RSSQSLLRSMGYNYLD (SEQ ID NO:24), RSSQSLLRSLGYNYLD (SEQ ID NO:25), RSSQSLLHSNGYNYLD (SEQ ID NO:26), or RSSQGLLRSNGYNYLD (SEQ ID NO:27). In one specific embodiment, the HVR-L1 comprises a sequence of RSSQSLLRSNGYNYLD (SEQ ID NO:8). In another specific embodiment, the HVR-L1 comprises a sequence of RSSQSLLRSTGYNYLD (SEQ ID NO:9) (as shown in Table 19).

In some embodiments, the HVR-L2 comprises a sequence according to Formula IV: LGSNRX1S (SEQ ID NO: 31), wherein X1 is A or V. In some embodiments, the HVR-L2 comprises a sequence selected from SEQ ID NOs: 29-30.

In some embodiments, the HVR-L3 comprises a sequence according to Formula V: MQQQEX1PLT (SEQ ID NO: 34), wherein X1 is A or T. In some embodiments, the HVR-L3 comprises a sequence selected from SEQ ID NOs: 32-33.

In some embodiments, the HVR-L1 comprises an amino acid sequence with at least about 90%, at least about 91%, at least about 92%, at least about 93%, at least about 94%, at least about 95%, at least about 96%, at least about 97%, at least about 98%, at least about 99%, or 100% identity to an amino acid sequence selected from SEQ ID NOs: 8-27. In some embodiments, the HVR-L1 comprises an amino acid sequence containing substitutions (e.g., conservative substitutions, insertions, or deletions relative to an amino acid sequence selected from SEQ ID NOs: 8-27), but retains the ability to bind to Sortilin. In certain embodiments, up to 1, up to 2, up to 3, up to 4, or up to 5 amino acids been substituted, inserted, and/or deleted in the HVR-L1 amino acid sequence selected from SEQ ID NOs: 8-27. In some embodiments, the HVR-L2 comprises an amino acid sequence with at least about 90%, at least about 91%, at least about 92%, at least about 93%, at least about 94%, at least about 95%, at least about 96%, at least about 97%, at least about 98%, at least about 99%, or 100% identity to an amino acid sequence selected from SEQ ID NOs: 29-30. In some embodiments, the HVR-L2 comprises an amino acid sequence containing substitutions (e.g., conservative substitutions, insertions, or deletions relative to an amino acid sequence selected from SEQ ID NOs: 29-30), but retains the ability to bind to Sortilin. In certain embodiments, up to 1, up to 2, up to 3, up to 4, or up to 5 amino acids been substituted, inserted, and/or deleted in the HVR-L2 amino acid sequence selected from SEQ ID NOs: 29-30. In some embodiments, the HVR-L3 comprises an amino acid sequence with at least about 90%, at least about 91%, at least about 92%, at least about 93%, at least about 94%, at least about 95%, at least about 96%, at least about 97%, at least about 98%, at least about 99%, or 100% identity to an amino acid sequence selected from SEQ ID NOs: 32-33. In some embodiments, the HVR-L3 comprises an amino acid sequence containing substitutions (e.g., conservative substitutions, insertions, or deletions relative to an amino acid sequence selected from SEQ ID NOs: 32-33), but retains the ability to bind to Sortilin. In certain embodiments, up to 1, up to 2, up to 3, up to 4, or up to 5 amino acids been substituted, inserted, and/or deleted in the HVR-L3 amino acid sequence selected from SEQ ID NOs: 32-33.

In some embodiments, the light chain variable region comprises an HVR-L1 comprising a sequence according to Formula III, an HVR-L2 comprising a sequence according to Formula IV, and an HVR-L3 comprising a sequence according to Formula V. In some embodiments, the light chain variable region comprises an HVR-L1 comprising a sequence selected from SEQ ID NOs: 8-27, an HVR-L2 comprising a sequence selected from SEQ ID NOs: 29-30, and an HVR-L3 comprising a sequence selected from SEQ ID NOs: 32-33.

In some embodiments, the light chain variable region comprises the HVR-L1, HVR-L2, and HVR-L3 of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, S-60-24, or any combination thereof (as shown in Tables 17-19).

In some embodiments, anti-Sortilin antibodies of the present disclosure include a light chain variable region, wherein the light chain variable region comprises one or more of: (a) an HVR-L1 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-L1 amino acid sequence of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, or S-60-24; (b) an HVR-L2 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-L2 amino acid sequence of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, or S-60-24; and (c) an HVR-L3 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-L3 amino acid sequence of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, or S-60-24.

In some embodiments, anti-Sortilin antibodies of the present disclosure comprise an HVR-L1 comprising the amino acid sequence RSSQSLLRSNGYNYLD (SEQ ID NO: 8), an HVR-L2 comprising the amino acid sequence LGSNRAS (SEQ ID NO: 29), and an HVR-L3 comprising the amino acid sequence MQQQEAPLT (SEQ ID NO: 32).

In some embodiments, anti-Sortilin antibodies of the present disclosure comprise an HVR-L1 comprising the amino acid sequence RSSQSLLRSTGYNYLD (SEQ ID NO: 9), an HVR-L2 comprising the amino acid sequence LGSNRAS (SEQ ID NO: 29), and an HVR-L3 comprising the amino acid sequence MQQQEAPLT (SEQ ID NO: 32).

C. Heavy Chain HVRs and Light Chain HVRs

In some embodiments, anti-Sortilin antibodies of the present disclosure include a heavy chain variable region comprising one or more (e.g., one or more, two or more, or all three) HVRs selected from HVR-H1, HVR-H2, and HVR-H3 (as shown in Tables 14-16), and a light chain variable region comprising one or more (e.g., one or more, two or more, or all three) HVRs selected from HVR-L1, HVR-L2, and HVR-L3 (as shown in Tables 17-19). In some embodiments, the heavy chain variable region comprises an HVR-H1, an HVR-H2, and an HVR-H3 (as shown in Tables 14-16), and the light chain variable region comprises an HVR-L1, an HVR-L2, and an HVR-L3 (as shown in Tables 17-19).

In some embodiments, the heavy chain variable region comprises an HVR-H1 comprising a sequence of YSISSGYYWG (SEQ ID NO: 1), an HVR-H2 comprising a sequence according to Formula I, and an HVR-H3 comprising a sequence according to Formula II, and the light chain variable region comprises an HVR-L1 comprising a sequence according to Formula III, an HVR-L2 comprising a sequence according to Formula IV, and an HVR-L3 comprising a sequence according to Formula V. In some embodiments, the heavy chain variable region comprises an HVR-H1 comprising a sequence of SEQ ID NO: 1, an HVR-H2 comprising a sequence selected from SEQ ID NOs: 2-3, and an HVR-H3 comprising a sequence selected from SEQ ID NOs: 5-6, and the light chain variable region comprises an HVR-L1 comprising a sequence selected from SEQ ID NOs: 8-27, an HVR-L2 comprising a sequence selected from SEQ ID NOs: 29-30, and an HVR-L3 comprising a sequence selected from SEQ ID NOs: 32-33.

In some aspects, the heavy chain variable region comprises an HVR-H1 comprising a sequence of SEQ ID NO: 1, an HVR-H2 comprising a sequence selected from SEQ ID NOs: 2-3, and an HVR-H3 comprising a sequence selected from SEQ ID NOs: 5-6, and the light chain variable region comprises an HVR-L1 comprising a sequence selected from SEQ ID NOs: 8-27, an HVR-L2 comprising a sequence selected from SEQ ID NOs: 29-30, and an HVR-L3 comprising a sequence of SEQ ID NO: 32.

In some embodiments, anti-Sortilin antibodies of the present disclosure comprise a heavy chain variable region comprising the HVR-H1, HVR-H2, and HVR-H3 of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, S-60-24, or any combination thereof (as shown in Tables 14-16); and a light chain variable region comprising the HVR-L1, HVR-L2, and HVR-L3 of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, S-60-24, or any combination thereof (as shown in Tables 17-19).

In some embodiments, anti-Sortilin antibodies of the present disclosure comprise a heavy chain variable region comprising an HVR-H1, HVR-H2, and HVR-H3 and a light chain variable region comprising an HVR-L1, HVR-L2, and HVR-L3, wherein the antibody comprises the HVR-H1, HVR-H2, HVR-H3, HVR-L1, HVR-L2, and HVR-L3 of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, or S-60-24 (as shown in Tables 14-19).

In some embodiments, anti-Sortilin antibodies of the present disclosure comprise a heavy chain variable region and a light chain variable region, wherein the heavy chain variable region comprises one or more of: (a) an HVR-H1 comprising an amino acid sequence with at least 90%, at least 91%, at least 92%, at least 93%, at least 94%, at least 95%, at least 96%, at least 97%, at least 98%, at least 99%, or 100% identity to an HVR-H1 amino acid sequence of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, or S-60-24; (b) an HVR-H2 comprising an amino acid sequence with at least 90%, at least 91%, at least 92%, at least 93%, at least 94%, at least 95%, at least 96%, at least 97%, at least 98%, at least 99%, or 100% identity to an HVR-H2 amino acid sequence of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-

15.14 [N33V], S-60-15.15 [N33A], S-60-15.16 [N33M], S-60-15.17 [N33L], S-60-16; S-60-18, S-60-19, or S-60-24; and (c) an HVR-H3 comprising an amino acid sequence with at least 90%, at least 91%, at least 92%, at least 93%, at least 94%, at least 95%, at least 96%, at least 97%, at least 98%, at least 99%, or 100% identity to an HVR-H3 amino acid sequence of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, or S-60-24; and wherein the light chain variable region comprises one or more of: (a) an HVR-L1 comprising an amino acid sequence with at least 90%, at least 91%, at least 92%, at least 93%, at least 94%, at least 95%, at least 96%, at least 97%, at least 98%, at least 99%, or 100% identity to an HVR-L1 amino acid sequence of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, or S-60-24; (b) an HVR-L2 comprising an amino acid sequence with at least 90%, at least 91%, at least 92%, at least 93%, at least 94%, at least 95%, at least 96%, at least 97%, at least 98%, at least 99%, or 100% identity to an HVR-L2 amino acid sequence of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, or S-60-24; and (c) an HVR-L3 comprising an amino acid sequence with at least 90%, at least 91%, at least 92%, at least 93%, at least 94%, at least 95%, at least 96%, at least 97%, at least 98%, at least 99%, or 100% identity to an HVR-L3 amino acid sequence of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, or S-60-24.

In some embodiments, an anti-Sortilin antibody of the present disclosure comprises a heavy chain variable region comprising the HVR-H1 comprising the amino acid sequence YSISSGYYWG (SEQ ID NO: 1), the HVR-H2 comprising the amino acid sequence TIYHSGSTYYNPSLKS (SEQ ID NO: 2), the HVR-H3 comprising the amino acid sequence ARQGSIQQGYYGMDV (SEQ ID NO: 5); and a light chain variable region comprising the HVR-L1 comprising the amino acid sequence RSSQSLLRSNGYNYLD (SEQ ID NO: 8), the HVR-L2 comprising the amino acid sequence LGSNRAS (SEQ ID NO: 29), and the HVR-L3 comprising the amino acid sequence MQQQEAPLT (SEQ ID NO: 32).

In some embodiments, an anti-Sortilin antibody of the present disclosure comprises a heavy chain variable region comprising the HVR-H1 comprising the amino acid sequence YSISSGYYWG (SEQ ID NO: 1), the HVR-H2 comprising the amino acid sequence TIYHSGSTYYNPSLKS (SEQ ID NO: 2), the HVR-H3 comprising the amino acid sequence ARQGSIQQGYYGMDV (SEQ ID NO: 5); and a light chain variable region comprising the HVR-L1 comprising the amino acid sequence RSSQSLLRSNGYNYLD (SEQ ID NO: 8), the HVR-L2 comprising the amino acid sequence LGSNRVS (SEQ ID NO: 30), and the HVR-L3 comprising the amino acid sequence MQQQETPLT (SEQ ID NO: 33).

In some embodiments, an anti-Sortilin antibody of the present disclosure comprises a heavy chain variable region comprising the HVR-H1 comprising the amino acid sequence YSISSGYYWG (SEQ ID NO: 1), the HVR-H2 comprising the amino acid sequence TIYHSGSTYYNPSLES (SEQ ID NO: 3), the HVR-H3 comprising the amino acid sequence ARQGSIQQGYYGMDV (SEQ ID NO: 5); and a light chain variable region comprising the HVR-L1 comprising the amino acid sequence RSSQSLLRSNGYNYLD (SEQ ID NO: 8), the HVR-L2 comprising the amino acid sequence LGSNRAS (SEQ ID NO: 29), and the HVR-L3 comprising the amino acid sequence MQQQEAPLT (SEQ ID NO: 32).

In some aspects, an anti-Sortilin antibody of the present disclosure comprises a heavy chain variable region comprising the HVR-H1 comprising the amino acid sequence YSISSGYYWG (SEQ ID NO: 1), the HVR-H2 comprising the amino acid sequence TIYHSGSTYYNPSLKS (SEQ ID NO: 2), the HVR-H3 comprising the amino acid sequence ARQGSIKQGYYGMDV (SEQ ID NO: 6); and a light chain variable region comprising the HVR-L1 comprising the amino acid sequence RSSQSLLRSNGYNYLD (SEQ ID NO: 8), the HVR-L2 comprising the amino acid sequence LGSNRAS (SEQ ID NO: 29), and the HVR-L3 comprising the amino acid sequence MQQQEAPLT (SEQ ID NO: 32).

In some aspects, an anti-Sortilin antibody of the present disclosure comprises a heavy chain variable region comprising the HVR-H1 comprising the amino acid sequence YSISSGYYWG (SEQ ID NO: 1), the HVR-H2 comprising the amino acid sequence TIYHSGSTYYNPSLKS (SEQ ID NO: 2), the HVR-H3 comprising the amino acid sequence ARQGSIKQGYYGMDV (SEQ ID NO: 6); and a light chain variable region comprising the HVR-L1 comprising the amino acid sequence RSSQSLLRSTGYNYLD (SEQ ID NO: 9), the HVR-L2 comprising the amino acid sequence LGSNRAS (SEQ ID NO: 29), and the HVR-L3 comprising the amino acid sequence MQQQEAPLT (SEQ ID NO: 32).

In some embodiments, an anti-Sortilin antibody of the present disclosure comprises a heavy chain variable region comprising the HVR-H1 comprising the amino acid sequence YSISSGYYWG (SEQ ID NO: 1), the HVR-H2 comprising the amino acid sequence TIYHSGSTYYNPSLKS (SEQ ID NO: 2), the HVR-H3 comprising the amino acid sequence ARQGSIKQGYYGMDV (SEQ ID NO: 6); and a light chain variable region comprising the HVR-L1 comprising the amino acid sequence RSSQSLLRSNGYNYLD (SEQ ID NO: 8), the HVR-L2 comprising the amino acid sequence LGSNRAS (SEQ ID NO: 29), and the HVR-L3 comprising the amino acid sequence MQQQETPLT (SEQ ID NO: 33).

In some embodiments, an anti-Sortilin antibody of the present disclosure comprises a heavy chain variable region comprising the HVR-H1 comprising the amino acid sequence YSISSGYYWG (SEQ ID NO: 1), the HVR-H2 comprising the amino acid sequence TIYHSGSTYYNPSLKS (SEQ ID NO: 2), the HVR-H3 comprising the amino acid sequence ARQGSIQQGYYGMDV (SEQ ID NO: 5); and a light chain variable region comprising the HVR-L1 comprising the amino acid sequence RSSQSLLHSNGYNYLD (SEQ ID NO: 26), the HVR-L2 comprising the amino acid sequence LGSNRAS (SEQ ID NO: 29), and the HVR-L3 comprising the amino acid sequence MQQQETPLT (SEQ ID NO: 33).

In some embodiments, an anti-Sortilin antibody of the present disclosure comprises a heavy chain variable region comprising the HVR-H1 comprising the amino acid sequence YSISSGYYWG (SEQ ID NO: 1), the HVR-H2 comprising the amino acid sequence TIYHSGSTYYNPSLKS (SEQ ID NO: 2), the HVR-H3 comprising the amino acid sequence ARQGSIKQGYYGMDV (SEQ ID NO: 6); and a light chain variable region comprising the HVR-L1 comprising the amino acid sequence RSSQGLLRSNGYNYLD (SEQ ID NO: 27), the HVR-L2 comprising the amino acid sequence LGSNRAS (SEQ ID NO: 29), and the HVR-L3 comprising the amino acid sequence MQQQEAPLT (SEQ ID NO: 32).

D. Heavy Chain Variable Region

In some embodiments, anti-Sortilin antibodies of the present disclosure include a heavy chain variable region comprising an amino acid sequence selected from SEQ ID NOs: 54-56. In some embodiments, the heavy chain variable region comprises an amino acid sequence with at least about 90%, at least about 91%, at least about 92%, at least about 93%, at least about 94%, at least about 95%, at least about 96%, at least about 97%, at least about 98%, at least about 99%, or 100% identity to an amino acid sequence selected from SEQ ID NOs: 54-56. In some embodiments, the heavy chain variable region comprises an amino acid sequence containing substitutions (e.g., conservative substitutions, insertions, or deletions relative to an amino acid sequence selected from SEQ ID NOs: 54-56), but retains the ability to bind to Sortilin. In certain embodiments, up to 1, up to 2, up to 3, up to 4, up to 5, up to 6, up to 7, up to 8, up to 9, or up to 10 amino acids been substituted, inserted, and/or deleted in the heavy chain variable region amino acid sequence selected from SEQ ID NOs: 54-56.

In some embodiments, the heavy chain variable region comprises the amino acid sequence of SEQ ID NO: 56.

In some embodiments, anti-Sortilin antibodies of the present disclosure include a heavy chain variable region of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, or S-60-24 (as shown in Table 30).

In some embodiments, anti-Sortilin antibodies of the present disclosure include a heavy chain variable region comprising an HVR-H1 comprising the amino acid sequence YSISSGYYWG (SEQ ID NO: 1), an HVR-H2 comprising the amino acid sequence TIYHSGSTYYNPSLKS (SEQ ID NO: 2), and an HVR-H3 comprising the amino acid sequence ARQGSIKQGYYGMDV (SEQ ID NO: 6).

E. Light Chain Variable Region

In some embodiments, anti-Sortilin antibodies of the present disclosure include a light chain variable region comprising an amino acid sequence selected from SEQ ID NOs: 57-80. In some embodiments, the light chain variable region comprises an amino acid sequence with at least about 90%, at least about 91%, at least about 92%, at least about 93%, at least about 94%, at least about 95%, at least about 96%, at least about 97%, at least about 98%, at least about 99%, or 100% identity to an amino acid sequence selected from SEQ ID NOs: 57-80. In some embodiments, the light chain variable region comprises an amino acid sequence containing substitutions (e.g., conservative substitutions, insertions, or deletions relative to an amino acid sequence selected from SEQ ID NOs: 57-80), but retains the ability to bind to Sortilin. In certain embodiments, up to 1, up to 2, up to 3, up to 4, up to 5, up to 6, up to 7, up to 8, up to 9, or up to 10 amino acids been substituted, inserted, and/or deleted in the light chain variable region amino acid sequence selected from SEQ ID NOs: 57-80.

In some embodiments, the light chain variable region includes the amino acid sequence of SEQ ID NO: 57. In some embodiments, the light chain variable region includes the amino acid sequence of SEQ ID NO: 60.

In some embodiments, anti-Sortilin antibodies of the present disclosure comprise a light chain variable region of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, or S-60-24 (as shown in Table 31).

In some embodiments, anti-Sortilin antibodies of the present disclosure include a light chain variable region comprising an HVR-L1 comprising the amino acid sequence RSSQSLLRSNGYNYLD (SEQ ID NO: 8), an HVR-L2 comprising the amino acid sequence LGSNRAS (SEQ ID NO: 29), and an HVR-L3 comprising the amino acid sequence MQQQEAPLT (SEQ ID NO: 32).

In some embodiments, anti-Sortilin antibodies of the present disclosure include a light chain variable region comprising an HVR-L1 comprising the amino acid sequence RSSQSLLRSTGYNYLD (SEQ ID NO: 9), an HVR-L2 comprising the amino acid sequence LGSNRAS (SEQ ID NO: 29), and an HVR-L3 comprising the amino acid sequence MQQQEAPLT (SEQ ID NO: 32).

F. Heavy Chain Variable Region and Light Chain Variable Region

In some aspects, an anti-Sortilin antibody of the present disclosure includes a heavy chain variable region comprising an amino acid sequence selected from the group consisting of SEQ ID NOs: 54-56; and/or a light chain variable region comprises an amino acid sequence selected from the group consisting of SEQ ID NOs: 57-80. In some embodiments, the heavy chain variable region comprises an amino acid sequence with at least about 90%, at least about 91%, at least about 92%, at least about 93%, at least about 94%, at least about 95%, at least about 96%, at least about 97%, at least about 98%, at least about 99%, or 100% identity to an amino acid sequence selected from SEQ ID NOs: 54-56, and the light chain variable region comprises an amino acid sequence with at least about 90%, at least about 91%, at least about 92%, at least about 93%, at least about 94%, at least about 95%, at least about 96%, at least about 97%, at least about 98%, at least about 99%, or 100% identity to an amino acid sequence selected from SEQ ID NOs: 57-80. In some embodiments, an anti-Sortilin antibody of the present disclosure includes a heavy chain variable region comprising an amino acid sequence containing substitutions (e.g., conservative substitutions, insertions, or deletions relative to an amino acid sequence selected from SEQ ID NOs: 54-56), and a light chain variable region comprising an amino acid sequence containing substitutions (e.g., conservative substitutions, insertions, or deletions relative to an amino acid sequence selected from SEQ ID NOs: 57-80), but retains the ability to bind to Sortilin. In certain embodiments, up to 1, up to 2, up to 3, up to 4, up to 5, up to 6, up to 7, up to 8, up to 9, or up to 10 amino acids been substituted, inserted, and/or deleted in the heavy chain variable region amino acid sequence selected from SEQ ID NOs: 54-56; and up to 1, up to 2, up to 3, up to 4, up to 5, up to 6, up to 7, up to 8, up to 9, or up to 10 amino acids been substituted, inserted, and/or deleted in the light chain variable region amino acid sequence selected from SEQ ID NOs: 57-80.

In some aspects, an anti-Sortilin antibody of the present disclosure includes a heavy chain variable region comprising an amino acid sequence selected from the group consisting of SEQ ID NOs: 54-56; and/or a light chain variable region comprises an amino acid sequence selected from the group consisting of SEQ ID NOs: 57-58, 60-78, and 80.

In some embodiments, an anti-Sortilin antibody of the present disclosure binds to a Sortilin protein, wherein the antibody includes a heavy chain variable region comprising the amino acid sequence of SEQ ID NO: 54, and a light chain variable region comprising the amino acid sequence of SEQ ID NO: 57; a heavy chain variable region comprising the amino acid sequence of SEQ ID NO: 54, and a light chain variable region comprising the amino acid sequence of SEQ ID NO: 58; a heavy chain variable region comprising the amino acid sequence of SEQ ID NO: 54, and a light chain variable region comprising the amino acid sequence of SEQ ID NO: 59; a heavy chain variable region comprising the amino acid sequence of SEQ ID NO: 55, and a light chain variable region comprising the amino acid sequence of SEQ ID NO: 57; a heavy chain variable region comprising the amino acid sequence of SEQ ID NO: 55, and a light chain variable region comprising the amino acid sequence of SEQ ID NO: 58; a heavy chain variable region comprising the amino acid sequence of SEQ ID NO: 56, and a light chain variable region comprising the amino acid sequence of SEQ ID NO: 57; a heavy chain variable region comprising the amino acid sequence of SEQ ID NO: 56, and a light chain variable region comprising the amino acid sequence of SEQ ID NO: 77; a heavy chain variable region comprising the amino acid sequence of SEQ ID NO: 56, and a light chain variable region comprising the amino acid sequence of SEQ ID NO: 78; a heavy chain variable region comprising the amino acid sequence of SEQ ID NO: 54, and a light chain variable region comprising the amino acid sequence of SEQ ID NO: 79; or a heavy chain variable region comprising the amino acid sequence of SEQ ID NO: 56, and a light chain variable region comprising the amino acid sequence of SEQ ID NO: 80.

In one aspect, an anti-Sortilin antibody of the present disclosure includes a heavy chain variable region having the amino acid sequence of SEQ ID NO: 56, and a light chain variable region having the amino acid sequence of SEQ ID NO: 57.

In one aspect, an anti-Sortilin antibody of the present disclosure includes a heavy chain variable region having the amino acid sequence of SEQ ID NO: 56, and a light chain variable region having the amino acid sequence of SEQ ID NO: 60.

In some embodiments, anti-Sortilin antibodies of the present disclosure comprise a heavy chain variable region of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, or S-60-24 (as shown in Table 30), and a light chain variable region of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, or S-60-24 (as shown in Table 31).

In some embodiments, anti-Sortilin antibodies of the present disclosure comprise a heavy chain variable region comprising the amino acid sequence of SEQ ID NO: 56, and a light chain variable region comprising an amino acid sequence selected from SEQ ID NOs: 56 and 60. In some embodiments, the antibody comprises a heavy chain variable region of S-60-15 [N33 (wt)] (as shown in Table 30), and a light chain variable region of antibody S-60-15 [N33 (wt)] (as shown in Table 31). In some embodiments, the antibody comprises a heavy chain variable region of S-60-15.1 [N33T] (as shown in Table 30), and a light chain variable region of antibody S-60-15.1 [N33T] (as shown in Table 31).

Exemplary Anti-Sortilin Antibodies

In some embodiments, the anti-Sortilin antibody is an anti-Sortilin monoclonal antibody comprising the heavy chain variable region and the light chain variable region of an antibody selected from S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, or S-60-24. In some embodiments, the anti-Sortilin antibody is an anti-Sortilin monoclonal antibody comprising the heavy chain and the light chain of an antibody selected from S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, or S-60-24.

(1) S-60-10

In some embodiments, anti-Sortilin antibodies of the present disclosure comprise a heavy chain variable domain and a light chain variable domain, wherein the heavy chain variable domain comprises an amino acid sequence with at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-10 or to the amino acid sequence of SEQ ID NO: 54; and/or the light chain variable domain comprises an amino acid sequence with at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-10 or to the amino acid sequence of SEQ ID NO: 57. In some embodiments, anti-Sortilin antibodies of the present disclosure comprise a heavy chain variable domain comprising an amino acid sequence with at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-10 or to the amino acid sequence of SEQ ID NO: 54, wherein the heavy chain variable domain comprises the HVR-H1, HVR-H2, and HVR-H3 amino acid sequences of antibody S-60-10. In some embodiments, anti-Sortilin antibodies of the present disclosure comprise a light chain variable domain comprising an amino acid sequence with at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-10 or to the amino acid sequence of SEQ ID NO: 57, wherein the light chain variable domain comprises the HVR-L1, HVR-L2, and HVR-L3 amino acid sequences of antibody S-60-10. In some embodiments, the anti-Sortilin antibody comprises a heavy chain variable domain (VH) sequence having at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-10 or to the amino acid sequence of SEQ ID NO: 54 and contains substitutions (e.g., conservative substitutions, insertions, or deletions relative to the reference sequence), but the anti-Sortilin antibody comprising that sequence retains the ability to bind to Sortilin. In certain embodiments, a total of 1 to 10 amino acids have been substituted, inserted, and/or deleted in the heavy chain variable domain amino acid sequence of antibody S-60-10 or the amino acid sequence of SEQ ID NO: 54. In certain embodiments, a total of 1 to 5 amino acids have been substituted, inserted and/or deleted in the heavy chain variable domain amino acid sequence of antibody S-60-10 or the amino acid sequence of SEQ ID NO: 54. In certain embodiments, substitutions, insertions, or deletions occur in regions outside the HVRs (i.e., in the FR regions). In some embodiments, the substitutions, insertions, or deletions occur in in the FR regions. Optionally, the anti-Sortilin antibody comprises the VH sequence of antibody S-60-10 or of SEQ ID NO: 54, including post-translational modifications of that sequence. In a particular embodiment, the VH comprises one, two or three HVRs selected from: (a) the HVR-H1 amino acid sequence of antibody S-60-10, (b) the HVR-H2 amino acid sequence of antibody S-60-10, and (c) the HVR-H3 amino acid sequence of antibody S-60-10. In some embodiments, anti-Sortilin antibodies of the present disclosure comprise a light chain variable domain (VL) sequence having at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-10 or to the amino acid sequence of SEQ ID NO: 57 and contains substitutions (e.g., conservative substitutions, insertions, or deletions relative to the reference sequence), but the anti-Sortilin antibody comprising that sequence retains the ability to bind to Sortilin. In certain embodiments, a total of 1 to 10 amino acids have been substituted, inserted, and/or deleted in the light chain variable domain amino acid sequence of antibody S-60-10 or the amino acid sequence of SEQ ID NO: 57. In certain embodiments, a total of 1 to 5 amino acids have been substituted, inserted and/or deleted in the light chain variable domain amino acid sequence of antibody S-60-10 or the amino acid sequence of SEQ ID NO: 57. In certain embodiments, substitutions, insertions, or deletions occur in regions outside the HVRs (i.e., in the FR regions). In some embodiments, the substitutions, insertions, or deletions occur in in the FR regions. Optionally, the anti-Sortilin antibody comprises the VL sequence of antibody S-60-10 or of SEQ ID NO: 57, including post-translational modifications of that sequence. In a particular embodiment, the VL comprises one, two or three HVRs selected from: (a) the HVR-L1 amino acid sequence of antibody S-60-10, (b) the HVR-L2 amino acid sequence of antibody S-60-10, and (c) the HVR-L3 amino acid sequence of antibody S-60-10.

In some embodiments, anti-Sortilin antibodies of the present disclosure comprise a heavy chain comprising the amino acid sequence of SEQ ID NO: 105 or SEQ ID NO: 106. In some embodiments, anti-Sortilin antibodies of the present disclosure comprise a light chain comprising the amino acid sequence of SEQ ID NO: 139. In some embodiments, anti-Sortilin antibodies of the present disclosure comprise a heavy chain comprising the amino acid sequence of SEQ ID NO: 105 or SEQ ID NO: 106 and a light chain comprising the amino acid sequence of SEQ ID NO: 139.

(2) S-60-11

In some embodiments, anti-Sortilin antibodies of the present disclosure comprise a heavy chain variable domain and a light chain variable domain, wherein the heavy chain variable domain comprises an amino acid sequence with at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-11 or to the amino acid sequence of SEQ ID NO: 54; and/or the light chain variable domain comprises an amino acid sequence with at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-11 or to the amino acid sequence of SEQ ID NO: 58. In some embodiments, anti-Sortilin antibodies of the present disclosure comprise a heavy chain variable domain comprising an amino acid sequence with at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-11 or to the amino acid sequence of SEQ ID NO: 54, wherein the heavy chain variable domain comprises the HVR-H1, HVR-H2, and HVR-H3 amino acid sequences of antibody S-60-11. In some embodiments, anti-Sortilin antibodies of the present disclosure comprise a light chain variable domain comprising an amino acid sequence with at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-11 or to the amino acid sequence of SEQ ID NO: 58, wherein the light chain variable domain comprises the HVR-L1, HVR-L2, and HVR-L3 amino acid sequences of antibody S-60-11. In some embodiments, the anti-Sortilin antibody comprises a heavy chain variable domain (VH) sequence having at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-11 or to the amino acid sequence of SEQ ID NO: 54 and contains substitutions (e.g., conservative substitutions, insertions, or deletions relative to the reference sequence), but the anti-Sortilin antibody comprising that sequence retains the ability to bind to Sortilin. In certain embodiments, a total of 1 to 10 amino acids have been substituted, inserted, and/or deleted in the heavy chain variable domain amino acid sequence of antibody S-60-11 or the amino acid sequence of SEQ ID NO: 54. In certain embodiments, a total of 1 to 5 amino acids have been substituted, inserted and/or deleted in the heavy chain variable domain amino acid sequence of antibody S-60-11 or the amino acid sequence of SEQ ID NO: 54. In certain embodiments, substitutions, insertions, or deletions occur in regions outside the HVRs (i.e., in the FR regions). In some embodiments, the substitutions, insertions, or deletions occur in in the FR regions. Optionally, the anti-Sortilin antibody comprises the VH sequence of antibody S-60-11 or of SEQ ID NO: 54, including post-translational modifications of that sequence. In a particular embodiment, the VH comprises one, two or three HVRs selected from: (a) the HVR-H1 amino acid sequence of antibody S-60-11, (b) the HVR-H2 amino acid sequence of antibody S-60-11, and (c) the HVR-H3 amino acid sequence of antibody S-60-11. In some embodiments, anti-Sortilin antibodies of the present disclosure comprise a light chain variable domain (VL) sequence having at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-11 or to the amino acid sequence of SEQ ID NO: 58 and contains substitutions (e.g., conservative substitutions, insertions, or deletions relative to the reference sequence), but the anti-Sortilin antibody comprising that sequence retains the ability to bind to Sortilin. In certain embodiments, a total of 1 to 10 amino acids have been substituted, inserted, and/or deleted in the light chain variable domain amino acid sequence of antibody S-60-11 or the amino acid sequence of SEQ ID NO: 58. In certain embodiments, a total of 1 to 5 amino acids have been substituted, inserted and/or deleted in the light chain variable domain amino acid sequence of antibody S-60-11 or the amino acid sequence of SEQ ID NO: 58. In certain embodiments, substitutions, insertions, or deletions occur in regions outside the HVRs (i.e., in the FR regions). In some embodiments, the substitutions, insertions, or deletions occur in in the FR regions. Optionally, the anti-Sortilin antibody comprises the VL sequence of antibody S-60-11 or of SEQ ID NO: 58, including post-translational modifications of that sequence. In a particular embodiment, the VL comprises one, two or three HVRs selected from: (a) the HVR-L1 amino acid sequence of antibody S-60-11, (b) the HVR-L2 amino acid sequence of antibody S-60-11, and (c) the HVR-L3 amino acid sequence of antibody S-60-11.

In some embodiments, anti-Sortilin antibodies of the present disclosure comprise a heavy chain comprising the amino acid sequence of SEQ ID NO: 105 or SEQ ID NO: 106. In some embodiments, anti-Sortilin antibodies of the present disclosure comprise a light chain comprising the amino acid sequence of SEQ ID NO: 140. In some embodiments, anti-Sortilin antibodies of the present disclosure comprise a heavy chain comprising the amino acid sequence of SEQ ID NO: 105 or SEQ ID NO: 106 and a light chain comprising the amino acid sequence of SEQ ID NO: 140.

(3) S-60-12

In some embodiments, anti-Sortilin antibodies of the present disclosure comprise a heavy chain variable domain and a light chain variable domain, wherein the heavy chain variable domain comprises an amino acid sequence with at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-12 or to the amino acid sequence of SEQ ID NO: 54; and/or the light chain variable domain comprises an amino acid sequence with at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-12 or to the amino acid sequence of SEQ ID NO: 59. In some embodiments, anti-Sortilin antibodies of the present disclosure comprise a heavy chain variable domain comprising an amino acid sequence with at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-12 or to the amino acid sequence of SEQ ID NO: 54, wherein the heavy chain variable domain comprises the HVR-H1, HVR-H2, and HVR-H3 amino acid sequences of antibody S-60-12. In some embodiments, anti-Sortilin antibodies of the present disclosure comprise a light chain variable domain comprising an amino acid sequence with at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-12 or to the amino acid sequence of SEQ ID NO: 59, wherein the light chain variable domain comprises the HVR-L1, HVR-L2, and HVR-L3 amino acid sequences of antibody S-60-12. In some embodiments, the anti-Sortilin antibody comprises a heavy chain variable domain (VH) sequence having at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-12 or to the amino acid sequence of SEQ ID NO: 54 and contains substitutions (e.g., conservative substitutions, insertions, or deletions relative to the reference sequence), but the anti-Sortilin antibody comprising that sequence retains the ability to bind to Sortilin. In certain embodiments, a total of 1 to 10 amino acids have been substituted, inserted, and/or deleted in the heavy chain variable domain amino acid sequence of antibody S-60-12 or the amino acid sequence of SEQ ID NO: 54. In certain embodiments, a total of 1 to 5 amino acids have been substituted, inserted and/or deleted in the heavy chain variable domain amino acid sequence of antibody S-60-12 or the amino acid sequence of SEQ ID NO: 54. In certain embodiments, substitutions, insertions, or deletions occur in regions outside the HVRs (i.e., in the FR regions). In some embodiments, the substitutions, insertions, or deletions occur in in the FR regions. Optionally, the anti-Sortilin antibody comprises the VH sequence of antibody S-60-12 or of SEQ ID NO: 54, including post-translational modifications of that sequence. In a particular embodiment, the VH comprises one, two or three HVRs selected from: (a) the HVR-H1 amino acid sequence of antibody S-60-12, (b) the HVR-H2 amino acid sequence of antibody S-60-12, and (c) the HVR-H3 amino acid sequence of antibody S-60-12. In some embodiments, anti-Sortilin antibodies of the present disclosure comprise a light chain variable domain (VL) sequence having at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-12 or to the amino acid sequence of SEQ ID NO: 59 and contains substitutions (e.g., conservative substitutions, insertions, or deletions relative to the reference sequence), but the anti-Sortilin antibody comprising that sequence retains the ability to bind to Sortilin. In certain embodiments, a total of 1 to 10 amino acids have been substituted, inserted, and/or deleted in the light chain variable domain amino acid sequence of antibody S-60-12 or the amino acid sequence of SEQ ID NO: 59. In certain embodiments, a total of 1 to 5 amino acids have been substituted, inserted and/or deleted in the light chain variable domain amino acid sequence of antibody S-60-12 or the amino acid sequence of SEQ ID NO: 59. In certain embodiments, substitutions, insertions, or deletions occur in regions outside the HVRs (i.e., in the FR regions). In some embodiments, the substitutions, insertions, or deletions occur in in the FR regions. Optionally, the anti-Sortilin antibody comprises the VL sequence of antibody S-60-12 or of SEQ ID NO: 59, including post-translational modifications of that sequence. In a particular embodiment, the VL comprises one, two or three HVRs selected from: (a) the HVR-L1 amino acid sequence of antibody S-60-12, (b) the HVR-L2 amino acid sequence of antibody S-60-12, and (c) the HVR-L3 amino acid sequence of antibody S-60-12.

In some embodiments, anti-Sortilin antibodies of the present disclosure comprise a heavy chain comprising the amino acid sequence of SEQ ID NO: 105 or SEQ ID NO: 106. In some embodiments, anti-Sortilin antibodies of the present disclosure comprise a light chain comprising the amino acid sequence of SEQ ID NO: 141. In some embodiments, anti-Sortilin antibodies of the present disclosure comprise a heavy chain comprising the amino acid sequence of SEQ ID NO: 105 or SEQ ID NO: 106 and a light chain comprising the amino acid sequence of SEQ ID NO: 141.

(4) S-60-13

In some embodiments, anti-Sortilin antibodies of the present disclosure comprise a heavy chain variable domain and a light chain variable domain, wherein the heavy chain variable domain comprises an amino acid sequence with at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-13 or to the amino acid sequence of SEQ ID NO: 55; and/or the light chain variable domain comprises an amino acid sequence with at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-13 or to the amino acid sequence of SEQ ID NO: 57. In some embodiments, anti-Sortilin antibodies of the present disclosure comprise a heavy chain variable domain comprising an amino acid sequence with at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-13 or to the amino acid sequence of SEQ ID NO: 55, wherein the heavy chain variable domain comprises the HVR-H1, HVR-H2, and HVR-H3 amino acid sequences of antibody S-60-13. In some embodiments, anti-Sortilin antibodies of the present disclosure comprise a light chain variable domain comprising an amino acid sequence with at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-13 or to the amino acid sequence of SEQ ID NO: 57, wherein the light chain variable domain comprises the HVR-L1, HVR-L2, and HVR-L3 amino acid sequences of antibody S-60-13. In some embodiments, the anti-Sortilin antibody comprises a heavy chain variable domain (VH) sequence having at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-13 or to the amino acid sequence of SEQ ID NO: 55 and contains substitutions (e.g., conservative substitutions, insertions, or deletions relative to the reference sequence), but the anti-Sortilin antibody comprising that sequence retains the ability to bind to Sortilin. In certain embodiments, a total of 1 to 10 amino acids have been substituted, inserted, and/or deleted in the heavy chain variable domain amino acid sequence of antibody S-60-13 or the amino acid sequence of SEQ ID NO: 55. In certain embodiments, a total of 1 to 5 amino acids have been substituted, inserted and/or deleted in the heavy chain variable domain amino acid sequence of antibody S-60-13 or the amino acid sequence of SEQ ID NO: 55. In certain embodiments, substitutions, insertions, or deletions occur in regions outside the HVRs (i.e., in the FR regions). In some embodiments, the substitutions, insertions, or deletions occur in in the FR regions. Optionally, the anti-Sortilin antibody comprises the VH sequence of antibody S-60-13 or of SEQ ID NO: 55, including post-translational modifications of that sequence. In a particular embodiment, the VH comprises one, two or three HVRs selected from: (a) the HVR-H1 amino acid sequence of antibody S-60-13, (b) the HVR-H2 amino acid sequence of antibody S-60-13, and (c) the HVR-H3 amino acid sequence of antibody S-60-13. In some embodiments, anti-Sortilin antibodies of the present disclosure comprise a light chain variable domain (VL) sequence having at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-13 or to the amino acid sequence of SEQ ID NO: 57 and contains substitutions (e.g., conservative substitutions, insertions, or deletions relative to the reference sequence), but the anti-Sortilin antibody comprising that sequence retains the ability to bind to Sortilin. In certain embodiments, a total of 1 to 10 amino acids have been substituted, inserted, and/or deleted in the light chain variable domain amino acid sequence of antibody S-60-13 or the amino acid sequence of SEQ ID NO: 57. In certain embodiments, a total of 1 to 5 amino acids have been substituted, inserted and/or deleted in the light chain variable domain amino acid sequence of antibody S-60-13 or the amino acid sequence of SEQ ID NO: 57. In certain embodiments, substitutions, insertions, or deletions occur in regions outside the HVRs (i.e., in the FR regions). In some embodiments, the substitutions, insertions, or deletions occur in in the FR regions. Optionally, the anti-Sortilin antibody comprises the VL sequence of antibody S-60-13 or of SEQ ID NO: 57, including post-translational modifications of that sequence. In a particular embodiment, the VL comprises one, two or three HVRs selected from: (a) the HVR-L1 amino acid sequence of antibody S-60-13, (b) the HVR-L2 amino acid sequence of antibody S-60-13, and (c) the HVR-L3 amino acid sequence of antibody S-60-13.

In some embodiments, anti-Sortilin antibodies of the present disclosure comprise a heavy chain comprising the amino acid sequence of SEQ ID NO: 135 or SEQ ID NO: 136. In some embodiments, anti-Sortilin antibodies of the present disclosure comprise a light chain comprising the amino acid sequence of SEQ ID NO: 139. In some embodiments, anti-Sortilin antibodies of the present disclosure comprise a heavy chain comprising the amino acid sequence of SEQ ID NO: 135 or SEQ ID NO: 136 and a light chain comprising the amino acid sequence of SEQ ID NO: 139.

(5) S-60-14

In some embodiments, anti-Sortilin antibodies of the present disclosure comprise a heavy chain variable domain and a light chain variable domain, wherein the heavy chain variable domain comprises an amino acid sequence with at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-14 or to the amino acid sequence of SEQ ID NO: 55; and/or the light chain variable domain comprises an amino acid sequence with at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-14 or to the amino acid sequence of SEQ ID NO: 58. In some embodiments, anti-Sortilin antibodies of the present disclosure comprise a heavy chain variable domain comprising an amino acid sequence with at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-14 or to the amino acid sequence of SEQ ID NO: 55, wherein the heavy chain variable domain comprises the HVR-H1, HVR-H2, and HVR-H3 amino acid sequences of antibody S-60-14. In some embodiments, anti-Sortilin antibodies of the present disclosure comprise a light chain variable domain comprising an amino acid sequence with at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-14 or to the amino acid sequence of SEQ ID NO: 58, wherein the light chain variable domain comprises the HVR-L1, HVR-L2, and HVR-L3 amino acid sequences of antibody S-60-14. In some embodiments, the anti-Sortilin antibody comprises a heavy chain variable domain (VH) sequence having at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-14 or to the amino acid sequence of SEQ ID NO: 55 and contains substitutions (e.g., conservative substitutions, insertions, or deletions relative to the reference sequence), but the anti-Sortilin antibody comprising that sequence retains the ability to bind to Sortilin. In certain embodiments, a total of 1 to 10 amino acids have been substituted, inserted, and/or deleted in the heavy chain variable domain amino acid sequence of antibody S-60-14 or the amino acid sequence of SEQ ID NO: 55. In certain embodiments, a total of 1 to 5 amino acids have been substituted, inserted and/or deleted in the heavy chain variable domain amino acid sequence of antibody S-60-14 or the amino acid sequence of SEQ ID NO: 55. In certain embodiments, substitutions, insertions, or deletions occur in regions outside the HVRs (i.e., in the FR regions). In some embodiments, the substitutions, insertions, or deletions occur in in the FR regions. Optionally, the anti-Sortilin antibody comprises the VH sequence of antibody S-60-14 or of SEQ ID NO: 55, including post-translational modifications of that sequence. In a particular embodiment, the VH comprises one, two or three HVRs selected from: (a) the HVR-H1 amino acid sequence of antibody S-60-14, (b) the HVR-H2 amino acid sequence of antibody S-60-14, and (c) the HVR-H3 amino acid sequence of antibody S-60-14. In some embodiments, anti-Sortilin antibodies of the present disclosure comprise a light chain variable domain (VL) sequence having at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-14 or to the amino acid sequence of SEQ ID NO: 58 and contains substitutions (e.g., conservative substitutions, insertions, or deletions relative to the reference sequence), but the anti-Sortilin antibody comprising that sequence retains the ability to bind to Sortilin. In certain embodiments, a total of 1 to 10 amino acids have been substituted, inserted, and/or deleted in the light chain variable domain amino acid sequence of antibody S-60-14 or the amino acid sequence of SEQ ID NO: 58. In certain embodiments, a total of 1 to 5 amino acids have been substituted, inserted and/or deleted in the light chain variable domain amino acid sequence of antibody S-60-14 or the amino acid sequence of SEQ ID NO: 58. In certain embodiments, substitutions, insertions, or deletions occur in regions outside the HVRs (i.e., in the FR regions). In some embodiments, the substitutions, insertions, or deletions occur in in the FR regions. Optionally, the anti-Sortilin antibody comprises the VL sequence of antibody S-60-14 or of SEQ ID NO: 58, including post-translational modifications of that sequence. In a particular embodiment, the VL comprises one, two or three HVRs selected from: (a) the HVR-L1 amino acid sequence of antibody S-60-14, (b) the HVR-L2 amino acid sequence of antibody S-60-14, and (c) the HVR-L3 amino acid sequence of antibody S-60-14.

In some embodiments, anti-Sortilin antibodies of the present disclosure comprise a heavy chain comprising the amino acid sequence of SEQ ID NO: 135 or SEQ ID NO: 136. In some embodiments, anti-Sortilin antibodies of the present disclosure comprise a light chain comprising the amino acid sequence of SEQ ID NO: 140. In some embodiments, anti-Sortilin antibodies of the present disclosure comprise a heavy chain comprising the amino acid sequence of SEQ ID NO: 135 or SEQ ID NO: 136 and a light chain comprising the amino acid sequence of SEQ ID NO: 140.

(6) S-60-15

In some embodiments, anti-Sortilin antibodies of the present disclosure comprise a heavy chain variable domain and a light chain variable domain, wherein the heavy chain variable domain comprises an amino acid sequence with at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-15 or to the amino acid sequence of SEQ ID NO: 56; and/or the light chain variable domain comprises an amino acid sequence with at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-15 or to the amino acid sequence of SEQ ID NO: 57. In some embodiments, anti-Sortilin antibodies of the present disclosure comprise a heavy chain variable domain comprising an amino acid sequence with at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-15 or to the amino acid sequence of SEQ ID NO: 56, wherein the heavy chain variable domain comprises the HVR-H1, HVR-H2, and HVR-H3 amino acid sequences of antibody S-60-15. In some embodiments, anti-Sortilin antibodies of the present disclosure comprise a light chain variable domain comprising an amino acid sequence with at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-15 or to the amino acid sequence of SEQ ID NO: 57, wherein the light chain variable domain comprises the HVR-L1, HVR-L2, and HVR-L3 amino acid sequences of antibody S-60-15. In some embodiments, the anti-Sortilin antibody comprises a heavy chain variable domain (VH) sequence having at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-15 or to the amino acid sequence of SEQ ID NO: 56 and contains substitutions (e.g., conservative substitutions, insertions, or deletions relative to the reference sequence), but the anti-Sortilin antibody comprising that sequence retains the ability to bind to Sortilin. In certain embodiments, a total of 1 to 10 amino acids have been substituted, inserted, and/or deleted in the heavy chain variable domain amino acid sequence of antibody S-60-15 or the amino acid sequence of SEQ ID NO: 56. In certain embodiments, a total of 1 to 5 amino acids have been substituted, inserted and/or deleted in the heavy chain variable domain amino acid sequence of antibody S-60-15 or the amino acid sequence of SEQ ID NO: 56. In certain embodiments, substitutions, insertions, or deletions occur in regions outside the HVRs (i.e., in the FR regions). In some embodiments, the substitutions, insertions, or deletions occur in in the FR regions. Optionally, the anti-Sortilin antibody comprises the VH sequence of antibody S-60-15 or of SEQ ID NO: 56, including post-translational modifications of that sequence. In a particular embodiment, the VH comprises one, two or three HVRs selected from: (a) the HVR-H1 amino acid sequence of antibody S-60-15, (b) the HVR-H2 amino acid sequence of antibody S-60-15, and (c) the HVR-H3 amino acid sequence of antibody S-60-15. In some embodiments, anti-Sortilin antibodies of the present disclosure comprise a light chain variable domain (VL) sequence having at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-15 or to the amino acid sequence of SEQ ID NO: 57 and contains substitutions (e.g., conservative substitutions, insertions, or deletions relative to the reference sequence), but the anti-Sortilin antibody comprising that sequence retains the ability to bind to Sortilin. In certain embodiments, a total of 1 to 10 amino acids have been substituted, inserted, and/or deleted in the light chain variable domain amino acid sequence of antibody S-60-15 or the amino acid sequence of SEQ ID NO: 57. In certain embodiments, a total of 1 to 5 amino acids have been substituted, inserted and/or deleted in the light chain variable domain amino acid sequence of antibody S-60-15 or the amino acid sequence of SEQ ID NO: 57. In certain embodiments, substitutions, insertions, or deletions occur in regions outside the HVRs (i.e., in the FR regions). In some embodiments, the substitutions, insertions, or deletions occur in in the FR regions. Optionally, the anti-Sortilin antibody comprises the VL sequence of antibody S-60-15 or of SEQ ID NO: 57, including post-translational modifications of that sequence. In a particular embodiment, the VL comprises one, two or three HVRs selected from: (a) the HVR-L1 amino acid sequence of antibody S-60-15, (b) the HVR-L2 amino acid sequence of antibody S-60-15, and (c) the HVR-L3 amino acid sequence of antibody S-60-15.

In some embodiments, anti-Sortilin antibodies of the present disclosure comprise a heavy chain comprising the amino acid sequence of SEQ ID NO: 137 or SEQ ID NO: 138. In some embodiments, anti-Sortilin antibodies of the present disclosure comprise a light chain comprising the amino acid sequence of SEQ ID NO: 139. In some embodiments, anti-Sortilin antibodies of the present disclosure comprise a heavy chain comprising the amino acid sequence of SEQ ID NO: 137 or SEQ ID NO: 138 and a light chain comprising the amino acid sequence of SEQ ID NO: 139.

(7) S-60-15.1

In some embodiments, anti-Sortilin antibodies of the present disclosure comprise a heavy chain variable domain and a light chain variable domain, wherein the heavy chain variable domain comprises an amino acid sequence with at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-15.1 or to the amino acid sequence of SEQ ID NO: 56; and/or the light chain variable domain comprises an amino acid sequence with at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-15.1 or to the amino acid sequence of SEQ ID NO: 60. In some embodiments, anti-Sortilin antibodies of the present disclosure comprise a heavy chain variable domain comprising an amino acid sequence with at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-15.1 or to the amino acid sequence of SEQ ID NO: 56, wherein the heavy chain variable domain comprises the HVR-H1, HVR-H2, and HVR-H3 amino acid sequences of antibody S-60-15.1. In some embodiments, anti-Sortilin antibodies of the present disclosure comprise a light chain variable domain comprising an amino acid sequence with at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-15.1 or to the amino acid sequence of SEQ ID NO: 60, wherein the light chain variable domain comprises the HVR-L1, HVR-L2, and HVR-L3 amino acid sequences of antibody S-60-15.1. In some embodiments, the anti-Sortilin antibody comprises a heavy chain variable domain (VH) sequence having at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-15.1 or to the amino acid sequence of SEQ ID NO: 56 and contains substitutions (e.g., conservative substitutions, insertions, or deletions relative to the reference sequence), but the anti-Sortilin antibody comprising that sequence retains the ability to bind to Sortilin. In certain embodiments, a total of 1 to 10 amino acids have been substituted, inserted, and/or deleted in the heavy chain variable domain amino acid sequence of antibody S-60-15.1 or the amino acid sequence of SEQ ID NO: 56. In certain embodiments, a total of 1 to 5 amino acids have been substituted, inserted and/or deleted in the heavy chain variable domain amino acid sequence of antibody S-60-15.1 or the amino acid sequence of SEQ ID NO: 56. In certain embodiments, substitutions, insertions, or deletions occur in regions outside the HVRs (i.e., in the FR regions). In some embodiments, the substitutions, insertions, or deletions occur in in the FR regions. Optionally, the anti-Sortilin antibody comprises the VH sequence of antibody S-60-15.1 or of SEQ ID NO: 56, including post-translational modifications of that sequence. In a particular embodiment, the VH comprises one, two or three HVRs selected from: (a) the HVR-H1 amino acid sequence of antibody S-60-15.1, (b) the HVR-H2 amino acid sequence of antibody S-60-15.1, and (c) the HVR-H3 amino acid sequence of antibody S-60-15.1. In some embodiments, anti-Sortilin antibodies of the present disclosure comprise a light chain variable domain (VL) sequence having at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-15.1 or to the amino acid sequence of SEQ ID NO: 60 and contains substitutions (e.g., conservative substitutions, insertions, or deletions relative to the reference sequence), but the anti-Sortilin antibody comprising that sequence retains the ability to bind to Sortilin. In certain embodiments, a total of 1 to 10 amino acids have been substituted, inserted, and/or deleted in the light chain variable domain amino acid sequence of antibody S-60-15.1 or the amino acid sequence of SEQ ID NO: 60. In certain embodiments, a total of 1 to 5 amino acids have been substituted, inserted and/or deleted in the light chain variable domain amino acid sequence of antibody S-60-15.1 or the amino acid sequence of SEQ ID NO: 60. In certain embodiments, substitutions, insertions, or deletions occur in regions outside the HVRs (i.e., in the FR regions). In some embodiments, the substitutions, insertions, or deletions occur in in the FR regions. Optionally, the anti-Sortilin antibody comprises the VL sequence of antibody S-60-15.1 or of SEQ ID NO: 60, including post-translational modifications of that sequence. In a particular embodiment, the VL comprises one, two or three HVRs selected from: (a) the HVR-L1 amino acid sequence of antibody S-60-15.1, (b) the HVR-L2 amino acid sequence of antibody S-60-15.1, and (c) the HVR-L3 amino acid sequence of antibody S-60-15.1.

In some embodiments, anti-Sortilin antibodies of the present disclosure comprise a heavy chain comprising the amino acid sequence of SEQ ID NO: 137 or SEQ ID NO: 138. In some embodiments, anti-Sortilin antibodies of the present disclosure comprise a light chain comprising the amino acid sequence of SEQ ID NO: 142. In some embodiments, anti-Sortilin antibodies of the present disclosure comprise a heavy chain comprising the amino acid sequence of SEQ ID NO: 137 or SEQ ID NO: 138 and a light chain comprising the amino acid sequence of SEQ ID NO: 142.

(8) S-60-16

In some embodiments, anti-Sortilin antibodies of the present disclosure comprise a heavy chain variable domain and a light chain variable domain, wherein the heavy chain variable domain comprises an amino acid sequence with at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-16 or to the amino acid sequence of SEQ ID NO: 56; and/or the light chain variable domain comprises an amino acid sequence with at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-16 or to the amino acid sequence of SEQ ID NO: 77. In some embodiments, anti-Sortilin antibodies of the present disclosure comprise a heavy chain variable domain comprising an amino acid sequence with at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-16 or to the amino acid sequence of SEQ ID NO: 56, wherein the heavy chain variable domain comprises the HVR-H1, HVR-H2, and HVR-H3 amino acid sequences of antibody S-60-16. In some embodiments, anti-Sortilin antibodies of the present disclosure comprise a light chain variable domain comprising an amino acid sequence with at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-16 or to the amino acid sequence of SEQ ID NO: 77, wherein the light chain variable domain comprises the HVR-L1, HVR-L2, and HVR-L3 amino acid sequences of antibody S-60-16. In some embodiments, the anti-Sortilin antibody comprises a heavy chain variable domain (VH) sequence having at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-16 or to the amino acid sequence of SEQ ID NO: 56 and contains substitutions (e.g., conservative substitutions, insertions, or deletions relative to the reference sequence), but the anti-Sortilin antibody comprising that sequence retains the ability to bind to Sortilin. In certain embodiments, a total of 1 to 10 amino acids have been substituted, inserted, and/or deleted in the heavy chain variable domain amino acid sequence of antibody S-60-16 or the amino acid sequence of SEQ ID NO: 56. In certain embodiments, a total of 1 to 5 amino acids have been substituted, inserted and/or deleted in the heavy chain variable domain amino acid sequence of antibody S-60-16 or the amino acid sequence of SEQ ID NO: 56. In certain embodiments, substitutions, insertions, or deletions occur in regions outside the HVRs (i.e., in the FR regions). In some embodiments, the substitutions, insertions, or deletions occur in in the FR regions. Optionally, the anti-Sortilin antibody comprises the VH sequence of antibody S-60-16 or of SEQ ID NO: 56, including post-translational modifications of that sequence. In a particular embodiment, the VH comprises one, two or three HVRs selected from: (a) the HVR-H1 amino acid sequence of antibody S-60-16, (b) the HVR-H2 amino acid sequence of antibody S-60-16, and (c) the HVR-H3 amino acid sequence of antibody S-60-16. In some embodiments, anti-Sortilin antibodies of the present disclosure comprise a light chain variable domain (VL) sequence having at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-16 or to the amino acid sequence of SEQ ID NO: 77 and contains substitutions (e.g., conservative substitutions, insertions, or deletions relative to the reference sequence), but the anti-Sortilin antibody comprising that sequence retains the ability to bind to Sortilin. In certain embodiments, a total of 1 to 10 amino acids have been substituted, inserted, and/or deleted in the light chain variable domain amino acid sequence of antibody S-60-16 or the amino acid sequence of SEQ ID NO: 77. In certain embodiments, a total of 1 to 5 amino acids have been substituted, inserted and/or deleted in the light chain variable domain amino acid sequence of antibody S-60-16 or the amino acid sequence of SEQ ID NO: 77. In certain embodiments, substitutions, insertions, or deletions occur in regions outside the HVRs (i.e., in the FR regions). In some embodiments, the substitutions, insertions, or deletions occur in in the FR regions. Optionally, the anti-Sortilin antibody comprises the VL sequence of antibody S-60-16 or of SEQ ID NO: 77, including post-translational modifications of that sequence. In a particular embodiment, the VL comprises one, two or three HVRs selected from: (a) the HVR-L1 amino acid sequence of antibody S-60-16, (b) the HVR-L2 amino acid sequence of antibody S-60-16, and (c) the HVR-L3 amino acid sequence of antibody S-60-16.

In some embodiments, anti-Sortilin antibodies of the present disclosure comprise a heavy chain comprising the amino acid sequence of SEQ ID NO: 137 or SEQ ID NO: 138. In some embodiments, anti-Sortilin antibodies of the present disclosure comprise a light chain comprising the amino acid sequence of SEQ ID NO: 131. In some embodiments, anti-Sortilin antibodies of the present disclosure comprise a heavy chain comprising the amino acid sequence of SEQ ID NO: 137 or SEQ ID NO: 138 and a light chain comprising the amino acid sequence of SEQ ID NO: 131.

(9) S-60-18

In some embodiments, anti-Sortilin antibodies of the present disclosure comprise a heavy chain variable domain and a light chain variable domain, wherein the heavy chain variable domain comprises an amino acid sequence with at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-18 or to the amino acid sequence of SEQ ID NO: 56; and/or the light chain variable domain comprises an amino acid sequence with at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-18 or to the amino acid sequence of SEQ ID NO: 78. In some embodiments, anti-Sortilin antibodies of the present disclosure comprise a heavy chain variable domain comprising an amino acid sequence with at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-18 or to the amino acid sequence of SEQ ID NO: 56, wherein the heavy chain variable domain comprises the HVR-H1, HVR-H2, and HVR-H3 amino acid sequences of antibody S-60-18. In some embodiments, anti-Sortilin antibodies of the present disclosure comprise a light chain variable domain comprising an amino acid sequence with at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-18 or to the amino acid sequence of SEQ ID NO: 78, wherein the light chain variable domain comprises the HVR-L1, HVR-L2, and HVR-L3 amino acid sequences of antibody S-60-18. In some embodiments, the anti-Sortilin antibody comprises a heavy chain variable domain (VH) sequence having at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-18 or to the amino acid sequence of SEQ ID NO: 56 and contains substitutions (e.g., conservative substitutions, insertions, or deletions relative to the reference sequence), but the anti-Sortilin antibody comprising that sequence retains the ability to bind to Sortilin. In certain embodiments, a total of 1 to 10 amino acids have been substituted, inserted, and/or deleted in the heavy chain variable domain amino acid sequence of antibody S-60-18 or the amino acid sequence of SEQ ID NO: 56. In certain embodiments, a total of 1 to 5 amino acids have been substituted, inserted and/or deleted in the heavy chain variable domain amino acid sequence of antibody S-60-18 or the amino acid sequence of SEQ ID NO: 56. In certain embodiments, substitutions, insertions, or deletions occur in regions outside the HVRs (i.e., in the FR regions). In some embodiments, the substitutions, insertions, or deletions occur in in the FR regions. Optionally, the anti-Sortilin antibody comprises the VH sequence of antibody S-60-18 or of SEQ ID NO: 56, including post-translational modifications of that sequence. In a particular embodiment, the VH comprises one, two or three HVRs selected from: (a) the HVR-H1 amino acid sequence of antibody S-60-18, (b) the HVR-H2 amino acid sequence of antibody S-60-18, and (c) the HVR-H3 amino acid sequence of antibody S-60-18. In some embodiments, anti-Sortilin antibodies of the present disclosure comprise a light chain variable domain (VL) sequence having at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-18 or to the amino acid sequence of SEQ ID NO: 78 and contains substitutions (e.g., conservative substitutions, insertions, or deletions relative to the reference sequence), but the anti-Sortilin antibody comprising that sequence retains the ability to bind to Sortilin. In certain embodiments, a total of 1 to 10 amino acids have been substituted, inserted, and/or deleted in the light chain variable domain amino acid sequence of antibody S-60-18 or the amino acid sequence of SEQ ID NO: 78. In certain embodiments, a total of 1 to 5 amino acids have been substituted, inserted and/or deleted in the light chain variable domain amino acid sequence of antibody S-60-18 or the amino acid sequence of SEQ ID NO: 78. In certain embodiments, substitutions, insertions, or deletions occur in regions outside the HVRs (i.e., in the FR regions). In some embodiments, the substitutions, insertions, or deletions occur in in the FR regions. Optionally, the anti-Sortilin antibody comprises the VL sequence of antibody S-60-18 or of SEQ ID NO: 78, including post-translational modifications of that sequence. In a particular embodiment, the VL comprises one, two or three HVRs selected from: (a) the HVR-L1 amino acid sequence of antibody S-60-18, (b) the HVR-L2 amino acid sequence of antibody S-60-18, and (c) the HVR-L3 amino acid sequence of antibody S-60-18.

In some embodiments, anti-Sortilin antibodies of the present disclosure comprise a heavy chain comprising the amino acid sequence of SEQ ID NO: 137 or SEQ ID NO: 138. In some embodiments, anti-Sortilin antibodies of the present disclosure comprise a light chain comprising the amino acid sequence of SEQ ID NO: 132. In some embodiments, anti-Sortilin antibodies of the present disclosure comprise a heavy chain comprising the amino acid sequence of SEQ ID NO: 137 or SEQ ID NO: 138 and a light chain comprising the amino acid sequence of SEQ ID NO: 132.

(10) S-60-19

In some embodiments, anti-Sortilin antibodies of the present disclosure comprise a heavy chain variable domain and a light chain variable domain, wherein the heavy chain variable domain comprises an amino acid sequence with at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-19 or to the amino acid sequence of SEQ ID NO: 54; and/or the light chain variable domain comprises an amino acid sequence with at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-19 or to the amino acid sequence of SEQ ID NO: 79. In some embodiments, anti-Sortilin antibodies of the present disclosure comprise a heavy chain variable domain comprising an amino acid sequence with at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-19 or to the amino acid sequence of SEQ ID NO: 54, wherein the heavy chain variable domain comprises the HVR-H1, HVR-H2, and HVR-H3 amino acid sequences of antibody S-60-19. In some embodiments, anti-Sortilin antibodies of the present disclosure comprise a light chain variable domain comprising an amino acid sequence with at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-19 or to the amino acid sequence of SEQ ID NO: 79, wherein the light chain variable domain comprises the HVR-L1, HVR-L2, and HVR-L3 amino acid sequences of antibody S-60-19. In some embodiments, the anti-Sortilin antibody comprises a heavy chain variable domain (VH) sequence having at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-19 or to the amino acid sequence of SEQ ID NO: 54 and contains substitutions (e.g., conservative substitutions, insertions, or deletions relative to the reference sequence), but the anti-Sortilin antibody comprising that sequence retains the ability to bind to Sortilin. In certain embodiments, a total of 1 to 10 amino acids have been substituted, inserted, and/or deleted in the heavy chain variable domain amino acid sequence of antibody S-60-19 or the amino acid sequence of SEQ ID NO: 54. In certain embodiments, a total of 1 to 5 amino acids have been substituted, inserted and/or deleted in the heavy chain variable domain amino acid sequence of antibody S-60-19 or the amino acid sequence of SEQ ID NO: 54. In certain embodiments, substitutions, insertions, or deletions occur in regions outside the HVRs (i.e., in the FR regions). In some embodiments, the substitutions, insertions, or deletions occur in in the FR regions. Optionally, the anti-Sortilin antibody comprises the VH sequence of antibody S-60-19 or of SEQ ID NO: 54, including post-translational modifications of that sequence. In a particular embodiment, the VH comprises one, two or three HVRs selected from: (a) the HVR-H1 amino acid sequence of antibody S-60-19, (b) the HVR-H2 amino acid sequence of antibody S-60-19, and (c) the HVR-H3 amino acid sequence of antibody S-60-19. In some embodiments, anti-Sortilin antibodies of the present disclosure comprise a light chain variable domain (VL) sequence having at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-19 or to the amino acid sequence of SEQ ID NO: 79 and contains substitutions (e.g., conservative substitutions, insertions, or deletions relative to the reference sequence), but the anti-Sortilin antibody comprising that sequence retains the ability to bind to Sortilin. In certain embodiments, a total of 1 to 10 amino acids have been substituted, inserted, and/or deleted in the light chain variable domain amino acid sequence of antibody S-60-19 or the amino acid sequence of SEQ ID NO: 79. In certain embodiments, a total of 1 to 5 amino acids have been substituted, inserted and/or deleted in the light chain variable domain amino acid sequence of antibody S-60-19 or the amino acid sequence of SEQ ID NO: 79. In certain embodiments, substitutions, insertions, or deletions occur in regions outside the HVRs (i.e., in the FR regions). In some embodiments, the substitutions, insertions, or deletions occur in in the FR regions. Optionally, the anti-Sortilin antibody comprises the VL sequence of antibody S-60-19 or of SEQ ID NO: 79, including post-translational modifications of that sequence. In a particular embodiment, the VL comprises one, two or three HVRs selected from: (a) the HVR-L1 amino acid sequence of antibody S-60-19, (b) the HVR-L2 amino acid sequence of antibody S-60-19, and (c) the HVR-L3 amino acid sequence of antibody S-60-19.

In some embodiments, anti-Sortilin antibodies of the present disclosure comprise a heavy chain comprising the amino acid sequence of SEQ ID NO: 105 or SEQ ID NO: 106. In some embodiments, anti-Sortilin antibodies of the present disclosure comprise a light chain comprising the amino acid sequence of SEQ ID NO: 133. In some embodiments, anti-Sortilin antibodies of the present disclosure comprise a heavy chain comprising the amino acid sequence of SEQ ID NO: 105 or SEQ ID NO: 106 and a light chain comprising the amino acid sequence of SEQ ID NO: 133.

(11) S-60-24

In some embodiments, anti-Sortilin antibodies of the present disclosure comprise a heavy chain variable domain and a light chain variable domain, wherein the heavy chain variable domain comprises an amino acid sequence with at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-24 or to the amino acid sequence of SEQ ID NO: 56; and/or the light chain variable domain comprises an amino acid sequence with at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-24 or to the amino acid sequence of SEQ ID NO: 80. In some embodiments, anti-Sortilin antibodies of the present disclosure comprise a heavy chain variable domain comprising an amino acid sequence with at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-24 or to the amino acid sequence of SEQ ID NO: 56, wherein the heavy chain variable domain comprises the HVR-H1, HVR-H2, and HVR-H3 amino acid sequences of antibody S-60-24. In some embodiments, anti-Sortilin antibodies of the present disclosure comprise a light chain variable domain comprising an amino acid sequence with at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-24 or to the amino acid sequence of SEQ ID NO: 80, wherein the light chain variable domain comprises the HVR-L1, HVR-L2, and HVR-L3 amino acid sequences of antibody S-60-24. In some embodiments, the anti-Sortilin antibody comprises a heavy chain variable domain (VH) sequence having at least 90%, at least 91%, at least 92%, at least 93%, at least 94%, at least 95%, at least 96%, at least 97%, at least 98%, at least 99%, or 100% identity to a heavy chain variable domain amino acid sequence of antibody S-60-24 or to the amino acid sequence of SEQ ID NO: 56 and contains substitutions (e.g., conservative substitutions, insertions, or deletions relative to the reference sequence), but the anti-Sortilin antibody comprising that sequence retains the ability to bind to Sortilin. In certain embodiments, a total of 1 to 10 amino acids have been substituted, inserted, and/or deleted in the heavy chain variable domain amino acid sequence of antibody S-60-24 or the amino acid sequence of SEQ ID NO: 56. In certain embodiments, a total of 1 to 5 amino acids have been substituted, inserted and/or deleted in the heavy chain variable domain amino acid sequence of antibody S-60-24 or the amino acid sequence of SEQ ID NO: 56. In certain embodiments, substitutions, insertions, or deletions occur in regions outside the HVRs (i.e., in the FR regions). In some embodiments, the substitutions, insertions, or deletions occur in in the FR regions. Optionally, the anti-Sortilin antibody comprises the VH sequence of antibody S-60-24 or of SEQ ID NO: 56, including post-translational modifications of that sequence. In a particular embodiment, the VH comprises one, two or three HVRs selected from: (a) the HVR-H1 amino acid sequence of antibody S-60-24, (b) the HVR-H2 amino acid sequence of antibody S-60-24, and (c) the HVR-H3 amino acid sequence of antibody S-60-24. In some embodiments, anti-Sortilin antibodies of the present disclosure comprise a light chain variable domain (VL) sequence having at least 90%, at least 91%, at least 92%, at least 93%, at least 94%, at least 95%, at least 96%, at least 97%, at least 98%, at least 99%, or 100% identity to a light chain variable domain amino acid sequence of antibody S-60-24 or to the amino acid sequence of SEQ ID NO: 80 and contains substitutions (e.g., conservative substitutions, insertions, or deletions relative to the reference sequence), but the anti-Sortilin antibody comprising that sequence retains the ability to bind to Sortilin. In certain embodiments, a total of 1 to 10 amino acids have been substituted, inserted, and/or deleted in the light chain variable domain amino acid sequence of antibody S-60-24 or the amino acid sequence of SEQ ID NO: 80. In certain embodiments, a total of 1 to 5 amino acids have been substituted, inserted and/or deleted in the light chain variable domain amino acid sequence of antibody S-60-24 or the amino acid sequence of SEQ ID NO: 80. In certain embodiments, substitutions, insertions, or deletions occur in regions outside the HVRs (i.e., in the FR regions). In some embodiments, the substitutions, insertions, or deletions occur in in the FR regions. Optionally, the anti-Sortilin antibody comprises the VL sequence of antibody S-60-24 or of SEQ ID NO: 80, including post-translational modifications of that sequence. In a particular embodiment, the VL comprises one, two or three HVRs selected from: (a) the HVR-L1 amino acid sequence of antibody S-60-24, (b) the HVR-L2 amino acid sequence of antibody S-60-24, and (c) the HVR-L3 amino acid sequence of antibody S-60-24.

In some embodiments, anti-Sortilin antibodies of the present disclosure comprise a heavy chain comprising the amino acid sequence of SEQ ID NO: 137 or SEQ ID NO: 138. In some embodiments, anti-Sortilin antibodies of the present disclosure comprise a light chain comprising the amino acid sequence of SEQ ID NO: 134. In some embodiments, anti-Sortilin antibodies of the present disclosure comprise a heavy chain comprising the amino acid sequence of SEQ ID NO: 137 or SEQ ID NO: 138 and a light chain comprising the amino acid sequence of SEQ ID NO: 134.

In some embodiments, an anti-Sortilin antibody of the present disclosure binds essentially the same Sortilin epitope as an antibody comprising the heavy chain variable domain and the light chain variable domain of an antibody selected from the group consisting of S-60-10, S-60-11, S-60-12, S-60-13, S-60-14, S-60-15 [N33 (wt)], S-60-15.1 [N33T], S-60-16, S-60-18, S-60-19, and S-60-24.

In some embodiments, the anti-Sortilin antibody is anti-Sortilin monoclonal antibody S-60-10. In some embodiments, the anti-Sortilin antibody is an isolated antibody which binds essentially the same Sortilin epitope as S-60-10. In some embodiments, the anti-Sortilin antibody is an isolated antibody comprising the heavy chain variable region of monoclonal antibody S-60-10. In some embodiments, the anti-Sortilin antibody is an isolated antibody comprising the light chain variable region of monoclonal antibody S-60-10. In some embodiments, the anti-Sortilin antibody is an isolated antibody comprising the heavy chain variable region and the light chain variable region of monoclonal antibody S-60-10.

In some embodiments, the anti-Sortilin antibody is anti-Sortilin monoclonal antibody S-60-11. In some embodiments, the anti-Sortilin antibody is an isolated antibody which binds essentially the same Sortilin epitope as S-60-11. In some embodiments, the anti-Sortilin antibody is an isolated antibody comprising the heavy chain variable region of monoclonal antibody S-60-11. In some embodiments, the anti-Sortilin antibody is an isolated antibody comprising the light chain variable region of monoclonal antibody S-60-11. In some embodiments, the anti-Sortilin antibody is an isolated antibody comprising the heavy chain variable region and the light chain variable region of monoclonal antibody S-60-11.

In some embodiments, the anti-Sortilin antibody is anti-Sortilin monoclonal antibody S-60-12. In some embodiments, the anti-Sortilin antibody is an isolated antibody which binds essentially the same Sortilin epitope as S-60-12. In some embodiments, the anti-Sortilin antibody is an isolated antibody comprising the heavy chain variable region of monoclonal antibody S-60-12. In some embodiments, the anti-Sortilin antibody is an isolated antibody comprising the light chain variable region of monoclonal antibody S-60-12. In some embodiments, the anti-Sortilin antibody is an isolated antibody comprising the heavy chain variable region and the light chain variable region of monoclonal antibody S-60-12.

In some embodiments, the anti-Sortilin antibody is anti-Sortilin monoclonal antibody S-60-13. In some embodiments, the anti-Sortilin antibody is an isolated antibody which binds essentially the same Sortilin epitope as S-60-13. In some embodiments, the anti-Sortilin antibody is an isolated antibody comprising the heavy chain variable region of monoclonal antibody S-60-13. In some embodiments, the anti-Sortilin antibody is an isolated antibody comprising the light chain variable region of monoclonal antibody S-60-13. In some embodiments, the anti-Sortilin antibody is an isolated antibody comprising the heavy chain variable region and the light chain variable region of monoclonal antibody S-60-13.

In some embodiments, the anti-Sortilin antibody is anti-Sortilin monoclonal antibody S-60-14. In some embodiments, the anti-Sortilin antibody is an isolated antibody which binds essentially the same Sortilin epitope as S-60-14. In some embodiments, the anti-Sortilin antibody is an isolated antibody comprising the heavy chain variable region of monoclonal antibody S-60-14. In some embodiments, the anti-Sortilin antibody is an isolated antibody comprising the light chain variable region of monoclonal antibody S-60-14. In some embodiments, the anti-Sortilin antibody is an isolated antibody comprising the heavy chain variable region and the light chain variable region of monoclonal antibody S-60-14.

In some embodiments, the anti-Sortilin antibody is anti-Sortilin monoclonal antibody S-60-15. In some embodiments, the anti-Sortilin antibody is an isolated antibody which binds essentially the same Sortilin epitope as S-60-15.

In some embodiments, the anti-Sortilin antibody is an isolated antibody comprising the heavy chain variable region of monoclonal antibody S-60-15. In some embodiments, the anti-Sortilin antibody is an isolated antibody comprising the light chain variable region of monoclonal antibody S-60-15. In some embodiments, the anti-Sortilin antibody is an isolated antibody comprising the heavy chain variable region and the light chain variable region of monoclonal antibody S-60-15.

In some embodiments, the anti-Sortilin antibody is anti-Sortilin monoclonal antibody S-60-15.1. In some embodiments, the anti-Sortilin antibody is an isolated antibody which binds essentially the same Sortilin epitope as S-60-15.1. In some embodiments, the anti-Sortilin antibody is an isolated antibody comprising the heavy chain variable region of monoclonal antibody S-60-15.1. In some embodiments, the anti-Sortilin antibody is an isolated antibody comprising the light chain variable region of monoclonal antibody S-60-15.1. In some embodiments, the anti-Sortilin antibody is an isolated antibody comprising the heavy chain variable region and the light chain variable region of monoclonal antibody S-60-15.1.

In some embodiments, the anti-Sortilin antibody is anti-Sortilin monoclonal antibody S-60-16. In some embodiments, the anti-Sortilin antibody is an isolated antibody which binds essentially the same Sortilin epitope as S-60-16. In some embodiments, the anti-Sortilin antibody is an isolated antibody comprising the heavy chain variable region of monoclonal antibody S-60-16. In some embodiments, the anti-Sortilin antibody is an isolated antibody comprising the light chain variable region of monoclonal antibody S-60-16. In some embodiments, the anti-Sortilin antibody is an isolated antibody comprising the heavy chain variable region and the light chain variable region of monoclonal antibody S-60-16.

In some embodiments, the anti-Sortilin antibody is anti-Sortilin monoclonal antibody S-60-18. In some embodiments, the anti-Sortilin antibody is an isolated antibody which binds essentially the same Sortilin epitope as S-60-18. In some embodiments, the anti-Sortilin antibody is an isolated antibody comprising the heavy chain variable region of monoclonal antibody S-60-18. In some embodiments, the anti-Sortilin antibody is an isolated antibody comprising the light chain variable region of monoclonal antibody S-60-18. In some embodiments, the anti-Sortilin antibody is an isolated antibody comprising the heavy chain variable region and the light chain variable region of monoclonal antibody S-60-18.

In some embodiments, the anti-Sortilin antibody is anti-Sortilin monoclonal antibody S-60-19. In some embodiments, the anti-Sortilin antibody is an isolated antibody which binds essentially the same Sortilin epitope as S-60-19. In some embodiments, the anti-Sortilin antibody is an isolated antibody comprising the heavy chain variable region of monoclonal antibody S-60-19. In some embodiments, the anti-Sortilin antibody is an isolated antibody comprising the light chain variable region of monoclonal antibody S-60-19. In some embodiments, the anti-Sortilin antibody is an isolated antibody comprising the heavy chain variable region and the light chain variable region of monoclonal antibody S-60-19.

In some embodiments, the anti-Sortilin antibody is anti-Sortilin monoclonal antibody S-60-24. In some embodiments, the anti-Sortilin antibody is an isolated antibody which binds essentially the same Sortilin epitope as S-60-24. In some embodiments, the anti-Sortilin antibody is an isolated antibody comprising the heavy chain variable region of monoclonal antibody S-60-24. In some embodiments, the anti-Sortilin antibody is an isolated antibody comprising the light chain variable region of monoclonal antibody S-60-24. In some embodiments, the anti-Sortilin antibody is an isolated antibody comprising the heavy chain variable region and the light chain variable region of monoclonal antibody S-60-24.

In certain embodiments, the anti-Sortilin antibody is an antagonist antibody. In certain embodiments, the anti-Sortilin antibody is an agonist antibody. In some embodiments, anti-Sortilin antibodies of the present disclosure are of the IgG class the IgM class, or the IgA class. In some embodiments, anti-Sortilin antibodies of the present disclosure are of the IgG class and have an IgG1, IgG2, IgG3, or IgG4 isotype.

Additional anti-Sortilin antibodies, e.g., antibodies that specifically bind to a Sortilin protein of the present disclosure, may be identified, screened, and/or characterized for their physical/chemical properties and/or biological activities by various assays known in the art.

Certain aspects of the present disclosure relate to the use of two or more anti-Sortilin antibodies that when utilized together display additive or synergistic effects, as compared to utilization of a corresponding single anti-Sortilin antibody.

In some embodiments, an anti-Sortilin antibody of the present disclosure is an antibody fragment that binds to a human Sortilin protein.

In some embodiments, an anti-Sortilin antibody of the present disclosure is an antibody fragment that binds to one or more human proteins selected from the group consisting of human Sortilin, a naturally occurring variant of human Sortilin, and a disease variant of human Sortilin.

In some embodiments, an anti-Sortilin antibody of the present disclosure is antibody fragment, wherein the antibody fragment is an Fab, Fab', Fab'-SH, F(ab')2, Fv, or scFv fragment.

Antibody Frameworks

In some embodiments, anti-Sortilin antibodies of the present disclosure comprise a heavy chain variable region comprising one or more (e.g., one or more, two or more, three or more, or all four) framework regions selected from VH FR1, VH FR2, VH FR3, and VH FR4 (as shown in Tables 20-23). In some embodiments, the VH FR1 comprises a sequence of QVQLQESGPGLVKPSETLSLTCAVSG (SEQ ID NO: 35). In some embodiments, the VH FR2 comprises a sequence of WIRQPPGKGLEWIG (SEQ ID NO: 36). In some embodiments, the VH FR3 comprises the sequence according to Formula VI: $X_1$VTISVDTSKNQFSLX$_2$LSSVTAADTAVYYC (SEQ ID NO: 39), wherein $X_1$ is Q or R, and $X_2$ is E or K. In some embodiments, VH FR3 comprises a sequence selected from the group consisting of SEQ ID NOs: 37-38. In some embodiments, VH FR4 comprises a sequence of WGQGTTVTVSS (SEQ ID NO: 40). In some embodiments, an antibody comprises a heavy chain variable region comprising a VH FR1 comprising the sequence of SEQ ID NO: 35, a VH FR2 comprising the sequence of SEQ ID NO: 36, a VH FR3 according to Formula VI, and a VH FR4 comprising the sequence of SEQ ID NO: 40.

In some embodiments, an antibody comprises a heavy chain variable region comprising a VH FR1 comprising the sequence of SEQ ID NO: 35, a VH FR2 comprising the sequence of SEQ ID NO: 36, a VH FR3 comprising the sequence selected from SEQ ID NOs: 37-38, and a VH FR4 comprising the sequence of SEQ ID NO: 40.

In some embodiments, anti-Sortilin antibodies of the present disclosure comprise a heavy chain variable region comprising a VH FR1, a VH FR2, a VH FR3, and VH FR4 of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, or S-60-24 (as shown in Tables 20-23).

In some embodiments, anti-Sortilin antibodies of the present disclosure comprise a light chain variable region comprising one or more (e.g., one or more, two or more, three or more, or all four) framework regions selected from VL FR1, VL FR2, VL FR3, and VL FR4 (as shown in Tables 24-27). In some embodiments, the VL FR1 comprises a sequence according to Formula VII: DIVMTQSPLSLPVTPGX$_1$X$_2$ASISC (SEQ ID NO: 44), wherein X$_1$ is E or G, and X$_2$ is P or S. In some embodiments, VL FR1 comprises a sequence selected from the group consisting of SEQ ID NOs: 41-43. In some embodiments, the VL FR2 comprises a sequence according to Formula VIII: WYLQKPGQX$_1$PQLLIY (SEQ ID NO: 47), wherein X$_1$ is S or P. In some embodiments, VL FR2 comprises a sequence selected from the group consisting of SEQ ID NOs: 45-46. In some embodiments, the VL FR3 comprises a sequence according to Formula IX: GVPDRX$_1$iSGSGSGT DFTLKISRX$_2$EAEDVGX$_3$YYC (SEQ ID NO: 52), wherein X$_1$ is F or L, X$_2$ is A or V, and X$_3$ is V or A. In some embodiments, VL FR3 comprises a sequence selected from the group consisting of SEQ ID NOs: 48-51. In some embodiments, the VL FR4 comprises a sequence of FGGGTKVEIK (SEQ ID NO: 53). In some embodiments, anti-Sortilin antibodies of the present disclosure comprise a light chain variable region comprising a VL FR1 comprising the sequence according to Formula VII, a VL FR2 comprising the sequence according to Formula VIII, a VL FR3 comprising the sequence according to Formula IX, and a VL FR4 comprising the sequence of SEQ ID NO: 53.

In some embodiments, anti-Sortilin antibodies of the present disclosure comprise a light chain variable region comprising a VL FR1 comprising the sequence selected from SEQ ID NOs: 41-43, a VL FR2 comprising the sequence selected from SEQ ID NOs: 45-46, a VL FR3 comprising the sequence selected from SEQ ID NOs: 48-51, and a VL FR4 comprising the sequence of SEQ ID NO: 53.

In some embodiments, anti-Sortilin antibodies of the present disclosure comprise a light chain variable region comprising a VL FR1, a VL FR2, a VL FR3, and VL FR4 of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, or S-60-24 (as shown in Tables 24-27).

In some embodiments, anti-Sortilin antibodies of the present disclosure comprise a heavy chain variable region comprising one or more (e.g., one or more, two or more, three or more, or all four) framework regions selected from VH FR1, VH FR2, VH FR3, and VH FR4 (as shown in Tables 20-23), and a light chain variable region comprising one or more (e.g., one or more, two or more, three or more, or all four) framework regions selected from VL FR1, VL FR2, VL FR3, and VL FR4 (as shown in Tables 24-27). In some embodiments, anti-Sortilin antibodies of the present disclosure comprise a heavy chain variable region comprising a VH FR1 comprising the sequence of SEQ ID NO: 35, a VH FR2 comprising the sequence of SEQ ID NO: 36, a VH FR3 according to Formula VI, and a VH FR4 comprising the sequence of SEQ ID NO: 40; and a light chain variable region comprising a VL FR1 comprising the sequence according to Formula VII, a VL FR2 comprising the sequence according to Formula VIII, a VL FR3 comprising the sequence according to Formula IX, and a VL FR4 comprising the sequence of SEQ ID NO: 53. In some embodiments, anti-Sortilin antibodies of the present disclosure comprise a heavy chain variable region comprising a VH FR1 comprising the sequence of SEQ ID NO: 35, a VH FR2 comprising the sequence of SEQ ID NO: 36, a VH FR3 comprising the sequence selected from SEQ ID NOs: 37-38, and a VH FR4 comprising the sequence of SEQ ID NO: 40; a light chain variable region comprising a VL FR1 comprising the sequence selected from SEQ ID NOs: 41-43, a VL FR2 comprising the sequence selected from SEQ ID NOs: 45-46, a VL FR3 comprising the sequence selected from SEQ ID NOs: 48-51, and a VL FR4 comprising the sequence of SEQ ID NO: 53.

In some embodiments, anti-Sortilin antibodies of the present disclosure comprise a heavy chain variable region comprising a VH FR1, a VH FR2, a VH FR3, and VH FR4 of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, or S-60-24 (as shown in Tables 20-23), and a light chain variable region comprising a VL FR1, a VL FR2, a VL FR3, and VL FR4 of antibody S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16; S-60-18, S-60-19, or S-60-24 (as shown in Tables 24-27).

Anti-Sortilin Antibody Activities

In certain aspects of any of the anti-Sortilin antibodies, anti-Sortilin antibodies of the present disclosure can inhibit one or more activities of a Sortilin protein, including, but not limited to, decreasing cellular levels of Sortilin (e.g., cell surface levels of Sortilin, intracellular levels of Sortilin, and/or total levels of Sortilin); increasing Progranulin levels (e.g., extracellular levels of Progranulin and/or cellular levels of Progranulin); and inhibiting the interaction (e.g., binding) between Progranulin and Sortilin. As contemplated herein, anti-Sortilin antibodies of the present disclosure may inhibit additional activities of a Sortilin protein, including but not limited to inhibiting interaction (e.g., binding) with one or more of pro-neurotrophins of the present disclosure (pro-neurotrophin-3, pro-neurotrophin-4/5, pro-NGF, pro-BDNF, etc.), neurotrophins of the present disclosure (neurotrophin-3, neurotrophin-4/5, NGF, BDNF, etc.), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), and receptor associated protein (RAP), decreasing secretion of PCSK9, decreasing production of beta amyloid peptide..

In certain embodiments, the present disclosure provides an anti-Sortilin antibody, wherein (a) the anti-Sortilin antibody increases extracellular levels of Progranulin, decreases cellular levels of Sortilin, inhibits interaction between Sortilin and Progranulin, or any combination thereof; (b) the anti-Sortilin antibody decreases cell surface levels of Sortilin, increases extracellular levels of Progranulin, inhibits interaction between Sortilin and Progranulin, or any combination thereof; (c) the anti-Sortilin antibody decreases cell surface levels of Sortilin, decreases intracellular levels of Sortilin, decreases total levels of Sortilin, or any combination thereof; (d) the anti-Sortilin antibody induces Sortilin degradation, Sortilin cleavage, Sortilin internalization, Sortilin down regulation, or any combination thereof; (e) the anti-Sortilin antibody decreases cellular levels of Sortilin and inhibits the interaction between Sortilin and Progranulin; (f) the anti-Sortilin antibody decreases cellular levels of Sortilin and increases cellular levels of Progranulin; and/or (g) the anti-Sortilin antibody increases the effective concentration of Progranulin.

In certain embodiments, the present disclosure provides an anti-Sortilin antibody, wherein the anti-Sortilin antibody decreases cell surface levels of Sortilin, increases extracellular levels of Progranulin, inhibits interaction between Sortilin and Progranulin, or any combination thereof.

In some embodiments, an anti-Sortilin antibody of the present disclosure (a) reduces cell surface levels of Sortilin with a half maximal effective concentration ($EC_{50}$) that is less than 150 pM, as measured by flow cytometry; (b) reduces cell surface levels of Sortilin by more than about 50% at 1.25 nM IgG, by more than about 80% at 0.63 nM IgG, or by more than about 69% at 150 nM IgG relative to control, as measured by flow cytometry; increases Progranulin secretion by more than about 1.13 fold over control at 0.63 nM IgG, or by more than about 1.22 fold over control at 50 nM IgG, as measured by standard ELISA; blocks binding of Progranulin to Sortilin with a half maximal effective concentration ($EC_{50}$) that is less than 0.325 nM, as measured by flow cytometry; (e) blocks binding of Progranulin to Sortilin by more than about 88% at 50 nM IgG, or by more than about 27.5% at 150 nM IgG relative to control, as measured by flow cytometry; or (f) any combination thereof (see, e.g., Examples 2-4).

In some embodiments, an anti-Sortilin antibody of the present disclosure (a) reduces cell surface levels of Sortilin with a half maximal effective concentration ($EC_{50}$) that is less than 681 pM, as measured by flow cytometry; (b) reduces cell surface levels of Sortilin by more than about 40% at 1.25 nM IgG, by more than about 29% at 0.6 nM IgG, or by more than about 62% at 150 nM IgG relative to control, as measured by flow cytometry; (c) increases Progranulin secretion by more than about 1.11 fold over control at 0.63 nM IgG, or by more than about 1.75 fold over control at 50 nM IgG, as measured by standard ELISA; (d) blocks binding of Progranulin to Sortilin with a half maximal effective concentration ($EC_{50}$) that is less than 0.751 nM, as measured by flow cytometry; (e) blocks binding of Progranulin to Sortilin by more than about 90% at 50 nM IgG, or by more than about 95% at 150 nM IgG relative to control, as measured by flow cytometry; or (f) any combination thereof (see, e.g., Examples 2-4). Decreasing Sortilin levels In some embodiments, anti-Sortilin antibodies of the present disclosure bind to a Sortilin protein of the present disclosure expressed on the surface of a cell and modulate (e.g., induce or inhibit) one or more Sortilin activities of the present disclosure after binding to the surface-expressed Sortilin protein.

In some embodiments, anti-Sortilin antibodies of the present disclosure decrease cellular levels of Sortilin in vitro. In some embodiments, anti-Sortilin antibodies of the present disclosure may decrease cellular levels of Sortilin in vivo (e.g., in the brain, and/or peripheral organs of an individual). In some embodiments, a decrease in cellular levels of Sortilin comprises a decrease in cell surface levels of Sortilin. As used herein, an anti-Sortilin antibody decreases cell surface levels of Sortilin if it induces a decrease at saturating antibody concentrations (e.g., 0.6 nM, 0.63 nM, 1.25 nM, 50 nM or 150 nM) and/or relative to a control antibody (e.g. an anti-Sortilin antibody having a heavy chain variable region and a light chain variable region corresponding to S-60) in cell surface levels of Sortilin as measured by any in vitro cell-based assays or suitable in vivo model described herein or known in the art. In some embodiments, a decrease in cellular levels of Sortilin comprises a decrease in intracellular levels of Sortilin. As contemplated herein, an anti-Sortilin antibody decreases intracellular levels of Sortilin if it induces a decrease at saturating antibody concentrations and/or relative to a control antibody (e.g. an anti-Sortilin antibody having a heavy chain variable region and a light chain variable region corresponding to S-60) in intracellular levels of Sortilin as measured by any in vitro cell-based assays or suitable in vivo model described herein or known in the art. In some embodiments, a decrease in cellular levels of Sortilin comprises a decrease in total levels of Sortilin. As contemplated herein, an anti-Sortilin antibody decreases total levels of Sortilin if it induces a decrease at saturating antibody concentrations and/or relative to a control antibody (e.g. an anti-Sortilin antibody having a heavy chain variable region and a light chain variable region corresponding to S-60) in total levels of Sortilin as measured by any in vitro cell-based assays or suitable in vivo model described herein or known in the art.

As used herein, levels of Sortilin may refer to expression levels of the gene encoding Sortilin; to expression levels of one or more transcripts encoding Sortilin; to expression levels of Sortilin protein; and/or to the amount of Sortilin protein present within cells and/or on the cell surface. Any methods known in the art for measuring levels of gene expression, transcription, translation, and/or protein abundance or localization may be used to determine the levels of Sortilin.

Cellular levels of Sortilin may refer to, without limitation, cell surface levels of Sortilin, intracellular levels of Sortilin, and total levels of Sortilin. In some embodiments, a decrease in cellular levels of Sortilin comprises decrease in cell surface levels of Sortilin. In some embodiments, anti-Sortilin antibodies of the present disclosure that decrease cellular levels of Sortilin (e.g., cell surface levels of Sortilin) have one or more of the following characteristics: (1) inhibits or reduces one or more Sortilin activities; (2) the ability to inhibit or reduce binding of a Sortilin to one or more of its ligands; (3) the ability to reduce Sortilin expression in Sortilin-expressing cells; (4) the ability to interact, bind, or recognize a Sortilin protein; (5) the ability to specifically interact with or bind to a Sortilin protein; and (6) the ability to treat, ameliorate, or prevent any aspect of a disease or disorder described or contemplated herein.

In some embodiments, an isolated anti-Sortilin antibody of the present disclosure induces downregulation of Sortilin. In some embodiments, an isolated anti-Sortilin antibody of the present disclosure induces cleavage of Sortilin. In some embodiments, an isolated anti-Sortilin antibody of the present disclosure induces internalization of Sortilin. In some embodiments, an isolated anti-Sortilin antibody of the present disclosure induces shedding of Sortilin. In some embodiments, an isolated anti-Sortilin antibody of the present disclosure induces degradation of Sortilin. In some embodiments, an isolated anti-Sortilin antibody of the present disclosure induces desensitization of Sortilin. In some embodiments, an isolated anti-Sortilin antibody of the present disclosure acts as a ligand mimetic to transiently activate Sortilin. In some embodiments, an isolated anti-Sortilin antibody of the present disclosure acts as a ligand mimetic and transiently activates Sortilin before inducing a decrease in cellular levels of Sortilin and/or inhibition of interaction (e.g., binding) between Sortilin and one or more Sortilin ligands. In some embodiments, an isolated anti-Sortilin antibody of the present disclosure acts as a ligand mimetic and transiently activates Sortilin before inducing degradation of Sortilin. In some embodiments, an isolated anti-Sortilin antibody of the present disclosure acts as a ligand mimetic and transiently activates Sortilin before inducing cleavage of Sortilin. In some embodiments, an isolated anti-Sortilin antibody of the present disclosure acts as a ligand mimetic and transiently activates Sortilin before inducing internalization of Sortilin. In some embodiments, an isolated anti-Sortilin antibody of the present disclosure acts as a ligand mimetic and transiently activates Sortilin before inducing shedding of Sortilin. In some embodiments, an isolated anti-Sortilin antibody of the present disclosure acts as a ligand mimetic and transiently activates Sortilin before inducing downregulation of Sortilin expression. In some embodiments, an isolated anti-Sortilin antibody of the present disclosure acts as a ligand mimetic and transiently activates Sortilin before inducing desensitization of Sortilin.

In certain embodiments, anti-Sortilin antibodies of the present disclosure may decrease cellular levels of Sortilin (e.g., cell surface levels of Sortilin, intracellular levels of Sortilin, and/or total levels of Sortilin) by inducing Sortilin degradation. Accordingly, in some embodiments, anti-Sortilin antibodies of the present disclosure induce Sortilin degradation.

Anti-Sortilin antibodies of the present disclosure may decrease cellular levels (e.g., cell surface levels) of Sortilin with a half-maximal effective concentration ($EC_{50}$) (e.g., when measured in vitro) in the picomolar range. In certain embodiments, the $EC_{50}$ of the antibody is less than about 680.9 pM. In certain embodiments, the $EC_{50}$ of the antibody is about 72.58 pM to about 680.9 nM. In certain embodiments, the $EC_{50}$ of the antibody is about 103.6 pM to about 680.9 nM. In certain embodiments, the $EC_{50}$ of the antibody is less than about 600 pM, 500 pM, 400 pM, 300 pM, 200 pM, 100 pM, 50 pM, 40 pM, 30 pM, 20 pM, 10 pM, 1 pM, or 0.5 pM.

In some embodiments, the $EC_{50}$ of the antibody is less than about or equal to about 675 pM, 650 pM, 625 pM, 600 pM, 575 pM, 550 pM, 525 pM, 500 pM, 475 pM, 450 pM, 425 pM, 400 pM, 375 pM, 350 pM, 325 pM, 300 pM, 275 pM, 250 pM, 225 pM, 200 pM, 175 pM, 150 pM, 125 pM, 100 pM, 90 pM, 80 pM, 70 pM, 60 pM, 50 pM, 40 pM, 30 pM, 20 pM, 10 pM, 9 pM, 8 pM, 7 pM, 6 pM, 5 pM, 4 pM, 3 pM, 2 pM, 1 pM, or 0.5 pM.

In some embodiments, the $EC_{50}$ of the antibody is less than about 680.9 pM. In some embodiments, the $EC_{50}$ of the antibody is greater than about or equal to about 0.1 pM, 0.5 pM, 1 pM, 10 pM, 20 pM, 30 pM, 40 pM, 50 pM, 60 pM, 70 pM, 80 pM, 90 pM, 100 pM, 125 pM, 150 pM, 175 pM, 200 pM, 225 pM, 250 pM, 275 pM, 300 pM, 325 pM, 350 pM, 375 pM, 400 pM, 425 pM, 450 pM, 475 pM, 500 pM, 525 pM, 550 pM, 575 pM, 600 pM, 625 pM, 650 pM, 675 pM. That is, the $EC_{50}$ of the antibody can be any of a range having an upper limit of about 675 pM, 650 nM, 650 pM, 625 pM, 600 pM, 575 pM, 550 pM, 525 pM, 500 pM, 475 pM, 450 pM, 425 pM, 400 pM, 375 pM, 350 pM, 325 pM, 300 pM, 275 pM, 250 pM, 225 pM, 200 pM, 175 pM, 150 pM, 125 pM, 100 pM, 90 pM, 80 pM, 70 pM, 60 pM, 50 pM, 40 pM, 30 pM, 20 pM, 10 pM, 1 pM, or 0.5 pM, and an independently selected lower limit of about 0.1 pM, 0.5 pM, 1 pM, 10 pM, 20 pM, 30 pM, 40 pM, 50 pM, 60 pM, 70 pM, 80 pM, 90 pM, 100 pM, 125 pM, 150 pM, 175 pM, 200 pM, 225 pM, 250 pM, 275 pM, 300 pM, 325 pM, 350 pM, 375 pM, 400 pM, 425 pM, 450 pM, 475 pM, 500 pM, 525 pM, 550 pM, 575 pM, 600 pM, 625 pM, 650 pM, or 675 pM, wherein the lower limit is less than the upper limit. In some embodiments, the $EC_{50}$ of the antibody is any of about 1 pM, 2 pM, 3 pM, 4 pM, 5 pM, 6 pM, 7 pM, 8 pM, 9 pM, 10 pM, 15 pM, 20 pM, 25 pM, 30 pM, 35 pM, 40 pM, 45 pM, 50 pM, 55 pM, 60 pM, 65 pM, 70 pM, 75 pM, 80 pM, 85 pM, 90 pM, 95 pM, 100 pM, 105 pM, 110 pM, 115 pM, 120 pM, 125 pM, 130 pM, 135 pM, 140 pM, 145 pM, 150 pM, 155 pM, 160 pM, 165 pM, 170 pM, 175 pM, 180 pM, 185 pM, 190 pM, 195 pM, or 200 pM.

In some embodiments, an anti-Sortilin antibody of the present disclosure reduces cell surface levels of Sortilin with a half maximal effective concentration ($EC_{50}$) that is less than 150 pM, as measured by flow cytometry. In some embodiments, the $EC_{50}$ of an anti-Sortilin antibody of the present disclosure is about 103.6 pM. In some embodiments, the $EC_{50}$ of an anti-Sortilin antibody of the present disclosure is about 72.58 pM.

In some embodiments, an anti-Sortilin antibody of the present disclosure reduces cell surface levels of Sortilin by more than about 40% at 1.25 nM IgG or by more than about 80% at 0.63 nM IgG, as measured by flow cytometry. In some embodiments, an anti-Sortilin antibody of the present disclosure reduces cell surface levels of Sortilin by about 60.92% at 1.25 nM IgG, as measured by flow cytometry. In some embodiments, an anti-Sortilin antibody of the present disclosure reduces cell surface levels of Sortilin by about 69.3% at 150 nM IgG, as measured by flow cytometry. In some embodiments, an anti-Sortilin antibody of the present disclosure reduces cell surface levels of Sortilin by about 70.3% at 150 nM IgG, as measured by flow cytometry.

Various methods of measuring antibody $EC_{50}$ values are known in the art, including, for example, by flow cytometry (See e.g., Example 2). In some embodiments, the $EC_{50}$ is measured in vitro using cells engineered to express human Sortilin. In some embodiments, the $EC_{50}$ is measured at a temperature of approximately 4° C. In some embodiments, the $EC_{50}$ is measured at a temperature of approximately 25° C. In some embodiments, the $EC_{50}$ is measured at a temperature of approximately 35° C. In some embodiments, the $EC_{50}$ is measured at a temperature of approximately 37° C. In some embodiments, the $EC_{50}$ is determined using a monovalent antibody (e.g., a Fab) or a full-length antibody in a monovalent form. In some embodiments, the $EC_{50}$ is determined using antibodies containing constant regions that demonstrate enhanced Fc receptor binding. In some embodiments, the $EC_{50}$ is determined using antibodies containing constant regions that demonstrate reduced Fc receptor binding.

In some embodiments, anti-Sortilin antibodies of the present disclosure have higher potencies in reducing cell surface levels of Sortilin relative to a control antibody (e.g. an anti-Sortilin antibody having a heavy chain variable region and a light chain variable region corresponding to S-60). In some embodiments, anti-Sortilin antibodies of the present disclosure decrease cellular levels (e.g., cell surface levels) of Sortilin with a lower $EC_{50}$ (e.g., as measured in vitro) than a control antibody (e.g. an anti-Sortilin antibody having a heavy chain variable region and a light chain variable region corresponding to S-60). In some embodiments, anti-Sortilin antibodies of the present disclosure decrease cellular levels (e.g., cell surface levels) of Sortilin with an $EC_{50}$ that is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% lower than the $EC_{50}$ of a control antibody (e.g. an anti-Sortilin antibody having a heavy chain variable region and a light chain variable region corresponding to S-60). In some embodiments, anti-Sortilin antibodies of the present disclosure decrease cellular levels (e.g., cell surface levels) of Sortilin with an $EC_{50}$ that is at least about 1-fold, at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 12.5-fold, at least about 15-fold, at least about 17.5-fold, at least about 20-fold, at least about 22.5-fold, at least about 25-fold, at least about 27.5-fold, at least about 30-fold, at least about 50-fold, or at least about 100-fold lower than the $EC_{50}$ of a control antibody (e.g. an anti-Sortilin antibody having a heavy chain variable region and a light chain variable region corresponding to S-60).

In some embodiments, anti-Sortilin antibodies of the present disclosure have an $EC_{50}$ that is at least 1.5-fold lower than control antibody (e.g. an anti-Sortilin antibody having a heavy chain variable region and a light chain variable region corresponding to S-60). In some embodiments, anti-Sortilin antibodies of the present disclosure have an $EC_{50}$ that is at least 1.1-fold lower than control antibody (e.g. an anti-Sortilin antibody having a heavy chain variable region and a light chain variable region corresponding to S-60).

In some embodiments, an anti-Sortilin antibody of the present disclosure (a) reduces cell surface levels of Sortilin with a half maximal effective concentration ($EC_{50}$) that is less than 681 pM, as measured by flow cytometry; (b) reduces cell surface levels of Sortilin by more than about 40% at 1.25 nM IgG, by more than about 29% at 0.6 nM IgG, or by more than about 62% at 150 nM IgG relative to control, as measured by flow cytometry; (c) increases Progranulin secretion by more than about 1.11 fold over control at 0.63 nM IgG, or by more than about 1.75 fold over control at 50 nM IgG, as measured by standard ELISA; (d) blocks binding of Progranulin to Sortilin with a half maximal effective concentration ($EC_{50}$) that is less than 0.751 nM, as measured by flow cytometry; (e) blocks binding of Progranulin to Sortilin by more than about 90% at 50 nM IgG, or by more than about 95% at 150 nM IgG relative to control, as measured by flow cytometry; or (f) any combination thereof (see, e.g., Examples 2-4).

Increasing Progranulin Levels

In some embodiments, anti-Sortilin antibodies of the present disclosure increase extracellular levels of Progranulin in vitro. In some embodiments, anti-Sortilin antibodies of the present disclosure may increase cellular levels of Progranulin or in vivo (e.g., in the brain, blood, and/or peripheral organs of an individual). As used herein, an anti-Sortilin antibody increases extracellular levels of Progranulin if it induces an increase at saturating antibody concentrations (e.g., 0.6 nM, 0.63 nM, 1.25 nM, 50 nM or 150 nM) and/or relative to a control antibody (e.g. an anti-Sortilin antibody having a heavy chain variable region and a light chain variable region corresponding to S-60) in extracellular levels of Progranulin as measured by any in vitro cell-based assays or in tissue-based (such as brain tissue-based) assays described herein or known in the art. As contemplated herein, an anti-Sortilin antibody increases cellular levels of Progranulin if it induces an increase at saturating antibody concentrations (e.g., 0.6 nM, 0.63 nM, 1.25 nM, 50 nM or 150 nM) and/or relative to a control antibody (e.g. an anti-Sortilin antibody having a heavy chain variable region and a light chain variable region corresponding to S-60) in cellular levels of Progranulin as measured by any in vitro cell-based assays or in tissue-based (such as brain tissue-based) assays described herein or known in the art.

As used herein, levels of Progranulin may refer to expression levels of the gene encoding Progranulin; to expression levels of one or more transcripts encoding Progranulin; to expression levels of Progranulin protein; and/or to the amount of Progranulin protein secreted from cells and/or present within cells. Any methods known in the art for measuring levels of gene expression, transcription, translation, protein abundance, protein secretion, and/or protein localization may used to determine the levels of Progranulin.

As used herein, Progranulin levels may refer to, without limitation, extracellular levels of Progranulin, intracellular levels of Progranulin, and total levels of Progranulin. In some embodiments, an increase in levels of Progranulin comprises an increase in extracellular levels of Progranulin.

In some embodiments, an anti-Sortilin antibody of the present disclosure increases Progranulin secretion by more than about 1.11 fold over control at 0.63 nM IgG, as measured by standard ELISA. In some embodiments, an anti-Sortilin antibody of the present disclosure increases Progranulin secretion by about 1.42 fold over control at 0.63 nM IgG, as measured by standard ELISA. In some embodiments, an anti-Sortilin antibody of the present disclosure increases Progranulin secretion by more than about 1.75 fold over control at 50 nM IgG, as measured by standard ELISA. In some embodiments, an anti-Sortilin antibody of the present disclosure increases Progranulin secretion by about 1.97 fold over control at 50 nM IgG, as measured by standard ELISA. In some embodiments, an anti-Sortilin antibody of the present disclosure increases Progranulin secretion by about 2.29 fold over control at 50 nM IgG, as measured by standard ELISA.

Various methods of measuring Progranulin secretion are known in the art, including, for example, by ELISA (See e.g., Examples 2 and 4). In some embodiments, the $EC_{50}$ is measured in vitro using cells expressing human Sortilin. In some embodiments, Progranulin secretion is determined using a monovalent antibody (e.g., a Fab) or a full-length antibody in a monovalent form. In some embodiments, Progranulin secretion is determined using antibodies containing constant regions that demonstrate enhanced Fc receptor binding. In some embodiments, Progranulin secretion is determined using antibodies containing constant regions that demonstrate reduced Fc receptor binding.

In some embodiments, anti-Sortilin antibodies of the present disclosure have higher potencies in increasing levels of Progranulin relative to a control antibody (e.g. an anti-Sortilin antibody having a heavy chain variable region and a light chain variable region corresponding to S-60). In some embodiments, anti-Sortilin antibodies of the present disclosure increase levels (e.g., extracellular levels) of Progranulin with a lower $EC_{50}$ (e.g., as measured in vitro) than a control antibody (e.g. an anti-Sortilin antibody having a heavy chain variable region and a light chain variable region corresponding to S-60). In some embodiments, anti-Sortilin antibodies of the present disclosure increase levels (e.g., extracellular levels) of Progranulin by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% than a control antibody (e.g. an anti-Sortilin antibody having a heavy chain variable region and a light chain variable region corresponding to S-60). In some embodiments, anti-Sortilin antibodies of the present disclosure increase levels (e.g., extracellular levels) of Progranulin by about 1-fold, at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 12.5-fold, at least about 15-fold, at least about 17.5-fold, at least about 20-fold, at least about 22.5-fold, at least about 25-fold, at least about 27.5-fold, at least about 30-fold, at least about 50-fold, or at least about 100-fold higher than a control antibody (e.g. an anti-Sortilin antibody having a heavy chain variable region and a light chain variable region corresponding to S-60).

In some embodiments, anti-Sortilin antibodies of the present disclosure increase Progranulin levels by about 1.1-fold higher than a control antibody (e.g. an anti-Sortilin antibody having a heavy chain variable region and a light chain variable region corresponding to S-60). In some embodiments, anti-Sortilin antibodies of the present disclosure increase Progranulin levels by about 1.3-fold higher than a control antibody (e.g. an anti-Sortilin antibody having a heavy chain variable region and a light chain variable region corresponding to S-60).

In some embodiments, anti-Sortilin antibodies of the present disclosure increase the effective concentration of Progranulin. The effective concentration of Progranulin refers to the concentration of Progranulin in plasma or cerebrospinal fluid. In some embodiments, an increase in the effective concentration of Progranulin is an increase of greater than 1.5 fold. In some embodiments, the effective concentration of Progranulin is increased for 7-28 days.

Decreasing Interaction Between Sortilin and Binding Partner

In certain embodiments, the anti-Sortilin antibodies inhibit interaction (e.g., binding) between a Sortilin protein of the present disclosure and one or more proteins selected from Progranulin, a pro-neurotrophin, a neurotrophin, pro-neurotrophin-3, neurotrophin-3, pro-neurotrophin-4/5, neurotrophin-4/5, pro-nerve growth factor (pro-NGF), nerve growth factor (NGF), pro-brain-derived neurotrophic factor (pro-BDNF), brain-derived neurotrophic factor (BDNF), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), PCSK9, and receptor associated protein (RAP), and/or naturally occurring variants. In a specific embodiment, anti-Sortilin antibodies of the present disclosure inhibit interaction (e.g., binding) between a Sortilin protein of the present disclosure and Progranulin.

In some embodiments, the anti-Sortilin antibodies may inhibit interaction (e.g., binding) between a Sortilin protein of the present disclosure and a neurotrophin of the present disclosure, such as a pro-neurotrophin, pro-neurotrophin-3, pro-neurotrophin-4/5, pro-NGF, pro-BDNF, neurotrophin-3, neurotrophin-4/5, NGF, and BDNF. In other embodiments, the anti-Sortilin antibodies may inhibit interaction (e.g., binding) between a Sortilin protein of the present disclosure and neurotensin. In other embodiments, the anti-Sortilin antibodies inhibit interaction (e.g., binding) between a Sortilin protein of the present disclosure and p75. In other embodiments, the anti-Sortilin antibodies may inhibit interaction (e.g., binding) between a Sortilin protein of the present disclosure and a Sort-pro. In other embodiments, the anti-Sortilin antibodies may inhibit interaction (e.g., binding) between a Sortilin protein of the present disclosure and APP. In other embodiments, the anti-Sortilin antibodies may inhibit the production of the A beta peptide. In other embodiments, the anti-Sortilin antibodies may inhibit the transport and secretion of PCSK9. In other embodiments, the anti-Sortilin antibodies may inhibit interaction (e.g., binding) between a Sortilin protein of the present disclosure and LpL. In other embodiments, the anti-Sortilin antibodies may inhibit interaction (e.g., binding) between a Sortilin protein of the present disclosure and APOA5. In other embodiments, the anti-Sortilin antibodies may inhibit interaction (e.g., binding) between a Sortilin protein of the present disclosure and APOE. In other embodiments, the anti-Sortilin antibodies may inhibit interaction (e.g., binding) between a Sortilin protein of the present disclosure and RAP.

In some embodiments, anti-Sortilin antibodies of the present disclosure bind to a Sortilin protein of the present disclosure expressed on the surface of cell and the naked antibodies inhibit interaction (e.g., binding) between the Sortilin protein and one or more Sortilin ligands. In some embodiments, anti-Sortilin antibodies of the present disclosure that bind to a Sortilin protein of the present inhibit interaction (e.g., binding) between the Sortilin protein and one or more Sortilin ligands by reducing the effective levels of Sortilin that is available to interact with these proteins either on the cell surface or inside the cell. In some embodiments, anti-Sortilin antibodies of the present disclosure that bind to a Sortilin protein of the present inhibit interaction (e.g., binding) between the Sortilin protein and one or more Sortilin ligands by inducing degradation of Sortilin.

A. Decreasing Interaction Between Sortilin and Progranulin

In some embodiments, anti-Sortilin antibodies of the present disclosure increase Progranulin levels and/or decrease cellular levels of Sortilin while blocking (e.g. inhibiting) the interaction (e.g., binding) between Sortilin and Progranulin. Accordingly, in some embodiments, anti-Sortilin antibodies of the present disclosure block the interaction (e.g., binding) between Sortilin and Progranulin. As used herein, an anti-Sortilin antibody blocks the interaction (e.g., binding) between Sortilin and Progranulin if it decreases Progranulin binding to Sortilin relative to a control antibody (e.g. an anti-Sortilin antibody having a heavy chain variable region and a light chain variable region corresponding to S-60) at saturating antibody concentrations (e.g., 0.6 nM, 0.63 nM, 1.25 nM, 50 nM or 150 nM) in any in vitro assay or cell-based culture assay described herein or known in the art.

Anti-Sortilin antibodies of the present disclosure may decrease Progranulin binding to Sortilin with a half-maximal effective concentration ($EC_{50}$) (e.g., when measured in vitro) in the picomolar range. In certain embodiments, the $EC_{50}$ of the antibody is less than about 2.2 nM. In certain embodiments, the $EC_{50}$ of the antibody is less than about 1.22 nM. In certain embodiments, the $EC_{50}$ of the antibody is less than about 751 pM. In certain embodiments, the $EC_{50}$ of the antibody is about 325 pM to about 751 nM. In certain embodiments, the $EC_{50}$ of the antibody is about 405 pM to about 751 nM. In certain embodiments, the $EC_{50}$ of the antibody is about 588 pM to about 751 nM. In certain embodiments, the $EC_{50}$ of the antibody is less than about 2.2 nM, 2.1 nM, 2.0 nM, 1.9 nM, 1.8 nM, 1.7 nM, 1.6 nM, 1.5 nM, 1.4 nM, 1.3 nM, 1.2 nM, 1.1 nM, 1.0 nM, 900 pM, 800 pM, 700 pM, 600 pM, 500 pM, 400 pM, 300 pM, 200 pM, 100 pM, 50 pM, 40 pM, 30 pM, 20 pM, 10 pM, 1 pM, or 0.5 pM.

In some embodiments, the $EC_{50}$ of the antibody for decreasing Progranulin binding to Sortilin is less than about or equal to about 2.2 nM, 2.1 nM, 2.0 nM, 1.9 nM, 1.8 nM, 1.7 nM, 1.6 nM, 1.5 nM, 1.4 nM, 1.3 nM, 1.2 nM, 1.1 nM, 1.0 nM, 900 pM, 800 pM, 700 pM, 600 pM, 500 pM, 475 pM, 450 pM, 425 pM, 400 pM, 375 pM, 350 pM, 325 pM, 300 pM, 275 pM, 250 pM, 225 pM, 200 pM, 175 pM, 150 pM, 125 pM, 100 pM, 90 pM, 80 pM, 70 pM, 60 pM, 50 pM, 40 pM, 30 pM, 20 pM, 10 pM, 9 pM, 8 pM, 7 pM, 6 pM, 5 pM, 4 pM, 3 pM, 2 pM, 1 pM, or 0.5 pM.

In some embodiments, the $EC_{50}$ of an anti-Sortilin antibody of the present disclosure is about 1.22 nM. In some embodiments, the $EC_{50}$ of an anti-Sortilin antibody of the present disclosure is about 588 pM. In some embodiments, the $EC_{50}$ of an anti-Sortilin antibody of the present disclosure is about 405 pM. In some embodiments, the $EC_{50}$ of an anti-Sortilin antibody of the present disclosure is about 325 pM.

Various methods of measuring antibody $EC_{50}$ values are known in the art, including, for example, by flow cytometry (See e.g., Example 3). In some embodiments, the $EC_{50}$ for decreasing Progranulin binding to Sortlin is measured in vitro using cells expressing human Sortilin. In some embodiments, the $EC_{50}$ is measured at a temperature of approximately 4° C. In some embodiments, the $EC_{50}$ is measured at a temperature of approximately 25° C. In some embodiments, the $EC_{50}$ is measured at a temperature of approximately 35° C. In some embodiments, the $EC_{50}$ is measured at a temperature of approximately 37° C. In some embodiments, the $EC_{50}$ for decreasing Progranulin binding to Sortlin is determined using a monovalent antibody (e.g., a Fab) or a full-length antibody in a monovalent form. In some embodiments, the $EC_{50}$ is determined using antibodies containing constant regions that demonstrate enhanced Fc receptor binding. In some embodiments, the $EC_{50}$ for decreasing Progranulin binding to Sortlin is determined using antibodies containing constant regions that demonstrate reduced Fc receptor binding.

In some embodiments, anti-Sortilin antibodies of the present disclosure have higher potencies in reducing Progranulin binding to Sortlin relative to a control antibody (e.g. an anti-Sortilin antibody having a heavy chain variable region and a light chain variable region corresponding to S-60). In some embodiments, anti-Sortilin antibodies of the present disclosure decrease Progranulin binding to Sortlin with a lower $EC_{50}$ (e.g., as measured in vitro) than a control antibody (e.g. an anti-Sortilin antibody having a heavy chain variable region and a light chain variable region corresponding to S-60). In some embodiments, anti-Sortilin antibodies of the present disclosure decrease Progranulin binding to Sortlin with an $EC_{50}$ that is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% lower than the $EC_{50}$ of a control antibody (e.g. an anti-Sortilin antibody having a heavy chain variable region and a light chain variable region corresponding to S-60). In some embodiments, anti-Sortilin antibodies of the present disclosure decrease Progranulin binding to Sortlin with an $EC_{50}$ that is at least about 1-fold, at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 12.5-fold, at least about 15-fold, at least about 17.5-fold, at least about 20-fold, at least about 22.5-fold, at least about 25-fold, at least about 27.5-fold, at least about 30-fold, at least about 50-fold, or at least about 100-fold lower than the $EC_{50}$ of a control antibody (e.g. an anti-Sortilin antibody having a heavy chain variable region and a light chain variable region corresponding to S-60).

In some embodiments, anti-Sortilin antibodies of the present disclosure have an $EC_{50}$ that is at least 1.3-fold lower than control antibody (e.g. an anti-Sortilin antibody having a heavy chain variable region and a light chain variable region corresponding to S-60). In some embodiments, anti-Sortilin antibodies of the present disclosure have an $EC_{50}$ that is at least 1.8-fold lower than control antibody (e.g. an anti-Sortilin antibody having a heavy chain variable region and a light chain variable region corresponding to S-60). In some embodiments, anti-Sortilin antibodies of the present disclosure have an $EC_{50}$ that is at least 1.9-fold lower than control antibody (e.g. an anti-Sortilin antibody having a heavy chain variable region and a light chain variable region corresponding to S-60). In some embodiments, anti-Sortilin antibodies of the present disclosure have an $EC_{50}$ that is at least 2.3-fold lower than control antibody (e.g. an anti-Sortilin antibody having a heavy chain variable region and a light chain variable region corresponding to S-60).

Any in vitro cell-based assays or suitable in vivo model described herein or known in the art may be used to measure inhibition or reduction of interaction (e.g., binding) between Sortilin and one or more Sortilin ligands. In some embodiments, anti-Sortilin antibodies of the present disclosure inhibit or reduce interaction (e.g., binding) between Sortilin and one or more Sortilin ligands by reducing Sortilin expression (e.g., by reducing cell surface levels of Sortilin). In some embodiments, anti-Sortilin antibodies of the present disclosure inhibit or reduce interaction (e.g., binding) between Sortilin and one or more Sortilin ligands by at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more at saturating antibody concentrations utilizing any in vitro assay or cell-based culture assay described herein or known in the art.

In some embodiments, an anti-Sortilin antibody of the present disclosure blocks Progranulin binding to Sortlin by more than about 90% at 50 nM IgG or by more than about 96% at 150 nM IgG, as measured by flow cytometry. In some embodiments, an anti-Sortilin antibody of the present disclosure blocks Progranulin binding to Sortlin by about 90.74% at 50 nM IgG, as measured by flow cytometry. In some embodiments, an anti-Sortilin antibody of the present disclosure blocks Progranulin binding to Sortlin by about 96.5% at 150 nM IgG, as measured by flow cytometry. In some embodiments, an anti-Sortilin antibody of the present disclosure blocks Progranulin binding to Sortlin by about 96.9% at 150 nM IgG, as measured by flow cytometry.

Decreasing Expression of Pro-Inflammatory Mediators

In some embodiments, anti-Sortilin antibodies of the present disclosure may decrease the expression of pro-inflammatory mediators after binding to a Sortilin protein expressed in a cell.

As used herein, pro-inflammatory mediators are proteins involved either directly or indirectly (e.g., by way of pro-inflammatory signaling pathways) in a mechanism that induces, activates, promotes, or otherwise decreases an inflammatory response. Any method known in the art for identifying and characterizing pro-inflammatory mediators may be used.

Examples of pro-inflammatory mediators include, without limitation, cytokines, such as type I and II interferons, IL-6, IL12p70, IL12p40, IL-1β, TNF-α, IL-8, CRP, IL-20 family members, IL-33, LIF, OSM, CNTF, GM-CSF, IL-11, IL-12, IL-17, IL-18, and CRP. Further examples of pro-inflammatory mediators include, without limitation, chemokines, such as CXCL1, CCL2, CCL3, CCL4, and CCL5.

In some embodiments, the anti-Sortilin antibodies of the present disclosure may decrease functional expression and/or secretion of pro-inflammatory mediators, IL-6, IL12p70, IL12p40, IL-1β, TNF-α, CXCL1, CCL2, CCL3, CCL4, and CCL5. In certain embodiments, decreased expression of the pro-inflammatory mediators occurs in macrophages, dendritic cells, monocytes, osteoclasts, Langerhans cells of skin, Kupffer cells, T cells, and/or microglial cells. Decreased expression may include, without limitation, a decrease in gene expression, a decrease in transcriptional expression, or a decrease in protein expression. Any method known in the art for determining gene, transcript (e.g., mRNA), and/or protein expression may be used. For example, Northern blot analysis may be used to determine pro-inflammatory mediator gene expression levels, RT-PCR may be used to determine the level of pro-inflammatory mediator transcription, and Western blot analysis may be used to determine pro-inflammatory mediator protein levels.

As used herein, a pro-inflammatory mediator may have decreased expression if its expression in one or more cells of a subject treated with a Sortilin agent, such as an agonist anti-Sortilin antibody of the present disclosure is more than the expression of the same pro-inflammatory mediator expressed in one or more cells of a corresponding subject that is not treated with the agonist anti-Sortilin antibody. In some embodiments, the anti-Sortilin antibody of the present disclosure may decrease pro-inflammatory mediator expression in one or more cells of a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to pro-inflammatory mediator expression in one or more cells of a corresponding subject that is not treated with the anti-Sortilin antibody. In other embodiments, the anti-Sortilin antibody may decrease pro-inflammatory mediator expression in one or more cells of a subject by at least at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to pro-inflammatory mediator expression in one or more cells of a corresponding subject that is not treated with the anti-Sortilin antibody.

In some embodiments, an anti-Sortilin antibody according to any of the above embodiments may incorporate any of the features, singly or in combination, as described in Sections 1-7 below:

(1) Anti-Sortilin Antibody Binding Affinity

In some embodiments of any of the antibodies provided herein, the antibody has a dissociation constant (Kd) of <1 μM, <100 nM, <10 nM, <1 nM, <0.1 nM, <0.01 nM, or <0.001 nM (e.g., $10^{-8}$ M or less, e.g., from $10^{-8}$ M to $10^{-13}$ M, e.g., from $10^{-9}$ M to $10^{-13}$ M).

Anti-Sortilin antibodies of the present disclosure may have nanomolar or even picomolar affinities for the target antigen (e.g., human Sortilin or mammalian Sortilin). In certain embodiments, the binding affinity of an anti-Sortilin antibody of the present disclosure for target antigen (e.g., human Sortilin or mammalian Sortilin) is measured by the dissociation constant, $K_D$. Dissociation constants may be determined through any analytical technique, including any biochemical or biophysical technique such as fluorescent activated cell sorting (FACS), flow cytometry, enzyme-linked immunosorbent assay (ELISA), surface plasmon resonance (SPR), BioLayer interferometry (see, e.g., Octet System by ForteBio), meso scale discover (see, e.g., MSD-SET), isothermal titration calorimetry (ITC), differential scanning calorimetry (DSC), circular dichroism (CD), stopped-flow analysis, and colorimetric or fluorescent protein melting analyses; or a cell binding assay. In some embodiments, the $K_D$ for Sortilin is determined at a temperature of approximately 25° C. In some embodiments, the dissociation constant ($K_D$) may be measured at 4° C. or room temperature utilizing, for example, FACS or BioLlayer interferometry assay.

In some embodiments, the $K_D$ for Sortilin is determined at a temperature of approximately 4° C. In some embodiments, the $K_D$ is determined using a monovalent antibody (e.g., a Fab) or a full-length antibody in a monovalent form. In some embodiments, the $K_D$ is determined using a bivalent antibody and monomeric recombinant Sortilin protein.

In certain embodiments, the $K_D$ of an anti-Sortilin antibody of the present disclosure for human Sortilin, mammalian Sortilin, or both, is measured using FACS as described herein (see, e.g., Examples 1 and 4). In certain embodiments, the $K_D$ of an anti-Sortilin antibody of the present disclosure for human Sortilin, mammalian Sortilin, or both, is measured using BioLayer Interferometry as described herein (see, e.g., Example 4).

In some embodiments, the anti-Sortilin antibody has a dissociation constant ($K_D$) for human Sortilin that is up to 2.5-fold lower than an anti-Sortilin antibody comprising a heavy chain variable region comprising the sequence of SEQ ID NO: 56 and a light chain variable region comprising the sequence of SEQ ID NO: 79, wherein the $K_D$ is determined by FACS (see, e.g., Example 1). In some embodiments, the anti-Sortilin antibody has a dissociation constant ($K_D$) for human Sortilin that ranges from about 1.10E-8 M to about 4.68E-10 M wherein the $K_D$ is determined by FACS (see, e.g., Example 1), or about 270 to about 2910 pM wherein the $K_D$ is determined by Bio-layer interferometry (see, e.g., Example 4).

In certain embodiments, the $K_D$ of an anti-Sortilin antibody of the present disclosure for human Sortilin, mammalian Sortilin, or both, may be less than 100 nM, less than 90 nM, less than 80 nM, less than 70 nM, less than 60 nM, less than 50 nM, less than 40 nM, less than 30 nM, less than 20 nM, less than 10 nM, less than 9 nM, less than 8 nM, less than 7 nM, less than 6 nM, less than 5 nM, less than 4 nM, less than 3 nM, less than 2 nM, less than 1 nM, less than 0.5 nM, less than 0.1 nM, less than 0.09 nM, less than 0.08 nM, less than 0.07 nM, less than 0.06 nM, less than 0.05 nM, less than 0.04 nM, less than 0.03 nM, less than 0.02 nM, less than 0.01 nM, less than 0.009 nM, less than 0.008 nM, less than 0.007 nM, less than 0.006 nM, less than 0.005 nM, less than 0.004 nM, less than 0.003 nM, less than 0.002 nM, less than 0.001 nM, or less than 0.001 nM.

The dissociation constants ($K_D$) of anti-Sortilin antibodies for human Sortilin, mammalian Sortilin, or both, may be less than 10 nM, less than 9.5 nM, less than 9 nM, less than 8.5 nM, less than 8 nM, less than 7.5 nM, less than 7 nM, less than 6.9 nM, less than 6.8 nM, less than 6.7 nM, less than 6.6 nM, less than 6.5 nM, less than 6.4 nM, less than 6.3 nM, less than 6.2 nM, less than 6.1 nM, less than 6 nM, less than 5.5 nM, less than 5 nM, less than 4.5 nM, less than 4 nM, less than 3.5 nM, less than 3 nM, less than 2.5 nM, less than 2 nM, less than 1.5 nM, less than 1 nM, less than 0.95 nM, less than 0.9 nM, less than 0.89 nM, less than 0.88 nM, less than 0.87 nM, less than 0.86 nM, less than 0.85 nM, less than 0.84 nM, less than 0.83 nM, less than 0.82 nM, less than 0.81 nM, less than 0.8 nM, less than 0.75 nM, less than 0.7 nM, less than 0.65 nM, less than 0.64 nM, less than 0.63 nM, less than 0.62 nM, less than 0.61 nM, less than 0.6 nM, less than 0.55 nM, less than 0.5 nM, less than 0.45 nM, less than 0.4 nM, less than 0.35 nM, less than 0.3 nM, less than 0.29 nM, less than 0.28 nM, less than 0.27 nM, less than 0.26 nM, less than 0.25 nM, less than 0.24 nM, less than 0.23 nM, less than 0.22 nM, less than 0.21 nM, less than 0.2 nM, less than 0.15 nM, less than 0.1 nM, less that 0.09 nM, less than 0.08 nM, less than 0.07 nM, less than 0.06 nM, less than 0.05 nM, less than 0.04 nM, less than 0.03 nM, less than 0.02 nM, less than 0.01 nM, less that 0.009 nM, less than 0.008 nM, less than 0.007 nM, less than 0.006 nM, less than 0.005 nM, less than 0.004 nM, less than 0.003 nM, less than 0.002 nM, or less than 0.001 nM.

In certain embodiments, the dissociation constant ($K_D$) of the antibody for Sortilin is from about 0.560 nM to about 1.63 nM, for example when the $K_D$ is determined by FACS. In certain embodiments, the dissociation constant ($K_D$) of the antibody for Sortilin is from about 0.270 nM to about 2.910 nM, for example when the $K_D$ is determined by BioLayer Interferometry. In some embodiments, the antibody has a dissociation constant ($K_D$) for human Sortilin, mouse Sortilin, or both, that ranges from about 0.36 nM to about 0.43 nM, or less than 1.02 nM. In some embodiments, the dissociation constant is less than 1.02 nM. In some embodiments, an anti-Sortilin antibody of the present disclosure has a dissociation constant for human Sortilin of 0.560 nM or less.

In one specific embodiment, an anti-Sortilin antibody of the present disclosure has a dissociation constant for human Sortilin of about 0.560 nM. In one specific embodiment, an anti-Sortilin antibody of the present disclosure has a dissociation constant for human Sortilin of about 0.423 nM. In one specific embodiment, an anti-Sortilin antibody of the present disclosure has a dissociation constant for human Sortilin of about 0.365 nM. In one specific embodiment, an anti-Sortilin antibody of the present disclosure has a dissociation constant for human Sortilin of about 0.344 nM. In one specific embodiment, an anti-Sortilin antibody of the present disclosure has a dissociation constant for human Sortilin of about 0.298 nM. In one specific embodiment, an anti-Sortilin antibody of the present disclosure has a dissociation constant for human Sortilin of about 0.270 nM. In another specific embodiment, an anti-Sortilin antibody of the present disclosure has a dissociation constant for human Sortilin of about 0.260 nM.

In some embodiments, anti-Sortilin antibodies of the present disclosure have a lower dissociation constant ($K_D$) for Sortilin than a control anti-Sortilin antibody (e.g., a control anti-Sortilin antibody comprising a heavy chain variable region and a light chain variable region corresponding to S-60. In some embodiments, anti-Sortilin antibodies of the present disclosure have a $K_D$ for a target (e.g., human Sortilin) that is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% lower than the $K_D$ of a control anti-Sortilin antibody for the target (e.g., a control anti-Sortilin antibody comprising a heavy chain variable region and a light chain variable region corresponding to S-60. In some embodiments, anti-Sortilin antibodies of the present disclosure have a $K_D$ for a target (e.g., human Sortilin) that is at least about 1-fold, at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 12.5-fold, at least about 15-fold, at least about 17.5-fold, at least about 20-fold, at least about 22.5-fold, at least about 25-fold, at least about 27.5-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, or at least about 1000-fold lower than the $K_D$ of a control anti-Sortilin antibody for the target (e.g., a control anti-Sortilin antibody comprising a heavy chain variable region and a light chain variable region corresponding to S-60.

In some embodiments, anti-Sortilin antibodies of the present disclosure have a $K_D$ for human Sortilin that is at least 100-fold lower than an anti-Sortilin antibody having a heavy chain variable region and a light chain variable region corresponding to S-60. In some embodiments, anti-Sortilin antibodies of the present disclosure have a $K_D$ for human Sortilin that is at least 50-fold lower than an anti-Sortilin antibody having a heavy chain variable region and a light chain variable region corresponding to S-60. In some embodiments, anti-Sortilin antibodies of the present disclosure have a $K_D$ for human Sortilin that is at least 10-fold lower than an anti-Sortilin antibody having a heavy chain variable region and a light chain variable region corresponding to S-60. In some embodiments, anti-Sortilin antibodies of the present disclosure have a $K_D$ for human Sortilin that is at least 5-fold lower than an anti-Sortilin antibody having a heavy chain variable region and a light chain variable region corresponding to S-60. In some embodiments, anti-Sortilin antibodies of the present disclosure have a $K_D$ for human Sortilin that is at least 2-fold lower than an anti-Sortilin antibody having a heavy chain variable region and a light chain variable region corresponding to S-60.

In a specific embodiment, an anti-Sortilin antibody of the present disclosure has a $K_D$ for human Sortilin that is about 2.79-fold lower than an anti-Sortilin antibody having a heavy chain variable region and a light chain variable region corresponding to S-60. In another specific embodiment, an anti-Sortilin antibody of the present disclosure has a $K_D$ for human Sortilin that is about 2.05-fold lower than an anti-Sortilin antibody having a heavy chain variable region and a light chain variable region corresponding to S-60.

(2) Antibody Fragments

In some embodiments of any of the antibodies provided herein, the antibody antibodies is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP404097; WO 1993/01161; Hudson et al. *Nat. Med.* 9:129-134 (2003). Triabodies and tetrabodies are also described in Hudson et al. *Nat. Med.* 9:129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (see, e.g., U.S. Pat. No. 6,248,516).

Antibody fragments can be made by various techniques, including but not limited to proteolytic digestion of an intact antibody as well as production by recombinant host cells (e.g., *E. coli* or phage), as described herein.

In some embodiments, the antibody fragment is used in combination with a second Sortilin antibody and/or with one or more antibodies that specifically bind a disease-causing protein selected from: amyloid beta or fragments thereof, Tau, IAPP, alpha-synuclein, TDP-43, FUS protein, prion protein, PrPSc, huntingtin, calcitonin, superoxide dismutase, ataxin, Lewy body, atrial natriuretic factor, islet amyloid polypeptide, insulin, apolipoprotein A1, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, proline-arginine (PR) repeat peptides, and any combination thereof.

(3) Chimeric and Humanized Antibodies

In some embodiments of any of the antibodies provided herein, the antibody is a chimeric antibody. Certain chimeric antibodies are described, e.g., in U.S. Pat. No. 4,816,567. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In some embodiments of any of the antibodies provided herein, the antibody is a humanized antibody. Typically, a non-human antibody is humanized to reduce immunogenicity to humans, while retaining the specificity and affinity of the parental non-human antibody. In certain embodiments, a humanized antibody is substantially non-immunogenic in humans. In certain embodiments, a humanized antibody has substantially the same affinity for a target as an antibody from another species from which the humanized antibody is derived. See, e.g., U.S. Pat. Nos. 5,530,101, 5,693,761; 5,693,762; and 5,585,089. In certain embodiments, amino acids of an antibody variable domain that can be modified without diminishing the native affinity of the antigen binding domain while reducing its immunogenicity are identified. See, e.g., U.S. Pat. Nos. 5,766,886 and 5,869,619. Generally, a humanized antibody comprises one or more variable domains in which HVRs (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), for example, to restore or improve antibody specificity or affinity.

Humanized antibodies and methods of making them are reviewed, for example, in Almagro et al. *Front. Biosci.* 13:161 9-1633 (2008), and are further described, e.g., in U.S. Pat. Nos. 5,821,337, 7,527,791, 6,982,321, and 7,087,409. Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA* 89:4285 (1992); and Presta et al., *J. Immunol.* 151:2623 (1993)); human mature (somatically mutated) framework regions or human germline framework regions (see, e.g., Almagro and Fransson *Front. Biosci.* 13:1619-1633 (2008)); and framework regions derived from screening FR libraries (see, e.g., Baca et al. *J. Biol. Chem.* 272:10678-10684 (1997) and Rosok et al. *J. Biol. Chem.* 271:22611-22618 (1996)).

(4) Human Antibodies

In some embodiments of any of the antibodies provided herein, the antibody is a human antibody. Human antibodies can be produced using various techniques known in the art. Human antibodies are described generally in van Dijk et al. *Curr. Opin. Pharmacol.* 5:368-74 (2001) and Lonberg *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge.

One can engineer mouse strains deficient in mouse antibody production with large fragments of the human Ig loci in anticipation that such mice would produce human antibodies in the absence of mouse antibodies. Large human Ig fragments can preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains can yield high affinity fully human antibodies against any antigen of interest, including human antigens. Using the hybridoma technology, antigen-specific human MAbs with the desired specificity can be produced and selected. Certain exemplary methods are described in U.S. Pat. No. 5,545,807, EP 546073, and EP 546073. See also, for example, U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology. Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.* 133:3001 (1984) and Boerner et al. *J. Immunol.* 147:86 (1991)). Human antibodies generated via human B-cell hybridoma technology are also described in Li et al. *Proc. Natl. Acad. Sci. USA,* 1 03:3557-3562 (2006). Additional methods include those described, for example, in U.S. Pat. No. 7,189,826 (describing production of monoclonal human IgM antibodies from hybridoma cell lines). Human hybridoma technology (Trioma technology) is also described in Vollmers et al. *Histology and Histopathology* 20(3):927-937 (2005) and Vollmers et al. *Methods and Findings in Experimental and Clinical Pharmacology* 27(3): 185-91 (2005). Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

In some embodiments of any of the antibodies provided herein, the antibody is a human antibody isolated by in vitro methods and/or screening combinatorial libraries for antibodies with the desired activity or activities. Suitable examples include but are not limited to phage display (CAT, Morphosys, Dyax, Biosite/Medarex, Xoma, Symphogen, Alexion (formerly Proliferon), Affimed) ribosome display (CAT), yeast-based platforms (Adimab), and the like. In certain phage display methods, repertoires of VH and VL genes are separately cloned by polymerase chain reaction (PCR) and recombined randomly in phage libraries, which can then be screened for antigen-binding phage as described in Winter et al. *Ann. Rev. Immunol.* 12: 433-455 (1994). For example, a variety of methods are known in the art for generating phage display libraries and screening such libraries for antibodies possessing the desired binding characteristics. See also Sidhu et al. *J. Mol. Biol.* 338(2): 299-310, 2004; Lee et al. *J. Mol. Biol.* 340(5): 1073-1093, 2004; Fellouse *Proc. Natl. Acad. Sci. USA* 101(34):12467-12472 (2004); and Lee et al. *J. Immunol. Methods* 284(-2):1 19-132 (2004). Phage typically display antibody fragments, either as single-chain Fv (scFv) fragments or as Fab fragments.

Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al. *EMBO J.* 12: 725-734 (1993). Finally, naive libraries can also be made synthetically by cloning unrearranged V-gene segments from stem cells, and using PCR primers comprising random sequence to encode the highly variable HVR3 regions and to accomplish rearrangement in vitro, as described by Hoogenboom et al. *J. Mol. Biol.,* 227: 381-388, 1992. Patent publications describing human antibody phage libraries include, for example: U.S. Pat. No. 5,750,373, and US Patent Publication Nos. 2007/0292936 and 2009/0002360. Antibodies isolated from human antibody libraries are considered human antibodies or human antibody fragments herein.

(5) Constant Regions Including Fc Regions

In some embodiments of any of the antibodies provided herein, the antibody comprises an Fc. In some embodiments, the Fc is a human IgG1, IgG2, IgG3, and/or IgG4 isotype. In some embodiments, the antibody is of the IgG class, the IgM class, or the IgA class.

In certain embodiments of any of the antibodies provided herein, the antibody has an IgG2 isotype. In some embodiments, the antibody contains a human IgG2 constant region. In some embodiments, the human IgG2 constant region includes an Fc region. In some embodiments, the antibody induces the one or more Sortilin activities or independently of binding to an Fc receptor. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has an IgG1 isotype. In some embodiments, the antibody contains a mouse IgG1 constant region. In some embodiments, the antibody contains a human IgG1 constant region. In some embodiments, the human IgG1 constant region includes an Fc region. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has an IgG4 isotype. In some embodiments, the antibody contains a human IgG4 constant region. In some embodiments, the human IgG4 constant region includes an Fc region. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has a hybrid IgG2/4 isotype. In some embodiments, the antibody includes an amino acid sequence comprising amino acids 118 to 260 according to EU numbering of human IgG2 and amino acids 261-447 according to EU numbering of human IgG4 (WO 1997/11971; WO 2007/106585).

In some embodiments, the Fc region increases clustering without activating complement as compared to a corresponding antibody comprising an Fc region that does not comprise the amino acid substitutions. In some embodiments, the antibody induces one or more activities of a target specifically bound by the antibody. In some embodiments, the antibody binds to Sortilin.

It may also be desirable to modify an anti-Sortilin antibody of the present disclosure to modify effector function and/or to increase serum half-life of the antibody. For example, the Fc receptor binding site on the constant region may be modified or mutated to remove or reduce binding affinity to certain Fc receptors, such as FcγRI, FcγRII, and/or FcγRIII to reduce Antibody-dependent cell-mediated cytotoxicity. In some embodiments, the effector function is impaired by removing N-glycosylation of the Fc region (e.g., in the CH2 domain of IgG) of the antibody. In some embodiments, the effector function is impaired by modifying regions such as 233-236, 297, and/or 327-331 of human IgG as described in WO 99/58572 and Armour et al. *Molecular Immunology* 40: 585-593 (2003); Reddy et al. *J. Immunology* 164:1925-1933 (2000). In other embodiments, it may also be desirable to modify an anti-Sortilin antibody of the present disclosure to modify effector function to increase finding selectivity toward the ITIM-containing FcgRIIb (CD32b) to increase clustering of Sortilin antibodies on adjacent cells without activating humoral responses including Antibody-dependent cell-mediated cytotoxicity and antibody-dependent cellular phagocytosis.

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule. Other amino acid sequence modifications.

(6) Multispecific Antibodies

Multispecific are antibodies that have binding specificities for at least two different epitopes, including those on the same or another polypeptide (e.g., one or more Sortilin polypeptides of the present disclosure). In some embodiments, the multispecific antibody can be a bispecific antibody. In some embodiments, the multispecific antibody can be a trispecific antibody. In some embodiments, the multispecific antibody can be a tetraspecific antibody. Such antibodies can be derived from full-length antibodies or antibody fragments (e.g., F(ab')$_2$ bispecific antibodies). In some embodiments, the multispecific antibody comprises a first antigen binding region which binds to first site on Sortilin and comprises a second antigen binding region which binds to a second site on Sortilin. In some embodiment, the multispecific antibodies comprises a first antigen binding region which binds to Sortilin and a second antigen binding region that binds to a second polypeptide.

Provided herein are multispecific antibodies comprises a first antigen binding region, wherein the first antigen binding region comprises the six HVRs of an antibody described herein, which binds to Sortilin and a second antigen binding region that binds to a second polypeptide. In some embodiments, the first antigen binding region comprises the V$_H$ or V$_L$ of an antibody described herein.

In some embodiments of any of the multispecific antibodies, the second polypeptide is a) an antigen facilitating transport across the blood-brain-barrier; (b) an antigen facilitating transport across the blood-brain-barrier selected from transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, and ANG1005; (c) a disease-causing protein selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein A1, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; (d) ligands and/or proteins expressed on immune cells, wherein the ligands and/or proteins selected from CD40, OX40, ICOS, CD28, CD137/4-1BB, CD27, GITR, PD-L1, CTLA-4, PD-L2, PD-1, B7-H3, B7-H4, HVEM, BTLA, KIR, GAL9, TIM3, A2AR, LAG-3, and phosphatidylserine; and/or (e) a protein, lipid, polysaccharide, or glycolipid expressed on one or more tumor cells and any combination thereof.

Numerous antigens are known in the art that facilitate transport across the blood-brain barrier (see, e.g., Gabathuler R. *Neurobiol. Dis.* 37:48-57 (2010)). Such second antigens include, without limitation, transferrin receptor (TR), insulin receptor (HIR), Insulin-like growth factor receptor (IGFR), low-density lipoprotein receptor related proteins 1 and 2 (LPR-1 and 2), diphtheria toxin receptor, including CRM197 (a non-toxic mutant of diphtheria toxin), llama single domain antibodies such as TMEM 30(A) (Flippase), protein transduction domains such as TAT, Syn-B, or penetratin, poly-arginine or generally positively charged peptides, Angiopep peptides such as ANG1005 (see, e.g., Gabathuler, 2010), and other cell surface proteins that are enriched on blood-brain barrier endothelial cells (see, e.g., Daneman et al. *PLoS One* 5(10):e13741 (2010)).

The multivalent antibodies may recognize the Sortilin antigen as well as without limitation additional antigens Aβ peptide, antigen or an α-synuclein protein antigen or, Tau protein antigen or, TDP-43 protein antigen or, prion protein antigen or, huntingtin protein antigen, or RAN, translation Products antigen, including the DiPeptide Repeats, (DPRs peptides) composed of glycine-alanine (GA), glycine-proline (GP), glycine-arginine (GR), proline-alanine (PA), or proline-arginine (PR), Insulin receptor, insulin like growth factor receptor. Transferrin receptor or any other antigen that facilitate antibody transfer across the blood brain barrier. In some embodiments, the second polypeptide is transferrin. In some embodiments, the second polypeptide is Tau. In some embodiments, the second polypeptide is Ap. In some embodiments, the second polypeptide is TREM2. In some embodiments, the second polypeptide is α-synuclein.

The multivalent antibody contains at least one polypeptide chain (and preferably two polypeptide chains), wherein the polypeptide chain or chains comprise two or more variable domains. For instance, the polypeptide chain or chains may comprise VD1-(X$_1$)$_n$-VD2-(X$_2$)$_n$-Fc, wherein VD1 is a first variable domain, VD2 is a second variable domain, Fc is one polypeptide chain of an Fc region, X$_1$ and X$_2$ represent an amino acid or polypeptide, and n is 0 or 1. Similarly, the polypeptide chain or chains may comprise V$_H$-C$_H$1-flexible linker-V$_H$-C$_H$1-Fc region chain; or V$_H$—C$_H$1-V$_H$-C$_H$1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Techniques for making multispecific antibodies include, but are not limited to, recombinant co-expression of two immunoglobulin heavy chain-light chain pairs having different specificities (see Milstein and Cuello *Nature* 305: 537 (1983), WO 93/08829, and Traunecker et al. *EMBO J.* 10:3655 (1991)), and "knob-in-hole" engineering (see, e.g., U.S. Pat. No. 5,731,168). See also WO 2013/026833 (CrossMab). Multi-specific antibodies may also be made by engineering electrostatic steering effects for making antibody Fc-heterodimeric molecules (WO 2009/089004A1); cross-linking two or more antibodies (see, e.g., U.S. Pat. No. 4,676,980); using leucine; using "diabody" technology for making bispecific antibody fragments (see, e.g., Hollinger et al. *Proc. Natl. Acad. Sci. USA* 90:6444-6448 (1993)); and using single-chain Fv (scFv) dimers (see, e.g., Gruber et al. *J. Immunol.* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g., US 2006/0025576). The antibody herein also includes a "Dual Acting FAb" or "DAF" comprising an antigen binding site that binds to multiple Sortilin (see, US 2008/0069820, for example).

(7) Antibodies with Improved Stability

Amino acid sequence modifications of anti-Sortilin antibodies of the present disclosure, or antibody fragments thereof to improve stability during manufacturing, storage, and in vivo administration, are also contemplated. For example, it may be desirable to reduce degradation of the antibodies or antibody fragments of the present disclosure through multiple pathways, including without limitation, oxidation and deamidation. Amino acid sequence variants of the antibodies or antibody fragments are prepared by introducing appropriate nucleotide changes into the nucleic acid encoding the antibodies or antibody fragments, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics (i.e., reduced susceptibility to degradation).

In some embodiments, the asparagine (N33) site in the HVR-L1 region of an anti-Sortilin antibody of the present disclosure may be susceptible to degradation by means of deamidation. In certain embodiments, the asparagine (N33) site in the HVR-L1 region of S-60-15 (SEQ ID NO:8) may be susceptible to deamidation. Upon deamidation, the asparagine (N33) site in the HVR-L1 region of S-60-15 results in an Asn to Asp/IsoAsp change. In certain embodiments, the asparagine (N33) site in the HVR-L1 region of S-60-15 may be substituted to prevent or reduce deamidation. Non-limiting exemplary amino acid sequence variants of S-60-15 having amino acid substitutions in the asparagine (N33) site of the HVR-L1 region include S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], or S-60-15.17 [N33L].

(8) Antibody Variants

In some embodiments of any of the antibodies provided herein, amino acid sequence variants of the antibodies are contemplated. For example, it may be desirable to improve the binding affinity and/or other biological properties of the antibody.

(i) Substitution, Insertion, and Deletion Variants

In some embodiments of any of the antibodies provided herein, antibody variants having one or more amino acid substitutions are provided. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody.

TABLE 37

Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Tyr |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro; and
(6) aromatic: Trp, Tyr, Phe.

For example, non-conservative substitutions can involve the exchange of a member of one of these classes for a member from another class. Such substituted residues can be introduced, for example, into regions of a human antibody that are homologous with non-human antibodies, or into the non-homologous regions of the molecule.

In making changes to the polypeptide or antibody described herein, according to certain embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al. *J. Mol. Biol.,* 157:105-131 (1982). It is known that certain amino acids can be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0±1); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One can also identify epitopes from primary amino acid sequences on the basis of hydrophilicity. These regions are also referred to as "epitopic core regions".

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

Amino acid sequence insertions include amino- and/or carboxyl-terminal fusions ranging in length from one residue to polypeptides comprising a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment, such as an Fv fragment).

(ii) Glycosylation Variants

In some embodiments of any of the antibodies provided herein, the antibody is altered to increase or decrease the extent to which the antibody is glycosylated. Addition or deletion of glycosylation sites to an antibody may be conveniently accomplished by altering the amino acid sequence such that one or more glycosylation sites is created or removed.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. Native antibodies produced by mammalian cells typically comprise a branched, biantennary oligosaccharide that is generally attached by an N-linkage to Asn297 according to Kabat numbering of the CH2 domain of the Fc region. The oligosaccharide may include various carbohydrates, for example, mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. See, e.g., US Patent Publication Nos. 2003/0157108 and 2004/0093621. Examples of publications related to "defucosylated" or "fucose-deficient" antibody variants include: US 2003/0157108; US 2003/0115614; US 2002/0164328; US 2004/0093621; US 2004/0132140; US 2004/0110704; US 2004/0110282; US 2004/0109865; Okazaki et al. *J. Mol. Biol.* 336:1239-1249 (2004); Yamane-Ohnuki et al. *Biotech. Bioeng.* 87:614 (2004). Examples of cell lines capable of producing defucosylated antibodies include Led 3 CHO cells deficient in protein fucosylation (Ripka et al. *Arch. Biochem. Biophys.* 249:533-545 (1986); US 2003/0157108), and knockout cell lines, such as alpha-1,6-fucosyltransferase gene, FUT8, knockout CHO cells (see, e.g., Yamane-Ohnuki et al. *Biotech. Bioeng.* 87: 614 (2004) and Kanda et al. *Biotechnol. Bioeng.* 94(4):680-688 (2006)).

(iii) Modified Constant Regions

In some embodiments of any of the antibodies provided herein, the antibody Fc is an antibody Fc isotypes and/or modifications. In some embodiments, the antibody Fc isotype and/or modification is capable of binding to Fc gamma receptor.

In some embodiments of any of the antibodies provided herein, the modified antibody Fc is an IgG1 modified Fc. In some embodiments, the IgG1 modified Fc comprises one or more modifications. For example, in some embodiments, the IgG1 modified Fc comprises one or more amino acid substitutions (e.g., relative to a wild-type Fc region of the same isotype). In some embodiments, the one or more amino acid substitutions are selected from N297A (Bolt S et al. (1993) *Eur J Immunol* 23:403-411), D265A (Shields et al. (2001) *R. J. Biol. Chem.* 276, 6591-6604), L234A, L235A (Hutchins et al. (1995) *Proc Natl Acad Sci USA*, 92:11980-11984; Alegre et al., (1994) *Transplantation* 57:1537-1543. 31; Xu et al., (2000) *Cell Immunol,* 200:16-26), G237A (Alegre et al. (1994) *Transplantation* 57:1537-1543. 31; Xu et al. (2000) *Cell Immunol,* 200:16-26), C226S, C229S, E233P, L234V, L234F, L235E (McEarchern et al., (2007) *Blood,* 109:1185-1192), P331S (Sazinsky et al., (2008) *Proc Natl Acad Sci USA* 2008, 105:20167-20172), S267E, L328F, A330L, M252Y, S254T, and/or T256E, where the amino acid position is according to the EU numbering convention. In some embodiments of any of the antibodies provided herein, the antibody is an IgG1 isotype and the Fc region comprises amino acid substitutions at positions L234A, L235A, and P331S, wherein the numbering of the residue position is according to EU numbering.

In some embodiments of any of the IgG1 modified Fc, the Fc comprises N297A mutation according to EU numbering. In some embodiments of any of the IgG1 modified Fc, the Fc comprises D265A and N297A mutations according to EU numbering. In some embodiments of any of the IgG1 modified Fc, the Fc comprises D270A mutations according to EU numbering. In some embodiments, the IgG1 modified Fc comprises L234A and L235A mutations according to EU numbering. In some embodiments of any of the IgG1 modified Fc, the Fc comprises L234A and G237A mutations according to EU numbering. In some embodiments of any of the IgG1 modified Fc, the Fc comprises L234A, L235A and G237A mutations according to EU numbering. In some embodiments of any of the IgG1 modified Fc, the Fc comprises one or more (including all) of P238D, L328E, E233, G237D, H268D, P271G and A330R mutations according to EU numbering. In some embodiments of any of the IgG1 modified Fc, the Fc comprises one or more of S267E/L328F mutations according to EU numbering. In some embodiments of any of the IgG1 modified Fc, the Fc comprises P238D, L328E, E233D, G237D, H268D, P271G and A330R mutations according to EU numbering. In some embodiments of any of the IgG1 modified Fc, the Fc comprises P238D, L328E, G237D, H268D, P271G and A330R mutations according to EU numbering. In some embodiments of any of the IgG1 modified Fc, the Fc comprises P238D, S267E, L328E, E233D, G237D, H268D, P271G and A330R mutations according to EU numbering. In some embodiments of any of the IgG1 modified Fc, the Fc comprises P238D, S267E, L328E, G237D, H268D, P271G and A330R mutations according to EU numbering. In some embodiments of any of the IgG1 modified Fc, the Fc comprises C226S, C229S, E233P, L234V, and L235A mutations according to EU numbering. In some embodiments of any of the IgG1 modified Fc, the Fc comprises L234F, L235E, and P331S mutations according to EU numbering. In some embodiments of any of the IgG1 modified Fc, the Fc comprises S267E and L328F mutations according to EU numbering. In some embodiments of any of the IgG1 modified Fc, the Fc comprises S267E mutations according to EU numbering. In some embodiments of any of the IgG1 modified Fc, the Fc comprises a substitute of the constant heavy 1 (CH1) and hinge region of IgG1 with CH1 and hinge region of IgG2 (amino acids 118-230 of IgG2 according to EU numbering) with a Kappa light chain.

In some embodiments of any of the IgG1 modified Fc, the Fc includes two or more amino acid substitutions that increase antibody clustering without activating complement as compared to a corresponding antibody having an Fc region that does not include the two or more amino acid substitutions. Accordingly, in some embodiments of any of the IgG1 modified Fc, the IgG1 modified Fc is an antibody comprising an Fc region, where the antibody comprises an amino acid substitution at position E430G and one or more amino acid substitutions in the Fc region at a residue position selected from: L234F, L235A, L235E, S267E, K322A, L328F, A330S, P331S, and any combination thereof according to EU numbering. In some embodiments, the IgG1 modified Fc comprises an amino acid substitution at positions E430G, L243A, L235A, and P331S according to EU numbering. In some embodiments, the IgG1 modified Fc comprises an amino acid substitution at positions E430G and P331S according to EU numbering. In some embodiments, the IgG1 modified Fc comprises an amino acid substitution at positions E430G and K322A according to EU numbering. In some embodiments, the IgG1 modified Fc comprises an amino acid substitution at positions E430G, A330S, and P331S according to EU numbering. In some embodiments, the IgG1 modified Fc comprises an amino acid substitution at positions E430G, K322A, A330S, and P331S according to EU numbering. In some embodiments, the IgG1 modified Fc comprises an amino acid substitution at positions E430G, K322A, and A330S according to EU numbering. In some embodiments, the IgG1 modified Fc comprises an amino acid substitution at positions E430G, K322A, and P331S according to EU numbering.

In some embodiments of any of the IgG1 modified Fc, the IgG1 modified Fc may further comprise herein may be combined with an A330L mutation (Lazar et al. *Proc Natl Acad Sci USA,* 103:4005-4010 (2006)), or one or more of L234F, L235E, and/or P331S mutations (Sazinsky et al. *Proc Natl Acad Sci USA,* 105:20167-20172 (2008)), according to the EU numbering convention, to eliminate complement activation. In some embodiments of any of the IgG1 modified Fc, the IgG1 modified Fc may further comprise one or more of A330L, A330S, L234F, L235E, and/or P331S according to EU numbering. In some embodiments of any of the IgG1 modified Fc, the IgG1 modified Fc may further comprise one or more mutations to enhance the antibody half-life in human serum (e.g., one or more (including all) of M252Y, S254T, and T256E mutations according to the EU numbering convention). In some embodiments of any of the IgG1 modified Fc, the IgG1 modified Fc may further comprise one or more of E430G, E430S, E430F, E430T, E345K, E345Q, E345R, E345Y, S440Y, and/or S440W according to EU numbering.

Other aspects of the present disclosure relate to antibodies having modified constant regions (i.e., Fc regions). An antibody dependent on binding to FcgR receptor to activate targeted receptors may lose its agonist activity if engineered to eliminate FcgR binding (see, e.g., Wilson et al. *Cancer Cell* 19:101-113 (2011); Armour at al. *Immunology* 40:585-593 (2003); and White et al. *Cancer Cell* 27:138-148

(2015)). As such, it is thought that an anti-Sortlin antibody of the present disclosure with the correct epitope specificity can activate the target antigen, with minimal adverse effects, when the antibody has an Fc domain from a human IgG2 isotype (CH1 and hinge region) or another type of Fc domain that is capable of preferentially binding the inhibitory FcgRIIB r receptors, or a variation thereof.

In some embodiments of any of the antibodies provided herein, the modified antibody Fc is an IgG2 modified Fc. In some embodiments, the IgG2 modified Fc comprises one or more modifications. For example, in some embodiments, the IgG2 modified Fc comprises one or more amino acid substitutions (e.g., relative to a wild-type Fc region of the same isotype). In some embodiments of any of the IgG2 modified Fc, the one or more amino acid substitutions are selected from V234A (Alegre et al. *Transplantation* 57:1537-1543 (1994); Xu et al. *Cell Immunol,* 200:16-26 (2000)); G237A (Cole et al. *Transplantation,* 68:563-571 (1999)); H268Q, V309L, A330S, P331S (US 2007/0148167; Armour et al. *Eur J Immunol* 29: 2613-2624 (1999); Armour et al. *The Haematology Journal* 1 (Suppl. 1):27 (2000); Armour et al. *The Haematology Journal* 1 (Suppl. 1):27 (2000)), C219S, and/or C220S (White et al. *Cancer Cell* 27, 138-148 (2015)); S267E, L328F (Chu et al. *Mol Immunol,* 45:3926-3933 (2008)); and M252Y, S254T, and/or T256E according to the EU numbering convention. In some embodiments of any of the IgG2 modified Fc, the Fc comprises an amino acid substitution at positions V234A and G237A according to EU numbering. In some embodiments of any of the IgG2 modified Fc, the Fc comprises an amino acid substitution at positions C219S or C220S according to EU numbering. In some embodiments of any of the IgG2 modified Fc, the Fc comprises an amino acid substitution at positions A330S and P331S according to EU numbering. In some embodiments of any of the IgG2 modified Fc, the Fc comprises an amino acid substitution at positions S267E and L328F according to EU numbering.

In some embodiments of any of the IgG2 modified Fc, the Fc comprises a C127S amino acid substitution according to the EU numbering convention (White et al., (2015) *Cancer Cell* 27, 138-148; Lightle et al. *Protein Sci.* 19:753-762 (2010); and WO 2008/079246). In some embodiments of any of the IgG2 modified Fc, the antibody has an IgG2 isotype with a Kappa light chain constant domain that comprises a C214S amino acid substitution according to the EU numbering convention (White et al. *Cancer Cell* 27:138-148 (2015); Lightle et al. *Protein Sci.* 19:753-762 (2010); and WO 2008/079246).

In some embodiments of any of the IgG2 modified Fc, the Fc comprises a C220S amino acid substitution according to the EU numbering convention. In some embodiments of any of the IgG2 modified Fc, the antibody has an IgG2 isotype with a Kappa light chain constant domain that comprises a C214S amino acid substitution according to the EU numbering convention.

In some embodiments of any of the IgG2 modified Fc, the Fc comprises a C219S amino acid substitution according to the EU numbering convention. In some embodiments of any of the IgG2 modified Fc, the antibody has an IgG2 isotype with a Kappa light chain constant domain that comprises a C214S amino acid substitution according to the EU numbering convention.

In some embodiments of any of the IgG2 modified Fc, the Fc includes an IgG2 isotype heavy chain constant domain 1 (CH1) and hinge region (White et al. *Cancer Cell* 27:138-148 (2015)). In certain embodiments of any of the IgG2 modified Fc, the IgG2 isotype CH1 and hinge region comprise the amino acid sequence of 118-230 according to EU numbering. In some embodiments of any of the IgG2 modified Fc, the antibody Fc region comprises a S267E amino acid substitution, a L328F amino acid substitution, or both, and/or a N297A or N297Q amino acid substitution according to the EU numbering convention.

In some embodiments of any of the IgG2 modified Fc, the Fc further comprises one or more amino acid substitution at positions E430G, E430S, E430F, E430T, E345K, E345Q, E345R, E345Y, S440Y, and S440W according to EU numbering. In some embodiments of any of the IgG2 modified Fc, the Fc may further comprise one or more mutations to enhance the antibody half-life in human serum (e.g., one or more (including all) of M252Y, S254T, and T256E mutations according to the EU numbering convention). In some embodiments of any of the IgG2 modified Fc, the Fc may further comprise A330S and P331S.

In some embodiments of any of the IgG2 modified Fc, the Fc is an IgG2/4 hybrid Fc. In some embodiments, the IgG2/4 hybrid Fc comprises IgG2 aa 118 to 260 and IgG4 aa 261 to 447. In some embodiments of any IgG2 modified Fc, the Fc comprises one or more amino acid substitutions at positions H268Q, V309L, A330S, and P331S according to EU numbering.

In some embodiments of any of the IgG1 and/or IgG2 modified Fc, the Fc comprises one or more additional amino acid substitutions selected from A330L, L234F; L235E, or P331S according to EU numbering; and any combination thereof.

In certain embodiments of any of the IgG1 and/or IgG2 modified Fc, the Fc comprises one or more amino acid substitutions at a residue position selected from C127S, L234A, L234F, L235A, L235E, S267E, K322A, L328F, A330S, P331S, E345R, E430G, S440Y, and any combination thereof according to EU numbering. In some embodiments of any of the IgG1 and/or IgG2 modified Fc, the Fc comprises an amino acid substitution at positions E430G, L243A, L235A, and P331S according to EU numbering. In some embodiments of any of the IgG1 and/or IgG2 modified Fc, the Fc comprises an amino acid substitution at positions E430G and P331S according to EU numbering. In some embodiments of any of the IgG1 and/or IgG2 modified Fc, the Fc comprises an amino acid substitution at positions E430G and K322A according to EU numbering. In some embodiments of any of the IgG1 and/or IgG2 modified Fc, the Fc comprises an amino acid substitution at positions E430G, A330S, and P331S according to EU numbering. In some embodiments of any of the IgG1 and/or IgG2 modified Fc, the Fc comprises an amino acid substitution at positions E430G, K322A, A330S, and P331S according to EU numbering. In some embodiments of any of the IgG1 and/or IgG2 modified Fc, the Fc comprises an amino acid substitution at positions E430G, K322A, and A330S according to EU numbering. In some embodiments of any of the IgG1 and/or IgG2 modified Fc, the Fc comprises an amino acid substitution at positions E430G, K322A, and P331S according to EU numbering. In some embodiments of any of the IgG1 and/or IgG2 modified Fc, the Fc comprises an amino acid substitution at positions S267E and L328F according to EU numbering. In some embodiments of any of the IgG1 and/or IgG2 modified Fc, the Fc comprises an amino acid substitution at position C127S according to EU numbering. In some embodiments of any of the IgG1 and/or IgG2 modified Fc, the Fc comprises an amino acid substitution at positions E345R, E430G and S440Y according to EU numbering.

In some embodiments of any of the antibodies provided herein, the modified antibody Fc is an IgG4 modified Fc. In some embodiments, the IgG4 modified Fc comprises one or more modifications. For example, in some embodiments, the IgG4 modified Fc comprises one or more amino acid substitutions (e.g., relative to a wild-type Fc region of the same isotype). In some embodiments of any of the IgG4 modified Fc, the one or more amino acid substitutions are selected from L235A, G237A, S229P, L236E (Reddy et al. *J Immunol* 164:1925-1933(2000)), S267E, E318A, L328F, M252Y, S254T, and/or T256E according to the EU numbering convention. In some embodiments of any of the IgG4 modified Fc, the Fc may further comprise L235A, G237A, and E318A according to the EU numbering convention. In some embodiments of any of the IgG4 modified Fc, the Fc may further comprise S228P and L235E according to the EU numbering convention. In some embodiments of any of the IgG4 modified Fc, the IgG4 modified Fc may further comprise S267E and L328F according to the EU numbering convention.

In some embodiments of any of the IgG4 modified Fc, the IgG4 modified Fc comprises may be combined with an S228P mutation according to the EU numbering convention (Angal et al. *Mol Immunol.* 30:105-108 (1993)) and/or with one or more mutations described in (Peters et al. *J Biol Chem.* 287(29):24525-33 (2012)) to enhance antibody stabilization.

In some embodiments of any of the IgG4 modified Fc, the IgG4 modified Fc may further comprise one or more mutations to enhance the antibody half-life in human serum (e.g., one or more (including all) of M252Y, S254T, and T256E mutations according to the EU numbering convention).

In some embodiments of any of the IgG4 modified Fc, the Fc comprises L235E according to EU numbering. In certain embodiments of any of the IgG4 modified Fc, the Fc comprises one or more amino acid substitutions at a residue position selected from C127S, F234A, L235A, L235E, S267E, K322A, L328F, E345R, E430G, S440Y, and any combination thereof, according to EU numbering. In some embodiments of any of the IgG4 modified Fc, the Fc comprises an amino acid substitution at positions E430G, L243A, L235A, and P331S according to EU numbering. In some embodiments of any of the IgG4 modified Fc, the Fc comprises an amino acid substitution at positions E430G and P331S according to EU numbering. In some embodiments of any of the IgG4 modified Fc, the Fc comprises an amino acid substitution at positions E430G and K322A according to EU numbering. In some embodiments of any of the IgG4 modified Fc, the Fc comprises an amino acid substitution at position E430 according to EU numbering. In some embodiments of any of the IgG4 modified Fc, the Fc region comprises an amino acid substitution at positions E430G and K322A according to EU numbering. In some embodiments of any of the IgG4 modified Fc, the Fc comprises an amino acid substitution at positions S267E and L328F according to EU numbering. In some embodiments of any of the IgG4 modified Fc, the Fc comprises an amino acid substitution at position C127S according to EU numbering. In some embodiments of any of the IgG4 modified Fc, the Fc comprises an amino acid substitution at positions E345R, E430G and S440Y according to EU numbering.

(9) Other Antibody Modifications

In some embodiments of any of the antibodies, the antibody is a derivative. The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen binding protein can have a greater circulating half-life than an antigen binding protein that is not chemically modified. In certain embodiments, a chemically modified antigen binding protein can have improved targeting capacity for desired cells, tissues, and/or organs. In some embodiments, a derivative antigen binding protein is covalently modified to include one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative antigen binding protein comprises one or more polymer, including, but not limited to, monomethoxy-polyethylene glycol, dextran, cellulose, copolymers of ethylene glycol/propylene glycol, carboxymethylcellulose, polyvinyl pyrrolidone, poly-1, 3-dioxolane, poly-1,3,6-trioxane, ethylene/maleic anhydride copolymer, polyaminoacids (either homopolymers or random copolymers), poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers.

In certain embodiments, a derivative is covalently modified with polyethylene glycol (PEG) subunits. In certain embodiments, one or more water-soluble polymer is bonded at one or more specific position, for example at the amino terminus, of a derivative. In certain embodiments, one or more water-soluble polymer is randomly attached to one or more side chains of a derivative. In certain embodiments, PEG is used to improve the therapeutic capacity for an antigen binding protein. In certain embodiments, PEG is used to improve the therapeutic capacity for a humanized antibody. Certain such methods are discussed, for example, in U.S. Pat. No. 6,133,426, which is hereby incorporated by reference for any purpose.

Peptide analogs are commonly used in the pharmaceutical industry as non-peptide drugs with properties analogous to those of the template peptide. These types of non-peptide compound are termed "peptide mimetics" or "peptidomimetics." Fauchere, *J. Adv. Drug Res.*, 15:29 (1986); and Evans et al. *J. Med. Chem.*, 30:1229 (1987), which are incorporated herein by reference for any purpose. Such compounds are often developed with the aid of computerized molecular modeling. Peptide mimetics that are structurally similar to therapeutically useful peptides can be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: —CH$_2$NH—, —CH$_2$S—, —CH$_2$—CH$_2$—, ——CH═CH-(cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) can be used in certain embodiments to generate more stable peptides. In addition, constrained peptides comprising a consensus sequence or a substantially identical consensus sequence variation can be generated by methods known in the art (Rizo and Gierasch *Ann. Rev. Biochem.*, 61:387 (1992), incorporated herein by reference for any purpose); for example, by adding internal cysteine residues capable of forming intramolecular disulfide bridges which cyclize the peptide.

Drug conjugation involves coupling of a biological active cytotoxic (anticancer) payload or drug to an antibody that specifically targets a certain tumor marker (e.g. a polypeptide that, ideally, is only to be found in or on tumor cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cancer. Due to this targeting, ideally the drug has lower side effects and gives a wider therapeutic window than other chemotherapeutic agents. Technics to conjugate antibodies are disclosed are known in the art (see, e.g., Jane de Lartigue OncLive Jul. 5, 2012; ADC Review on antibody-drug conjugates; and Ducry et al. *Bioconjugate Chemistry* 21 (1):5-13 (2010).

Binding Assays and Other Assays

Anti-Sortilin antibodies of the present disclosure may be tested for antigen binding activity, e.g., by known methods such as ELISA, surface plasmon resonance (SPR), Western blot, flow cytometry, FACS, Bio-layer interferometry etc.

In some embodiments, competition assays may be used to identify an antibody that competes with any of the antibodies described herein. In some embodiments, competition assays may be used to identify an antibody that competes with any of the antibodies listed in Tables 1-30, or comprising the heavy chain variable region and the light chain variable region of an antibody selected from S-60, S-60-1, S-60-2, S-60-3, S-60-4, S-60-7, S-60-8, S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16, S-60-18, S-60-19, and S-60-24 for binding to Sortilin. In certain embodiments, such a competing antibody binds to the same epitope (e.g., a linear or a conformational epitope) that is bound by any of the antibodies listed in Tables 1-30, or comprising the heavy chain variable region and the light chain variable region of an antibody selected from S-60, S-60-1, S-60-2, S-60-3, S-60-4, S-60-7, S-60-8, S-60-10, S-60-11, S-60-12, S-60-13, S-60-14, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16, S-60-18, S-60-19, and S-60-24. Detailed exemplary methods for mapping an epitope to which an antibody binds are provided in Morris (1996) "Epitope Mapping Protocols," in *Methods in Molecular Biology* vol. 66 (Humana Press, Totowa, NJ).

In an exemplary competition assay, immobilized Sortilin or cells expressing Sortilin on a cell surface are incubated in a solution comprising a first labeled antibody that binds to Sortilin (e.g., human or non-human primate) and a second unlabeled antibody that is being tested for its ability to compete with the first antibody for binding to Sortilin. The second antibody may be present in a hybridoma supernatant. As a control, immobilized Sortilin or cells expressing Sortilin is incubated in a solution comprising the first labeled antibody but not the second unlabeled antibody. After incubation under conditions permissive for binding of the first antibody to Sortilin, excess unbound antibody is removed, and the amount of label associated with immobilized Sortilin or cells expressing Sortilin is measured. If the amount of label associated with immobilized Sortilin or cells expressing Sortilin is substantially reduced in the test sample relative to the control sample, then that indicates that the second antibody is competing with the first antibody for binding to Sortilin. See, Harlow and Lane (1988) *Antibodies: A Laboratory Manual* ch. 14 (Cold Spring Harbor Laboratory, Cold Spring Harbor, NY).

Ligand Binding Assays

Further provided herein are methods of screening for anti-Sortilin antibodies that bind His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe314, Ser316, Arg325, Arg326, Ile327, Phe350, Tyr351, Ser352, Ile353, Asn373, Ser379, Arg382, Tyr386, Ser595, and/or Glu700 of human Sortilin (SEQ ID NO: 81); or to amino acid residues of a mammalian Sortilin that corresponds to one or more amino acid residues His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe314, Ser316, Arg325, Arg326, Ile327, Phe350, Tyr351, Ser352, Ile353, Asn373, Ser379, Arg382, Tyr386, Ser595, and/or Glu700 of SEQ ID NO: 81, thereby blocking the interactions between Sortilin and a Sortilin ligand (e.g., Progranulin, pro-neurotrophin, pro-NGF, pro-BDNF, pro-NT3, p75, APP, LpL, APOA5, APOE). In some embodiments, a peptide library can be synthesized in which a Sortilin protein is dissected into consecutive 15-mer and 25-mer peptides separated by one amino acid residue and subsequently spotted onto filters. Binding of a Sortilin ligand can then then tested for its ability to interact with the receptor peptide or with peptides that are, for example, mutated at His131, Val132, Pro133, Leu134, Val135, Ile136, Met137, Thr138, Arg196, Phe198, Arg199, Phe203, Lys205, Phe207, Thr210, Thr218, Tyr222, Ser223, Ser227, Ser242, Lys243, Lys248, Lys254, Lys260, Ser305, Phe306, Gly307, Arg311, Phe314, Ser316, Arg325, Arg326, Ile327, Phe350, Tyr351, Ser352, Ile353, Asn373, Ser379, Arg382, Tyr386, Ser595, and/or Glu700 of human Sortilin libraries in the presence or absence of the anti-Sortilin antibodies by SPOT binding analysis (e.g., Frank, R and Overwin, H (1996) *Methods. Mol. Biol.* 66, 149-169; Reineke, U et al., (2002) *J. Immunol. Methods* 267, 13-26; and Andersen, O S et al., (2010) *J, Biological Chemistry* 285, 12210-12222).

Further provided herein are methods of screening for anti-Sortilin antibodies that block interactions (e.g., binding) Sortilin and a Sortilin ligand (e.g., Progranulin, pro-neurotrophin, pro-NGF, pro-BDNF, pro-NT3, p75, APP, LpL, APOA5, APOE). In some embodiments, the interaction between Sortilin and Sortilin ligands (e.g., Progranulin, pro-neurotrophin, pro-NGF, pro-BDNF, pro-NT3, p75, APP, LpL, APOA5, APOE) may be characterized using surface plasmon resonance analysis (e.g., Skeldal, S et al., (2012) *J Biol Chem.*, 287:43798; and Andersen, O S et al., (2010) *The Journal Of Biological Chemistry*, 285, 12210-12222, a pull-down assay (e.g., Andersen, O S et al., (2010) *The Journal*

Of Biological Chemistry, 285, 12210-12222, cellulose-bound proteins (e.g., Andersen, O S et al., (2010) *The Journal Of Biological Chemistry*, 285, 12210-12222), a proximity ligation assay (e.g., Gustafsen, C et al., (2013) *The Journal of Neuroscience*, 33:64-71), and/or alkaline phosphatase-tagged ligands in cell binding assays (e.g., Hu, F et al., (2010) *Neuron* 68, 654-667).

Cell-Based Assays

Further provided herein are methods of screening for a Sortilin binding antagonist, such as an anti-Sortilin antibody, that include contacting an agent (e.g., an anti-Sortilin antibody) with a cell expressing a Sortilin protein on its cell surface. In some embodiments, the agent and cell are further contacted with a Sortilin ligand of the present disclosure. In some embodiments, the cell itself expresses a Sortilin ligand of the present disclosure. The cell-based methods are particularly suited for screening and validating Sortilin binding antagonists (e.g., anti-Sortilin antibodies) by assessing the effect on the interaction between Sortilin and a Sortilin ligand in the context of a cell.

Accordingly, certain aspects of the present disclosure relate to a cell expressing a Sortilin protein of the present disclosure on its cell surface. In some embodiments, the cell endogenously expresses a Sortilin protein of the present disclosure. In some embodiments, the cell is recombinantly engineered to express a Sortilin protein of the present disclosure. In any of these embodiments, the Sortilin protein of the present disclosure (whether endogenous or recombinant) encoded by the polynucleotide will preferably include at least protein domains required for post-translational processing, membrane translocation, and targeting to the cell surface, including without limitation a signal peptide and a transmembrane domain. In some embodiments, the signal peptide and/or transmembrane domain may refer to the endogenous Sortilin signal peptide and/or transmembrane domain. In other embodiments, the signal peptide and/or transmembrane domain may refer to an exogenous signal peptide and/or transmembrane domain known to promote cell surface expression in the desired host cell. In preferred embodiments, the Sortilin protein will also contain a domain sufficient for binding a Sortilin ligand of the present disclosure.

In these embodiments, any cell that expresses a Sortilin protein of the present disclosure on its cell surface may be used. In some embodiments, the cell endogenously expresses a Sortilin protein of the present disclosure on its cell surface. In some embodiments, the cell is recombinantly engineered to express a Sortilin protein of the present disclosure on its cell surface. Any suitable Sortilin ligand of the present disclosure may be used, such that it retains the ability to bind to the Sortilin protein expressed on the cell surface. The Sortilin ligand need not be fluorescently labeled. Levels of Sortilin ligand may be detected by any assay known in the art, including without limitation ELISA, SPR, Western blotting, mass spectrometry, immunoprecipitation, peptide microarray, and so forth.

In some embodiments, the methods disclosed herein involve culturing a cell that expresses both a Sortilin protein on its cell surface and a Sortilin ligand in a media under conditions in which the Sortilin protein and the Sortilin ligand are expressed and the Sortilin ligand is released into the media; contacting the cell with an agent (e.g., an anti-Sortilin antibody) under conditions in which the Sortilin protein is capable of binding to the Sortilin ligand; and detecting an increase in the level of the Sortilin ligand in the media, as compared to the level of the Sortilin ligand in the media in the absence of the agent. An increase in the level of the Sortilin ligand indicates that the agent is a Sortilin binding antagonist. Without wishing to be bound to theory, it is thought that the interaction between the Sortilin protein expressed on the cell surface and the secreted Sortilin ligand will result in endocytosis and lysosomal degradation of the Sortilin ligand. Therefore, it is thought that decreasing this interaction (e.g., by addition of a Sortilin binding antagonist of the present disclosure) leads to an increase in the level of the Sortilin ligand in the media over time.

In these embodiments, any cell that expresses a Sortilin protein of the present disclosure on its cell surface and expresses and secretes a Sortilin ligand of the present disclosure may be used. In some embodiments, the cell may endogenously express a Sortilin protein of the present disclosure on its cell surface. In some embodiments, the cell may endogenously express and secrete a Sortilin ligand of the present disclosure. In some embodiments, the cell is a U-251 cell, and the Sortilin ligand is a Progranulin protein. In some embodiments, the cell may be recombinantly engineered to express a Sortilin protein of the present disclosure on its cell surface. In some embodiments, the cell may be recombinantly engineered to express and secrete a Sortilin ligand of the present disclosure.

In any of the cell-based assays described herein, a Sortilin ligand of the present disclosure may be used. In some embodiments, the Sortilin ligand is a Progranulin protein. The Sortilin ligand may be a full-length protein, or it may be a Sortilin-binding peptide fragment thereof.

Nucleic Acids, Vectors, and Host Cells

Anti-Sortilin antibodies of the present disclosure may be produced using recombinant methods and compositions, e.g., as described in U.S. Pat. No. 4,816,567. In some embodiments, isolated nucleic acids having a nucleotide sequence encoding any of the anti-Sortilin antibodies of the present disclosure are provided. Such nucleic acids may encode an amino acid sequence comprising the $V_L$ and/or an amino acid sequence comprising the $V_H$ Of the anti-Sortilin antibody (e.g., the light and/or heavy chains of the antibody). In some embodiments, one or more vectors (e.g., expression vectors) comprising such nucleic acids are provided. In some embodiments, a host cell comprising such nucleic acid is also provided. In some embodiments, the host cell comprises (e.g., has been transduced with): (1) a vector comprising a nucleic acid that encodes an amino acid sequence comprising the $V_L$ of the antibody and an amino acid sequence comprising the $V_H$ of the antibody, or (2) a first vector comprising a nucleic acid that encodes an amino acid sequence comprising the $V_L$ of the antibody and a second vector comprising a nucleic acid that encodes an amino acid sequence comprising the $V_H$ of the antibody. In some embodiments, the host cell is eukaryotic, e.g., a Chinese Hamster Ovary (CHO) cell or lymphoid cell (e.g., Y0, NS0, Sp20 cell). Host cells of the present disclosure also include, without limitation, isolated cells, in vitro cultured cells, and ex vivo cultured cells.

Methods of making an anti-Sortilin antibody of the present disclosure are provided. In some embodiments, the method includes culturing a host cell of the present disclosure comprising a nucleic acid encoding the anti-Sortilin antibody, under conditions suitable for expression of the antibody. In some embodiments, the antibody is subsequently recovered from the host cell (or host cell culture medium).

For recombinant production of an anti-Sortilin antibody of the present disclosure, a nucleic acid encoding the anti-Sortilin antibody is isolated and inserted into one or more vectors for further cloning and/or expression in a host cell.

Such nucleic acid may be readily isolated and sequenced using conventional procedures (e.g., by using oligonucleotide probes that are capable of binding specifically to genes encoding the heavy and light chains of the antibody).

Suitable vectors comprising a nucleic acid sequence encoding any of the anti-Sortilin antibodies of the present disclosure, or cell-surface expressed fragments or polypeptides thereof polypeptides (including antibodies) described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones comprising the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Suitable host cells for cloning or expression of antibody-encoding vectors include prokaryotic or eukaryotic cells. For example, anti-Sortilin antibodies of the present disclosure may be produced in bacteria, in particular when glycosylation and Fc effector function are not needed. For expression of antibody fragments and polypeptides in bacteria (e.g., U.S. Pat. Nos. 5,648,237, 5,789,199, and 5,840,523. After expression, the antibody may be isolated from the bacterial cell paste in a soluble fraction and can be further purified.

In addition to prokaryotes, eukaryotic microorganisms, such as filamentous fungi or yeast, are also suitable cloning or expression hosts for antibody-encoding vectors, including fungi and yeast strains whose glycosylation pathways have been "humanized," resulting in the production of an antibody with a partially or fully human glycosylation pattern (e.g., Gerngross *Nat. Biotech.* 22:1409-1414 (2004); and Li et al. *Nat. Biotech.* 24:210-215 (2006)).

Suitable host cells for the expression of glycosylated antibody can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (e.g., U.S. Pat. Nos. 5,959,177, 6,040,498, 6,420,548, 7,125,978, and 6,417,429, describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al. *J. Gen Virol.* 36:59 (1977)); baby hamster kidney cells (BHK); mouse sertoli cells (TM4 cells as described, e.g., in *Mather, Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al. *Annals N.Y. Acad. Sci.* 383:44-68 (1982); MRC 5 cells; and FS4 cells. Other useful mammalian host cell lines include Chinese hamster ovary (CHO) cells, including DHFR-CHO cells (Urlaub et al. *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, NJ), pp. 255-268 (2003).

Pharmaceutical Compositions

Provided herein are pharmaceutical compositions and/or pharmaceutical formulations comprising the anti-Sortilin antibodies of the present disclosure and a pharmaceutically acceptable carrier.

In some embodiments, pharmaceutically acceptable carrier preferably are nontoxic to recipients at the dosages and concentrations employed. The antibodies described herein may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols. Pharmaceutically acceptable carriers can include, depending on the formulation desired, pharmaceutically-acceptable, non-toxic carriers of diluents, which are vehicles commonly used to formulate pharmaceutical compositions for animal or human administration. In certain embodiments, the pharmaceutical composition can comprise formulation materials for modifying, maintaining or preserving, for example, the pH, osmolarity, viscosity, clarity, color, isotonicity, odor, sterility, stability, rate of dissolution or release, adsorption or penetration of the composition.

In certain embodiments, pharmaceutically acceptable carriers include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. Further examples of formulations that are suitable for various types of administration can be found in *Remington: The Science and Practice of Pharmacy*, Pharmaceutical Press 22nd ed. (2013). For a brief review of methods for drug delivery, see, *Langer, Science* 249:1527-1533 (1990).

Formulations suitable for parenteral administration include aqueous and non-aqueous, isotonic sterile injection solutions, which can comprise antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Formulations may be optimized for retention and stabilization in the brain or central nervous system. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the antibody, such as an anti-Sortilin antibody of the present disclosure, in a biodegradable or bioerodible implant. The rate of release of the therapeutically active agent is controlled by the rate of transport through the polymeric matrix, and the biodegradation of the implant. Implants may be particles, sheets, patches, plaques, fibers, microcapsules and the like and may be of any size or shape compatible with the selected site of insertion. Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the subject invention. Hydrogels are typically a copolymer material, characterized by the ability to imbibe a liquid.

Pharmaceutical Dosages

An antibody provided herein (and any additional therapeutic agent) can be administered by any suitable means, including parenteral, intrapulmonary, intranasal, intralesional administration, intracerobrospinal, intracranial, intraspinal, intrasynovial, intrathecal, oral, topical, or inhalation routes. Parenteral infusions include intramuscular, intravenous administration as a bolus or by continuous infusion over a period of time, intraarterial, intra-articular, intraperitoneal, or subcutaneous administration. In some embodiments, the administration is intravenous administration. In some embodiments, the administration is subcutaneous. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies provided herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

Dosages for a particular anti-Sortilin antibody may be determined empirically in individuals who have been given one or more administrations of the anti-Sortilin antibody. Individuals are given incremental doses of an anti-Sortilin antibody. To assess efficacy of an anti-Sortilin antibody, a clinical symptom of any of the diseases, disorders, or conditions of the present disclosure (e.g., frontotemporal dementia, Alzheimer's disease, vascular dementia, seizures, retinal dystrophy, a traumatic brain injury, a spinal cord injury, long-term depression, atherosclerotic vascular diseases, and undesirable symptoms of normal aging) can be monitored.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 µg/kg to 15 mg/kg (e.g., 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g., every week or every three weeks (e.g., such that the patient receives from about two to about twenty, or e.g., about six doses of the antibody). In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. An initial higher loading dose, followed by one or more lower doses may be administered. However, other dosage regimens may be useful. The progress of this therapy is easily monitored by conventional techniques and assays.

Therapeutic Uses

In certain aspects, anti-Sortilin antibodies of the present disclosure can be used for preventing, reducing risk for, or treating an individual having a disease, disorder, or injury. Anti-Sortilin antibodies of the present disclosure can be used to prevent, reduce risk of, or treat cell death (e.g., neuronal cell death), frontotemporal dementia, Alzheimer's disease, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotrophic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, intervertebral disc degeneration, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arthritis, multiple sclerosis, metabolic disorder, obesity, insulin resistance, type 2 diabetes, tissue or vascular damage, an injury, and/or one or more undesirable symptoms of normal aging.

In certain aspects, provided herein is a method of preventing, reducing risk for, or treating an individual having a disease, disorder, or injury, comprising administering to an individual in need thereof a therapeutically effective amount of an anti-Sortilin antibody of the present disclosure. In some embodiments, the disease, disorder or injury is selected from the group consisting of frontotemporal dementia, progressive supranuclear palsy, Alzheimer's disease, vascular dementia, seizures, retinal dystrophy, amyotrophic lateral sclerosis, traumatic brain injury, a spinal cord injury, dementia, stroke, Parkinson's disease, acute disseminated encephalomyelitis, retinal degeneration, age related macular degeneration, glaucoma, multiple sclerosis, septic shock, bacterial infection, arthritis, and osteoarthritis.

Certain aspects of the present disclosure provide methods of increasing Progranulin levels in an individual in need thereof, such as in the brain, blood, and/or peripheral organs of the individual, by administering to the individual a therapeutically effective amount of one or more anti-Sortilin antibodies of the present disclosure. Other aspects of the present disclosure provide methods of increasing extracellular levels of Progranulin, by contacting one or more cells with one or more anti-Sortilin antibodies of the present disclosure. In some embodiments, levels of Progranulin are increased without decreasing cellular levels of Sortilin. Other aspects of the present disclosure provide methods of decreasing cellular levels of Sortilin in an individual in need thereof, such as in the brain and/or peripheral organs of the individual, by administering to the individual a therapeutically effective amount of one or more anti-Sortilin antibodies of the present disclosure. Other aspects of the present disclosure provide methods of decreasing cellular levels of Sortilin of one or more cells, comprising contacting one or more cells with one or more anti-Sortilin antibodies of the present disclosure.

Further aspects of the present disclosure provide methods for increasing the effective concentrations of Progranulin and/or reducing the effective concentrations of a neurotrophin of the present disclosure (e.g., pro-neurotrophin-3, pro-neurotrophin-4/5, pro-neurotrophins, pro-NGF, pro-BDNF, neurotrophin-3, neurotrophin-4/5, NGF, BDNF, etc.), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), PCSK9, and receptor associated protein (RAP) in an individual in need thereof, by administering to the individual a therapeutically effective amount of an anti-Sortilin antibody of the present disclosure to inhibit the interaction between Sortilin and Progranulin, a neurotrophin of the present disclosure (e.g., pro-neurotrophins, pro-neurotrophin-3, pro-neurotrophin-4/5, pro-NGF, pro-BDNF, neurotrophin-3, neurotrophin-4/5, NGF, BDNF, etc.), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), and/or receptor associated protein (RAP).

The present disclosure also provides methods of inhibiting the interaction between Sortilin and Progranulin, a neurotrophin of the present disclosure (e.g., pro-neurotrophins, pro-neurotrophin-3, pro-neurotrophin-4/5, pro-NGF, pro-BDNF, neurotrophin-3, neurotrophin-4/5, NGF, BDNF, etc.), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), PCSK9, and/or receptor associated protein (RAP); as well as one or more activities of Sortilin, Progranulin, a neurotrophin of the present disclosure (e.g., pro-neurotrophins, pro-neurotrophin-3, pro-neurotrophin-4/5, pro-NGF, pro-BDNF, neurotrophin-3, neurotrophin-4/5, NGF, BDNF, etc.), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), and/or receptor associated protein (RAP) in an individual by administering to the individual a therapeutically effective amount of an anti-Sortilin antibody of the present disclosure.

In certain aspects, provided herein is a method of preventing, reducing risk for, or treating an individual having a disease, disorder, or injury, comprising administering to an individual in need thereof a therapeutically effective amount of an anti-Sortilin antibody of the present disclosure.

As disclosed herein, anti-Sortilin antibodies of the present disclosure may be used for preventing, reducing risk, or treating frontotemporal dementia, Alzheimer's disease, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotrophic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, intervertebral disc degeneration, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arthritis, multiple sclerosis, metabolic disorder, obesity, insulin resistance, type 2 diabetes, tissue or vascular damage, an injury, and one or more undesirable symptoms of normal aging.

In some embodiments, the present disclosure provides methods of preventing, reducing risk, or treating an individual having frontotemporal dementia, Alzheimer's disease, vascular dementia, seizures, retinal dystrophy, a traumatic brain injury, a spinal cord injury, long-term depression, atherosclerotic vascular diseases, undesirable symptoms of normal aging, dementia, mixed dementia, Creutzfeldt-Jakob disease, normal pressure hydrocephalus, amyotrophic lateral sclerosis, Huntington's disease, taupathy disease, stroke, acute trauma, chronic trauma, lupus, acute and chronic colitis, Crohn's disease, inflammatory bowel disease, ulcerative colitis, malaria, essential tremor, central nervous system lupus, Behcet's disease, Parkinson's disease, dementia with Lewy bodies, multiple system atrophy, intervertebral disc degeneration, Shy-Drager syndrome, progressive supranuclear palsy, cortical basal ganglionic degeneration, acute disseminated encephalomyelitis, granulomartous disorders, Sarcoidosis, diseases of aging, age related macular degeneration, glaucoma, retinitis pigmentosa, retinal degeneration, respiratory tract infection, sepsis, eye infection, systemic infection, inflammatory disorders, arthritis, multiple sclerosis, metabolic disorder, obesity, insulin resistance, type 2 diabetes, tissue or vascular damage, an injury, and one or more undesirable symptoms of normal aging, in an individual in need thereof by administering to the individual a therapeutically effective amount of an anti-Sortilin antibody of the present disclosure to: (i) inhibit the interaction between Sortilin and Progranulin, a neurotrophin of the present disclosure (e.g., pro-neurotrophins, pro-neurotrophin-3, pro-neurotrophin-4/5, pro-NGF, pro-BDNF, neurotrophin-3, neurotrophin-4/5, NGF, BDNF, etc.), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), and/or receptor associated protein (RAP); and/or (ii) inhibit one or more activities of Sortilin, Progranulin, a neurotrophin of the present disclosure (e.g., pro-neurotrophins, pro-neurotrophin-3, pro-neurotrophin-4/5, pro-NGF, pro-BDNF, neurotrophin-3, neurotrophin-4/5, NGF, BDNF, etc.), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), and/or receptor associated protein (RAP). In some embodiments, the present disclosure provides methods of inducing wound healing in an individual in need thereof by administering to the individual a therapeutically effective amount of an anti-Sortilin antibody of the present disclosure.

The present disclosure also provides methods of promoting cell survival, such as neuronal cell survival, by administering an anti-Sortilin antibody of the present disclosure to inhibit the interaction between Sortilin and Progranulin, a neurotrophin of the present disclosure (e.g., pro-neurotrophins, pro-neurotrophin-3, pro-neurotrophin-4/5, pro-NGF, pro-BDNF, neurotrophin-3, neurotrophin-4/5, NGF, BDNF, etc.), neurotensin, p75, amyloid precursor protein (APP), and the A beta peptide. The anti-Sortilin antibody may be administered to cells in vitro to promote cell survival. Alternatively, the anti-Sortilin antibody may be administered in vivo (e.g., by administering the antibody to an individual) to promote cell survival.

In certain aspects, provided herein is a method of inhibiting one or more of neuroinflammation, axonopathy characterized by short axonal outgrowth and aberrant branching, microglial activation, and inflammatory response, comprising administering to the individual a therapeutically effective amount of an anti-Sortilin antibody of the present disclosure.

The present disclosure provides methods of inhibiting neuroinflammation, axonopathy characterized by short axonal outgrowth and aberrant branching, microglial activation, and inflammatory response and promoting wound healing, autophagy and the clearance of aggregate proteins by administering an anti-Sortilin antibody of the present disclosure to inhibit the interaction between Sortilin and Progranulin, a neurotrophin of the present disclosure (e.g., pro-neurotrophins, pro-neurotrophin-3, pro-neurotrophin-4/5, pro-NGF, pro-BDNF, neurotrophin-3, neurotrophin-4/5, NGF, BDNF, etc.), neurotensin, p75, amyloid precursor protein (APP), and the A beta peptide. The anti-Sortilin antibody may be administered to cells in vitro. Alternatively, the anti-Sortilin antibody may be administered in vivo (e.g., by administering the antibody to an individual).

In certain aspects, provided herein is a method of promoting one or more of wound healing, autophagy, and clearance of aggregate proteins, comprising administering to the individual a therapeutically effective amount of an anti-Sortilin antibody of the present disclosure.

In certain aspects, provided herein is a method of preventing, reducing risk, or treating an individual having arthritis, comprising administering to the individual a therapeutically effective amount of an anti-Sortilin antibody of the present disclosure.

The present disclosure also provides methods of decreasing expression of one or more pro-inflammatory mediators by administering to an individual in need thereof an anti-Sortilin antibody of the present disclosure. In some embodiments, the one or more pro-inflammatory mediators are selected from IL-6, IL12p70, IL12p40, IL-1β, TNF-α, CXCL1, CCL2, CCL3, CCL4, and CCL5.

In some embodiments, a method of the present disclosure includes an anti-Sortilin antibody comprising two or more anti-Sortilin antibodies.

Dementia

Dementia is a non-specific syndrome (i.e., a set of signs and symptoms) that presents as a serious loss of global cognitive ability in a previously unimpaired person, beyond what might be expected from normal ageing. Dementia may be static as the result of a unique global brain injury. Alternatively, dementia may be progressive, resulting in long-term decline due to damage or disease in the body. While dementia is much more common in the geriatric population, it can also occur before the age of 65. Cognitive areas affected by dementia include, without limitation, memory, attention span, language, and problem solving. Generally, symptoms must be present for at least six months to before an individual is diagnosed with dementia.

Exemplary forms of dementia include, without limitation, frontotemporal dementia, Alzheimer's disease, vascular dementia, semantic dementia, and dementia with Lewy bodies.

Without wishing to be bound by theory, it is believed that administering an anti-Sortilin antibody of the present disclosure can prevent, reduce the risk, and/or treat dementia. In some embodiments, administering an anti-Sortilin antibody may induce one or more Progranulin activities in an individual having dementia (e.g., neurotrophic and/or survival activity on neurons, and anti-inflammatory activity).

Frontotemporal Dementia

Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. The clinical features of FTD include memory deficits, behavioral abnormalities, personality changes, and language impairments (Cruts, M. & Van Broeckhoven, C., *Trends Genet.* 24:186-194 (2008); Neary, D., et al., *Neurology* 51:1546-1554 (1998); Ratnavalli, E., Brayne, C., Dawson, K. & Hodges, J. R., *Neurology* 58:1615-1621 (2002)).

A substantial portion of FTD cases are inherited in an autosomal dominant fashion, but even in one family, symptoms can span a spectrum from FTD with behavioral disturbances, to Primary Progressive Aphasia, to Cortico-Basal Ganglionic Degeneration. FTD, like most neurodegenerative diseases, can be characterized by the pathological presence of specific protein aggregates in the diseased brain. Historically, the first descriptions of FTD recognized the presence of intraneuronal accumulations of hyperphosphorylated Tau protein in neurofibrillary tangles or Pick bodies. A causal role for the microtubule associated protein Tau was supported by the identification of mutations in the gene encoding the Tau protein in several families (Hutton, M., et al., *Nature* 393:702-705 (1998). However, the majority of FTD brains show no accumulation of hyperphosphorylated Tau but do exhibit immunoreactivity to ubiquitin (Ub) and TAR DNA binding protein (TDP43) (Neumann, M., et al., *Arch. Neurol.* 64:1388-1394 (2007)). A majority of those FTD cases with Ub inclusions (FTD-U) were shown to carry mutations in the Progranulin gene.

Progranulin mutations result in haploinsufficiency and are known to be present in nearly 50% of familial FTD cases, making Progranulin mutation a major genetic contributor to FTD. Without wishing to be bound by theory, it is believed that the loss-of-function heterozygous character of Progranulin mutations indicates that in healthy individuals, Progranulin expression plays a dose-dependent, critical role in protecting healthy individuals from the development of FTD. Accordingly, increasing levels of Progranulin by inhibiting the interaction between Sortilin and Progranulin, can prevent, reduce the risk, and/or treat FTD.

In some embodiments, administering an anti-Sortilin antibody of the present disclosure, can prevent, reduce the risk, and/or treat FTD. In some embodiments, administering an anti-Sortilin antibody may modulate one or more Sortilin activities in an individual having FTD.

Alzheimer's Disease

Alzheimer's disease (AD) is the most common form of dementia. There is no cure for the disease, which worsens as it progresses, and eventually leads to death. Most often, AD is diagnosed in people over 65 years of age. However, the less-prevalent early-onset Alzheimer's can occur much earlier.

Common symptoms of Alzheimer's disease include, behavioral symptoms, such as difficulty in remembering recent events; cognitive symptoms, confusion, irritability and aggression, mood swings, trouble with language, and long-term memory loss. As the disease progresses bodily functions are lost, ultimately leading to death. Alzheimer's disease develops for an unknown and variable amount of time before becoming fully apparent, and it can progress undiagnosed for years.

It has been shown that Sortilin binds to amyloid precursor protein (APP) and the APP processing enzyme BACE1. Without wishing to be bound by theory, it is believed that these interactions are involved in Alzheimer's disease. Accordingly, and without wishing to be bound by theory, it is believed that anti-Sortilin antibodies of the present disclosure can be utilized to inhibit such interactions and prevent, reduce the risk of, or treat Alzheimer's disease in individuals in need thereof.

In some embodiments, and without wishing to be bound by theory, it is believed that anti-Sortilin antibodies of the present disclosure that inhibit the interaction between Sortilin and neurotrophins of the present disclosure (e.g., pro-neurotrophins, pro-neurotrophin-3, pro-neurotrophin-4/5, pro-NGF, pro-BDNF, neurotrophin-3, neurotrophin-4/5, NGF, BDNF, etc.), p75, amyloid precursor protein (APP), and/or the A beta peptide, or that inhibit one or more activities of Sortilin can be utilized to prevent, reduce the risk of, or treat Alzheimer's disease in individuals in need thereof.

In some embodiments, administering an anti-Sortilin antibody of the present disclosure can prevent, reduce the risk, and/or treat Alzheimer's disease. In some embodiments, administering an anti-Sortilin antibody may modulate one or more Sortilin activities in an individual having Alzheimer's disease.

Vascular Dementia

Vascular dementia (VaD) is a subtly progressive worsening of memory and other cognitive functions that is believed to be due to cerebrovascular disease (vascular disease within the brain). Cerebrovascular disease is the progressive change in our blood vessels (vasculature) in the brain (cerebrum). The most common vascular change associated with age is the accumulation of cholesterol and other substances in the blood vessel walls. This results in the thickening and hardening of the walls, as well as narrowing of the vessels, which can result in a reduction or even a complete stopping of blood flow to brain regions supplied by the affected artery. Vascular dementia patients often present with similar symptoms to Alzheimer's disease (AD) patients. However, the related changes in the brain are not due to AD pathology but to chronic reduced blood flow in the brain, eventually resulting in dementia. VaD is considered one of the most common types of dementia in older adults. Symptoms of VaD include difficulties with memory, difficulty with organization and solving complex problems, slowed thinking, distraction or "absent mindedness," difficulty retrieving words from memory, changes in mood or behavior such as depression, irritability, or apathy, and hallucinations or delusions.

Without wishing to be bound by theory, it is believed that one or more activities of Sortilin, or one or more interactions between Sortilin and Progranulin, neurotrophins of the present disclosure (e.g., pro-neurotrophins, pro-neurotrophin-3, pro-neurotrophin-4/5, pro-NGF, pro-BDNF, neurotrophin-3, neurotrophin-4/5, NGF, BDNF, etc.), neurotensin, lipoprotein lipase, apolipoprotein AV, and/or receptor-associated protein are involved in vascular dementia. Accordingly, and without wishing to be bound by theory, it is believed that anti-Sortilin antibodies of the present disclosure that inhibit the interaction between Sortilin and neurotrophins of the present disclosure (e.g., pro-neurotrophins, pro-neurotrophin-3, pro-neurotrophin-4/5, pro-NGF, pro-BDNF, neurotrophin-3, neurotrophin-4/5, NGF, BDNF, etc.), neurotensin, p75, Sortilin propeptide (Sort-pro), amyloid precursor protein (APP), the A beta peptide, lipoprotein lipase (LpL), apolipoprotein AV (APOA5), apolipoprotein E (APOE), and/or receptor associated protein (RAP); or that inhibit one or more activities of Sortilin can be utilized to prevent, reduce the risk of, or treat vascular dementia in individuals in need thereof.

In some embodiments, administering an anti-Sortilin antibody of the present disclosure can prevent, reduce the risk, and/or treat VaD. In some embodiments, administering an anti-Sortilin antibody may modulate one or more Sortilin activities in an individual having VaD.

Seizures, Retinal Dystrophy, Traumatic Brain Injuries, Spinal Cord Injuries, and Long-Term Depression As used herein, retinal dystrophy refers to any disease or condition that involves the degeneration of the retinal. Such diseases or conditions may lead to loss of vision or complete blindness.

As used herein, seizures also include epileptic seizures, and refer to a transient symptom of abnormal excessive or synchronous neuronal activity in the brain. The outward effect can be as dramatic as a wild thrashing movement or as mild as a brief loss of awareness. Seizures can manifest as an alteration in mental state, tonic or clonic movements, convulsions, and various other psychic symptoms.

Traumatic brain injuries (TBI), may also be known as intracranial injuries. Traumatic brain injuries occur when an external force traumatically injures the brain. Traumatic brain injuries can be classified based on severity, mechanism (closed or penetrating head injury), or other features (e.g., occurring in a specific location or over a widespread area).

Spinal cord injuries (SCI) include any injury to the spinal cord that is caused by trauma instead of disease. Depending on where the spinal cord and nerve roots are damaged, the symptoms can vary widely, from pain to paralysis to incontinence. Spinal cord injuries are described at various levels of "incomplete", which can vary from having no effect on the patient to a "complete" injury which means a total loss of function.

Long-term depression (LTD) is an activity-dependent reduction in the efficacy of neuronal synapses lasting hours or longer following a long patterned stimulus. Long-term depression can occur in many areas of the central nervous system with varying mechanisms depending upon brain region and developmental progress. Long-term depression can occur in the hippocampus, cerebellum, and in different types of neurons that release various neurotransmitters. Without wishing to be bound by theory, it is believed that long-term depression may be associated with neurodegeneration, dementia, and Alzheimer's disease.

It has been shown that pro-neurotrophins (e.g., pro-neurotrophin-4/5, neurotrophin-4/5, pro-NGF, pro-BDNF, etc.) play a role in seizures, retinal dystrophy, traumatic brain injury, spinal cord injury, and long-term depression.

Accordingly, and without wishing to be bound by theory, it is believed that anti-Sortilin antibodies of the present disclosure that inhibit the interaction between Sortilin and neurotrophins of the present disclosure (e.g., pro-neurotrophins, pro-neurotrophin-3, pro-neurotrophin-4/5, pro-NGF, pro-BDNF, neurotrophin-3, neurotrophin-4/5, NGF, BDNF, etc.); or that inhibit one or more activities of Sortilin can be utilized to prevent, reduce the risk of, or treat seizures, retinal dystrophy, traumatic brain injuries, spinal cord injuries, and/or long-term depression in individuals in need thereof.

In some embodiments, administering an anti-Sortilin antibody of the present disclosure can prevent, reduce the risk, and/or treat seizures, retinal dystrophy, traumatic brain injuries, spinal cord injuries, and/or long-term depression. In some embodiments, administering an anti-Sortilin antibody may modulate one or more Sortilin activities in an individual having seizures, retinal dystrophy, traumatic brain injuries, spinal cord injuries, and/or long-term depression.

Atherosclerotic Vascular Diseases

As used herein, "atherosclerotic vascular disease," "ASVD," and "atherosclerosis" are used interchangeably and refer to any condition in which an artery wall thickens as a result of the accumulation of fatty materials such as cholesterol, lipids, and triglyceride. Atherosclerotic vascular diseases include, without limitation, any ASVD-associated condition, disorder, or disease, including without limitation, thromboembolism, stroke, ischemia, infarctions, coronary thrombosis, myocardial infarction (e.g., heart attack), and claudication.

As disclosed herein, Sortilin proteins of the present disclosure are involved in lipid regulation, by binding lipid-associated proteins, such as receptor associated protein, lipoprotein lipase and apopolipoproteins APOA5 and APOE.

Accordingly, and without wishing to be bound by theory, it is believed that anti-Sortilin antibodies of the present disclosure that inhibit the interaction between Sortilin and lipoprotein lipase (LpL), apolipoprotein AV (APOA5), apolipoprotein E (APOE), and/or receptor associated protein (RAP); or that inhibit one or more activities of Sortilin can be utilized to prevent, reduce the risk of, or treat one or more atherosclerotic vascular disease in individuals in need thereof.

In some embodiments, administering an anti-Sortilin antibody of the present disclosure can prevent, reduce the risk, and/or treat atherosclerotic vascular disease. In some embodiments, administering an anti-Sortilin antibody may modulate one or more Sortilin activities in an individual having atherosclerotic vascular disease.

Undesirable Symptoms of Aging

As used herein, undesirable symptoms of aging include, without limitation, memory loss, behavioral changes, dementia, Alzheimer's disease, retinal degeneration, atherosclerotic vascular diseases, hearing loss, and cellular breakdown.

In some embodiments, and without wishing to be bound by theory, it is believed that anti-Sortilin antibodies of the present disclosure that inhibit the interaction between Sortilin and Progranulin, neurotrophins of the present disclosure (e.g., pro-neurotrophins, pro-neurotrophin-3, pro-neurotrophin-4/5, pro-NGF, pro-BDNF, neurotrophin-3, neurotrophin-4/5, NGF, BDNF, etc.), neurotensin, p75, lipoprotein lipase (LpL), apolipoprotein AV (APOA5), and/or receptor associated protein (RAP); or that inhibit one or more activities of Sortilin can be utilized to prevent, reduce the risk of, or treat one or more undesirable symptoms of aging.

In some embodiments, administering an anti-Sortilin antibody of the present disclosure can prevent, reduce the risk, and/or treat one or more undesirable symptoms of aging. In some embodiments, administering an anti-Sortilin antibody may modulate one or more Sortilin activities in an individual having one or more undesirable symptoms of aging.

Amyotrophic Lateral Sclerosis (ALS)

As used herein, amyotrophic lateral sclerosis (ALS) or, motor neuron disease or, Lou Gehrig's disease are used interchangeably and refer to a debilitating disease with varied etiology characterized by rapidly progressive weakness, muscle atrophy and fasciculations, muscle spasticity, difficulty speaking (dysarthria), difficulty swallowing (dysphagia), and difficulty breathing (dyspnea).

PGRN haploinsufficiency due to heterozygous loss-of-function mutations in the GRN gene results in a reduction of CSF PGRN levels and is causal for the development of frontotemporal dementia (FTD) with TDP-43 pathology (Sleegers et al., (2009) Ann Neurol 65:603; Smith et al., (2012) Am J Hum Genet 90:1102). TDP-43 has also been identified as a major pathological protein in ALS, suggesting a similarity between ALS and FTD.

For example, over twenty dominant mutations in TDP-43 have been identified in sporadic and familial ALS patients (Lagier-Tourenne et al., (2009) Cell 136:1001) and TDP-43 positive aggregates are found in approximately 95% of ALS cases (Prasad et al., (2019) Front Mol Neurosci 12:25). Furthermore, ALS risk genes, such as MOBP, C9ORF72, MOBKL2B, NSF and FUS, can also cause FTD (Karch et al., (2018) JAMA Neurol 75:860). In addition, both PGRN and C9ORF72 mutations are associated with abnormal microglial activation, which appears to be another common pathology of FTD and ALS (Haukedal et al., (2019) J Mol Biol 431:1818). Other evidence also suggests that ALS and FTD are closely related conditions with overlapping genetic, neuropathological, and clinical features (Weishaupt et al., (2016) Trends Mol Med 22:769; McCauley et al., (2018) Acta Neuropathol 137:715). Taken together, these results suggest that both diseases could benefit from shared treatments and that PGRN genetic variability acts as a modifier of the course of ALS.

In some embodiments, and without wishing to be bound by theory, it is believed that anti-Sortilin antibodies of the present disclosure that inhibit the interaction between Sortilin and Progranulin, neurotrophins of the present disclosure (e.g., pro-neurotrophins, pro-neurotrophin-3, pro-neurotrophin-4/5, pro-NGF, pro-BDNF, neurotrophin-3, neurotrophin-4/5, NGF, BDNF, etc.), neurotensin, p75, lipoprotein lipase (LpL), apolipoprotein AV (APOA5), and/or receptor associated protein (RAP); or that inhibit one or more activities of Sortilin can be utilized to prevent, or treat one or more undesirable symptoms of ALS In some embodiments, administering an anti-Sortilin antibody of the present disclosure can prevent, reduce the risk, and/or treat ALS. In some embodiments, administering an anti-Sortilin antibody may modulate one or more Sortilin activities in an individual having ALS.

Depression

As used herein, depression or, major depressive disorder (MDD), clinical depression, major depression, unipolar depression, unipolar disorder, recurrent depression or, dysthymia, are used interchangeably and refer to a mental disorder characterized by episodes of all-encompassing low mood accompanied by low self-esteem and loss of interest or pleasure in normally enjoyable activities.

Accordingly, and without wishing to be bound by theory, it is believed that anti-Sortilin antibodies of the present disclosure that inhibit the interaction between Sortilin and Progranulin, neurotrophins of the present disclosure (e.g., pro-neurotrophins, pro-neurotrophin-3, pro-neurotrophin-4/5, pro-NGF, pro-BDNF, neurotrophin-3, neurotrophin-4/5, NGF, BDNF, etc.), neurotensin, p75, lipoprotein lipase (LpL), apolipoprotein AV (APOA5), and/or receptor associated protein (RAP); or that inhibit one or more activities of Sortilin can be utilized to prevent, or treat one or more undesirable symptoms of depression.

In some embodiments, administering an anti-Sortilin antibody of the present disclosure can prevent, reduce the risk, and/or treat depression. In some embodiments, administering an anti-Sortilin antibody may modulate one or more Sortilin activities in an individual having depression.

Parkinson's Disease

Parkinson's disease, which may be referred to as idiopathic or primary parkinsonism, hypokinetic rigid syndrome (HRS), or paralysis agitans, is a neurodegenerative brain disorder that affects motor system control. The progressive death of dopamine-producing cells in the brain leads to the major symptoms of Parkinson's. Most often, Parkinson's disease is diagnosed in people over 50 years of age. Parkinson's disease is idiopathic (having no known cause) in most people. However, genetic factors also play a role in the disease.

Symptoms of Parkinson's disease include, without limitation, tremors of the hands, arms, legs, jaw, and face, muscle rigidity in the limbs and trunk, slowness of movement (bradykinesia), postural instability, difficulty walking, neuropsychiatric problems, changes in speech or behavior, depression, anxiety, pain, psychosis, dementia, hallucinations, and sleep problems.

In some embodiments, administering an anti-Sortilin antibody of the present disclosure can prevent, reduce the risk, and/or treat Parkinson's disease. In some embodiments, administering an anti-Sortilin antibody may induce one or more Progranulin activities in an individual having Parkinson's disease. In some embodiments, administering an anti-Sortilin antibody may modulate one or more Sortilin activities in an individual having Parkinson's disease.

Huntington's Disease

Huntington's disease (HD) is an inherited neurodegenerative disease caused by an autosomal dominant mutation in the Huntingtin gene (HTT). Expansion of a cytokine-adenine-guanine (CAG) triplet repeat within the Huntingtin gene results in production of a mutant form of the Huntingtin protein (Htt) encoded by the gene. This mutant Huntingtin protein (mHtt) is toxic and contributes to neuronal death. Symptoms of Huntington's disease most commonly appear between the ages of 35 and 44, although they can appear at any age.

Symptoms of Huntington's disease, include, without limitation, motor control problems, jerky, random movements (chorea), abnormal eye movements, impaired balance, seizures, difficulty chewing, difficulty swallowing, cognitive problems, altered speech, memory deficits, thinking difficulties, insomnia, fatigue, dementia, changes in personality, depression, anxiety, and compulsive behavior.

In some embodiments, administering an anti-Sortilin antibody of the present disclosure can prevent, reduce the risk, and/or treat Huntington's disease. In some embodiments, administering an anti-Sortilin antibody may induce one or more Progranulin activities in an individual having Huntington's disease. In some embodiments, administering an anti-Sortilin antibody may modulate one or more Sortilin activities in an individual having Huntington's disease.

Taupathy Disease

Taupathy diseases, or Tauopathies, are a class of neurodegenerative disease caused by aggregation of the microtubule-associated protein tau within the brain. Alzheimer's disease (AD) is the most well-known taupathy disease, and involves an accumulation of tau protein within neurons in the form of insoluble neurofibrillary tangles (NFTs). Other taupathy diseases and disorders include progressive supranuclear palsy, dementia pugilistica (chromic traumatic encephalopathy), frontotemporal dementia and parkinsonism linked to chromosome 17, Lytico-Bodig disease (Parkinson-dementia complex of Guam), Tangle-predominant dementia, Ganglioglioma and gangliocytoma, Meningioangiomatosis, Subacute sclerosing panencephalitis, lead encephalopathy, tuberous sclerosis, Hallervorden-Spatz disease, lipofuscinosis, Pick's disease, corticobasal degeneration, Argyrophilic grain disease (AGD), Huntington's disease, and frontotemporal lobar degeneration.

In some embodiments, administering an anti-Sortilin antibody of the present disclosure, can prevent, reduce the risk, and/or treat taupathy disease. In some embodiments, administering an anti-Sortilin antibody may induce one or more Progranulin activities in an individual having a taupathy disease. In some embodiments, administering an anti-Sortilin antibody may modulate one or more Sortilin activities in an individual having a taupathy disease.

Multiple Sclerosis

Multiple sclerosis (MS) can also be referred to as disseminated sclerosis or encephalomyelitis disseminata. MS is an inflammatory disease in which the fatty myelin sheaths around the axons of the brain and spinal cord are damaged, leading to demyelination and scarring as well as a broad spectrum of signs and symptoms.

Symptoms of MS include, without limitation, changes in sensation, such as loss of sensitivity or tingling; pricking or numbness, such as hypoesthesia and paresthesia; muscle weakness; clonus; muscle spasms; difficulty in moving; difficulties with coordination and balance, such as ataxia; problems in speech, such as dysarthria, or in swallowing, such as dysphagia; visual problems, such as nystagmus, optic neuritis including phosphenes, and diplopia; fatigue; acute or chronic pain; and bladder and bowel difficulties; cognitive impairment of varying degrees; emotional symptoms of depression or unstable mood; Uhthoffs phenomenon, which is an exacerbation of extant symptoms due to an exposure to higher than usual ambient temperatures; and Lhermitte's sign, which is an electrical sensation that runs down the back when bending the neck.

In some embodiments, administering an anti-Sortilin antibody of the present disclosure can prevent, reduce the risk, and/or treat multiple sclerosis. In some embodiments, administering an anti-Sortilin antibody may induce one or more Progranulin activities in an individual having multiple sclerosis. In some embodiments, administering an anti-Sortilin antibody may modulate one or more Sortilin activities in an individual having multiple sclerosis.

Glaucoma and Macular Degeneration

Glaucoma describes, without limitation, a group of diseases that are characterized by a damaged optic nerve, resulting in vision loss and blindness. Glaucoma is usually caused by increased fluid pressure (=intraocular pressure) in the anterior chamber underneath the cornea. Glaucoma results in the successive loss of retinal ganglion cells that are important for vision. Age-related macular degeneration usually affects older people and primarily causes loss of vision in the macula, the central field of vision. Macular degeneration causes, without limitation, drusen, pigmentary changes, distorted vision, hemorrhages of the eye, atrophy, reduced visual acuity, blurred vision, central scotomas, reduced color vision and reduced contrast sensitivity.

Without wishing to be bound by theory, it is believed that administering an anti-Sortilin antibody of the present disclosure can prevent, reduce the risk, and/or treat glaucoma and macular degeneration. In some embodiments, administering an anti-Sortilin antibody may induce one or more Progranulin activities in an individual having glaucoma or macular degeneration. In some embodiments, administering an anti-Sortilin antibody may modulate one or more Sortilin activities in an individual having glaucoma or macular degeneration.

Degenerative Disc Disease (DDD)

Degenerative disc disease (DDD) describes, without limitation, a group of diseases in which intervertebral disc (IVD) undergoes extensive morphological as well as biomechanical changes, and usually manifests clinically in patients with lower back pain. Degenerative discs typically show degenerative fibrocartilage and clusters of chondrocytes, suggestive of repair. Inflammation may or may not be present. The pathologic findings in DDD include protrusion, spondylolysis, and/or subluxation of vertebrae (sponylolisthesis) and spinal stenosis.

Without wishing to be bound by theory, it is believed that administering an anti-Sortilin antibody of the present disclosure can prevent, reduce the risk, and/or treat DDD. In some embodiments, administering an anti-Sortilin antibody may induce one or more Progranulin activities in an individual having DDD. In some embodiments, administering an anti-Sortilin antibody may modulate one or more Sortilin activities in an individual having DDD.

Pain

Pain describes, without limitation, neuropathic pain arising from nerve injury, e.g., from trauma or disease. Such injury may include injury to peripheral nerves and/or the spinal cord. Sortilin antagonists have been shown to alleviate neuropathic pain. (Richner M et al. (2019) *Sci. Adv.* 5: eaav9946.)

Kits/Articles of Manufacture

Provided herein are articles of manufacture (e.g., kit) comprising an anti-Sortilin antibody described herein. Article of manufacture may include one or more containers comprising an antibody described herein. Containers may be any suitable packaging including, but is not limited to, vials, bottles, jars, flexible packaging (e.g., sealed Mylar or plastic bags), and the like. The containers may be unit doses, bulk packages (e.g., multi-dose packages) or sub-unit doses.

In some embodiments, the kits may further include a second agent. In some embodiments, the second agent is a pharmaceutically-acceptable buffer or diluting agent including, but not limited to, such as bacteriostatic water for injection (BWFI), phosphate-buffered saline, Ringer's solution and dextrose solution. In some embodiments, the second agent is a pharmaceutically active agent.

In some embodiments of any of the articles of manufacture, the article of manufactures further include instructions for use in accordance with the methods of this disclosure. The instructions generally include information as to dosage, dosing schedule, and route of administration for the intended treatment. In some embodiments, these instructions comprise a description of administration of the isolated antibody of the present disclosure (e.g., an anti-Sortilin antibody described herein) to prevent, reduce risk, or treat an individual having a disease, disorder, or injury selected from dementia, frontotemporal dementia, Alzheimer's disease, gauche's disease, vascular dementia, seizures, retinal dystrophy, a traumatic brain injury, a spinal cord injury, atherosclerotic vascular diseases, undesirable symptoms of normal aging, amyotrophic lateral sclerosis (ALS), long-term depression, Parkinson's disease, Huntington's disease, Taupathy disease, multiple sclerosis, age related macular degeneration, glaucoma, degenerative disc disease (DDD), Creutzfeldt-Jakob disease, normal pressure hydrocephalus, Nasu-Hakola disease, stroke, acute trauma, chronic trauma, lupus, acute and chronic colitis, Crohn's disease, inflammatory bowel disease, ulcerative colitis, malaria, essential tremor, central nervous system lupus, Behcet's disease, mixed dementia, dementia with Lewy bodies, multiple system atrophy, Shy-Drager syndrome, progressive supranuclear palsy, cortical basal ganglionic degeneration, acute disseminated encephalomyelitis, granulomatous disorders, sarcoidosis, diseases of aging, retinitis pigmentosa, retinal degeneration, respiratory tract infection, sepsis, eye infection, systemic infection, lupus, arthritis, and wound healing, according to any methods of this disclosure. In some embodiments, the disease, disorder, or injury is frontotemporal dementia. In some embodiments, the instructions include instructions for use of the anti-Sortilin antibody and the second agent (e.g., second pharmaceutically active agent).

Diagnostic Uses

The isolated antibodies of the present disclosure (e.g., an anti-Sortilin antibody described herein) also have diagnostic utility. This disclosure therefore provides for methods of using the antibodies of this disclosure, or functional fragments thereof, for diagnostic purposes, such as the detection of a Sortilin protein in an individual or in tissue samples derived from an individual.

In some embodiments, the individual is a human. In some embodiments, the individual is a human patient suffering from, or at risk for developing a disease, disorder, or injury of the present disclosure. In some embodiments, the diagnostic methods involve detecting a Sortilin protein in a biological sample, such as a biopsy specimen, a tissue, or a cell. An anti-Sortilin antibody described herein is contacted with the biological sample and antigen-bound antibody is detected. For example, a biopsy specimen may be stained with an anti-Sortilin antibody described herein in order to detect and/or quantify disease-associated cells. The detection method may involve quantification of the antigen-bound antibody. Antibody detection in biological samples may occur with any method known in the art, including immunofluorescence microscopy, immunocytochemistry, immunohistochemistry, ELISA, FACS analysis, immunoprecipitation, or micro-positron emission tomography. In certain embodiments, the antibody is radiolabeled, for example with $^{18}F$ and subsequently detected utilizing micro-positron emission tomography analysis. Antibody-binding may also be quantified in a patient by non-invasive techniques such as positron emission tomography (PET), X-ray computed tomography, single-photon emission computed tomography (SPECT), computed tomography (CT), and computed axial tomography (CAT).

In other embodiments, an isolated antibody of the present disclosure (e.g., an anti-Sortilin antibody described herein) may be used to detect and/or quantify, for example, microglia in a brain specimen taken from a preclinical disease model (e.g., a non-human disease model). As such, an isolated antibody of the present disclosure (e.g., an anti-Sortilin antibody described herein) may be useful in evaluating therapeutic response after treatment in a model for a nervous system disease or injury such as frontotemporal dementia, Alzheimer's disease, vascular dementia, seizures, retinal dystrophy, atherosclerotic vascular diseases, Nasu-Hakola disease, or multiple sclerosis, as compared to a control.

The present disclosure will be more fully understood by reference to the following Examples. They should not, however, be construed as limiting the scope of the present disclosure. All citations throughout the disclosure are hereby expressly incorporated by reference.

EXAMPLES

Examples 1-3 describe the generation of affinity-matured variants of an anti-human Sortilin antibody, S-60, and the characterization of those variants with respect to not only their binding affinity for SORT1 but also their biological activity in down-regulating SORT1 expression, increasing PGRN secretion, and blocking PGRN-SORT1 binding. Surprisingly, it was found that improved biological activity did not necessarily correlate with increased affinity.

Example 1: Generation of S-60 Variants and Measurement of SORT1 Binding Affinity The purpose of the following Example was to generate affinity-matured variants of an anti-human Sortilin antibody, S-60, and to characterize the binding of the affinity-matured antibodies to human Sortilin (SORT1).

S-60 Affinity Matured Variants

Affinity-matured antibodies against human Sortilin (SORT1) were generated and their binding to SORT1 measured. The anti-SORT1 antibody, S-60, as well as S-60-1, S-60-2, S-60-3, S-60-4, S-60-5, S-60-6, S-60-7, S-60-8, and S-60-9 have been described in WO2016164637. The $V_H$ and $V_L$ sequences for S-60-9 and S60 in WO2016164637 are identical, and S-60 will be used herein to refer to the antibody. The $V_H$ and $V_L$ sequences for S-60-5, S-60-6, and S-60-7 in WO2016164637 are identical, and S-60-7 will be used herein to refer to the antibody. S-60 was found to be both a potent downregulator of SORT1 levels and a potent blocker of binding between SORT1 and PGRN (see, e.g., Tables 8-10 and FIGS. 6A and 10D in WO2016164637). Therefore, S-60 was selected for further affinity maturation.

The anti-SORT1 variants S-60-10, S-60-11, S-60-12, S-60-13, S-60-14, S-60-15, S-60-16, S-60-18, S-60-19, and S-60-24 were generated as described below.

Production of S-60 Affinity Matured Variants

The anti-SORT1 antibody S-60 was affinity-matured. Briefly, diversified antibody libraries were created in yeast for each of the starting parental antibodies. The diversity in the first round of affinity maturation was created by utilizing standard molecular cloning techniques to combine the parental heavy chain HVR-H3 and light chain (LC) with pre-existing genetic diversity in the HVR-H1 and HVR-H2 regions of the heavy chain (HC) (termed "H1/H2" optimization). For the second round of affinity maturation, both heavy chain variable region ($V_H$) and light chain variable region ($V_L$) sequences were optimized, with a particular focus on HVR-H3.

Selection pressures used for screening the libraries included human SORT1 antigen equilibrium titration, parental antibody Fab competition kinetics, and the use of polyspecificity reagent deselection. FACS flow cytometry was then employed to visualize and select antibodies, using standard techniques (see, e.g., Chao et al. *Nature Protocols*, 2006). The desired population was then carried forward into additional selection rounds.

The affinity-matured anti-SORT1 antibodies were purified as follows: clones were grown to saturation and then induced for 48 h at 30° C. with shaking. After induction, yeast cells were pelleted and the supernatants were harvested for purification. Immunoglobulins were purified using a Protein A column and eluted with acetic acid, pH 2.0. Fab fragments were generated by papain digestion and purified over CaptureSelect IgG-CH1 affinity matrix (LifeTechnologies).

Measurement of Binding Affinity to SORT1

The anti-SORT1 antibody S-60 and affinity-matured variants thereof were tested and compared in a SORT1 binding assay. For the binding assay, stable HEK293T cells expressing human SORT1 were harvested by trypsinization, washed in PBS, counted and plated on 96-well u-bottom plates at $1\times10^5$ cells/well. The plates were spun at 1,400 rpm for 3 minutes and primary anti-SORT1 or control antibodies were added in FACS buffer (PBS+2 FBS) and incubated on ice for one hour. Cells were subsequently centrifuged as before and washed thrice with FACS buffer. Cells were then incubated with anti-human APC conjugated secondary antibody (BD Biosciences) in FACS buffer for 30 minutes on ice. Cells were again washed three times with FACS buffer and analyzed on a BD FACS Canto or an Intellicyt Flow Cytometer. Binding was measured as median fluorescent intensity (MFI) in the PE channel of the GFP positive cell population.

Results

The binding affinities of the anti-SORT1 antibodies to SORT1 are shown below in Table 1. All antibodies were tested on the huIgG1 backbone.

TABLE 1

Binding Affinity to SORT1.

| Antibody ID | $K_D$ (M) | Fold change from S-60 |
|---|---|---|
| S-60 | 1.15E−09* | |
| S-60-1 | 7.221E−09 | 0.16 |
| S-60-2 | 1.101E−08 | 0.10 |
| S-60-3 | 8.56E−10* | 1.34 |
| S-60-4 | 6.34E−10 | 1.81 |
| S-60-7 | 7.87E−10 | 1.46 |
| S-60-8 | 4.68E−10 | 2.46 |
| S-60-10 | 6.5E−10 | 1.77 |
| S-60-11 | 6.5E−10 | 1.77 |
| S-60-12 | 8.9E−10 | 1.29 |
| S-60-13 | 7.5E−10 | 1.53 |
| S-60-14 | 1.05E−09 | 1.10 |
| S-60-15 | 5.60E−10 | 2.05 |
| S-60-16 | 7.80E−10 | 1.47 |
| S-60-18 | 1.63E−09 | 0.71 |
| S-60-19 | 8.00E−10 | 1.44 |
| S-60-24 | 7.55E−10* | 1.52 |

*Note:
$K_D$ values represent the average of two experiments.

Anti-SORT1 antibodies S-60-3, S-60-4, S-60-7, S-60-8, S-60-10, S-60-11, S-60-13, S-60-15, S-60-16, S-60-19, and S-60-24 showed significantly improved affinity for binding to SORT1 compared to S-60. In particular, S-60-8 and S-60-15 demonstrated the highest binding affinities to SORT1 of the tested variants, having a 2.46- and 2.05- increased fold change, respectively, compared to the binding affinity of the parental antibody, S-60.

Example 2: Effect of S-60 Variants on SORT1 Expression and PGRN Secretion

The purpose of the following Example was to characterize the effect of affinity-matured variants of an anti-human SORT1 antibody, S-60, on SORT1 expression and extracellular levels of Progranulin (PGRN).

SORT1 Expression and PGRN Secretion Assays

Affinity matured variants of S-60 were generated as described in Example 1 and were subsequently screened by FACS for their abilities to downregulate SORT1 and to elevate extracellular levels of PGRN. In order to assay the effect of the anti-SORT1 antibodies on SORT1 expression and PGRN secretion, U251 cells that endogenously express SORT1 and secrete PGRN were incubated with anti-SORT1 antibody S-60 and affinity-matured variants. Cell surface levels of SORT1 at different antibody concentrations were measured by FACS as follows: anti-SORT1 antibody S-60 and affinity-matured variants were added to U251 cells seeded at 3×10³ cells/well in 96 well plates with a serial dilution from 0.023 nM to 150 nM. After 72 h, cells were harvested with Trypsin, washed in PBS and labeled with Dylight-650 conjugated anti-SORT1 antibody S-2-11 (described in WO2016164637) to quantify the levels of SORT1 protein remaining. After cells were incubated with 5 pg/ml S-2-11 conjugated to DyLight-650 (Invitrogen) for one hour on ice, cells were washed three times in PBS+2 FBS and binding was quantified using a FACSCanto™ or Intellicyt Flow cytometer as median fluorescence intensity (MFI) of APC.

The amount of PGRN secreted into the cell supernatant over the course of the 72h was measured by standard ELISA as follows: cells were harvested and the media was collected; the concentration of PGRN in the media samples was measured using an R&D Systems human PGRN Duoset ELISA kit, according to manufacturer's instructions. Data were analyzed in Microsoft Excel and GraphPad Prism.

Results

The half maximal effective concentration ($EC_{50}$) for down-regulation (DR) of cell surface levels of SORT1 for each of the tested S-60 variants is shown in Table 2. SORT1 DR was quantified for each S-60 variant tested and expressed as a percent of the control (untreated cells) (Tables 2-4). Additionally, the level of extracellular PGRN secretion was quantified and expressed as a fold change relative to the untreated control as shown in Tables 2-4. Independent experiments are represented in separate tables (Tables 2-4). All antibodies were tested on the huIgG1 WT backbone.

TABLE 2

Percent SORT1 Downregulation (DR) and PGRN Secretion for S-60, S-60-1, S-60-2, S-60-3, S-60-4, S-60-7, and S-60-8

| Antibody ID | DR $EC_{50}$ (M) | DR at 0.6 nM antibody (IgG) | PGRN secretion (fold over control) 0.62 or 0.63 nM antibody (IgG) |
|---|---|---|---|
| S-60 | 6.81E−10 | 29.3 | 1.38 |
| S-60-1 | 2.73E−10 | 50.4 | 1.60 |
| S-60-2 | 4.20E−10 | 40.3 | 1.75 |
| S-60-3 | 2.69E−10 | 43.0 | 1.77 |
| S-60-4 | 4.18E−10 | 39.6 | 1.61 |
| S-60-7 | 4.47E−10 | 32.6 | 1.40 |
| S-60-8 | 5.76E−10 | 32.0 | 1.54 |

TABLE 3

Percent SORT1 Downregulation (DR) and PGRN Secretion for S-60, S-60-3, S-60-24, S-60-15, S-60-16, S-60-18, and S-60-19.

| Antibody ID | DR at 1.25 nM antibody (IgG) | PGRN secretion (fold over control), 0.63 nM antibody (IgG) |
|---|---|---|
| S-60 | 40.17 | 1.11 |
| S-60-3 | 61.50 | 1.32 |
| S-60-24 | 65.20 | 1.35 |
| S-60-15 | 60.92 | 1.42 |
| S-60-16 | 70.14 | 1.42 |
| S-60-18 | 51.33 | 1.13 |
| S-60-19 | 55.46 | 1.35 |

TABLE 4

Percent SORT1 Downregulation (DR) and PGRN Secretion for S-60-24, S-60-10, S-60-11, S-60-12, S-60-13, and S-60-14.

| Antibody ID | DR at 0.63 nM antibody (IgG) | PGRN secretion (fold over control), 0.63 nM antibody (IgG) |
|---|---|---|
| S-60-24 | 81.48 | 1.62 |
| S-60-10 | 85.41 | 1.85 |
| S-60-11 | 88.76 | 1.89 |
| S-60-12 | 87.38 | 1.89 |

TABLE 4-continued

Percent SORT1 Downregulation (DR) and PGRN Secretion for
S-60-24, S-60-10, S-60-11, S-60-12, S-60-13, and S-60-14.

| Antibody ID | DR at 0.63 nM antibody (IgG) | PGRN secretion (fold over control), 0.63 nM antibody (IgG) |
|---|---|---|
| S-60-13 | 82.33 | 1.77 |
| S-60-14 | 80.47 | 1.81 |

In a first experiment analyzing the SORT1 DR $EC_{50}$, the percent of SORT1 DR using a saturating antibody concentration of 0.6 nM IgG, and PGRN secretion using a saturating antibody concentration of 0.62 or 0.63 nM IgG, the following variants were tested: S-60, S-60-1, S-60-2, S-60-3, S-60-4, S-60-7, and S-60-8. As shown in Table 2, S-60-3 demonstrated the lowest DR $EC_{50}$ (0.269 nM) and the highest PGRN secretion, a 1.77-fold increase relative to the control, and an improvement over S-60, which showed a 1.38-fold increase over the control. Using 0.6 nM IgG, S-60-1 exhibited the most substantial effect on SORT1 expression of the variants tested, down-regulating SORT1 by 50.4% compared to the control, whereas S-60 down-regulated SORT1 by 29.3%.

In a subsequent experiment, the percent of DR using a saturating antibody concentration of 1.25 nM IgG, and PGRN secretion using a saturating antibody concentration of 0.63 nM IgG was analyzed for the following variants: S-60, S-60-3, S-60-24, S-60-15, S-60-16, S-60-18, and S-60-19. As shown in Table 3, both S-60-15 and S-60-16 demonstrated the highest levels of extracellular PGRN secretion with a 1.42-fold increase compared to the control, an improvement over S-60 which showed a 1.11-fold increase over the control. Indeed, these two variants also significantly reduced SORT1 expression compared to S-60, down-regulating SORT1 by 60.92% and 70.14%, respectively, relative to the control, whereas S-60 downregulated SORT1 by only 40.17%.

In a third experiment, the percent of DR using a saturating antibody concentration of 0.63 nM IgG, and PGRN secretion using a saturating antibody concentration of 0.63 nM IgG was analyzed for the following variants: S-60-24, S-60-10, S-60-11, S-60-12, S-60-13, and S-60-14. As shown in Table 4, S-60-11 and S-60-12 displayed the highest amount of extracellular PGRN secretion with a 1.89-fold increase compared to the control. S-60-11 also demonstrated the highest SORT1 DR at 0.63 nM IgG, down-regulating SORT1 by 88.76% relative to the control.

Conclusion

As shown in Table 1 in Example 1, S-60-8 and S-60-15 demonstrated the highest affinities for binding to SORT1 compared to S-60 and the other S-60 variants tested with the lowest $K_D$ values of 4.68E-10M and 5.60E-10, respectively. However, when compared to a specific variant, S-60-3, having a higher $K_D$ value of 8.56E-10M (Table 1), S-60-8 displayed a smaller increase in PGRN secretion (Table 2) while S-60-15 displayed a higher fold increase in PGRN secretion than did S-60-3 (Table 3). Additionally, S-60-8 (at a saturating concentration of 0.6 nM IgG) demonstrated a smaller percent reduction of SORT1 expression (Table 2) compared to S-60-3 and S-60-15 (at a saturating concentration of 1.25 nM IgG), which down-regulated SORT1 by 61.50% and 60.92%, respectively (Table 3). Thus, S-60-15 performed better than S-60-3 with respect to increasing PGRN secretion and exhibited a similar effect compared to S-60-3 in down-regulating cell surface levels of SORT1, whereas S-60-8 performed worse than S-60-3 with respect to increasing PGRN secretion and down-regulating cell surface levels of SORT1.

The results of this study indicate that the relative efficacy of anti-SORT1 S-60 antibody variants with respect to down-regulating SORT1 expression or increasing PGRN secretion was not predicted by their relative binding affinities for Sortilin.

Furthermore, S-60-15 showed the greatest increase in PGRN secretion compared to S-60 and certain S-60 variants (Table 3, last column), including S-60-3. S-60-3, in turn, showed increased PGRN secretion relative to S-60-1, -2, -4, -7, and -8 (Table 2, last column). Therefore S-60-15 is an effective antibody for increasing PGRN secretion relative to those S-60 variants. The ability to increase PGRN secretion is an important property in selecting a therapeutic antibody for treatment of diseases such as FTD and other pathologies in which PGRN deficiency plays a direct causal role. Such an antibody would be useful in restoring PGRN levels to, or closer to, wild-type levels, thereby treating the disease. Moreover, this property is an important pharmacodynamic parameter in assessing antibody activity in vivo (see below, Example 5).

Example 3: S-60 Variants Block Binding of PGRN to SORT1

The purpose of the following Example was to characterize the effect of affinity-matured variants of an anti-human SORT1 antibody, S-60, on the binding interaction between SORT1 and a natural ligand, PGRN.

SORT1-PGRN Blocking Assay

The ability of S-60 variants to block the binding of PGRN to SORT1 was also tested. Recombinant human PGRN (PGRN) (Adipogen) was biotinylated with an EZ-Link Micro NHS-PEG4 kit from ThermoScientific/Pierce according to the manufacturer's instructions. A stable cell line expressing full-length untagged human SORT1 (SORT1) was established by viral infection of HEK293T cells, and positive selection with hygromycin (Genscript custom project). As control cells, parental HEK293T cells were utilized.

SORT1-expressing cells or control cells were harvested and washed in PBS. Biotinylated human PGRN was added in PBS+2% FBS with or without a titration of anti-SORT1 antibodies or control human IgG1 isotype antibodies and incubated on ice for 2h. After washing cells 3 times in PBS+2% FBS, cells were incubated in Streptavidin-APC (BD Biosciences, 1:100) on ice for 30 min. Then cells were washed again, resuspended in PBS+2% FBS and analyzed on a FACSCanto™ flow cytometer (BD Biosciences, Mississauga, ON). PGRN binding was measured as the median fluorescence intensity (MFI) of APC of the SORT1 expressing cell population. Binding of biotinylated PGRN to SORT1 expressed on HEK293T cells was measured by FACS in absence or presence of S-60 and its variant antibodies.

Results

The half maximal effective concentration ($EC_{50}$) for blocking PGRN binding to SORT1 for each of the tested S-60 variants is shown in Tables 5-7. Additionally, the maximum level of blocking PGRN to SORT1 was quantified and expressed as a percentage of the maximum block achieved using a saturating concentration of 50 nM IgG or 150 nM IgG (Table 5-7). Independent experiments are shown in separate tables below.

TABLE 5

Blocking of PGRN binding to SORT1 expressed on HEK293T cells for S-60-1, S-60-2, S-60-3, S-60-4, S-60-7, S-60-8, and S-60.

| Antibody ID | PGRN binding block $EC_{50}$ (nM) | PGRN binding block (% max at 150 nM antibody (IgG)) |
|---|---|---|
| S-60-1 | 5.986 | 95.2 |
| S-60-2 | 7.509 | 94.5 |
| S-60-3 | 0.733 | 95.5 |
| S-60-4 | 0.584 | 95.7 |
| S-60-7 | 0.944 | 96.5 |
| S-60-8 | 0.985 | 95.6 |
| S-60 | 0.751 | 95.9 |

TABLE 6

Blocking of PGRN binding to SORT1 expressed on HEK293T cells for S-60, S-60-3, S-60-24, S-60-15, S-60-16, S-60-18, and S-60-19.

| Antibody ID | PGRN binding block $EC_{50}$ (M) | PGRN binding block (% max at 50 nM antibody (IgG)) |
|---|---|---|
| S-60 | 2.20E−09 | 90.13 |
| S-60-3 | 1.76E−09 | 90.44 |
| S-60-24 | 1.11E−09 | 88.94 |
| S-60-15 | 1.22E−09 | 90.74 |
| S-60-16 | 1.20E−09 | 90.44 |
| S-60-18 | 2.27E−09 | 89.33 |
| S-60-19 | 1.53E−09 | 90.15 |

TABLE 7

Blocking of PGRN binding to SORT1 expressed on HEK293T cells for S-60-24, S-60-10, S-60-11, S-60-12, S-60-13, and S-60-14.

| Antibody ID | PGRN binding block $EC_{50}$ (M) | PGRN binding block (% max at 50 nM antibody (IgG)) |
|---|---|---|
| S-60-24 | 4.70E−10 | 95.64 |
| S-60-10 | 4.60E−10 | 93.84 |
| S-60-11 | 4.10E−10 | 94.97 |
| S-60-12 | 6.10E−10 | 93.26 |
| S-60-13 | 5.60E−10 | 93.83 |
| S-60-14 | 6.00E−10 | 93.67 |

In a first experiment analyzing the PGRN binding block $EC_{50}$ and the percentage of PGRN binding block to SORT1 with a saturating concentration of 150 nM IgG, the following variants were tested: S-60-1, S-60-2, S-60-3, S-60-4, S-60-7, S-60-8, and S-60. As shown in Table 5, S-60-4 demonstrated the lowest $EC_{50}$ value (0.584 nM), achieving a 95.7% block of PGRN binding to SORT1. Of the variants analyzed, S-60-7 displayed the greatest reduction in the PGRN binding, blocking 96.5% of PGRN binding to SORT1, though it displayed lower efficiency at blocking PGRN binding (higher $EC_{50}$ value) than S-60 and variants S-60-3 and S-60-4.

In a subsequent experiment analyzing the PGRN binding block $EC_{50}$ and the percentage of PGRN binding block to SORT1 with a saturating concentration of 50 nM IgG, the following variants were tested: S-60, S-60-3, S-60-24, S-60-15, S-60-16, S-60-18, and S-60-19. As shown in Table 6, S-60-24, S-60-15, and S-60-16 displayed the lowest $EC_{50}$ values compared to S-60, ranging from 1.11 nM to 1.22 nM. Furthermore, the S-60-15 variant demonstrated the strongest potency compared to S-60, achieving a 90.74% block of PGRN binding to SORT1.

In a third experiment, the following variants were tested: S-60-24, S-60-10, S-60-11, S-60-12, S-60-13, and S-60-14. As shown in Table 7, S-60-11 demonstrated the lowest $EC_{50}$ (0.410 nM), achieving a 94.97% block of PGRN binding to SORT1. Of the variants analyzed, S-60-24 displayed the greatest reduction in the PGRN binding, blocking 95.64% of PGRN binding to SORT1.

Conclusion

As shown in Table 1 in Example 1, both S-60-8 and S-60-15 demonstrated the highest affinities for binding to SORT1 relative to S-60 and the other S-60 variants tested, with S-60-8 having the highest affinity for SORT1. However, when compared to S-60, S-60-8 displayed a lower efficiency at blocking binding to PGRN (higher $EC_{50}$ value relative to S-60) (Table 5) whereas S-60-15 displayed a higher efficiency at blocking binding to PGRN (reduced $EC_{50}$ value relative to S-60) (Table 6). Moreover, S-60-8 demonstrated a smaller percent maximal blocking of PGRN binding to SORT1 compared to S-60 (Table 5) whereas S-60-15 demonstrated a greater percent maximal blocking of PGRN binding to SORT1 relative to S-60 (Table 6). Thus, S-60-15 performed better than S-60-8 when compared to S-60 with respect to $EC_{50}$ value in blocking PGRN binding to SORT1 and the maximum percentage of blocking PGRN binding to SORT1, despite the fact that S-60-8 showed higher affinity binding to SORT1 compared to S-60-15.

Thus, the results of this study indicate, unexpectedly, that the relative efficacy of anti-SORT1 S-60 antibody variants with respect to blocking the degree of PGRN binding to SORT1 was not predicted by their relative binding affinities for SORT1.

Example 4: S-60-15 Stability and Stress Testing Analysis

The purpose of the following Example was to characterize S-60-15, an affinity-matured variant of S-60 described in previous Examples, for stability under various stress testing conditions.

Stability of a therapeutic antibody is important for clinical efficacy. During manufacturing, storage, and in vivo administration, therapeutic antibodies are at risk for degradation via multiple pathways. The factors that are responsible for such degradation remain poorly understood. Given that S-60-15 demonstrated a high binding affinity for SORT1 (see Example 1), effectively reduced cell surface levels of SORT1 and increased extracellular PGRN secretion (see Example 2), as well substantially blocked PGRN binding to SORT1 (see Example 3), and unexpectedly performed these functional tests better than S-60-8 which showed higher affinity for SORT1, S-60-15 was further evaluated for stability.

pH and Temperature Stress Testing

In order to measure the stability of the amino acid residues within S-60-15, samples of S-60-15 were subjected to pH and temperature stress conditions to emulate stress conditions that occur during manufacturing, storage, and in vivo administration. Briefly, individual samples of S-60-15 were subjected to stress testing at pH 3.5 or pH 5.0 and at 40° C. or 50° C. The samples were tested at various time points—0, 1, 3 and 5 days for the two pH conditions, and 0, 7, 14 and 30 days for the high temperature stress conditions—by treatment with DTT and IAA followed by trypsin digestion. The digested samples were analyzed by Liquid Chromatography with Mass Spectroscopy detection using a Waters ACQUITY UPLC coupled to a Xevo G2-XS QTOF mass spectrometer using a BEH C18 column. Results are shown in Table 8.

TABLE 8

Stoichiometry Percentage Table (% of each peptide with the modifier). Deamid (deamidation); Oxid (oxidation); CAM (carbamido methyl).

| S-60-15 Peptide | Modifier | Non-stress | pH 5 d0 | pH 5 d1 | pH 5 d3 | pH 5 d5 | pH 3.5 d0 | pH 3.5 d1 | pH 3.5 d3 | pH 3.5 d5 | T40 d7 | T40 d14 | T40 d30 | T50 d7 | T50 d14 | T50 d30 |
|---|---|---|---|---|---|---|---|---|---|---|---|---|---|---|---|---|
| NQFSLK (SEQ ID NO: 87) | Deamid | 1.3 | 1.5 | 1.5 | 1.5 | 0.9 | 1.5 | 1.4 | 1.5 | 1.4 | 1.3 | 1.3 | 1.3 | 1.3 | 1.3 | 1.4 |
| QGYYGMDVWGQGTTVTVSSAS TK (SEQ ID NO: 88) | Oxid M(1) | 6.2 | 6.8 | 6.2 | 6.6 | 8.8 | 6.2 | 6.8 | 6.6 | 6.4 | 5.7 | 5.1 | 5.6 | 5.1 | 5.4 | 1.3 |
| QGYYGMDVWGQGTTVT VSSASTK (SEQ ID NO: 88) | Deamid Q(1) | 0.5 | 0.6 | 0.6 | 0.6 | 0.7 | 0.6 | 0.6 | 0.6 | 0.6 | 0.8 | 1.0 | 1.0 | 1.4 | 2.3 | 3.6 |
| DYFPEPVTVSWNSGALTSGV HTFPAVLQSSGLYSLSSVVTV PSSSLGTK (SEQ ID NO: 89) | Deamid N(1) | 3.3 | 3.3 | 3.3 | 3.3 | 3.8 | 3.4 | 3.4 | 3.4 | 3.2 | 3.2 | 3.1 | 0.0 | 3.2 | 3.1 | 3.2 |
| DYFPEPVTVSWNSGALTSGV HTFPAVLQSSGLYSLSSVVTV PSSSLGTK (SEQ ID NO: 89) | Oxid M(1) | 0.3 | 0.4 | 0.4 | 0.4 | 0.4 | 0.4 | 0.4 | 0.3 | 0.3 | 0.4 | 0.5 | 0.8 | 0.7 | 1.0 | 1.5 |
| DTLMISR (SEQ ID NO: 90) | Oxid M(1) | 3.1 | 3.6 | 3.4 | 3.5 | 3.5 | 3.6 | 3.1 | 3.4 | 3.3 | 4.0 | 4.4 | 5.8 | 5.2 | 7.2 | 12.2 |
| TPEVTCVVVDVSQEDPEV QFNWYVDGVEVHNAK (SEQ ID NO: 91) | Deamid N(1) | 1.4 | 1.1 | 1.2 | 1.3 | 1.7 | 1.5 | 1.2 | 1.4 | 1.3 | 0.2 | 0.3 | 1.3 | 1.1 | 0.2 | 5.2 |
| VVSVLTVLHQDWLNGK (SEQ ID NO: 92) | Deamid N(1) | 7.8 | 7.2 | 6.7 | 6.9 | 6.5 | 7.0 | 6.9 | 7.0 | 6.8 | 8.1 | 8.4 | 9.2 | 9.3 | 12.6 | 12.0 |
| EPQVYTLPPSQEEMTK (SEQ ID NO: 93) | Oxid. M(1) | 0.3 | 0.3 | 0.0 | 0.0 | 1.5 | 0.2 | 0.4 | 0.4 | 0.5 | 0.8 | 0.0 | 0.0 | 0.8 | 1.3 | 1.1 |
| NQVSLTCLVK (SEQ ID NO: 94) | Deamid N(1), CAMC(1) | 1.9 | 2.1 | 2.0 | 2.0 | 1.7 | 2.0 | 2.0 | 2.0 | 1.9 | 1.9 | 2.1 | 1.9 | 2.1 | 2.5 | 2.0 |
| GFYPSDIAVEWESNGQPENNYK (SEQ ID NO: 95) | Deamid N(1) | 5.2 | 4.9 | 5.1 | 5.0 | 6.4 | 5.0 | 5.0 | 5.2 | 4.9 | 7.0 | 8.9 | 9.6 | 11.1 | 19.0 | 45.9 |
| WQEGNVFSCSVMHEALH NHYTQK (SEQ ID NO: 96) | Deamid N(1) | 3.8 | 4.0 | 4.0 | 4.0 | 4.4 | 3.9 | 3.0 | 4.0 | 3.9 | 3.7 | 3.7 | 3.9 | 3.9 | 4.4 | 6.7 |
| WQEGNVFSCSVMHEALH NHYTQK (SEQ ID NO: 96) | CAMC(1), Oxid. M(1) | 1.6 | 1.8 | 1.8 | 1.8 | 1.9 | 1.8 | 1.8 | 1.9 | 1.8 | 1.8 | 1.9 | 2.6 | 2.2 | 2.6 | 5.1 |
| DIVMTQSPLSLPVTPGEPASISCR (SEQ ID NO: 97) | CAM C(1), Oxid. M(1) | 0.7 | 0.8 | 0.8 | 0.8 | 0.8 | 0.8 | 0.7 | 0.8 | 0.7 | 0.8 | 0.8 | 1.1 | 0.8 | 0.8 | 2.0 |

TABLE 8-continued

Stoichiometry Percentage Table (% of each peptide with the modifier). Deamid (deamidation); Oxid (oxidation); CAM (carbamido methyl).

| S-60-15 Peptide | Modifier | Non-stress | pH 5 d0 | pH 5 d1 | pH 5 d3 | pH 5 d5 | pH 3.5 d0 | pH 3.5 d1 | pH 3.5 d3 | pH 3.5 d5 | T40 d7 | T40 d14 | T40 d30 | T50 d7 | T50 d14 | T50 d30 |
|---|---|---|---|---|---|---|---|---|---|---|---|---|---|---|---|---|
| SSQSLLR (SEQ ID NO: 98) | Deamid Q(1) | 6.8 | 6.1 | 5.2 | 5.4 | 6.5 | 6.0 | 5.4 | 6.7 | 5.8 | 7.3 | 6.9 | 7.0 | 6.8 | 7.2 | 6.6 |
| SNGYNYLDWYLQKPGQSP QLLIYLGSNR (SEQ ID NO: 99) | Deamid N(1) | 11.2 | 9.3 | 9.4 | 9.3 | 12.4 | 9.8 | 9.7 | 9.8 | 9.6 | 15.7 | 20.3 | 21.9 | 30.7 | 45.4 | 65.6 |
| AEAEDVGVYYCMQQEAP LTFGGGTK (SEQ ID NO: 100) | CAM C(1), Oxid. M(1) | 0.5 | 0.7 | 0.7 | 0.7 | 0.7 | 0.7 | 0.7 | 0.7 | 0.7 | 0.5 | 0.6 | 1.1 | 0.8 | 1.1 | 2.1 |
| SGTASVVCLLNNFYPR (SEQ ID NO: 101) | Deamid N(1) | 2.6 | 2.8 | 2.9 | 2.8 | 3.1 | 2.8 | 2.7 | 2.8 | 2.7 | 2.6 | 2.7 | 2.5 | 2.6 | 3.0 | 3.4 |
| VDNALQSGNSQESVTEQDSK (SEQ ID NO: 102) | Deamid N(1) | 0.3 | 0.4 | 0.4 | 0.4 | 0.4 | 0.3 | 0.4 | 0.4 | 0.4 | 0.5 | 0.5 | 0.5 | 0.6 | 0.8 | 1.3 |

Amino acids having the potential to incur post-translational modifications (PTMs) upon stress were identified, and the corresponding peptide fragments generated from the stressed samples were tracked kinetically. The results confirm that two asparagine-glycine sites, one in the Fc region of the heavy chain (SEQ ID NO:11) and one in the Fab region of the light chain (SEQ ID NO:15) of S-60-15, were the most susceptible to PTM, exhibiting 45.9% and 65.6% deamidation, respectively, after being subjected to 50° C. storage for 30 days. No other PTM or cleavage site exhibited notable PTM or degradation upon stress testing.

Deamidation of the Asparagine (N33) Site

Any deamidation in the Fc region of the heavy chain of S-60-15 should not affect the binding affinity of S-60-15 to SORT1, as that region does not directly interact with SORT1. However, the asparagine (N33) site in the Fab region of S-60-15 is in the HVR-L1 (SEQ ID NO:8), the complementarity determining region of the light chain, which participates in antigen binding. Thus, deamidation of the asparagine (N33) site in the Fab region of S-60-15 may affect the binding affinity of S-60-15 to SORT1. Upon deamidation, the asparagine (N33) site in the Fab region of S-60-15 undergoes an Asn to Asp/IsoAsp change.

Site-directed mutagenesis was utilized to test the effects of the deamidation of the asparagine (N33) site in the Fab region of S-60-15 and the potential amino acid substitution to reduce the likelihood of degradation and deamidation and resulting manufacturing liability. Seventeen different point mutations to the HVR-L1 N33 position of S-60-15 huIgG1 were produced and sequenced using standard procedures. The Glm3 or G1m(f) allotype with L234A/L235A/P331S ("LALAPS" motif) mutations was used as a background (Jefferis R and Lefranc M-P, Mabs, 2009 July-August; 1(4): 332-338). The LALAPS point mutations are intended to improve overall safety by minimizing effector functions such as Fc gamma receptor binding, complement activation, and antibody dependent cell mediated cytotoxicity (ADCC). Reduction of Fc gamma receptor binding, complement activation and ADCC as a result of LALAPS mutations have been observed in various experiments (data not shown). Bio-layer interferometry (BLI) data was collected at a rate of 5 Hz at 25° C. on a Pall ForteBio Octet RED96 instrument. Data analysis was performed using ForteBio Data Analysis Software, version 9.0. Standard kinetic buffer (PBS, 0.1 BSA, 0.02 Tween-20, pH 7.2) was used for the assay and for preparing reagents. For all assays, sensor tips were equilibrated in buffer prior to analysis.

For the initial off-rate screen, S-60-15 LALAPS N33 and N33X mutants (1 pg/mL, 300 s loading time) were captured on Anti-Human IgG Fc Capture Dip and Read Biosensors (Pall ForteBio, Menlo Park, CA). Twenty nM histidine-tagged human SORT1 (R&D Systems, Minneapolis, MN) was then bound to the captured anti-SORT1 surface (200 s association time, 1200 s dissociation time). The resulting BLI signal was obtained as the difference in response from the reference (1 pg/mL S60-15+0 nM SORT1) sensor. A zero-ligand control (0 pg/mL IgG+20 nM SORT1) showed no measurable non-specific binding of antigen to the sensor tip surface. Full, local fitting using a 1:1 interaction model was applied to extract association and dissociation rate constants ($k_a$ and $k_d$, respectively) for each N33 mutant. Affinity constants ($K_D$) were calculated from the ratio $k_d/k_a$. Different amino acid substitutions were made at N33 and tested for binding to SORT1 in an off-rate screen (under non-stress conditions) as shown in Table 9.

TABLE 9

Extracted $k_a$, $k_d$, and $K_D$ for S-60-15 N33X Mutants binding to SORT1

| S-60-15 Variants | $k_a$ (Ms)$^{-1}$ | $k_d$ (s$^{-1}$) | $K_D$ (pM) |
|---|---|---|---|
| S-60-15 [N33 (wt)] | 5.12E+05 | 1.41E−04 | 270 |
| S-60-15.1 [N33T] | 4.7E+05 | 1.67E−04 | 344 |
| S-60-15.2 [N33S] | 5.63E+05 | 2.47E−04 | 440 |
| S-60-15.3 [N33G] | 4.98E+05 | 4.11E−04 | 825 |
| S-60-15.4 [N33R] | 5.24E+05 | 4.60E−04 | 880 |
| S-60-15.5 [N33D] | 5.90E+05 | 6.10E−04 | 1000 |
| S-60-15.6 [N33H] | 5.48E+05 | 4.60E−04 | 823 |
| S-60-15.7 [N33K] | 5.63E+05 | 5.47E−04 | 965 |
| S-60-15.8 [N33Q] | 6.09E+05 | 6.53E−04 | 905 |
| S-60-15.9 [N33Y] | 5.11E+05 | 6.75E−04 | 1285 |
| S-60-15.10 [N33E] | 6.76E+05 | 4.30E−03 | 2007 |
| S-60-15.11 [N33W] | 6.01E+05 | 5.79E−04 | 960 |
| S-60-15.12 [N33F] | 2.80E+05 | 8.16E−04 | 2910 |
| S-60-15.13 [N33I] | 4.91E+05 | 2.28E−04 | 460 |
| S-60-15.14 [N33V] | 4.45E+05 | 3.06E−04 | 690 |
| S-60-15.15 [N33A] | 4.93E+05 | 3.15E−04 | 625 |
| S-60-15.16 [N33M] | 4.95E+05 | 4.23E−04 | 850 |
| S-60-15.17 [N33L] | 4.12E+05 | 4.25E−04 | 1030 |

Note:
$k_a$, $k_d$, and $K_D$ represent an average value from multiple experiments.

Screening this N33X mutant panel showed that the S-60-15.5 antibody (N33D), which mimics deamidation of N33, led to a significant reduction in binding, with a $K_D$ of 1000 pM compared to 270 pM for N33 wild-type (wt) (Table 9). In contrast, the S-60-15.1 antibody (N33T) had the best retention of S-60-15 affinity to SORT1, displaying the smallest $K_D$ difference from wild-type in the panel (Table 9).

In addition, complete kinetic analysis using multiple concentrations of SORT1 was performed for S-60-15.1 [N33T] as huIgG1 and huIgG1 LALAPS in an independent experiment. The kinetic data are displayed in Table 10. Kinetic data demonstrate that S60-15.1 [N33T] is a high affinity antibody both as huIgG1 and huIgG1 LALAPS.

TABLE 10

SORT1-binding kinetic data for S-60-15.1 [N33T] as huIgG1 and huIgG1 LALAPS.

| Antibody ID | $k_a$ (Ms)$^{-1}$ | $k_d$ (s$^{-1}$) | $K_D$ (pM) |
|---|---|---|---|
| S-60-15.1 [N33T] | 5.99E+05 | 1.79E−04 | 298 |
| S-60-15.1 [N33T] LALAPS | 4.79E+05 | 1.27E−04 | 260 |

Cell Binding and Functionality

S-60-15.1 [N33T], both as huIgG1 and huIgG1 LALAPS, and S-60-15.5 [N33D] were subsequently tested for cell binding and functionality as described below.

Affinity matured antibodies S-60, S-60-15.1 [N33T] and S-60-15.5 [N33D] were tested side-by-side for binding to human SORT1 expressed on HEK293T cells as described earlier. The results are shown in Table 11. S-60-15.1 [N33T] as huIgG1 or huIgG1 LALAPS showed a higher affinity than S-60 (Table 11), with a lower $K_d$ and a higher $B_{max}$. The Fc variant did not appear to have an effect on affinity, having only marginal differences in $K_d$ and $B_{max}$ of S-60-15.1 [N33T] huIgG1 vs. huIgG1 LALAPS. The completely deamidated version of S-60-15.5 [N33D] did not show any significant binding (Table 11, N.B. (No Binding)) to human SORT1 expressing cells, suggesting that amidation of the N33 residue is essential for target binding.

TABLE 11

Cell binding affinity values as measured by FACS.

| Antibody ID | $K_d$ (nM) | $B_{max}$ (MFI) |
|---|---|---|
| S60 | 1.02 | 758381 |
| S-60-15.5 [N33D] | N.B. | N.B. |
| S-60-15.1 [N33T] | 0.3651 | 791996 |
| S-60-15.1 [N33T] LALAPS | 0.4231 | 792791 |

U251 cells that endogenously express SORT1 and secrete PGRN were incubated with anti-SORT1 antibody S-60, S-60-15.1 [N33T] or S-60-15.5 [N33D] at different concentrations, and cell surface levels of SORT1 were measured by FACS as described in Example 2. The control was untreated cells. In order to quantify the percentage of Sortilin downregulation, a saturating antibody concentration of 150 nM IgG was used. For quantification of PGRN secretion, a saturating antibody concentration of 50 nM IgG was utilized. Results are shown in Table 12. S-60-15.1 [N33T] as huIgG1 or huIgG1 LALAPS resulted in significant downregulation of SORT1 and an increase in PGRN secretion. Both the level of downregulation of SORT1 and the level of increase in PGRN secretion were significantly improved in S-60-15.1 [N33T] as huIgG1 or huIgG1 LALAPS as compared to S-60. S-60-15.1 [N33T] as huIgG1 displayed only a minor reduction in $EC_{50}$ and percent SORT1 downregulation, having a minor fold increase in PGRN secretion compared to S-60-15.1 [N33T] as huIgG1 LALAPS. In contrast, the completely deamidated version of S-60-15.5 [N33D] performed worse than S-60 in each of these functional assays; it did not show significant downregulation of SORT1 and had only minimal change in secreted PGRN levels.

TABLE 12

Downregulation (DR) of cell surface SORT1 by S60 antibody variants.

| Antibody ID | $EC_{50}$ (pM) | % DR at 150 nM antibody (IgG) | PGRN secretion, fold over control at 50 nM antibody (IgG) |
|---|---|---|---|
| S-60 | 680.9 | 62.5 | 1.75 |
| S-60-15.5 [N33D] | n.d. | 3.4 | 1.22 |
| S-60-15.1 [N33T] | 72.58 | 69.3 | 2.29 |
| S-60-15.1 [N33T] LALAPS | 103.6 | 70.3 | 1.97 |

Binding of biotinylated PGRN to SORT1 expressed on HEK293T cells was measured by FACS in the absence or presence of anti-SORT1 antibody S-60, S-60-15.1 [N33T] and S-60-15.5 [N33D] as described in Example 3. Results are shown in Table 13. A saturating antibody concentration of 150 nM IgG was used for quantifying the percentage of blocking of PGRN binding to SORT1.

TABLE 13

Block of PGRN binding to SORT1 expressed on HEK293T cells.

| Antibody ID | $EC_{50}$ (nM) | Percentage block at 150 nM antibody (IgG) |
|---|---|---|
| S60 | 0.751 | 95.9 |
| S-60-15.5 [N33D] | 0.588 | 27.5 |
| S-60-15.1 [N33T] | 0.325 | 96.5 |
| S-60-15.1 [N33T] LALAPS | 0.405 | 96.9 |

The S-60-15.1 [N33T] variants, both with and without LALAPS, displayed the lowest $EC_{50}$ values and the highest level of blocking PGRN binding to SORT1 as compared to S-60-15.5 as well as compared to S-60. Thus, S-60-15.1 [N33T] performed better than S-60 and S-60-15.5 in blocking PGRN binding to SORT1.

In summary, S-60-15 was found to undergo extensive deamidation at N33 under storage stress (see Table 8), which increases the likelihood of degradation and resulting manufacturing liability. The previously described anti-SORT1 antibody S-60 and variants S-60-1, S-60-2, S-60-3, S-60-4, S-60-7, and S-60-8 also contain an asparagine at position 33 in the $V_L$. In particular, the location of the N33 deamidation site within the HVR-L1 site is likely to affect the binding of S-60-15 to SORT1. S-60-15.1 [N33T], one of several tested S-60-15 variants, retained significant binding affinity to SORT1 as compared to S-60-15 (see Table 9) and showed significantly improved binding affinity to SORT1 as compared to S-60 (see Table 11; compare to S-60-15 WT in Table 1). This high retention of binding affinity was unexpected for an antibody having a non-preferred substitution within HVR-L1 because the HVR-L1 residues may contact antigen. Also, unexpectedly, the S-60-15.1 [N33T] variant retained increased downregulation of SORT1, increased secretion of PGRN, and increased blocking of PGRN binding to SORT1 as compared to S-60 (see Tables 12 and 13). These results were also unexpected because a non-preferred substitution in an HVR sequence would likewise have been expected to negatively affect the functional characteristics of an antibody. Instead, S-60-15.1 [N33T] retains the desirable properties of downregulating cell-surface SORT1, increasing PGRN secretion, and blocking binding of PGRN to SORT1 in addition to being more stable than previously described antibodies by removal of a manufacturing liability at position 33 in the $V_L$.

Example 5: Anti-Sortilin Antibody PK and PD in Non-Human Primates

In this Example, the pharmacokinetics (PK) and pharmacodynamics (PD) of intravenously (IV) administered anti-Sortilin antibody S-60-15.1 [N33T] LALAPS were determined in non-human primates.

Materials and Methods

Single Dose Pharmacokinetic and Pharmacodynamic Studies

For single dose pharmacokinetic studies, cynomolgus monkeys were administered anti-Sortilin antibody by single IV dose of 5 mg/kg, 20 mg/kg, 60 mg/kg, or 200 mg/kg on Day 0 (n=3 animals per dose). Blood and CSF were drawn from the animals at multiple time-points thereafter to obtain anti-Sortilin antibody concentrations in plasma and cerebrospinal fluid (CSF), which are measurements of anti-Sortilin antibody pharmacokinetics. Progranulin (PGRN) concentration and the levels of Sortilin (SORT1) on white blood cells (WBCs), which are measurements of pharmacodynamics, were also determined.

Anti-Sortilin antibody concentrations were assayed using an ELISA assay with anti-Sortilin antibody-specific anti-idiotypic antibodies. PGRN concentrations were assayed with a commercially-available ELISA kit. Levels of SORT1 on white blood cells were assayed using an ELISA assay, and normalized to protein concentration.

Results

Table 14 provides the plasma mean $C_{max}$, mean AUC, and $t_{1/2}$ for each of the tested anti-Sortilin antibody doses.

TABLE 14

$C_{max}$, mean AUC, and $t_{1/2}$ for the indicated anti-Sortilin antibody doses (n = 3 for each dose).

| Antibody Dose | Mean $C_{max}$ (µg/ml) | Mean AUC (µg × hr/ml) | t½ hours |
|---|---|---|---|
| 5 mg/kg | 156 | 2,870 | 4.7 |
| 20 mg/kg | 697 | 26,500 | 13.3 |
| 60 mg/kg | 2,570 | 118,000 | 42 |
| 200 mg/kg | 7,910 | 366,000 | 73.6 |

As shown in FIG. 1A, SORT1 expression levels in peripheral white blood cells decreased after treatment of non-human primates with any of the anti-Sortilin antibody doses tested. The higher anti-Sortilin antibody doses (60 mg/kg, 200 mg/kg) resulted in both an earlier and more prolonged decrease of SORT1 levels in peripheral white blood cells compared to lower anti-Sortilin antibody doses (5 mg/kg, 20 mg/kg).

Figure 1B:
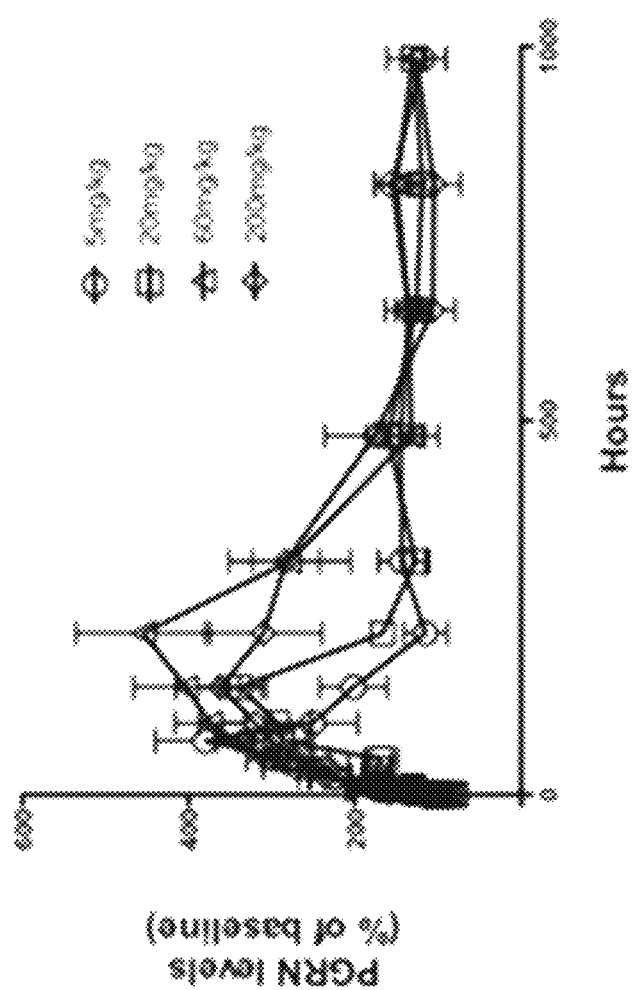

The levels of PGRN increased in the plasma of non-human primates administered a single IV injection of anti-Sortilin antibody in a time- and dose-dependent manner (FIG. 1B). In particular, plasma PGRN levels increased 3- to 4-fold at $C_{max}$, compared to baseline levels, for all anti-Sortilin antibody doses tested. Plasma PGRN levels remained elevated for longer periods of time at the higher antibody doses. Additionally, increased plasma PGRN levels were correlated with decreased expression levels of SORT1 in peripheral white blood cells.

Figure 1C:
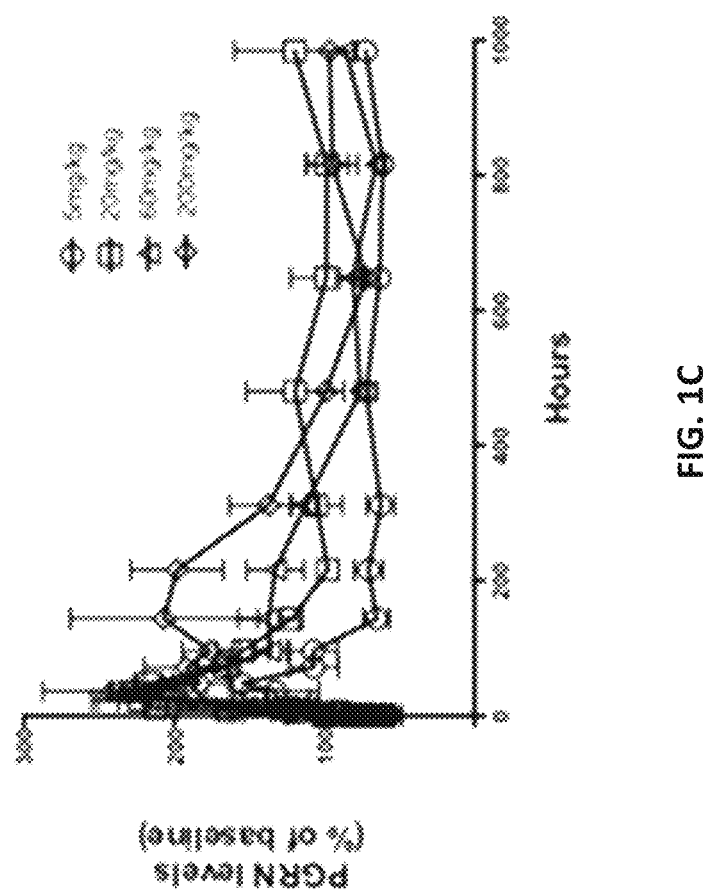

The levels of PGRN in CSF were also increased in non-human primates administered a single IV injection of anti-Sortilin antibody. As shown in FIG. 1C, CSF PGRN levels increased 2- to 3-fold above baseline in animals administered either 20 mg/kg, 60 mg/kg, or 200 mg/kg. As observed with plasma PGRN levels, CSF PGRN levels remained elevated over time in the higher antibody dose groups.

Table 15 provides the CSF mean $C_{max}$, mean AUC, and $t_{1/2}$ for each of the tested anti-Sortilin antibody doses in non-human primates. Anti-Sortilin antibody CSF concentrations were on average around 0.1% the amount observed in plasma.

TABLE 15

Anti-Sortilin antibody CSF PK parameters and estimated half-life in non-human primates.

| [1] Dose Level | $C_{max}$ (µg/mL) | AUC$_{all}$ (h*µg/mL) | CL (mL/h/kg) | $t_{1/2}$ hours (days) |
|---|---|---|---|---|
| 5 mg/kg | 20 | 184 | 20692 | 32.3 (1.34) |
| 20 mg/kg | 2243 | 35717 | 745 | 23.8 (1) |
| 60 mg/kg | 6842 | 113573 | 623 | 38.3 (1.6) |
| 200 mg/kg | 4595 | 349187 | 1037 | 72.4 (3.02) |

Repeat Dose Pharmacokinetic and Pharmacodynamic Studies

Further pharmacokinetic and pharmacodynamic studies were performed in non-human primates administered anti-Sortilin antibody following a repeat-dose regimen. In these studies, animals (2 males and 2 females) were administered anti-Sortilin antibody at a dose of 60 mg/kg once per week for four weeks. At various timepoints thereafter, SORT1 expression levels in peripheral white blood cells were determined. In addition, plasma and CSF levels of the anti-Sortilin antibody, were determined.

Figure 2A:
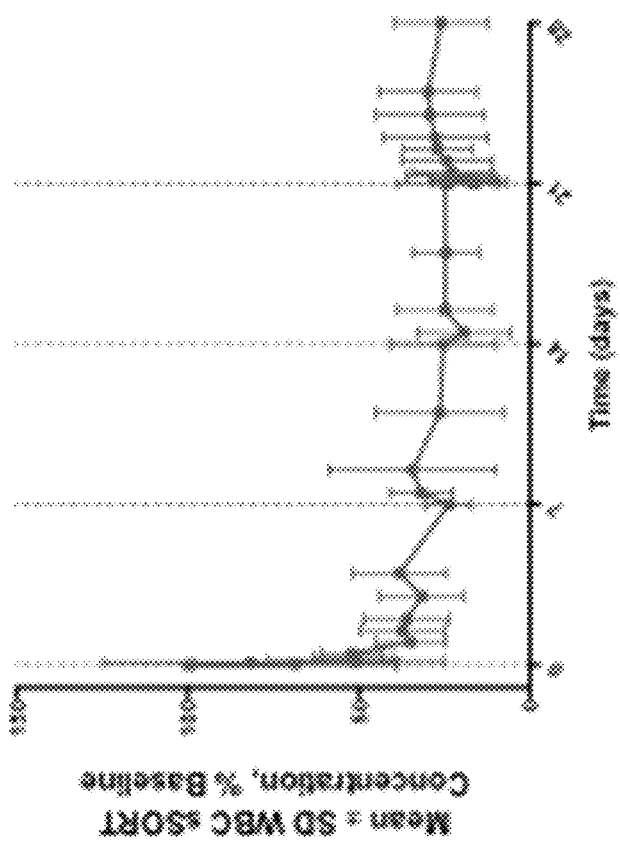
FIGS. 2A-2C provide pharmacokinetic and pharmacodynamic studies of non-human primates administered repeat doses of anti-Sortilin antibody S-60-15.1 [N33T] LALAPS. Animals (2 males and 2 females) were administered anti-Sortilin antibody S-60-15.1 [N33T] LALAPS at a dose of 60 mg/kg once per week for four weeks. The days on which dosing occurred are represented by the vertical dashed lines.
Figure 2B:
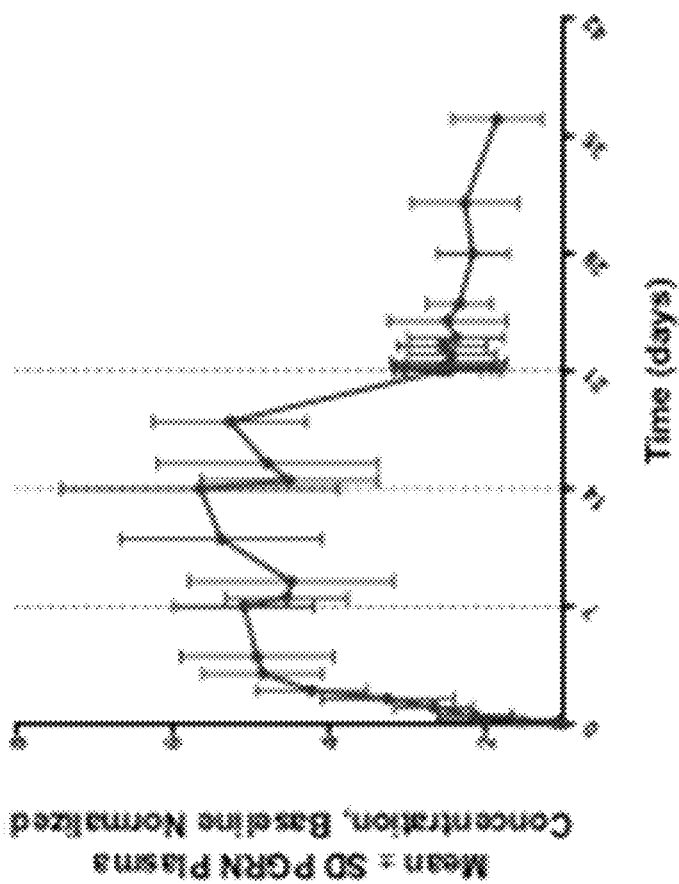
Figure 2C:
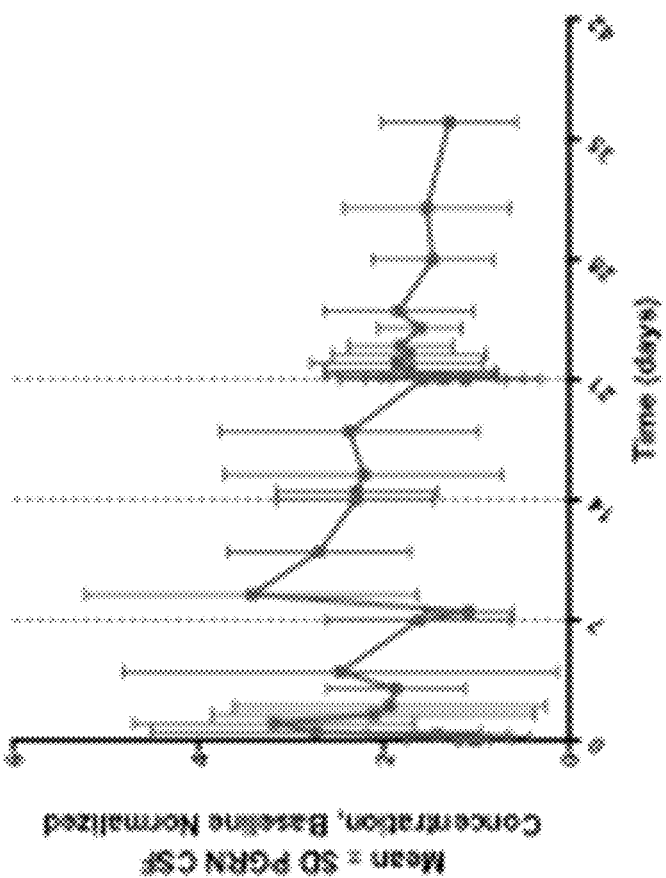

As shown in FIG. 2A, SORT1 levels in peripheral white blood cells remained decreased throughout the duration of the study. Plasma PGRN levels increased to 5- to 6-fold above baseline at peak levels (FIG. 2B). A decrease in plasma PGRN was observed following the fourth and final administration of anti-Sortilin antibody; however, the plasma PGRN levels remained elevated by 2-fold above baseline. Additionally, CSF PGRN levels were increased 3- to 4-fold above baseline (FIG. 2C).

The systemic anti-Sortilin antibody exposure, assessed by mean Cmax and AUC$_{0-168}$, was 2100 µg/mL and 114,000 µg/mL×hr on Day 1, and 3020 µg/mL and 174,000 µg/mL× hr on Day 22. These results showed that exposure was higher on Day 22 compared to Day 1, indicating some accumulation of the antibody.

CSF concentration of anti-Sortilin antibody in these animals ranged from 0.03% to 0.12% of that observed in plasma, consistent with the distribution of other antibodies in the CSF (Pestalozzi et al., (2000) J Clin Oncol 18(11): 2349-51; Petereit et al., (2009) Mult Scler 15(2):189-92).

Taken together, these results indicate that the S-60-15.1 [N33T] variant, in spite of having a relatively short half-life, has sustained activity in vivo, decreasing SORT1 levels in peripheral white blood cells and increasing plasma and CSF PGRN levels.

Moreover, IV administration of S-60-15.1 [N33T] to cynomolgous monkeys in both a 4-week and a 26-week repeat dose toxicology study was well tolerated at up to 200 mg/kg weekly, and there were no adverse findings that would preclude the conduct of clinical studies in humans based on those and other toxicology studies which included assessments of cytokine release, mortality, body weight, respiratory rate and depth, and local tolerability at injection site. Therefore, S-60-15.1 [N33T] is suitable for testing in human clinical studies of FTD and other indications as contemplated herein.

Lack of adverse findings with respect to toxicity from administration of an anti-Sortilin antibody was surprising in view of the fact that Sortilin acts as a receptor of several ligands and has multiple roles in cellular transport and signaling (Nykjaer, A et al., (2012) Trends Neurosci 35: 261-270). Due to Sortilin's multiple ligands and functional roles, administration of an anti-Sortilin antibody might have been expected to cause off-target effects; however, the S-60-15.1 [N33T] antibody was well tolerated at the administered doses.

```
Sequences of the V_H regions of the S-60 antibody variants, alignment to S-60, and HVR locations
S-60         (SEQ ID NO: 56)  QVQLQESGPGLVKPSETLSLTCAVSGYSISSGYYWGWIRQPPGKGLEWIGTIYHSGSTYY 60

S-60-1       (SEQ ID NO: 107) QVQLQESGPGLVKPSETLSLTCAVSGYSISSVRYWGWIRQPPGKGLEWIGSIYHSGSTYY 60

S-60-2       (SEQ ID NO: 108) QVQLQESGPGLVKPSETLSLTCAVSGYSISSVRYWGWIRQPPGKGLEWIGAIYPSGSTYY 60
```

```
S-60-3       (SEQ ID NO: 109)  QVQLQESGPGLVKPSETLSLTCAVSGYSISSGYYWGWIRQPPGKGLEWIGTIYHSGSTYY  60
S-60-4       (SEQ ID NO: 110)  QVQLQESGPGLVKPSETLSLTCAVSGYSISSGYYWGWIRQPPGKGLEWIGTIYHSGSTYY  60
S-60-7       (SEQ ID NO: 111)  QVQLQESGPGLVKPSETLSLTCAVSGYSISSGYYWGWIRQPPGKGLEWIGTIYHSGSTYY  60
S-60-8       (SEQ ID NO: 112)  QVQLQESGPGLVKPSETLSLTCAVSGYSISSGYYWGWIRQPPGKGLEWIGTIYHSGSTYY  60
S-60-10      (SEQ ID NO: 54)   QVQLQESGPGLVKPSETLSLTCAVSGYSISSGYYWGWIRQPPGKGLEWIGTIYHSGSTYY  60
S-60-11      (SEQ ID NO: 54)   QVQLQESGPGLVKPSETLSLTCAVSGYSISSGYYWGWIRQPPGKGLEWIGTIYHSGSTYY  60
S-60-12      (SEQ ID NO: 54)   QVQLQESGPGLVKPSETLSLTCAVSGYSISSGYYWGWIRQPPGKGLEWIGTIYHSGSTYY  60
S-60-13      (SEQ ID NO: 55)   QVQLQESGPGLVKPSETLSLTCAVSGYSISSGYYWGWIRQPPGKGLEWIGTIYHSGSTYY  60
S-60-14      (SEQ ID NO: 55)   QVQLQESGPGLVKPSETLSLTCAVSGYSISSGYYWGWIRQPPGKGLEWIGTIYHSGSTYY  60
S-60-15      (SEQ ID NO: 56)   QVQLQESGPGLVKPSETLSLTCAVSGYSISSGYYWGWIRQPPGKGLEWIGTIYHSGSTYY  60
S-60-15.1    (SEQ ID NO: 56)   QVQLQESGPGLVKPSETLSLTCAVSGYSISSGYYWGWIRQPPGKGLEWIGTIYHSGSTYY  60
S-60-16      (SEQ ID NO: 56)   QVQLQESGPGLVKPSETLSLTCAVSGYSISSGYYWGWIRQPPGKGLEWIGTIYHSGSTYY  60
S-60-18      (SEQ ID NO: 56)   QVQLQESGPGLVKPSETLSLTCAVSGYSISSGYYWGWIRQPPGKGLEWIGTIYHSGSTYY  60
S-60-19      (SEQ ID NO: 54)   QVQLQESGPGLVKPSETLSLTCAVSGYSISSGYYWGWIRQPPGKGLEWIGTIYHSGSTYY  60
S-60-24      (SEQ ID NO: 56)   QVQLQESGPGLVKPSETLSLTCAVSGYSISSGYYWGWIRQPPGKGLEWIGTIYHSGSTYY  60

S-60 Alignment                 ***************************** *****************:** ******

S-60 HVR H1  (SEQ ID NO: 1)    -------------------------YSISSGYYWG-------------------------
S-60 HVR H2  (SEQ ID NO: 2)    ------------------------------------------------TIYHSGSTYY

S-60         (SEQ ID NO: 56 cont.)   NPSLKSRVTISVDTSKNQFSLKLSSVTAADTAVYYCARQGSIKQGYYGMDVWGQGTTVTVSS  122
S-60-1       (SEQ ID NO: 107 cont.)  NPSLKSRVTISVDTSKNQFSLKLSSVTAADTAVYYCARQGSIKQGYYGMDVWGQGTTVTVSS  122
S-60-2       (SEQ ID NO: 108 cont.)  NPSLKSRVTISVDTSKNQFSLKLSSVTAADTAVYYCARQGSIKQGYYGMDVWGQGTTVTVSS  122
S-60-3       (SEQ ID NO: 109 cont.)  NPSLKSRVTISVDTSKNQFSLKLSSVTAADTAVYYCARQGSIKQGYYGMDVWGQGTTVTVSS  122
S-60-4       (SEQ ID NO: 110 cont.)  NPSLKSRVTISVDTSKNQFSLKLSSVTAADTAVYYCARQGSIKQGYYGMDVWGQGTTVTVSS  122
S-60-7       (SEQ ID NO: 111 cont.)  NPSLKSRVTISVDTSKNQFSLKLSSVTAADTAVYYCARQGSIKQGYYGMDVWGQGTTVTVSS  122
S-60-8       (SEQ ID NO: 112 cont.)  NPSLKSRVTISVDTSKNQFSLKLSSVTAADTAVYYCARQGSIKQGYYGMDVWGQGTTVTVSS  122
S-60-10      (SEQ ID NO: 54 cont.)   NPSLKSQVTISVDTSKNQFSLELSSVTAADTAVYYCARQGSIQQGYYGMDVWGQGTTVTVSS  122
S-60-11      (SEQ ID NO: 54 cont.)   NPSLKSQVTISVDTSKNQFSLELSSVTAADTAVYYCARQGSIQQGYYGMDVWGQGTTVTVSS  122
S-60-12      (SEQ ID NO: 54 cont.)   NPSLKSQVTISVDTSKNQFSLELSSVTAADTAVYYCARQGSIQQGYYGMDVWGQGTTVTVSS  122
S-60-13      (SEQ ID NO: 55 cont.)   NPSLESRVTISVDTSKNQFSLKLSSVTAADTAVYYCARQGSIQQGYYGMDVWGQGTTVTVSS  122
S-60-14      (SEQ ID NO: 55 cont.)   NPSLESRVTISVDTSKNQFSLKLSSVTAADTAVYYCARQGSIQQGYYGMDVWGQGTTVTVSS  122
S-60-15      (SEQ ID NO: 56 cont.)   NPSLKSRVTISVDTSKNQFSLKLSSVTAADTAVYYCARQGSIKQGYYGMDVWGQGTTVTVSS  122
S-60-15.1    (SEQ ID NO: 56 cont.)   NPSLKSRVTISVDTSKNQFSLKLSSVTAADTAVYYCARQGSIKQGYYGMDVWGQGTTVTVSS  122
S-60-16      (SEQ ID NO: 56 cont.)   NPSLKSRVTISVDTSKNQFSLKLSSVTAADTAVYYCARQGSIKQGYYGMDVWGQGTTVTVSS  122
S-60-18      (SEQ ID NO: 56 cont.)   NPSLKSRVTISVDTSKNQFSLKLSSVTAADTAVYYCARQGSIKQGYYGMDVWGQGTTVTVSS  122
S-60-19      (SEQ ID NO: 54 cont.)   NPSLKSQVTISVDTSKNQFSLELSSVTAADTAVYYCARQGSIQQGYYGMDVWGQGTTVTVSS  122
S-60-24      (SEQ ID NO: 56 cont.)   NPSLKSRVTISVDTSKNQFSLKLSSVTAADTAVYYCARQGSIKQGYYGMDVWGQGTTVTVSS  122

S-60 Alignment                       ****:*:*************:*************:******************

S-60 HVR H2  (SEQ ID NO: 2 cont.)    NPSLKS-------------------------------------------------------
S-60 HVR H3  (SEQ ID NO: 6)          ----------------------------------ARQGSIKQGYYGMDV-----------

Sequences of the V_L regions of the S-60 antibody variants, alignment to S-60, and HVR locations
S-60         (SEQ ID NO: 79)   DIVMTQSPLSLPVTPGEPASISCRSSQSLLHSNGYNYLDWYLQKPGQSPQLLIYLGSNRA  60
```

```
S-60-1      (SEQ ID NO: 113)  DIVMTQSPLSLPVTPGEPASISCRSSQSLLHSNGYNYLDWYLQKPGQSPQLLIYLGSNRA  60
S-60-2      (SEQ ID NO: 114)  DIVMTQSPLSLPVTPGEPASISCRSSQSLLHSNGYNYLDWYLQKPGQSPQLLIYLGSNRA  60
S-60-3      (SEQ ID NO: 115)  DIVMTQSPLSLPVTPGEPASISCRSSQSLLRSNGYNYLDWYLQKPGQPPQLLIYLGSNRV  60
S-60-4      (SEQ ID NO: 116)  DIVMTQSPLSLPVTPGESASISCRSSQGLLRSNGYNYLDWYLQKPGQSPQLLIYLGSNRA  60
S-60-7      (SEQ ID NO: 117)  DIVMTQSPLSLPVTPGEPASISCRSSQSLLRSNGYNYLDWYLQKPGQSPQLLIYLGSNRA  60
S-60-8      (SEQ ID NO: 118)  DIVMTQSPLSLPVTPGGPASISCRSSQSLLRSNGYNYLDWYLQKPGQSPQLLIYLGSNRA  60
S-60-10     (SEQ ID NO: 57)   DIVMTQSPLSLPVTPGEPASISCRSSQSLLRSNGYNYLDWYLQKPGQSPQLLIYLGSNRA  60
S-60-11     (SEQ ID NO: 58)   DIVMTQSPLSLPVTPGEPASISCRSSQSLLRSNGYNYLDWYLQKPGQSPQLLIYLGSNRA  60
S-60-12     (SEQ ID NO: 59)   DIVMTQSPLSLPVTPGEPASISCRSSQSLLRSNGYNYLDWYLQKPGQPPQLLIYLGSNRV  60
S-60-13     (SEQ ID NO: 57)   DIVMTQSPLSLPVTPGEPASISCRSSQSLLRSNGYNYLDWYLQKPGQSPQLLIYLGSNRA  60
S-60-14     (SEQ ID NO: 58)   DIVMTQSPLSLPVTPGEPASISCRSSQSLLRSNGYNYLDWYLQKPGQSPQLLIYLGSNRA  60
S-60-15     (SEQ ID NO: 57)   DIVMTQSPLSLPVTPGEPASISCRSSQSLLRSNGYNYLDWYLQKPGQSPQLLIYLGSNRA  60
S-60-15.1   (SEQ ID NO: 60)   DIVMTQSPLSLPVTPGEPASISCRSSQSLLRSTGYNYLDWYLQKPGQSPQLLIYLGSNRA  60
S-60-16     (SEQ ID NO: 77)   DIVMTQSPLSLPVTPGEPASISCRSSQSLLRSNGYNYLDWYLQKPGQSPQLLIYLGSNRA  60
S-60-18     (SEQ ID NO: 78)   DIVMTQSPLSLPVTPGGPASISCRSSQSLLRSNGYNYLDWYLQKPGQSPQLLIYLGSNRA  60
S-60-19     (SEQ ID NO: 79)   DIVMTQSPLSLPVTPGEPASISCRSSQSLLHSNGYNYLDWYLQKPGQSPQLLIYLGSNRA  60
S-60-24     (SEQ ID NO: 80)   DIVMTQSPLSLPVTPGESASISCRSSQGLLRSNGYNYLDWYLQKPGQSPQLLIYLGSNRA  60

S-60 Alignment                ***************  *********.**:****************  **********.

S-60 HVR L1 (SEQ ID NO: 27)   -----------------------RSSQSLLHSNGYNYLD---------------------
S-60 HVR L2 (SEQ ID NO: 29)   ------------------------------------------------------LGSNRA

S-60        (SEQ ID NO: 79 cont.)   SGVPDRFSGSGSGTDFTLKISRVEAEDVGVYYCMQQQETPLTFGGGTKVEIK  112
S-60-1      (SEQ ID NO: 113 cont.)  SGVPDRFSGSGSGTDFTLKISRVEAEDVGVYYCMQQQETPLTFGGGTKVEIK  112
S-60-2      (SEQ ID NO: 114 cont.)  SGVPDRFSGSGSGTDFTLKISRVEAEDVGVYYCMQQQETPLTFGGGTKVEIK  112
S-60-3      (SEQ ID NO: 115 cont.)  SGVPDRFSGSGSGTDFTLKISRVEAEDVGVYYCMQQQETPLTFGGGTKVEIK  112
S-60-4      (SEQ ID NO: 116 cont.)  SGVPDRFSGSGSGTDFTLKISRVEAEDVGVYYCMQQQETPLTFGGGTKVEIK  112
S-60-7      (SEQ ID NO: 117 cont.)  SGVPDRFSGSGSGTDFTLKISRVEAEDVGVYYCMQQQETPLTFGGGTKVEIK  112
S-60-8      (SEQ ID NO: 118 cont.)  SGVPDRFSGSGSGTDFTLKISRVEAEDVGVYYCMQQQETPLTFGGGTKVEIK  112
S-60-10     (SEQ ID NO: 57 cont.)   SGVPDRFSGSGSGTDFTLKISRAEAEDVGVYYCMQQQEAPLTFGGGTKVEIK  112
S-60-11     (SEQ ID NO: 58 cont.)   SGVPDRFSGSGSGTDFTLKISRVEAEDVGVYYCMQQQEAPLTFGGGTKVEIK  112
S-60-12     (SEQ ID NO: 59 cont.)   SGVPDRFSGSGSGTDFTLKISRVEAEDVGVYYCMQQQETPLTFGGGTKVEIK  112
S-60-13     (SEQ ID NO: 57 cont.)   SGVPDRFSGSGSGTDFTLKISRAEAEDVGVYYCMQQQEAPLTFGGGTKVEIK  112
S-60-14     (SEQ ID NO: 58 cont.)   SGVPDRFSGSGSGTDFTLKISRVEAEDVGVYYCMQQQEAPLTFGGGTKVEIK  112
S-60-15     (SEQ ID NO: 57 cont.)   SGVPDRFSGSGSGTDFTLKISRAEAEDVGVYYCMQQQEAPLTFGGGTKVEIK  112
S-60-15.1   (SEQ ID NO: 60 cont.)   SGVPDRFSGSGSGTDFTLKISRAEAEDVGVYYCMQQQEAPLTFGGGTKVEIK  112
S-60-16     (SEQ ID NO: 77 cont.)   SGVPDRFSGSGSGTDFTLKISRVEAEDVGAYYCMQQQEAPLTFGGGTKVEIK  112
S-60-18     (SEQ ID NO: 78 cont.)   SGVPDRLSGSGSGTDFTLKISRVEAEDVGVYYCMQQQETPLTFGGGTKVEIK  112
S-60-19     (SEQ ID NO: 79 cont.)   SGVPDRFSGSGSGTDFTLKISRVEAEDVGVYYCMQQQETPLTFGGGTKVEIK  112
S-60-24     (SEQ ID NO: 80 cont.)   SGVPDRFSGSGSGTDFTLKISRVEAEDVGVYYCMQQQEAPLTFGGGTKVEIK  112

S-60 Align.                           ******:************.******.*******:*************

S-60 HVR L2 (SEQ ID NO: 29 cont.)   S---------------------------------------------------
S-60 HVR L3 (SEQ ID NO: 33)        ---------------------------------MQQQETPLT----------
```

TABLE 16

Heavy chain HVR H1 sequences of anti-SORT1 antibodies

| Ab(s) | HVR H1 | SEQ ID NO: |
|---|---|---|
| S-60; S-60-10; S-60-11; S-60-12; S-60-13; S-60-14; S-60-15 [N33 (wt)]; S-60-15.1 [N33T]; S-60-15.2 [N33S]; S-60-15.3 [N33G]; S-60-15.4 [N33R]; S-60-15.5 [N33D]; S-60-15.6 [N33H]; S-60-15.7 [N33K]; S-60-15.8 [N33Q]; S-60-15.9 [N33Y]; S-60-15.10 [N33E]; S-60-15.11 [N33W]; S-60-15.12 [N33F]; S-60-15.13 [N33I]; S-60-15.14 [N33V]; S-60-15.15 [N33A]; S-60-15.16 [N33M]; S-60-15.17 [N33L]; S-60-16; S-60-18; S-60-19; S-60-24 | YSISSGYYWG | 1 |

TABLE 17

Heavy chain HVR H2 sequences of anti-SORT1 antibodies

| Ab(s) | HVR H2 | SEQ ID NO: |
|---|---|---|
| S-60; S-60-10; S-60-11; S-60-12; S-60-15 [N33 (wt)]; S-60-15.1 [N33T]; S-60-15.2 [N33S]; S-60-15.3 [N33G]; S-60-15.4 [N33R]; S-60-15.5 [N33D]; S-60-15.6 [N33H]; S-60-15.7 [N33K]; S-60-15.8 [N33Q]; S-60-15.9 [N33Y]; S-60-15.10 [N33E]; S-60-15.11 [N33W]; S-60-15.12 [N33F]; S-60-15.13 [N33I]; S-60-15.14 [N33V]; S-60-15.15 [N33A]; S-60-15.16 [N33M]; S-60-15.17 [N33L]; S-60-16; S-60-18; S-60-19; S-60-24 | TIYHSGSTYYNPSLKS | 2 |
| S-60-13; S-60-14 | TIYHSGSTYYNPSLES | 3 |
| Formula I | TIYHSGSTYYNPSLX$_1$S<br>X$_1$ is K or E | 4 |

TABLE 18

Heavy chain HVR H3 sequences of anti-SORT1 antibodies

| Ab(s) | HVR H3 | SEQ ID NO: |
|---|---|---|
| S-60-10; S-60-11; S-60-12; S-60-13; S-60-14; S-60-19 | ARQGSIQQGYYGMDV | 5 |
| S-60; S-60-15 [N33 (wt)]; S-60-15.1 [N33T]; S-60-15.2 [N33S]; S-60-15.3 [N33G]; S-60-15.4 [N33R]; S-60-15.5 [N33D]; S-60-15.6 [N33H]; S-60-15.7 [N33K]; S-60-15.8 [N33Q]; S-60-15.9 [N33Y]; S-60-15.10 [N33E]; S-60-15.11 [N33W]; S-60-15.12 [N33F]; S-60-15.13 [N33I]; S-60-15.14 [N33V]; S-60-15.15 [N33A]; S-60-15.16 [N33M]; S-60-15.17 [N33L]; S-60-16; S-60-18; S-60-24 | ARQGSIKQGYYGMDV | 6 |
| Formula II | ARQGSIX$_1$QGYYGMDV<br>X$_1$ is Q or K | 7 |

TABLE 19

Light chain HVR L1 sequences of anti-SORT1 antibodies

| Ab(s) | HVRL1 | SEQ ID NO: |
|---|---|---|
| S-60-10; S-60-11; S-60-12; S-60-13; S-60-14; S-60-15 [N33 (wt)]; S-60-16; S-60-18 | RSSQSLLRSNGYNYLD | 8 |
| S-60-15.1 [N33T] | RSSQSLLRSTGYNYLD | 9 |

TABLE 19-continued

Light chain HVR L1 sequences of anti-SORT1 antibodies

| Ab(s) | HVRL1 | SEQ ID NO: |
|---|---|---|
| S-60-15.2 [N33S] | RSSQSLLRSSGYNYLD | 10 |
| S-60-15.3 [N33G] | RSSQSLLRSGGYNYLD | 11 |
| S-60-15.4 [N33R] | RSSQSLLRSRGYNYLD | 12 |
| S-60-15.5 [N33D] | RSSQSLLRSDGYNYLD | 13 |
| S-60-15.6 [N33H] | RSSQSLLRSHGYNYLD | 14 |
| S-60-15.7 [N33K] | RSSQSLLRSKGYNYLD | 15 |
| S-60-15.8 [N33Q] | RSSQSLLRSQGYNYLD | 16 |
| S-60-15.9 [N33Y] | RSSQSLLRSYGYNYLD | 17 |
| S-60-15.10 [N33E] | RSSQSLLRSEGYNYLD | 18 |
| S-60-15.11 [N33W] | RSSQSLLRSWGYNYLD | 19 |
| S-60-15.12 [N33F] | RSSQSLLRSEGYNYLD | 20 |
| S-60-15.13 [N33I] | RSSQSLLRSIGYNYLD | 21 |
| S-60-15.14 [N33V] | RSSQSLLRSVGYNYLD | 22 |
| S-60-15.15 [N33A] | RSSQSLLRSAGYNYLD | 23 |
| S-60-15.16 [N33M] | RSSQSLLRSMGYNYLD | 24 |
| S-60-15.17 [N33L] | RSSQSLLRSEGYNYLD | 25 |
| S-60; S-60-19 | RSSQSLLHSNGYNYLD | 26 |
| S-60-24 | RSSQGLLRSNGYNYLD | 27 |
| Formula III | RSSQX$_1$LLX$_2$SX$_3$GYNYLD<br>X$_1$ is S or G<br>X$_2$ is R or H<br>X$_3$ is N, T, S, G, R, D, H, K, Q, Y, E, W, F, I, V, A, M, or L | 28 |

TABLE 20

Light chain HVR L2 sequences of anti-SORT1 antibodies

| Ab(s) | HVR L2 | SEQ ID NO: |
|---|---|---|
| S-60; S-60-10; S-60-11; S-60-13; S-60-14; S-60-15 [N33 (wt)]; S-60-15.1 [N33T]; S-60-15.2 [N33S]; S-60-15.3 [N33G]; S-60-15.4 [N33R]; S-60-15.5 [N33D]; S-60-15.6 [N33H]; S-60-15.7 [N33K]; S-60-15.8 [N33Q]; S-60-15.9 | LGSNRAS | 29 |

TABLE 20-continued

Light chain HVR L2 sequences of anti-SORT1 antibodies

| Ab(s) | HVR L2 | SEQ ID NO: |
|---|---|---|
| [N33Y]; S-60-15.10 [N33E]; S-60-15.11 [N33W]; S-60-15.12 [N33F]; S-60-15.13 [N33I]; S-60-15.14 [N33V]; S-60-15.15 [N33A]; S-60-15.16 [N33M]; S-60-15.17 [N33L]; S-60-16; S-60-18; S-60-19; S-60-24 | | |
| S-60-12 | LGSNRVS | 30 |
| Formula IV | LGSNRX$_1$S<br>X$_1$ is A or V | 31 |

TABLE 21

Light chain HVR L3 sequences of anti-SORT1 antibodies

| Ab(s) | HVR L3 | SEQ ID NO: |
|---|---|---|
| S-60-10; S-60-11; S-60-13; S-60-14; S-60-15 [N33 (wt)]; S-60-15.1 [N33T]; S-60-15.2 [N33S]; S-60-15.3 [N33G]; S-60-15.4 [N33R]; S-60-15.5 [N33D]; S-60-15.6 [N33H]; S-60-15.7 [N33K]; S-60-15.8 [N33Q]; S-60-15.9 [N33Y]; S-60-15.10 [N33E]; S-60-15.11 [N33W]; S-60-15.12 [N33F]; S-60-15.13 [N33I]; S-60-15.14 [N33V]; S-60-15.15 [N33A]; S-60-15.16 [N33M]; S-60-15.17 [N33L]; S-60-16; S-60-24 | MQQQEAPLT | 32 |
| S-60; S-60-12; S-60-18; S-60-19 | MQQQETPLT | 33 |
| Formula V | MQQQEX$_1$PLT<br>X$_1$ is A or T | 34 |

TABLE 22

Heavy chain framework 1 sequences of anti-SORT1 antibodies

| Ab(s) | VH FR1 | SEQ ID NO: |
|---|---|---|
| S-60-10; S-60-11; S-60-12; S-60-13; S-60-14; S-60-15 [N33 (wt)]; S-60-15.1 [N33T]; S-60-15.2 [N33S]; S-60-15.3 [N33G]; S-60-15.4 [N33R]; S-60-15.5 [N33D]; S-60-15.6 [N33H]; S-60-15.7 [N33K]; S-60-15.8 [N33Q]; S-60-15.9 [N33Y]; S-60-15.10 [N33E]; S-60-15.11 [N33W]; S-60-15.12 [N33F]; S-60-15.13 [N33I]; S-60-15.14 [N33V]; S-60-15.15 [N33A]; S-60-15.16 [N33M]; S-60-15.17 [N33L]; S-60-16; S-60-18; S-60-19; S-60-24 | QVQLQESGPGLVKP SETLSLTCAVSG | 35 |

TABLE 23

Heavy chain framework 2 sequences of anti-SORT1 antibodies

| Ab(s) | VH FR2 | SEQ ID NO: |
|---|---|---|
| S-60-10; S-60-11; S-60-12; S-60-13; S-60-14; S-60-15 [N33 (wt)]; S-60-15.1 [N33T]; S-60-15.2 [N33S]; S-60-15.3 [N33G]; S-60-15.4 [N33R]; S-60-15.5 [N33D]; S-60-15.6 [N33H]; S-60-15.7 [N33K]; S-60-15.8 [N33Q]; S-60-15.9 [N33Y]; S-60-15.10 [N33E]; S-60-15.11 [N33W]; S-60-15.12 [N33F]; S-60-15.13 [N33I]; S-60-15.14 [N33V]; S-60-15.15 [N33A]; S-60-15.16 [N33M]; S-60-15.17 [N33L]; S-60-16; S-60-18; S-60-19; S-60-24 | WIRQPPGKGLEWIG | 36 |

TABLE 24

Heavy chain framework 3 sequences of anti-SORT1 antibodies

| Ab(s) | VH FR3 | SEQ ID NO: |
|---|---|---|
| S-60-10; S-60-11; S-60-12; S-60-19 | QVTISVDTSKNQFSLELSSVTAADTAVYYC | 37 |
| S-60-13; S-60-14; S-60-15 [N33 (wt)]; S-60-15.1 [N33T]; S-60-15.2 [N33S]; S-60-15.3 [N33G]; S-60-15.4 [N33R]; S-60-15.5 [N33D]; S-60-15.6 [N33H]; S-60-15.7 [N33K]; S-60-15.8 [N33Q]; S-60-15.9 [N33Y]; S-60-15.10 [N33E]; S-60-15.11 [N33W]; S-60-15.12 [N33F]; S-60-15.13 [N33I]; S-60-15.14 [N33V]; S-60-15.15 [N33A]; S-60-15.16 [N33M]; S-60-15.17 [N33L]; S-60-16; S-60-18; S-60-24 | RVTISVDTSKNQFSLKLSSVTAADTAVYYC | 38 |
| Formula VI | $X_1$VTISVDTSKNQFSLX$_2$LSSVTAADTAVYYC<br>$X_1$ is Q or R<br>$X_2$ is E or K | 39 |

TABLE 25

Heavy chain framework 4 sequences of anti-SORT1 antibodies

| Ab(s) | VH FR4 | SEQ ID NO: |
|---|---|---|
| S-60-10; S-60-11; S-60-12; S-60-13; S-60-14; S-60-15 [N33 (wt)]; S-60-15.1 [N33T]; S-60-15.2 [N33S]; S-60-15.3 [N33G]; S-60-15.4 [N33R]; S-60-15.5 [N33D]; S-60-15.6 [N33H]; S-60-15.7 [N33K]; S-60-15.8 [N33Q]; S-60-15.9 [N33Y]; S-60-15.10 [N33E]; S-60-15.11 [N33W]; S-60-15.12 [N33F]; S-60-15.13 [N33I]; S-60-15.14 [N33V]; S-60-15.15 [N33A]; S-60-15.16 [N33M]; S-60-15.17 [N33L]; S-60-16; S-60-18; S-60-19; S-60-24 | WGQGTTVTVSS | 40 |

TABLE 26

Light chain framework 1 sequences of anti-SORT1 antibodies

| Ab(s) | VL FR1 | SEQ ID NO: |
|---|---|---|
| S-60-10; S-60-11; S-60-12; S-60-13; S-60-14; S-60-15 [N33 (wt)]; S-60-15.1 [N33T]; S-60-15.2 [N33S]; S-60-15.3 [N33G]; S-60-15.4 [N33R]; S-60-15.5 [N33D]; S-60-15.6 [N33H]; S-60-15.7 [N33K]; S-60-15.8 [N33Q]; S-60-15.9 [N33Y]; S-60-15.10 [N33E]; S-60-15.11 [N33W]; S-60-15.12 [N33F]; S-60-15.13 [N33I]; S-60-15.14 [N33V]; S-60-15.15 [N33A]; S-60-15.16 [N33M]; S-60-15.17 [N33L]; S-60-16; S-60-19 | DIVMTQSPLSLPVTPGEPASISC | 41 |
| S-60-18 | DIVMTQSPLSLPVTPGGPASISC | 42 |
| S-60-24 | DIVMTQSPLSLPVTPGESASISC | 43 |
| Formula VII | DIVMTQSPLSLPVTPGX$_1$X$_2$ASISC<br>$X_1$ is E or G<br>$X_2$ is P or S | 44 |

TABLE 27

Light chain framework 2 sequences of anti-SORT1 antibodies

| Ab(s) | VL FR2 | SEQ ID NO: |
|---|---|---|
| S-60-10; S-60-11; S-60-13; S-60-14; S-60-15 [N33 (wt)]; S-60-15.1 [N33T]; S-60-15.2 [N33S]; S-60-15.3 [N33G]; S-60-15.4 [N33R]; S-60-15.5 [N33D]; S-60-15.6 [N33H]; S-60-15.7 [N33K]; S-60-15.8 [N33Q]; S-60-15.9 [N33Y]; S-60-15.10 [N33E]; S-60-15.11 [N33W]; S-60-15.12 [N33F]; S-60-15.13 [N33I]; S-60-15.14 [N33V]; S-60-15.15 [N33A]; S-60-15.16 [N33M]; S-60-15.17 [N33L]; S-60-16; S-60-18; S-60-19; S-60-24 | WYLQKPGQSPQLLIY | 45 |
| S-60-12 | WYLQKPGQPPQLLIY | 46 |
| Formula VIII | WYLQKPGQX$_1$PQLLIY<br>X$_1$ is S or P | 47 |

TABLE 28

Light chain framework 3 sequences of anti-SORT1 antibodies

| Ab(s) | VL FR3 | SEQ ID NO: |
|---|---|---|
| S-60-10; S-60-13; S-60-15 [N33 (wt)]; S-60-15.1 [N33T]; S-60-15.2 [N33S]; S-60-15.3 [N33G]; S-60-15.4 [N33R]; S-60-15.5 [N33D]; S-60-15.6 [N33H]; S-60-15.7 [N33K]; S-60-15.8 [N33Q]; S-60-15.9 [N33Y]; S-60-15.10 [N33E]; S-60-15.11 [N33W]; S-60-15.12 [N33F]; S-60-15.13 [N33I]; S-60-15.14 [N33V]; S-60-15.15 [N33A]; S-60-15.16 [N33M]; S-60-15.17 [N33L] | GVPDRFSGSGSGTDFTLKISRAEAEDVGVYYC | 48 |
| S-60-11; S-60-12; S-60-14; S-60-19; S-60-24 | GVPDRFSGSGSGTDFTLKISRVEAEDVGVYYC | 49 |
| S-60-16 | GVPDRFSGSGSGTDFTLKISRVEAEDVGAYYC | 50 |
| S-60-18 | GVPDRLSGSGSGTDFTLKISRVEAEDVGVYYC | 51 |
| Formula IX | GVPDRX$_1$SGSGSGTDFTLKISRX$_2$EAEDVGX$_3$YYC<br>X$_1$ is F or L<br>X$_2$ is A or V<br>X$_3$ is V or A | 52 |

TABLE 29

Light chain framework 4 sequences of anti-SORT1 antibodies

| Ab(s) | VL FR4 | SEQ ID NO: |
|---|---|---|
| S-60-10; S-60-11; S-60-12; S-60-13; S-60-14; S-60-15 [N33 (wt)]; S-60-15.1 [N33T]; S-60-15.2 [N33S]; S-60-15.3 [N33G]; S-60-15.4 [N33R]; S-60-15.5 [N33D]; S-60-15.6 [N33H]; S-60-15.7 [N33K]; S-60-15.8 [N33Q]; S-60-15.9 [N33Y]; S-60-15.10 [N33E]; S-60-15.11 [N33W]; S-60-15.12 [N33F]; S-60-15.13 [N33I]; S-60-15.14 [N33V]; S-60-15.15 [N33A]; S-60-15.16 [N33M]; S-60-15.17 [N33L]; S-60-16; S-60-18; S-60-19; S-60-24 | FGGGTKVEIK | 53 |

TABLE 30

Heavy chain variable region sequences of anti-SORT1 antibodies

| Ab(s) | HCVR | SEQ ID NO: |
|---|---|---|
| S-60-10, S-60-11, S-60-12, S-60-19 | QVQLQESGPGLVKPSETLSLTCAVSG YSISSGYYWGWIRQPPGKGLEWIGTIY HSGSTYYNPSLKSQVTISVDTSKNQFS LELSSVTAADTAVYYCARQGSIQQGY YGMDVWGQGTTVTVSS | 54 |
| S-30-13, S-60-14 | QVQLQESGPGLVKPSETLSLTCAVSG YSISSGYYWGWIRQPPGKGLEWIGTIY HSGSTYYNPSLESRVTISVDTSKNQFS LKLSSVTAADTAVYYCARQGSIQQGY YGMDVWGQGTTVTVSS | 55 |
| S-60, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16, S-60-18, S-60-24 | QVQLQESGPGLVKPSETLSLTCAVSG YSISSGYYWGWIRQPPGKGLEWIGTIY HSGSTYYNPSLKSRVTISVDTSKNQFS LKLSSVTAADTAVYYCARQGSIKQGY YGMDVWGQGTTVTVSS | 56 |

TABLE 31

Light chain variable region sequences of anti-SORT1 antibodies

| Ab(s) | LCVR | SEQ ID NO: |
|---|---|---|
| S-60-10; S-60-13; S-60-15 [N33 (wt)] | DIVMTQSPLSLPVTPGEPASISCRSSQS LLRSNGYNYLDWYLQKPGQSPQLLIY LGSNRASGVPDRFSGSGSGTDFTLKIS RAEAEDVGVYYCMQQQEAPLTFGGG TKVEIK | 57 |
| S-60-11; S-60-14 | DIVMTQSPLSLPVTPGEPASISCRSSQS LLRSNGYNYLDWYLQKPGQSPQLLIY LGSNRASGVPDRFSGSGSGTDFTLKIS RVEAEDVGVYYCMQQQEAPLTFGGG TKVEIK | 58 |
| S-60-12 | DIVMTQSPLSLPVTPGEPASISCRSSQS LLRSNGYNYLDWYLQKPGQPPQLLIY LGSNRVSGVPDRFSGSGSGTDFTLKIS RVEAEDVGVYYCMQQQETPLTFGGG TKVEIK | 59 |
| S-60-15.1 [N33T] | DIVMTQSPLSLPVTPGEPASISCRSSQS LLRSTGYNYLDWYLQKPGQSPQLLIY LGSNRASGVPDRFSGSGSGTDFTLKIS RAEAEDVGVYYCMQQQEAPLTFGGG TKVEIK | 60 |
| S-60-15.2 [N33S] | DIVMTQSPLSLPVTPGEPASISCRSSQS LLRSSGYNYLDWYLQKPGQSPQLLIY LGSNRASGVPDRFSGSGSGTDFTLKIS RAEAEDVGVYYCMQQQEAPLTFGGG TKVEIK | 61 |
| S-60-15.3 [N33G] | DIVMTQSPLSLPVTPGEPASISCRSSQS LLRSGGYNYLDWYLQKPGQSPQLLIY LGSNRASGVPDRFSGSGSGTDFTLKIS RAEAEDVGVYYCMQQQEAPLTFGGG TKVEIK | 62 |
| S-60-15.4 [N33R] | DIVMTQSPLSLPVTPGEPASISCRSSQS LLRSRGYNYLDWYLQKPGQSPQLLIY LGSNRASGVPDRFSGSGSGTDFTLKIS RAEAEDVGVYYCMQQQEAPLTFGGG TKVEIK | 63 |

TABLE 31-continued

Light chain variable region sequences of anti-SORT1 antibodies

| Ab(s) | LCVR | SEQ ID NO: |
|---|---|---|
| S-60-15.5 [N33D] | DIVMTQSPLSLPVTPGEPASISCRSSQS LLRSDGYNYLDWYLQKPGQSPQLLIY LGSNRASGVPDRFSGSGSGTDFTLKIS RAEAEDVGVYYCMQQQEAPLTFGGG TKVEIK | 64 |
| S-60-15.6 [N33H] | DIVMTQSPLSLPVTPGEPASISCRSSQS LLRSHGYNYLDWYLQKPGQSPQLLIY LGSNRASGVPDRFSGSGSGTDFTLKIS RAEAEDVGVYYCMQQQEAPLTFGGG TKVEIK | 65 |
| S-60-15.7 [N33K] | DIVMTQSPLSLPVTPGEPASISCRSSQS LLRSKGYNYLDWYLQKPGQSPQLLIY LGSNRASGVPDRFSGSGSGTDFTLKIS RAEAEDVGVYYCMQQQEAPLTFGGG TKVEIK | 66 |
| S-60-15.8 [N33Q] | DIVMTQSPLSLPVTPGEPASISCRSSQS LLRSQGYNYLDWYLQKPGQSPQLLIY LGSNRASGVPDRFSGSGSGTDFTLKIS RAEAEDVGVYYCMQQQEAPLTFGGG TKVEIK | 67 |
| S-60-15.9 [N33Y] | DIVMTQSPLSLPVTPGEPASISCRSSQS LLRSYGYNYLDWYLQKPGQSPQLLIY LGSNRASGVPDRFSGSGSGTDFTLKIS RAEAEDVGVYYCMQQQEAPLTFGGG TKVEIK | 68 |
| S-60-15.10 [N33E] | DIVMTQSPLSLPVTPGEPASISCRSSQS LLRSEGYNYLDWYLQKPGQSPQLLIY LGSNRASGVPDRFSGSGSGTDFTLKIS RAEAEDVGVYYCMQQQEAPLTFGGG TKVEIK | 69 |
| S-60-15.11 [N33W] | DIVMTQSPLSLPVTPGEPASISCRSSQS LLRSWGYNYLDWYLQKPGQSPQLLI YLGSNRASGVPDRFSGSGSGTDFTLKI SRAEAEDVGVYYCMQQQEAPLTFGG GTKVEIK | 70 |
| S-60-15.12 [N33F] | DIVMTQSPLSLPVTPGEPASISCRSSQS LLRSEGYNYLDWYLQKPGQSPQLLIY LGSNRASGVPDRFSGSGSGTDFTLKIS RAEAEDVGVYYCMQQQEAPLTFGGG TKVEIK | 71 |
| S-60-15.13 [N33I] | DIVMTQSPLSLPVTPGEPASISCRSSQS LLRSIGYNYLDWYLQKPGQSPQLLIY LGSNRASGVPDRFSGSGSGTDFTLKIS RAEAEDVGVYYCMQQQEAPLTFGGG TKVEIK | 72 |
| S-60-15.14 [N33V] | DIVMTQSPLSLPVTPGEPASISCRSSQS LLRSVGYNYLDWYLQKPGQSPQLLIY LGSNRASGVPDRFSGSGSGTDFTLKIS RAEAEDVGVYYCMQQQEAPLTFGGG TKVEIK | 73 |
| S-60-15.15 [N33A] | DIVMTQSPLSLPVTPGEPASISCRSSQS LLRSAGYNYLDWYLQKPGQSPQLLIY LGSNRASGVPDRFSGSGSGTDFTLKIS RAEAEDVGVYYCMQQQEAPLTFGGG TKVEIK | 74 |
| S-60-15.16 [N33M] | DIVMTQSPLSLPVTPGEPASISCRSSQS LLRSMGYNYLDWYLQKPGQSPQLLIY LGSNRASGVPDRFSGSGSGTDFTLKIS RAEAEDVGVYYCMQQQEAPLTFGGG TKVEIK | 75 |
| S-60-15.17 [N33L] | DIVMTQSPLSLPVTPGEPASISCRSSQS LLRSLGYNYLDWYLQKPGQSPQLLIY LGSNRASGVPDRFSGSGSGTDFTLKIS | 76 |

TABLE 31-continued

Light chain variable region sequences of anti-SORT1 antibodies

| Ab(s) | LCVR | SEQ ID NO: |
|---|---|---|
|  | RAEAEDVGVYYCMQQQEAPLTFGGG TKVEIK |  |
| S-60-16 | DIVMTQSPLSLPVTPGEPASISCRSSQS LLRSNGYNYLDWYLQKPGQSPQLLIY LGSNRASGVPDRFSGSGSGTDFTLKIS RVEAEDVGAYYCMQQQEAPLTFGGG TKVEIK | 77 |
| S-60-18 | DIVMTQSPLSLPVTPGGPASISCRSSQS LLRSNGYNYLDWYLQKPGQSPQLLIY LGSNRASGVPDRLSGSGSGTDFTLKIS RVEAEDVGVYYCMQQQETPLTFGGG TKVEIK | 78 |
| S-60, S-60-19 | DIVMTQSPLSLPVTPGEPASISCRSSQS LLHSNGYNYLDWYLQKPGQSPQLLIY LGSNRASGVPDRFSGSGSGTDFTLKIS RVEAEDVGVYYCMQQQETPLTFGGG TKVEIK | 79 |
| S-60-24 | DIVMTQSPLSLPVTPGESASISCRSSQG LLRSNGYNYLDWYLQKPGQSPQLLIY LGSNRASGVPDRFSGSGSGTDFTLKIS RVEAEDVGVYYCMQQQEAPLTFGGG TKVEIK | 80 |

TABLE 32

Sortilin amino acid sequences

| Description | Sequence | SEQ ID NO |
|---|---|---|
| Human Sortilin |        10           20          30          40          50<br>MERPWGAADG LSRWPHGLGL LLLLQLLPPS TLSQDRLDAP PPPAAPLPRW<br>       60           70          80          90         100<br>SGPIGVSWGL RAAAAGGAFP RGGRWRRSAP GEDEECGRVR DFVAKLANNT<br>      110        120        130        140        150<br>HQHVFDDLRG SVSLSWVGDS TGVILVLTTF HVPLVIMTFG QSKLYRSEDY<br>      160        170        180        190        200<br>GKNFKDITDL INNTFIRTEF GMAIGPENSG KVVLTAEVSG GSRGGRIFRS<br>      210        220        230        240        250<br>SDFAKNFVQT DLPFHPLTQM MYSPQNSDYL LALSTENGLW VSKNFGGKWE<br>      260        270        280        290        300<br>EIHKAVCLAK WGSDNTIFFT TYANGSCKAD LGALELWRTS DLGKSFKTIG<br>      310        320        330        340        350<br>VKIYSFGLGG RFLFASVMAD KDTTRRIHVS TDQGDTWSMA QLPSVGQEQF<br>      360        370        380        390        400<br>YSILAANDDM VFMHVDEPGD TGFGTIFTSD DRGIVYSKSL DRHLYTTTGG<br>      410        420        430        440        450<br>ETDFTNVTSL RGVYITSVLS EDNSIQTMIT FDQGGRWTHL RKPENSECDA<br>      460        470        480        490        500<br>TAKNKNECSL HIHASYSISQ KLNVPMAPLS EPNAVGIVIA HGSVGDAISV<br>      510        520        530        540        550<br>MVPDVYISDD GGYSWTKMLE GPHYYTILDS GGIIVAIEHS SRPINVIKFS<br>      560        570        580        590        600<br>TDEGQCWQTY TFTRDPIYFT GLASEPGARS MNISIWGFTE SFLTSOWVSY<br>      610        620        630        640        650<br>TIDFKDILER NCEEKDYTIW LAHSTDPEDY EDGCILGYKE QFLRLRKSSV<br>      660        670        680        690        700<br>CQNGRDYVVT KQPSICLCSL EDFLCDFGYY RPENDSKCVE QPELKGHDLE<br>      710        720        730        740        750<br>FCLYGREEHL TTNGYRKIPG DKCQGGVNPV REVKDLKKKC TSNFLSPEKQ<br>      760        770        780        790        800<br>NSKSNSVPII LAIVGLMLVT WAGVLIVKK YVCGGRFLVH RYSVLQQHAE<br>      810        820        830<br>ANGVDGVDAL DTASHTNKSG YHDDSDEDLL E | 81 |
| Mouse Sortilin | MERPRGAADG LLRWPLGLLL LLQLLPPAAV GQDRLDAPPP PAPPLLRWAG<br>PVGVSWGLRA AAPGGPVPRA GRWRRGAPAE DQDCGRLPDF IAKLTNNTHQ<br>HVFDDLSGSV SLSWVGDSTG VILVLTTFQV PLVIVSFGQS KLYRSEDYGK | 82 |

TABLE 32-continued

Sortilin amino acid sequences

| Description | Sequence | SEQ ID NO |
|---|---|---|
| | NFKDITNLIN NTFIRTEFGM AIGPENSGKV ILTAEVSGGS RGGRVFRSSD<br>FAKNFVQTDL PFHPLTQMMY SPQNSDYLLA LSTENGLWVS KNFGEKWEEI<br>HKAVCLAKWG PNNIIFFTTH VNGSCKADLG ALELWRTSDL GKTFKTIGVK<br>IYSFGLGGRF LFASVMADKD TTRRIHVSTD QGDTWSMAQL PSVGQEQFYS<br>ILAANEDMVF MHVDEPGDTG FGTIFTSDDR GIVYSKSLDR HLYTTTGGET<br>DFTNVTSLRG VYITSTLSED NSIQSMITFD QGGRWEHLRK PENSKCDATA<br>KNKNECSLHI HASYSISQKL NVPMAPLSEP NAVGIVIAHG SVGDAISVMV<br>PDVYISDDGG YSWAKMLEGP HYYTILDSGG IIVAIEHSNR PINVIKFSTD<br>EGQCWQSYVF TQEPIYFTGL ASEPGARSMN ISIWGFTESF ITRQWVSYTV<br>DFKDILERNC EEDDYTTWLA HSTDPGDYKD GCILGYKEQF LRLRKSSVCQ<br>NGRDYVVAKQ PSVCPCSLED FLCDFGYFRP ENASECVEQP ELKGHELEFC<br>LYGKEEHLTT NGYRKIPGDK CQGGMNPARE VKDLKKKCTS NFLNPTKQNS<br>KSNSVPIILA IVGLMLVTVV AGVLIVKKYV CGGRFLVHRY SVLQQHAEAD<br>GVEALDSTSH AKSGYHDDSD EDLLE | |
| Rat Sortilin | MERPRGAADG LLRWPLGLLL LLQLLPPAAV GQDRLDAPPP PAPPLLRWAG<br>PVGVSWGLRA AAPGGPVPRA GRWRRGAPAE DQDCGRLPDF IAKLTNNTHQ<br>HVFDDLSGSV SLSWVGDSTG VILVLTTFQV PLVIVSFGQS KLYRSEDYGK<br>NFKDITNLIN NTFIRTEFGM AIGPENSGKV ILTAEVSGGS RGGRVFRSSD<br>FAKNFVQTDL PFHPLTQMMY SPQNSDYLLA LSTENGLWVS KNFGEKWEEI<br>HKAVCLAKWG PNNIIFFTTH VNGSCKADLG ALELWRTSDL GKTFKTIGVK<br>IYSFGLGGRF LFASVMADKD TTRRIHVSTD QGDTWSMAQL PSVGQEQFYS<br>ILAANDDMVF MHVDEPGDTG FGTIFTSDDR GIVYSKSLDR HLYTTTGGET<br>DFTNVTSLRG VYITSTLSED NSIQSMITFD QGGRWEHLQK PENSKCDATA<br>KNKNECSLHI HASYSISQKL NVPMAPLSEP NAVGIVIAHG SVGDAISVMV<br>PDVYISDDGG YSWAKMLEGP HYYTILDSGG IIVAIEHSNR PINVIKFSTD<br>EGQCWQSYVF SQEPVYFTGL ASEPGARSMN ISIWGFTESF LTRQWVSYTI<br>DFKDILERNC EENDYTTWLA HSTDPGDYKD GCILGYKEQF LRLRKSSVCQ<br>NGRDYVVAKQ PSICPCSLED FLCDFGYFRP ENASECVEQP ELKGHELEFC<br>LYGKEEHLTT NGYRKIPGDR CQGGMNPARE VKDLKKKCTS NFLNPKKQNS<br>KSSSVPIILA IVGLMLVTVV AGVLIVKKYV CGGRFLVHRY SVLQQHAEAD<br>GVEALDTASH AKSGYHDDSD EDLLE | 83 |

TABLE 33

S-60-15 peptide sequences

| Description | Sequence | SEQ ID NO |
|---|---|---|
| Asp-box motif | (S/T)-X-(D/N)-X-X-X-X-(W/F/Y)<br>X is any amino acid | 84 |
| Asp-box motif | X-X-(S/T)-X-(D/N)-X-G-X-(T/S)-(W/F/Y)-X<br>X is any amino acid | 85 |
| Asp-box motif in human Sortilin (residues 200-207) | SSDFAKNF | 86 |
| S-60-15 Peptide | N̲QFSLK | 87 |
| S-60-15 Peptide | Q̲GYYGM̲DVWGQ̲GTTVTVSSASTK | 88 |
| S-60-15 Peptide | DYFPEPVTVSW̲N̲SGALTSGVHTFPAVLQSSGLYSLSSVVT<br>VPSSSLGTK | 89 |
| S-60-15 Peptide | DTLM̲ISR | 90 |
| S-60-15 Peptide | TPEVTCVVVDVSQEDPEVQFNWYVDGVEVHN̲AK | 91 |
| S-60-15 Peptide | VVSVLTVLHQDWLN̲GK | 92 |
| S-60-15 Peptide | EPQVYTLPPSQEEM̲TK | 93 |

TABLE 33-continued

S-60-15 peptide sequences

| Description | Sequence | SEQ ID NO |
|---|---|---|
| S-60-15 Peptide | NQVSLTCLVK | 94 |
| S-60-15 Peptide | GFYPSDIAVEWESNGQPENNYK | 95 |
| S-60-15 Peptide | WQEGNVFSCSVMHEALHNHYTQK | 96 |
| S-60-15 Peptide | DIVMTQSPLSLPVTPGEPASISCR | 97 |
| S-60-15 Peptide | SSQSLLR | 98 |
| S-60-15 Peptide | SNGYNYLDWYLQKPGQSPQLLIYLGSNR | 99 |
| S-60-15 Peptide | AEAEDVGVYYCMQQQEAPLTFGGGTK | 100 |
| S-60-15 Peptide | SGTASWCLLNNFYPR | 101 |
| S-60-15 Peptide | VDNALQSGNSQESVTEQDSK | 102 |

TABLE 34

Fc domain amino acid sequences

| Description | Sequence | SEQ ID NO |
|---|---|---|
| hnIgG1 LALAPS Fc | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGGPSVFLFPPKPKDTLMISRTPE VTCVVVDVSHEDPEVKFNWYVDGVEVHNAKTKPREEQYNSTYRV VSVLTVLHQDWLNGKEYKCKVSNKALPASIEKTISKAKGQPREPQV YTLPPSRDELTKNQVSLTCLVKGFYPSDIAVEWESNGQPENNYKTT PPVLDSDGSFFLYSKLTVDKSRWQQGNVFSCSVMHEALHNHYTQK SLSLSPGK | 103 |
| hnIgG1 LALAPS Fc without C-terminal lysine | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGGPSVFLFPPKPKDTLMISRTPE VTCVVVDVSHEDPEVKFNWYVDGVEVHNAKTKPREEQYNSTYRV VSVLTVLHQDWLNGKEYKCKVSNKALPASIEKTISKAKGQPREPQV YTLPPSRDELTKNQVSLTCLVKGFYPSDIAVEWESNGQPENNYKTT PPVLDSDGSFFLYSKLTVDKSRWQQGNVFSCSVMHEALHNHYTQK SLSLSPG | 104 |

TABLE 35

Full-length heavy chain amino acid sequences

| Description | Sequence | SEQ ID NO |
|---|---|---|
| S-60-10, S-60-11, S-60-12, S-60-19 with Fc LALAPS with C-terminal Lysine | QVQLQESGPGLVKPSETLSLTCAVSGYSISSGYYWGW IRQPPGKGLEWIGTIYHSGSTYYNPSLKSQVTISVDTS KNQFSLELSSVTAADTAVYYCARQGSIQQGYYGMDV WGQGTTVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKKVEP KSCDKTHTCPPCPAPEAAGGPSVFLFPPKPKDTLMISR TPEVTCVVVDVSHEDPEVKFNWYVDGVEVHNAKTK | 105 |

TABLE 35-continued

Full-length heavy chain amino acid sequences

| Description | Sequence | SEQ ID NO |
|---|---|---|
| | PREEQYNSTYRVVSVLTVLHQDWLNGKEYKCKVSN KALPASIEKTISKAKGQPREPQVYTLPPSRDELTKNQV SLTCLVKGFYPSDIAVEWESNGQPENNYKTTPPVLDS DGSFFLYSKLTVDKSRWQQGNVFSCSVMHEALHNH YTQKSLSLSPGK | |
| S-60-10, S-60-11, S-60-12, S-60-19 with Fc LALAPS without C-terminal Lysine | QVQLQESGPGLVKPSETLSLTCAVSGYSISSGYYWGW IRQPPGKGLEWIGTIYHSGSTYYNPSLKSQVTISVDTS KNQFSLELSSVTAADTAVYYCARQGSIQQGYYGMDV WGQGTTVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKKVEP KSCDKTHTCPPCPAPEAAGGPSVFLFPPKPKDTLMISR TPEVTCVVVDVSHEDPEVKFNWYVDGVEVHNAKTK PREEQYNSTYRVVSVLTVLHQDWLNGKEYKCKVSN KALPASIEKTISKAKGQPREPQVYTLPPSRDELTKNQV SLTCLVKGFYPSDIAVEWESNGQPENNYKTTPPVLDS DGSFFLYSKLTVDKSRWQQGNVFSCSVMHEALHNH YTQKSLSLSPG | 106 |
| S-60-13, S-60-14 with Fc LALAPS with C-terminal Lysine | QVQLQESGPGLVKPSETLSLTCAVSGYSISSGYYWGW IRQPPGKGLEWIGTIYHSGSTYYNPSLESRVTISVDTSK NQFSLKLSSVTAADTAVYYCARQGSIQQGYYGMDV WGQGTTVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKKVEP KSCDKTHTCPPCPAPEAAGGPSVFLFPPKPKDTLMISR TPEVTCVVVDVSHEDPEVKFNWYVDGVEVHNAKTK PREEQYNSTYRVVSVLTVLHQDWLNGKEYKCKVSN KALPASIEKTISKAKGQPREPQVYTLPPSRDELTKNQV SLTCLVKGFYPSDIAVEWESNGQPENNYKTTPPVLDS DGSFFLYSKLTVDKSRWQQGNVFSCSVMHEALHNH YTQKSLSLSPGK | 135 |
| S-60-13, S-60-14 with Fc LALAPS without C-terminal Lysine | QVQLQESGPGLVKPSETLSLTCAVSGYSISSGYYWGW IRQPPGKGLEWIGTIYHSGSTYYNPSLESRVTISVDTSK NQFSLKLSSVTAADTAVYYCARQGSIQQGYYGMDV WGQGTTVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKKVEP KSCDKTHTCPPCPAPEAAGGPSVFLFPPKPKDTLMISR TPEVTCVVVDVSHEDPEVKFNWYVDGVEVHNAKTK PREEQYNSTYRVVSVLTVLHQDWLNGKEYKCKVSN KALPASIEKTISKAKGQPREPQVYTLPPSRDELTKNQV SLTCLVKGFYPSDIAVEWESNGQPENNYKTTPPVLDS DGSFFLYSKLTVDKSRWQQGNVFSCSVMHEALHNH YTQKSLSLSPG | 136 |
| S-60, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], S-60-15.14 [N33V], S-60-15.15 [N33A], S-60-15.16 [N33M], S-60-15.17 [N33L], S-60-16, S-60-18, S-60-24 with Fc LALAPS with C-terminal Lysine | QVQLQESGPGLVKPSETLSLTCAVSGYSISSGYYWGW IRQPPGKGLEWIGTIYHSGSTYYNPSLKSRVTISVDTS KNQFSLKLSSVTAADTAVYYCARQGSIKQGYYGMD VWGQGTTVTVSSASTKGPSVFPLAPSSKSTSGGTAAL GCLVKDYFPEPVTVSWNSGALTSGVHTFPAVLQSSGL YSLSSVVTVPSSSLGTQTYICNVNHKPSNTKVDKKVE PKSCDKTHTCPPCPAPEAAGGPSVFLFPPKPKDTLMIS RTPEVTCVVVDVSHEDPEVKFNWYVDGVEVHNAKT KPREEQYNSTYRVVSVLTVLHQDWLNGKEYKCKVS NKALPASIEKTISKAKGQPREPQVYTLPPSRDELTKNQ VSLTCLVKGFYPSDIAVEWESNGQPENNYKTTPPVLD SDGSFFLYSKLTVDKSRWQQGNVFSCSVMHEALHNH YTQKSLSLSPGK | 137 |
| S-60, S-60-15 [N33 (wt)], S-60-15.1 [N33T], S-60-15.2 [N33S], S-60-15.3 [N33G], S-60-15.4 [N33R], S-60-15.5 [N33D], S-60-15.6 [N33H], S-60-15.7 [N33K], S-60-15.8 [N33Q], S-60-15.9 [N33Y], S-60-15.10 [N33E], S-60-15.11 [N33W], S-60-15.12 [N33F], S-60-15.13 [N33I], | QVQLQESGPGLVKPSETLSLTCAVSGYSISSGYYWGW IRQPPGKGLEWIGTIYHSGSTYYNPSLKSRVTISVDTS KNQFSLKLSSVTAADTAVYYCARQGSIKQGYYGMD VWGQGTTVTVSSASTKGPSVFPLAPSSKSTSGGTAAL GCLVKDYFPEPVTVSWNSGALTSGVHTFPAVLQSSGL YSLSSVVTVPSSSLGTQTYICNVNHKPSNTKVDKKVE PKSCDKTHTCPPCPAPEAAGGPSVFLFPPKPKDTLMIS RTPEVTCVVVDVSHEDPEVKFNWYVDGVEVHNAKT KPREEQYNSTYRVVSVLTVLHQDWLNGKEYKCKVS NKALPASIEKTISKAKGQPREPQVYTLPPSRDELTKNQ | 138 |

TABLE 35-continued

Full-length heavy chain amino acid sequences

| Description | Sequence | SEQ ID NO |
|---|---|---|
| S-60-15.14 [N33V], S-60-15.15 [N33A], S-60-15.16 [N33M], S-60-15.17 [N33L], S-60-16, S-60-18, S-60-24 with Fc LALAPS without C-terminal Lysine | VSLTCLVKGFYPSDIAVEWESNGQPENNYKTTPPVLD SDGSFFLYSKLTVDKSRWQQGNVFSCSVMHEALHNH YTQKSLSLSPG | |

TABLE 36

Full-length light chain amino acid sequences

| Description | Sequence | SEQ ID NO |
|---|---|---|
| S-60-10; S-60-13; S-60-15 [N33 (wt)] | DIVMTQSPLSLPVTPGEPASIS CRSSQSLLRSNGYNYLDWYL QKPGQSPQLLIYLGSNRASGV PDRFSGSGSGTDFTLKISRAEA EDVGVYYCMQQQEAPLTFGG GTKVEIKRTVAAPSVFIFPPSD EQLKSGTASVVCLLNNFYPRE AKVQWKVDNALQSGNSQES VTEQDSKDSTYSLSSTLTLSK ADYEKHKVYACEVTHQGLSS PVTKSFNRGEC | 139 |
| S-60-11; S-60-14 | DIVMTQSPLSLPVTPGEPASIS CRSSQSLLRSNGYNYLDWYL QKPGQSPQLLIYLGSNRASGV PDRFSGSGSGTDFTLKISRVEA EDVGVYYCMQQQEAPLTFGG GTKVEIKRTVAAPSVFIFPPSD EQLKSGTASVVCLLNNFYPRE AKVQWKVDNALQSGNSQES VTEQDSKDSTYSLSSTLTLSK ADYEKHKVYACEVTHQGLSS PVTKSFNRGEC | 140 |
| S-60-12 | DIVMTQSPLSLPVTPGEPASIS CRSSQSLLRSNGYNYLDWYL QKPGQPPQLLIYLGSNRVSGV PDRFSGSGSGTDFTLKISRVEA EDVGVYYCMQQQETPLTFGG GTKVEIKRTVAAPSVFIFPPSD EQLKSGTASVVCLLNNFYPRE AKVQWKVDNALQSGNSQES VTEQDSKDSTYSLSSTLTLSK ADYEKHKVYACEVTHQGLSS PVTKSFNRGEC | 141 |
| S-60-15.1 [N33T] | DIVMTQSPLSLPVTPGEPASIS CRSSQSLLRSTGYNYLDWYL QKPGQSPQLLIYLGSNRASGV PDRFSGSGSGTDFTLKISRAEA EDVGVYYCMQQQEAPLTFGG GTKVEIKRTVAAPSVFIFPPSD EQLKSGTASVVCLLNNFYPRE AKVQWKVDNALQSGNSQES VTEQDSKDSTYSLSSTLTLSK ADYEKHKVYACEVTHQGLSS PVTKSFNRGEC | 142 |
| S-60-15.2 [N33S] | DIVMTQSPLSLPVTPGEPASIS CRSSQSLLRSSGYNYLDWYL QKPGQSPQLLIYLGSNRASGV PDRFSGSGSGTDFTLKISRAEA EDVGVYYCMQQQEAPLTFGG GTKVEIKRTVAAPSVFIFPPSD EQLKSGTASVVCLLNNFYPRE AKVQWKVDNALQSGNSQES VTEQDSKDSTYSLSSTLTLSK ADYEKHKVYACEVTHQGLSS PVTKSFNRGEC | 143 |
| S-60-15.3 [N33G] | DIVMTQSPLSLPVTPGEPASIS CRSSQSLLRSGGYNYLDWYL QKPGQSPQLLIYLGSNRASGV PDRFSGSGSGTDFTLKISRAEA EDVGVYYCMQQQEAPLTFGG GTKVEIKRTVAAPSVFIFPPSD EQLKSGTASVVCLLNNFYPRE AKVQWKVDNALQSGNSQES VTEQDSKDSTYSLSSTLTLSK ADYEKHKVYACEVTHQGLSS PVTKSFNRGEC | 144 |
| S-60-15.4 [N33R] | DIVMTQSPLSLPVTPGEPASIS CRSSQSLLRSRGYNYLDWYL QKPGQSPQLLIYLGSNRASGV PDRFSGSGSGTDFTLKISRAEA EDVGVYYCMQQQEAPLTFGG GTKVEIKRTVAAPSVFIFPPSD EQLKSGTASVVCLLNNFYPRE AKVQWKVDNALQSGNSQES VTEQDSKDSTYSLSSTLTLSK ADYEKHKVYACEVTHQGLSS PVTKSFNRGEC | 145 |
| S-60-15.5 [N33D] | DIVMTQSPLSLPVTPGEPASIS CRSSQSLLRSDGYNYLDWYL QKPGQSPQLLIYLGSNRASGV PDRFSGSGSGTDFTLKISRAEA EDVGVYYCMQQQEAPLTFGG GTKVEIKRTVAAPSVFIFPPSD EQLKSGTASVVCLLNNFYPRE AKVQWKVDNALQSGNSQES VTEQDSKDSTYSLSSTLTLSK ADYEKHKVYACEVTHQGLSS PVTKSFNRGEC | 146 |
| S-60-15.6 [N33H] | DIVMTQSPLSLPVTPGEPASIS CRSSQSLLRSHGYNYLDWYL QKPGQSPQLLIYLGSNRASGV PDRFSGSGSGTDFTLKISRAEA EDVGVYYCMQQQEAPLTFGG GTKVEIKRTVAAPSVFIFPPSD EQLKSGTASVVCLLNNFYPRE AKVQWKVDNALQSGNSQES VTEQDSKDSTYSLSSTLTLSK ADYEKHKVYACEVTHQGLSS PVTKSFNRGEC | 119 |
| S-60-15.7 [N33K] | DIVMTQSPLSLPVTPGEPASIS CRSSQSLLRSKGYNYLDWYL QKPGQSPQLLIYLGSNRASGV PDRFSGSGSGTDFTLKISRAEA EDVGVYYCMQQQEAPLTFGG GTKVEIKRTVAAPSVFIFPPSD EQLKSGTASVVCLLNNFYPRE AKVQWKVDNALQSGNSQES | 120 |

TABLE 36-continued

Full-length light chain amino acid sequences

| Description | Sequence | SEQ ID NO |
|---|---|---|
| | VTEQDSKDSTYSLSSTLTLSK ADYEKHKVYACEVTHQGLSS PVTKSFNRGEC | |
| S-60-15.8 [N33Q] | DIVMTQSPLSLPVTPGEPASIS CRSSQSLLRSQGYNYLDWYL QKPGQSPQLLIYLGSNRASGV PDRFSGSGSGTDFTLKISRAEA EDVGVYYCMQQEAPLTFGG GTKVEIKRTVAAPSVFIFPPSD EQLKSGTASVVCLLNNFYPRE AKVQWKVDNALQSGNSQES VTEQDSKDSTYSLSSTLTLSK ADYEKHKVYACEVTHQGLSS PVTKSFNRGEC | 121 |
| S-60-15.9 [N33Y] | DIVMTQSPLSLPVTPGEPASIS CRSSQSLLRSYGYNYLDWYL QKPGQSPQLLIYLGSNRASGV PDRFSGSGSGTDFTLKISRAEA EDVGVYYCMQQEAPLTFGG GTKVEIKRTVAAPSVFIFPPSD EQLKSGTASVVCLLNNFYPRE AKVQWKVDNALQSGNSQES VTEQDSKDSTYSLSSTLTLSK ADYEKHKVYACEVTHQGLSS PVTKSFNRGEC | 122 |
| S-60-15.10 [N33E] | DIVMTQSPLSLPVTPGEPASIS CRSSQSLLRSEGYNYLDWYL QKPGQSPQLLIYLGSNRASGV PDRFSGSGSGTDFTLKISRAEA EDVGVYYCMQQEAPLTFGG GTKVEIKRTVAAPSVFIFPPSD EQLKSGTASVVCLLNNFYPRE AKVQWKVDNALQSGNSQES VTEQDSKDSTYSLSSTLTLSK ADYEKHKVYACEVTHQGLSS PVTKSFNRGEC | 123 |
| S-60-15.11 [N33W] | DIVMTQSPLSLPVTPGEPASIS CRSSQSLLRSWGYNYLDWYL QKPGQSPQLLIYLGSNRASGV PDRFSGSGSGTDFTLKISRAEA EDVGVYYCMQQEAPLTFGG GTKVEIKRTVAAPSVFIFPPSD EQLKSGTASVVCLLNNFYPRE AKVQWKVDNALQSGNSQES VTEQDSKDSTYSLSSTLTLSK ADYEKHKVYACEVTHQGLSS PVTKSFNRGEC | 124 |
| S-60-15.12 [N33F] | DIVMTQSPLSLPVTPGEPASIS CRSSQSLLRSFGYNYLDWYL QKPGQSPQLLIYLGSNRASGV PDRFSGSGSGTDFTLKISRAEA EDVGVYYCMQQEAPLTFGG GTKVEIKRTVAAPSVFIFPPSD EQLKSGTASVVCLLNNFYPRE AKVQWKVDNALQSGNSQES VTEQDSKDSTYSLSSTLTLSK ADYEKHKVYACEVTHQGLSS PVTKSFNRGEC | 125 |
| S-60-15.13 [N33I] | DIVMTQSPLSLPVTPGEPASIS CRSSQSLLRSIGYNYLDWYLQ KPGQSPQLLIYLGSNRASGVP DRFSGSGSGTDFTLKISRAEAE DVGVYYCMQQEAPLTFGGG TKVEIKRTVAAPSVFIFPPSDE QLKSGTASVVCLLNNFYPREA KVQWKVDNALQSGNSQESVT EQDSKDSTYSLSSTLTLSKAD YEKHKVYACEVTHQGLSSPV TKSFNRGEC | 126 |
| S-60-15.14 [N33V] | DIVMTQSPLSLPVTPGEPASIS CRSSQSLLRSVGYNYLDWYL QKPGQSPQLLIYLGSNRASGV PDRFSGSGSGTDFTLKISRAEA EDVGVYYCMQQEAPLTFGG GTKVEIKRTVAAPSVFIFPPSD EQLKSGTASVVCLLNNFYPRE AKVQWKVDNALQSGNSQES VTEQDSKDSTYSLSSTLTLSK ADYEKHKVYACEVTHQGLSS PVTKSFNRGEC | 127 |
| S-60-15.15 [N33A] | DIVMTQSPLSLPVTPGEPASIS CRSSQSLLRSAGYNYLDWYL QKPGQSPQLLIYLGSNRASGV PDRFSGSGSGTDFTLKISRAEA EDVGVYYCMQQEAPLTFGG GTKVEIKRTVAAPSVFIFPPSD EQLKSGTASVVCLLNNFYPRE AKVQWKVDNALQSGNSQES VTEQDSKDSTYSLSSTLTLSK ADYEKHKVYACEVTHQGLSS PVTKSFNRGEC | 128 |
| S-60-15.16 [N33M] | DIVMTQSPLSLPVTPGEPASIS CRSSQSLLRSMGYNYLDWYL QKPGQSPQLLIYLGSNRASGV PDRFSGSGSGTDFTLKISRAEA EDVGVYYCMQQEAPLTFGG GTKVEIKRTVAAPSVFIFPPSD EQLKSGTASVVCLLNNFYPRE AKVQWKVDNALQSGNSQES VTEQDSKDSTYSLSSTLTLSK ADYEKHKVYACEVTHQGLSS PVTKSFNRGEC | 129 |
| S-60-15.17 [N33L] | DIVMTQSPLSLPVTPGEPASIS CRSSQSLLRSLGYNYLDWYL QKPGQSPQLLIYLGSNRASGV PDRFSGSGSGTDFTLKISRAEA EDVGVYYCMQQEAPLTFGG GTKVEIKRTVAAPSVFIFPPSD EQLKSGTASVVCLLNNFYPRE AKVQWKVDNALQSGNSQES VTEQDSKDSTYSLSSTLTLSK ADYEKHKVYACEVTHQGLSS PVTKSFNRGEC | 130 |
| S-60-16 | DIVMTQSPLSLPVTPGEPASIS CRSSQSLLRSNGYNYLDWYL QKPGQSPQLLIYLGSNRASGV PDRFSGSGSGTDFTLKISRVEA EDVGAYYCMQQEAPLTFGG GTKVEIKRTVAAPSVFIFPPSD EQLKSGTASVVCLLNNFYPRE AKVQWKVDNALQSGNSQES VTEQDSKDSTYSLSSTLTLSK ADYEKHKVYACEVTHQGLSS PVTKSFNRGEC | 131 |
| S-60-18 | DIVMTQSPLSLPVTPGGPASIS CRSSQSLLRSNGYNYLDWYL QKPGQSPQLLIYLGSNRASGV PDRLSGSGSGTDFTLKISRVEA EDVGVYYCMQQETPLTFGG GTKVEIKRTVAAPSVFIFPPSD EQLKSGTASVVCLLNNFYPRE AKVQWKVDNALQSGNSQES VTEQDSKDSTYSLSSTLTLSK ADYEKHKVYACEVTHQGLSS PVTKSFNRGEC | 132 |
| S-60, S-60-19 | DIVMTQSPLSLPVTPGEPASIS CRSSQSLLHSNGYNYLDWYL QKPGQSPQLLIYLGSNRASGV PDRFSGSGSGTDFTLKISRVEA | 133 |

TABLE 36-continued

Full-length light chain amino acid sequences

| Description | Sequence | SEQ ID NO |
|---|---|---|
| | EDVGVYYCMQQQETPLTFGG GTKVEIKRTVAAPSVFIFPPSD EQLKSGTASVVCLLNNFYPRE AKVQWKVDNALQSGNSQES VTEQDSKDSTYSLSSTLTLSK ADYEKHKVYACEVTHQGLSS PVTKSFNRGEC | |
| S-60-24 | DIVMTQSPLSLPVTPGESASIS CRSSQGLLRSNGYNYLDWYL QKPGQSPQLLIYLGSNRASGV PDRFSGSGSGTDFTLKISRVEA EDVGVYYCMQQQEAPLTFGG GTKVEIKRTVAAPSVFIFPPSD EQLKSGTASVVCLLNNFYPRE AKVQWKVDNALQSGNSQES VTEQDSKDSTYSLSSTLTLSK ADYEKHKVYACEVTHQGLSS PVTKSFNRGEC | 134 |

What is claimed is:

1. A method of treating an individual having a disease, disorder, or injury, comprising administering to the individual a therapeutically effective amount of an antibody that binds to a sortilin protein, wherein the disease, disorder, or injury is selected from the group consisting of frontotemporal dementia, dementia, Alzheimer's disease, amyotrophic lateral sclerosis, Parkinson's disease, stroke, and arthritis, wherein the antibody comprises a heavy chain variable region and a light chain variable region, wherein:

(a) the heavy chain variable region comprises an HVR-H1 comprising the amino acid sequence YSISSGYYWG (SEQ ID NO: 1), an HVR-H2 comprising the amino acid sequence TIYHSGSTYYNPSLKS (SEQ ID NO: 2), an HVR-H3 comprising the amino acid sequence ARQGSIQQGYYGMDV (SEQ ID NO: 5); and the light chain variable region comprises an HVR-L1 comprising the amino acid sequence RSSQSLLRSNGYNYLD (SEQ ID NO: 8), an HVR-L2 comprising the amino acid sequence LGSNRAS (SEQ ID NO: 29), and an HVR-L3 comprising the amino acid sequence MQQQEAPLT (SEQ ID NO: 32);

(b) the heavy chain variable region comprises an HVR-H1 comprising the amino acid sequence YSISSGYYWG (SEQ ID NO: 1), an HVR-H2 comprising the amino acid sequence TIYHSGSTYYNPSLKS (SEQ ID NO: 2), an HVR-H3 comprising the amino acid sequence ARQGSIQQGYYGMDV (SEQ ID NO: 5); and the light chain variable region comprises an HVR-L1 comprising the amino acid sequence RSSQSLLRSNGYNYLD (SEQ ID NO: 8), an HVR-L2 comprising the amino acid sequence LGSNRVS (SEQ ID NO: 30), and an HVR-L3 comprising the amino acid sequence MQQQETPLT (SEQ ID NO: 33);

(c) the heavy chain variable region comprises an HVR-H1 comprising the amino acid sequence YSISSGYYWG (SEQ ID NO: 1), an HVR-H2 comprising the amino acid sequence TIYHSGSTYYNPSLES (SEQ ID NO: 3), an HVR-H3 comprising the amino acid sequence ARQGSIQQGYYGMDV (SEQ ID NO: 5); and the light chain variable region comprises an HVR-L1 comprising the amino acid sequence RSSQSLLRSNGYNYLD (SEQ ID NO: 8), an HVR-L2 comprising the amino acid sequence LGSNRAS (SEQ ID NO: 29), and an HVR-L3 comprising the amino acid sequence MQQQEAPLT (SEQ ID NO: 32);

(d) the heavy chain variable region comprises an HVR-H1 comprising the amino acid sequence YSISSGYYWG (SEQ ID NO: 1), an HVR-H2 comprising the amino acid sequence TIYHSGSTYYNPSLKS (SEQ ID NO: 2), an HVR-H3 comprising the amino acid sequence ARQGSIKQGYYGMDV (SEQ ID NO: 6); and the light chain variable region comprises an HVR-L1 comprising the amino acid sequence RSSQSLLRSNGYNYLD (SEQ ID NO: 8), an HVR-L2 comprising the amino acid sequence LGSNRAS (SEQ ID NO: 29), and an HVR-L3 comprising the amino acid sequence MQQQEAPLT (SEQ ID NO: 32);

(e) the heavy chain variable region comprises an HVR-H1 comprising the amino acid sequence YSISSGYYWG (SEQ ID NO: 1), an HVR-H2 comprising the amino acid sequence TIYHSGSTYYNPSLKS (SEQ ID NO: 2), an HVR-H3 comprising the amino acid sequence ARQGSIKQGYYGMDV (SEQ ID NO: 6); and the light chain variable region comprises an HVR-L1 comprising the amino acid sequence RSSQSLLRSTGYNYLD (SEQ ID NO: 9), an HVR-L2 comprising the amino acid sequence LGSNRAS (SEQ ID NO: 29), and an HVR-L3 comprising the amino acid sequence MQQQEAPLT (SEQ ID NO: 32);

(f) the heavy chain variable region comprises an HVR-H1 comprising the amino acid sequence YSISSGYYWG (SEQ ID NO: 1), an HVR-H2 comprising the amino acid sequence TIYHSGSTYYNPSLKS (SEQ ID NO: 2), an HVR-H3 comprising the amino acid sequence ARQGSIKQGYYGMDV (SEQ ID NO: 6); and the light chain variable region comprises an HVR-L1 comprising the amino acid sequence RSSQSLLRSNGYNYLD (SEQ ID NO: 8), an HVR-L2 comprising the amino acid sequence LGSNRAS (SEQ ID NO: 29), and an HVR-L3 comprising the amino acid sequence MQQQETPLT (SEQ ID NO: 33);

(g) the heavy chain variable region comprises an HVR-H1 comprising the amino acid sequence YSISSGYYWG (SEQ ID NO: 1), an HVR-H2 comprising the amino acid sequence TIYHSGSTYYNPSLKS (SEQ ID NO: 2), an HVR-H3 comprising the amino acid sequence ARQGSIQQGYYGMDV (SEQ ID NO: 5); and the light chain variable region comprises an HVR-L1 comprising the amino acid sequence RSSQSLLHSNGYNYLD (SEQ ID NO: 26), an HVR-L2 comprising the amino acid sequence LGSNRAS (SEQ ID NO: 29), and an HVR-L3 comprising the amino acid sequence MQQQETPLT (SEQ ID NO: 33);

(h) the heavy chain variable region comprises an HVR-H1 comprising the amino acid sequence YSISSGYYWG (SEQ ID NO: 1), an HVR-H2 comprising the amino acid sequence TIYHSGSTYYNPSLKS (SEQ ID NO: 2), an HVR-H3 comprising the amino acid sequence ARQGSIKQGYYGMDV (SEQ ID NO: 6); and the light chain variable region comprises an HVR-L1 comprising the amino acid sequence RSSQGLLRSNGYNYLD (SEQ ID NO: 27), an HVR-L2 comprising the amino acid sequence LGSNRAS (SEQ ID NO: 29), and an HVR-L3 comprising the amino acid sequence MQQQEAPLT (SEQ ID NO: 32);

(i) the heavy chain variable region comprises an HVR-H1 comprising the amino acid sequence YSISSGYYWG (SEQ ID NO: 1), an HVR-H2 comprising the amino acid sequence TIYHSGSTYYNPSLKS (SEQ ID NO: 2), an HVR-H3 comprising the amino acid sequence ARQGSIKQGYYGMDV (SEQ ID NO: 6); and the light chain variable region comprises an HVR-L1 comprising the amino acid sequence RSSQSLLRSSGYNYLD (SEQ ID NO: 10), an HVR-L2 comprising the amino acid sequence LGSNRAS (SEQ ID NO: 29), and an HVR-L3 comprising the amino acid sequence MQQQEAPLT (SEQ ID NO: 32); or (j) the heavy chain variable region comprises an HVR-H1 comprising the amino acid sequence YSISSGYYWG (SEQ ID NO: 1), an HVR-H2 comprising the amino acid sequence TIYHSGSTYYNPSLKS (SEQ ID NO: 2), an HVR-H3 comprising the amino acid sequence ARQGSIKQGYYGMDV (SEQ ID NO: 6); and the light chain variable region comprises an HVR-L1 comprising the amino acid sequence RSSQSLLRSIGYNYLD (SEQ ID NO: 21), an HVR-L2 comprising the amino acid sequence LGSNRAS (SEQ ID NO: 29), and an HVR-L3 comprising the amino acid sequence MQQQEAPLT (SEQ ID NO: 32).

2. The method of claim 1, wherein the disease, disorder, or injury is arthritis.

3. The method of claim 1, wherein the disease, disorder, or injury is Alzheimer's disease.

4. The method of claim 1, wherein the disease, disorder, or injury is frontotemporal dementia.

5. The method of claim 1, wherein the disease, disorder, or injury is amyotrophic lateral sclerosis.

6. The method of claim 1, wherein the disease, disorder, or injury is Parkinson's disease.

7. The method of claim 1, wherein the individual has one or more mutations in the gene encoding progranulin.

8. The method of claim 7, wherein the individual is heterozygous for one or more loss-of-function mutations in the gene encoding progranulin.

9. The method of claim 1, wherein the antibody is in a pharmaceutical composition comprising the antibody and a pharmaceutically acceptable carrier.

10. The method of claim 1, wherein the antibody:
(a) decreases cell surface levels of sortilin more than the level of decrease caused by an anti-sortilin antibody comprising a heavy chain variable region comprising the sequence of SEQ ID NO: 56 and a light chain variable region comprising the sequence of SEQ ID NO: 79;
(b) increases extracellular levels of progranulin more than the level of increase caused by an anti-sortilin antibody comprising a heavy chain variable region comprising the sequence of SEQ ID NO: 56 and a light chain variable region comprising the sequence of SEQ ID NO: 79;
(c) inhibits the interaction between sortilin expressed on a cell and progranulin more than the level of inhibition caused by an anti-sortilin antibody comprising a heavy chain variable region comprising the sequence of SEQ ID NO: 56 and a light chain variable region comprising the sequence of SEQ ID NO: 79; or
(d) any combination of (a)-(c).

11. The method of claim 1, wherein:
(a) the antibody has a dissociation constant ($K_D$) for human sortilin that is at least 1.1-fold lower than an anti-sortilin antibody comprising a heavy chain variable region comprising the sequence of SEQ ID NO: 56 and a light chain variable region comprising the sequence of SEQ ID NO: 79, wherein the $K_D$ is determined by FACS; and/or
(b) the antibody has a dissociation constant ($K_D$) for human sortilin that ranges from about 5.0E-10 M to about 1.0E-9 M wherein the $K_D$ is determined by FACS, or about 250-500 pM wherein the $K_D$ is determined by Bio-layer interferometry.

12. The method of claim 1, wherein the antibody comprises a heavy chain variable region and a light chain variable region, wherein: the heavy chain variable region comprises an HVR-H1 comprising the amino acid sequence YSISSGYYWG (SEQ ID NO: 1), an HVR-H2 comprising the amino acid sequence TIYHSGSTYYNPSLKS (SEQ ID NO: 2), and an HVR-H3 comprising the amino acid sequence ARQGSIKQGYYGMDV (SEQ ID NO: 6); and the light chain variable region comprises an HVR-L1 comprising the amino acid sequence RSSQSLLRSTGYNYLD (SEQ ID NO: 9), an HVR-L2 comprising the amino acid sequence LGSNRAS (SEQ ID NO: 29), and an HVR-L3 comprising the amino acid sequence MQQQEAPLT (SEQ ID NO: 32).

13. The method of claim 1, wherein the antibody comprises a heavy chain variable region and a light chain variable region, wherein: the heavy chain variable region comprises an HVR-H1 comprising the amino acid sequence YSISSGYYWG (SEQ ID NO: 1), an HVR-H2 comprising the amino acid sequence TIYHSGSTYYNPSLKS (SEQ ID NO: 2), and an HVR-H3 comprising the amino acid sequence ARQGSIKQGYYGMDV (SEQ ID NO: 6); and the light chain variable region comprises an HVR-L1 comprising the amino acid sequence RSSQSLLRSNGYNYLD (SEQ ID NO: 8), an HVR-L2 comprising the amino acid sequence LGSNRAS (SEQ ID NO: 29), and an HVR-L3 comprising the amino acid sequence MQQQEAPLT (SEQ ID NO: 32).

14. The method of claim 1, wherein the antibody comprises:
(a) a heavy chain variable region comprising the amino acid sequence of SEQ ID NO: 54, and a light chain variable region comprising the amino acid sequence of SEQ ID NO: 57;

(b) a heavy chain variable region comprising the amino acid sequence of SEQ ID NO: 54, and a light chain variable region comprising the amino acid sequence of SEQ ID NO: 58;

(c) a heavy chain variable region comprising the amino acid sequence of SEQ ID NO: 54, and a light chain variable region comprising the amino acid sequence of SEQ ID NO: 59;

(d) a heavy chain variable region comprising the amino acid sequence of SEQ ID NO: 55, and a light chain variable region comprising the amino acid sequence of SEQ ID NO: 57;

(e) a heavy chain variable region comprising the amino acid sequence of SEQ ID NO: 55, and a light chain variable region comprising the amino acid sequence of SEQ ID NO: 58;

(f) a heavy chain variable region comprising the amino acid sequence of SEQ ID NO: 56, and a light chain variable region comprising the amino acid sequence of SEQ ID NO: 57;

(g) a heavy chain variable region comprising the amino acid sequence of SEQ ID NO: 56, and a light chain variable region comprising the amino acid sequence of SEQ ID NO: 77;

(h) a heavy chain variable region comprising the amino acid sequence of SEQ ID NO: 56, and a light chain variable region comprising the amino acid sequence of SEQ ID NO: 78;

(i) a heavy chain variable region comprising the amino acid sequence of SEQ ID NO: 54, and a light chain variable region comprising the amino acid sequence of SEQ ID NO: 79;

(j) a heavy chain variable region comprising the amino acid sequence of SEQ ID NO: 56, and a light chain variable region comprising the amino acid sequence of SEQ ID NO: 80;

(k) a heavy chain variable region comprising the amino acid sequence of SEQ ID NO: 56, and a light chain variable region comprising the amino acid sequence of SEQ ID NO: 60;

(l) a heavy chain variable region comprising the amino acid sequence of SEQ ID NO: 56, and a light chain variable region comprising the amino acid sequence of SEQ ID NO: 61; or (m) a heavy chain variable region comprising the amino acid sequence of SEQ ID NO: 56, and a light chain variable region comprising the amino acid sequence of SEQ ID NO: 72.

15. The method of claim 1, wherein the antibody comprises a heavy chain variable region comprising the amino acid sequence of SEQ ID NO: 56 and a light chain variable region comprising the amino acid sequence of SEQ ID NO: 60.

16. The method of claim 1, wherein the antibody comprises a heavy chain variable region comprising the amino acid sequence of SEQ ID NO: 56 and a light chain variable region comprising the amino acid sequence of SEQ ID NO: 57.

17. The method of claim 1, wherein the antibody comprises a heavy chain comprising the amino acid sequence of SEQ ID NO: 137 and a light chain comprising the amino acid sequence of SEQ ID NO: 142.

18. The method of claim 1, wherein the antibody comprises a heavy chain comprising the amino acid sequence of SEQ ID NO: 138 and a light chain comprising the amino acid sequence of SEQ ID NO: 142.

19. The method of claim 1, wherein the antibody is of the IgG class, the IgM class, or the IgA class.

20. The method of claim 19, wherein the antibody is of the IgG class and has an IgG1, IgG2, IgG3, or IgG4 isotype.

21. The method of claim 20, wherein:

(a) the antibody has an IgG1 or IgG2 isotype and comprises an Fc region comprising an amino acid substitution at position P331S, wherein the numbering of the residue position is according to EU numbering;

(b) the antibody has an IgG1 isotype and comprises an Fc region comprising amino acid substitutions at positions L234A, L235A, and P331S, wherein the numbering of the residue position is according to EU numbering;

(c) the antibody has an IgG1, IgG2, or IgG4 isotype and comprises an Fc region comprising an amino acid substitution at position N297A, wherein the numbering of the residue position is according to EU numbering; or (d) the antibody has an IgG1, IgG2, or IgG4 isotype and comprises an Fc region comprises an amino acid substitution at positions S267E and L328F, wherein the numbering of the residue position is according to EU numbering.

22. The method of claim 20, wherein the antibody has an IgG1 isotype and comprises an Fc region comprising amino acid substitutions at positions L234A, L235A, and P331S, wherein the numbering of the residue position is according to EU numbering.

23. The method of claim 1, wherein the sortilin protein is a human sortilin protein.

24. The method of claim 23, wherein the human sortilin protein comprises the amino acid sequence of SEQ ID NO: 81.

25. The method of claim 1, wherein the sortilin protein is a wild-type protein, a naturally occurring variant, or a disease variant.

26. The method of claim 1, wherein the antibody is a human antibody, a bispecific antibody, a monoclonal antibody, a multivalent antibody, or a conjugated antibody.

27. The method of claim 26, wherein the antibody is a bispecific antibody recognizing a first antigen and a second antigen.

28. The method of claim 27, wherein the first antigen is the sortilin protein and the second antigen is an antigen facilitating transport across the blood-brain-barrier.

29. The method of claim 28, wherein the second antigen is selected from the group consisting of transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30 (A), a protein transduction domain, TAT, Syn-B, penetratin, a poly-arginine peptide, an angiopep peptide, basigin, Glut1, CD98hc, and ANG1005.

30. The method of claim 1, wherein the antibody is an antibody fragment that binds to a human sortilin protein.

31. The method of claim 30, wherein the antibody fragment is a Fab, Fab', Fab'-SH, F (ab') 2, Fv, or scFv fragment.

32. The method of claim 1, wherein the individual is a human.

33. The method of claim 1, wherein the disease, disorder, or injury is a stroke.

34. The method of claim 1, wherein the disease, disorder, or injury is dementia.

35. A method of treating an individual having or at risk for frontotemporal dementia, comprising administering to the individual a therapeutically effective amount of an antibody that binds to a sortilin protein, wherein the antibody comprises a heavy chain variable region and a light chain variable region, wherein the heavy chain variable region comprises an HVR-H1 comprising the amino acid sequence YSISSGYYWG (SEQ ID NO: 1), an HVR-H2 comprising the amino acid sequence TIYHSGSTYYNPSLKS (SEQ ID NO: 2), an HVR-H3 comprising the amino acid sequence ARQGSIKQGYYGMDV (SEQ ID NO: 6); and the light chain variable region comprises an HVR-L1 comprising the amino acid sequence RSSQSLLRSTGYNYLD (SEQ ID NO: 9), an HVR-L2 comprising the amino acid sequence LGSNRAS (SEQ ID NO: 29), and an HVR-L3 comprising the amino acid sequence MQQQEAPLT (SEQ ID NO: 32).

36. The method of claim 35, wherein the antibody has an IgG1 isotype and comprises an Fc region comprising amino acid substitutions at positions L234A, L235A, and P331S, wherein the numbering of the residue position is according to EU numbering.

37. The method of claim 35, wherein the individual has one or more mutations in the gene encoding progranulin.

38. The method of claim 37, wherein the individual is heterozygous for one or more loss-of-function mutations in the gene encoding progranulin.

39. A method of treating an individual having or at risk for frontotemporal dementia, comprising administering to the individual a therapeutically effective amount of an antibody that binds to a sortilin protein, wherein the antibody comprises a heavy chain variable region comprising the amino acid sequence of SEQ ID NO: 56 and a light chain variable region comprising the amino acid sequence of SEQ ID NO: 60.

40. The method of claim 39, wherein the antibody has an IgG1 isotype and comprises an Fc region comprising amino acid substitutions at positions L234A, L235A, and P331S, wherein the numbering of the residue position is according to EU numbering.

41. The method of claim 35, wherein the individual has or is at risk for frontotemporal dementia associated with one or more mutations in the gene encoding progranulin.

42. The method of claim 39, wherein the individual has or is at risk for frontotemporal dementia associated with one or more mutations in the gene encoding progranulin.

43. The method of claim 39, wherein the individual has one or more mutations in the gene encoding progranulin.

44. The method of claim 43, wherein the individual is heterozygous for one or more loss-of-function mutations in the gene encoding progranulin.

45. A method of treating an individual having or at risk for frontotemporal dementia, comprising administering to the individual a therapeutically effective amount of an antibody that binds to a sortilin protein, wherein the antibody comprises a heavy chain comprising the amino acid sequence of SEQ ID NO: 137 and a light chain comprising the amino acid sequence of SEQ ID NO: 142.

46. The method of claim 45, wherein the individual has or is at risk for frontotemporal dementia associated with one or more mutations in the gene encoding progranulin.

47. The method of claim 45, wherein the individual has one or more mutations in the gene encoding progranulin.

48. The method of claim 47, wherein the individual is heterozygous for one or more loss-of-function mutations in the gene encoding progranulin.

49. A method of treating an individual having or at risk for frontotemporal dementia, comprising administering to the individual a therapeutically effective amount of an antibody that binds to a sortilin protein, wherein the antibody comprises a heavy chain comprising the amino acid sequence of SEQ ID NO: 138 and a light chain comprising the amino acid sequence of SEQ ID NO: 142.

50. The method of claim 49, wherein the individual has or is at risk for frontotemporal dementia associated with one or more mutations in the gene encoding progranulin.

51. The method of claim 49, wherein the individual has one or more mutations in the gene encoding progranulin.

52. The method of claim 51, wherein the individual is heterozygous for one or more loss-of-function mutations in the gene encoding progranulin.

\* \* \* \* \*